US012304928B2

(12) United States Patent
Weidenbacher et al.

(10) Patent No.: US 12,304,928 B2
(45) Date of Patent: May 20, 2025

(54) EPITOPE RESTRICTION FOR ANTIBODY SELECTION

(71) Applicants: CZ Biohub SF LLC, San Francisco, CA (US); The Board of Trustees of the Leland Stanford Junior University, Stanford, CA (US)

(72) Inventors: Payton Weidenbacher, Stanford, CA (US); Peter S. Kim, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 1074 days.

(21) Appl. No.: 17/053,230

(22) PCT Filed: May 17, 2019

(86) PCT No.: PCT/US2019/032945
§ 371 (c)(1),
(2) Date: Nov. 5, 2020

(87) PCT Pub. No.: WO2019/222674
PCT Pub. Date: Nov. 21, 2019

(65) Prior Publication Data

US 2021/0139542 A1 May 13, 2021

Related U.S. Application Data

(60) Provisional application No. 62/780,595, filed on Dec. 17, 2018, provisional application No. 62/688,939, filed on Jun. 22, 2018, provisional application No. 62/673,617, filed on May 18, 2018.

(51) Int. Cl.

| | |
|---|---|
| ***A61K 39/00*** | (2006.01) |
| ***C07K 1/107*** | (2006.01) |
| ***C07K 14/005*** | (2006.01) |
| ***C07K 16/10*** | (2006.01) |

(52) U.S. Cl.
CPC ............ *C07K 14/005* (2013.01); *A61K 39/00* (2013.01); *C07K 1/1072* (2013.01); *C07K 16/1018* (2013.01); *C07K 16/1063* (2013.01); *C07K 2317/35* (2013.01); *C12N 2740/16122* (2013.01); *C12N 2760/16122* (2013.01)

(58) Field of Classification Search
None
See application file for complete search history.

(56) References Cited

U.S. PATENT DOCUMENTS

| | | |
|---|---|---|
| 9,441,019 B2 | 9/2016 | Nabel et al. |
| 2010/0092505 A1 | 4/2010 | Bianchi et al. |

FOREIGN PATENT DOCUMENTS

| | | | |
|---|---|---|---|
| WO | 2010/045321 | A2 | 4/2010 |
| WO | 2013/043729 | A1 | 3/2013 |
| WO | 2013044203 | A2 | 3/2013 |
| WO | 2016/205704 | A1 | 12/2016 |
| WO | 2016205704 | A2 | 12/2016 |

OTHER PUBLICATIONS

Medina et al. "Glycosylations in the globular head of the hemagglutinin protein modulate the virulence and antigenic properties of the H1N1 influenza viruses," Sci Transl Med, May 29, 2013, Pagegs. 1-23, vol. 5.
Weidenbacher et al. "Protect, modify, deprotect (PMD): Astrategy for creating vaccines to elicit antibodies targeting a specificepitope," Proc Natl Acad Sci USA, Apr. 29, 2019, pp. 9947-9952, vol. 116, No. 20.
International Search Report, Application No. PCT/US2019/032945, Aug. 12, 2019, 4 pages.
Written Opinion, Application No. PCT/US2019/032945, Aug. 12, 2019, 6 pages.
Burton et al., "Broadly Neutralizing Anti bodies to HIV and Their Rolein Vaccine Design", Annu. Rev. Immunol., 2016, pp. 635-659, (34).
Bergström et al., "Epitope Specific Suppression of IgG Responses by Passively Administered Specific IgG: Evidence of Epitope Masking", Front. Immunol., Mar. 6, 2017, pp. 1-12.
McClements et al., "Immunization with DNA vaccines encoding glycoprotein D or glycoprotein B, alone or in combination, induces protective immunity in animal models of herpes simplex virus-2 disease", Proc. Natl. Acad. Sci. USA, Oct. 1996, pp. 11414-11420, vol. 93.
Lutz et al., "Unmodified mRNA in LNPs constitutes a competitive technologyfor prophylactic vaccines", NPJ Vaccines, Oct. 19, 2017, pp. 1-9, (2), Article No. 29.
Konigsberg et al., "The development of IL-2 conjugated liposomes for therapeutic purposes", Biochimica et Biophysica Acta (BBA)—Biomembranes, Mar. 13, 1998, pp. 243-251, vol. 1370, Issue 2.
Benacerraf et al., "Studies on Hypersensitivity—I. Delayed and Arthus-type Skin Reactivity to Protein Conjugates in Guinea Pigs", Immunology. Jan. 1959, pp. 53-63, 2(1).

(Continued)

*Primary Examiner* — Ruixiang Li
(74) *Attorney, Agent, or Firm* — Kilpatrick Townsend & Stockton LLP

(57) ABSTRACT

Provided are methods of producing antigenic proteins and antigenic protein complexes and compositions and vaccines produced from such methods. Also provided are methods of immunizing a subject using such compositions and vaccines. The antigenic proteins and protein complexes of this disclosure are useful as vaccine immunogens that can direct the immune system of a subject immunized with such vaccine immunogens to generate antibodies against a specific region, or epitope, of a protein that is known to be productive or neutralizing in the case of an infection. Also provided are methods of screening for B cells expressing antibodies that bind specifically to a particular, desired epitope (target region). Compositions and kits comprising one or more antigenic protein, protein complexes, binding partners, and polynucleotides encoding any thereof, are also described.

13 Claims, 43 Drawing Sheets

Specification includes a Sequence Listing.

(56) References Cited

OTHER PUBLICATIONS

Jardine et al., "Rational HIVimmunogen design to target specific germline B cell receptors", Science, May 10, 2013, pp. 711-716, 340 (6133).
Salmaso et al., "Preparation and characterization of active site protected poly (ethylene glycol)-avidin bioconjugates", Biochim. Biophys. Acta-Gen. Subj. Oct. 30, 2005, pp. 57-66, vol. 1726, Issue 1. (https://www.sciencedirect.com/science/article/pii/S0304416505001212).
Uhr et al., "Regulatory Effect of Antibody onthe Immune Response", Adv. Immunol. 1968, vol. 8, pp. 81-127.
Moller., Studies on the Mechanism of immuno logical enhancement of tumor homografts. I. Specificity of Immunologic Enhancement:, JNCI30, Jun. 1963, vol. 30, Issue 6, pp. 1153-1175.
Kanekiyo et al., "Self-assembling influenza nanoparticle vaccines elicit broadly neutralizing HIN1 antibodies", Nature , May 22, 2013, 499(7456), pp. 102-106.
Sutton et al., "Protective efficacy of influenza group 2 hemagglutinin stem-fragment immunogen vaccines", NPJ Vaccines, Dec. 15, 2017, vol. 2, Article 35, pp. 1-11.
Impagliazzo et al., "A stable trimeric influenza hemagglutinin stemas a broadly protective immunogen", Science, Sep. 18, 2015, 349(6254), pp. 1301-1306.
Lee et al., "Design and Structure of an Engineered Disulfide-Stabilized Influenza Virus Hemagglutinin Trimer",J. of Virology, Apr. 29, 2015, 89(14) , pp. 7417-7420.
Mallajosyula et al., "Hemagglutinin sequence conservation guided stem immunogen design from influenza A H3 subtype", Front. Immunol., Jun. 26, 2015, vol. 6, Article 329, pp. 1-12.
Yassine et al., "Hemagglutinin-stem nanoparticles generate heterosubtypic influenza protection", Nature Medicine, 2015 (21), pp. 1065-1070.
Jardine et al., "Rational HIV Immunogen Designto Target Specific Germline B Cell Receptors", Science, May 10, 2013, 340(6133) , pp. 711-716.
McGuire et al., Diverse Recombinant HIV-1 Envs Fail To Activate B Cells Expressing the Germline B Cell Receptors of the Broadly Neutralizing Anti-HIV-1 Antibodies PG9 and 447-52D, J. of Virology, Mar. 2014, 88(5), pp. 2645-2657.
Sanders et al., "A Next-Generation Cleaved, Soluble HIV-1 Env Trimer, BG505 SOSIP.664 gp 140, Expresses Multiple Epitopes for Broadly Neutralizing but Not Non-Neutralizing Antibodies", PLoS Pathology, Sep. 19, 2013, 9(9):e1003618, pp. 1-20.
Georgiev et al., "Single-Chain Soluble BG505.SOSIP gp 140 Trimers as Structural and Antigenic Mimics of Mature Closed HIV-1 Env", 2015, J. of Virology 89(10):5318-5329.
Kwon et al., "Crystalstructure, conformational fixation and entry-related interactions of mature ligand-free HIV-1 Env", Nature Struct. Mol. Biol., Jun. 22, 2015, 22(7), pp. 522-531.
Chuang et al., "Structure-Based Design of a Soluble Prefusion-Closed HIV-1 Env Trimer with Reduced CD4 Affinity and Improved Immunogenicity", J. Virol., May 2017, 91(10), pp. 1-18.
Joyce et al., "Soluble Prefusion Closed DS-SOSIP.664-Env Trimers of Diverse HIV-1 Strains", Cell Reports, Dec. 5, 2017, vol. 21, Issue 10, pp. 2992-3002.
Rutten et al., "A Universal Approach to Optimize the Folding and Stability of Prefusion-Closed HIV-1 Envelope Trimers", Cell Reports, Apr. 10, 2018, vol. 23, Issue 2, pp. 584-595.
McLellan et al., "Structure-Based Design of a Fusion Glycoprotein Vaccine for Respiratory Syncy tial Virus", Science, Nov. 1, 2013, 342(6158), pp. 592-598.
Finn, "Bacterialpolysaccharide-protein conjugate vaccines", British Medical Bulletin, Jan. 1, 2004, vol. 70, Issue 1, pp. 1-14.
Kadam & Wilson, "A small-molecule fragment that emulates binding of receptor and broadly neutralizing antibodies to influenza A hemagglutinin", Proc. Natl. Acad. Sci. U.S.A., 2018, 115(16): 1-6.
Bernard & Francis (2014). "Chemical strategies for the covalent modification of filamentous phage", Front. Microbiol. Dec. 23, 2014, 5:734, pp. 1-7.
Gilmore et al., "N-terminal protein modification through a biomimetic transamination reaction", Angew. Chem. Int. Ed. Engl., Aug. 11, 2006, vol. 45, Issue 32, pp. 5307-5311.
Liu & Schultz, "Adding new chemistries to the genetic code", Annu. Rev. Biochem. 2010, vol. 79, pp. 413-444.
Berge et al., "Pharmaceutical Salts",*J. Pharm. Sci.*, Jan. 1977, vol. 66, Issue 1, pp. 1-19.
McClements, "Immunization with DNA vaccines encoding glycoprotein D or glycoprotein B, alone or in combination, induces protective immunity in animalmodels of herpes simplexvirus-2 disease", Proc. Natl. Acad. Sci. USA, Oct. 15, 1996, 93 (21), pp. 11414-11420.
Lutz et al., "Unmodified mRNA in LNPs constitutes a competitive technology for prophylactic vaccines", NPJ Vaccines, Oct. 19, 2017, vol. 2, Art. 29, pp. 1-9.
Whittle et al., "Flow Cytometry Reveals that H5N1 Vaccination Elicits Cross-Reactive Stem-Directed Antibodies from Multiple Ig Heavy-Chain Lineages", J Virol., Apr. 2014, 88(8), pp. 4047-4057.
Han et al., "A long noncoding RNA protects the heart from pathological hypertrophy", Nature, Aug. 10, 2014, vol. 514, Issue 7520, pp. 102-106.
Doud et al., Accurate Measurement of the Effects of All Amino-Acid Mutations on Influenza Hemagglutinin, Viruses, Jun. 3, 2016, 8(6):155, pp. 1-17.

FIG. 2A

Anti-HEWL Bispecific Antibody (Purified)

(SEQ ID NO: 1)
SEVQLQQSGAELMKPGASVKISCKASGYTFSDYWIEWVKQRPGHGLEWIGEILPGSGSTNYHE
RFKGKATFTADTSSSTAYMQLNSLTSEDSGVYYCLHGNYDFDGWGQGTTLTVSSASTKGPSVK
LEEGEFSEARVSMDIVLTQSPAIMSASPGEKVTMTCSASSSVNYMYWYQQKSGTSPKRWI
YDTSKLASGVPVRFSGSGSGTSYSLTISSMETEDAATYYCQQWGRNPTFGGGTKLEIKRT
VAAPSGGSPSGQAGAAASESLFVSNHAYGGSSQVQLQQSGAELVRPGASVKLSCKASG
YTFISYWINWVKQRPGQGLEWIGNIYPSDSYTNYNQKFKDKATLTVDKSSSTAYMQLSSP
TSEDSAVYYCTRDDNYGAMDYWGQGTTVTVSSASTKGPSVKLEEGEFSEARVSDIELTQSP
SYLVASPGETITINCRASKSISKSLAWYQEKPGKTNNLLIYSGSTLQSGIPSRFSGSGSGTD
FTLTISSLEPEDFAMYICQQHNEYPWTFGGGTKLEIKRKRTVAAPSGAAALEHHHHHH

Anti-HEWL Bispecific Antibody (Expressed)

(SEQ ID NO: 2)
MKYLLPTAAAGLLLLAAQPAMASEVQLQQSGAELMKPGASVKISCKASGYTFSDYWIEW
VKQRPGHGLEWIGEILPGSGSTNYHERFKGKATFTADTSSSTAYMQLNSLTSEDSGVYYCLHG
NYDFDGWGQGTTLTVSSASTKGPSVKLEEGEFSEARVSMDIVLTQSPAIMSASPGEKVTMT
CSASSSVNYMYWYQQKSGTSPKRWIYDTSKLASGVPVRFSGSGSGTSYSLTISSMETEDA
ATYYCQQWGRNPTFGGGTKLEIKRTVAAPSGGSPSGQAGAAASESLFVSNHAYGGSSQ
VQLQQSGAELVRPGASVKLSCKASGYTFISYWINWVKQRPGQGLEWIGNIYPSDSYTNYN
QKFKDKATLTVDKSSSTAYMQLSSPTSEDSAVYYCTRDDNYGAMDYWGQGTTVTVSSAS
TKGPSVKLEEGEFSEARVSDIELTQSPSYLVASPGETITINCRASKSISKSLAWYQEKPGKT
NNLLIYSGSTLQSGIPSRFSGSGSGTDFTLTISSLEPEDFAMYICQQHNEYPWTFGGGTKL
EIKRKRTVAAPSGAAALEHHHHHH

| | |
|---|---|
| *HyHEL-5 HC Variable Region* | **Muscle Aldolase Linker** |
| *Yol-Tag* | ***D11.15 HC Variable Region*** |
| ***HyHEL-5 LC Variable Region*** | D11.15 LC Variable Region |
| **PelB Signal Sequence** | |

FIG. 2B

H5 HA Trispec HC (Purified)

(SEQ ID NO: 3)
QVQLQESGPGLVKPSGTVSLTCAVSGGSISSSYWWSWVRQPPGKGLEWIGEIYHSGNTNYNPS
LKSRVTISVDKSKNLFSLKLSSVTAADTAVYYCARVALFDILTGGWFDPWGQGTLVTVSSASTK
GPSVKLEEGEFSEARVYELTQPPSVSVSPGQTVNITCSGDTLGDKYVCWYQQKPGQSPVL
VIYQDTKRPSGIPERFSGSNSGDTATLTVSGTQAMDEADYYCQAWDSSSFVFGTGTKVT
VLGGSGGPSGQAGAAASESLFVSNHAYGGSGGEVHLQQSGPELVKPGASVKMSCKTSGYT
FTEYTIHWMKQSHGKSLEWIGGIFPNNGDTTYNQKFKVRATLTVGRSSSTAYMDLRSLT
SEDSAVYYCVRNYGSSYGYFDVWGAGTTVTVSSASTKGPSVFPLAPSSKSTSGGTAALGC
LVKDYFPEPVTVSWNSGALTSGVHTFPAVLQSSGLYSLSSVVTVPSSSLGTQTYICNVNH
KPSNTKVDKKVEPKSCDKTHT

H5 HA Trispec HC (Expressed)

(SEQ ID NO: 4)
MGWSCIILFLVATATGVHSQVQLQESGPGLVKPSGTVSLTCAVSGGSISSSYWWSWVR
QPPGKGLEWIGEIYHSGNTNYNPSLKSRVTISVDKSKNLFSLKLSSVTAADTAVYYCAR
VALFDILTGGWFDPWGQGTLVTVSSASTKGPSVKLEEGEFSEARVYELTQPPSVSVSPG
QTVNITCSGDTLGDKYVCWYQQKPGQSPVLVIYQDTKRPSGIPERFSGSNSGDTATLTVS
GTQAMDEADYYCQAWDSSSFVFGTGTKVTVLGGSGGPSGQAGAAASESLFVSNHAYGGS
GGEVHLQQSGPELVKPGASVKMSCKTSGYTFTEYTIHWMKQSHGKSLEWIGGIFPNNG
DTTYNQKFKVRATLTVGRSSSTAYMDLRSLTSEDSAVYYCVRNYGSSYGYFDVWGAGTT
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHT

Signal Sequence YolTag ScFv Linker *ScFv – FAb Linker*
*H5.3 HC Variable Region* *H5.3 LC Variable Region*
*H5M9 HC Variable Region* H5M9 HC Constant Region 1

FIG. 2C

H5 HA Trispec LC (Purified)

(SEQ ID NO: 5)
EVQLVQSGAEVKKPGESLRISCAGFAYSSTYFWISWVRQMPGKCPEWMGRIDPTDSYINYSPS
FQGHVTISVDRSASTVYLQWSSLKASDTAMYYCAYHRRGHFYGSGSAWDWFESWGQGTLVTV
SSRTVGPSVKLEEGEFSEARVEIVLTQSPLTLSVSPGERATLSCRASQSVSSNLAWYQQMP
GQAPRLLIYGASTRATGIPARLSGSASGTEFTLTISSLQSEDFAVYYCQQYNNWPYTFGC
GTKLEIKGGSGGPSGQAGAAASESLFVSNHAYGGSGGDIVLTQSPGSLTVSLGQRATISCRA
SESVDNFGKSFMHWYQQKPGQSPKLLIYRASNREFGIPARFNGSGSGTDFALTINPVEA
DDVATYFCQQSNEDPRTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTH
QGLSSPVTKSFNRGEC

H5 HA Trispec LC (Expressed)

(SEQ ID NO: 6)
MGWSCIILFLVATATGVHSEVQLVQSGAEVKKPGESLRISCAGFAYSSTYFWISWVRQMPG
KCPEWMGRIDPTDSYINYSPSFQGHVTISVDRSASTVYLQWSSLKASDTAMYYCAYHRRGHFY
GSGSAWDWFESWGQGTLVTVSSRTVGPSVKLEEGEFSEARVEIVLTQSPLTLSVSPGERAT
LSCRASQSVSSNLAWYQQMPGQAPRLLIYGASTRATGIPARLSGSASGTEFTLTISSLQSE
DFAVYYCQQYNNWPYTFGCGTKLEIKGGSGGPSGQAGAAASESLFVSNHAYGGSGGDIVL
TQSPGSLTVSLGQRATISCRASESVDNFGKSFMHWYQQKPGQSPKLLIYRASNREFGIPA
RFNGSGSGTDFALTINPVEADDVATYFCQQSNEDPRTFGGGTKLEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

Signal Sequence YolTag ScFv Linker *ScFv – FAb Linker*
*65C6 HC Variable Region* *65C6 Variable Region*
*H5M9 LC Variable Region* H5M9 LC Constant Region

FIG. 2D

Alternate H5 HA Trispec HC (Purified)

(SEQ ID NO: 7)
*EVQLVESGAEVKKPGSSVKVSCRASGTFYKYAINWVRQAPGQCLEWMGGIIPFFGTTNYAAKF*
*QGRLTITADGSTNTAYMQLDSLRSEDTAVYYCAGPSITESHYCLDCAAKDYYYGLDVWGQGTT*
*VTVSS*ASTKGPSVKLEEGEFSEARV*QSVLTQPPSASGTPGQSVTISCSGSRSNIGGNTVNW*
*YQHLPGMAPKLLIYSSNQRSSGVPDRFSGSKSGTSASLAISGLQSEDDADYYCASWDDSL*
*NGVVFGCGTKLTVLGGGSGGPSGQAGAAASESLFVSNHAYGGSGGEVHLQQSGPELVKPG*
*ASVKMSCKTSGYTFTEYTIHWMKQSHGKSLEWIGGIFPNNGDTTYNQKFKVRATLTVGR*
*SSSTAYMDLRSLTSEDSAVYYCVRNYGSSYGYFDVWGAGTTVTVSS*ASTKGPSVFPLAPS
SKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHT

Alternate H5 HA Trispec HC (Expressed)

(SEQ ID NO: 8)
MGWSCIILFLVATATGVHSEVQLVESGAEVKKPGSSVKVSCRASGTFYKYAINWVRQ
APGQCLEWMGGIIPFFGTTNYAAKFQGRLTITADGSTNTAYMQLDSLRSEDTAVYYCAG
PSITESHYCLDCAAKDYYYGLDVWGQGTTVTVSSASTKGPSVKLEEGEFSEARVQSVLT
QPPSASGTPGQSVTISCSGSRSNIGGNTVNWYQHLPGMAPKLLIYSSNQRSSGVPDRFSG
SKSGTSASLAISGLQSEDDADYYCASWDDSLNGVVFGCGTKLTVLG*GGSGGPSGQAGAA*
*ASESLFVSNHAYGGSGG**EVHLQQSGPELVKPGASVKMSCKTSGYTFTEYTIHWMKQSHG*
*KSLEWIGGIFPNNGDTTYNQKFKVRATLTVGRSSSTAYMDLRSLTSEDSAVYYCVRNYGS*
*SYGYFDVWGAGTTVTVSS*ASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPK
SCDKTHT

Signal Sequence YolTag ScFv Linker *ScFv – FAb Linker*
*F045-092 HC Variable Region* *F045-092 LC Variable Region*
*H5M9 HC Variable Region* H5M9 HC Constant Region 1

FIG. 2E

Medi8852 LC Reduced Affinity Protein (Purified)

(SEQ ID NO: 9)
DIQMTQSPSSLSASVGDRVTITCRTSQSLSSATHWYQQKPGKAPKLLIYAASSRGSGVPS
RFSGSGSGTDFTLTISSLQPEDFATYYCQQSRTFGQGTKVEIKRTVAAPSVFIFPPSDEQLK
SGTASVVCLLNNFYPREAKVQWKVDNALQSGNSQESVTEQDSKDSTYSLSSTLTLSKA
DYEKHKVYACEVTHQGLSSPVTKSFNRGEC

Medi8852 LC Reduced Affinity Protein (Expressed)

(SEQ ID NO: 10)
MGWSCIILFLVATATGVHSDIQMTQSPSSLSASVGDRVTITCRTSQSLSSATHWYQQKP
GKAPKLLIYAASSRGSGVPSRFSGSGSGTDFTLTISSLQPEDFATYYCQQSRTFGQGTKVE
IKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Signal Sequence Ala Mutation Constant Region

FIG. 2F

Medi8852 HC Reduced Affinity Protein (Purified)

(SEQ ID NO: 11)
QVQLQQSGPGLVKPSQTLSLTCAISGDSVSSYNAVWNWIRQSPSRGLEWLGATAYRSG
WYNDYAESVKSRITINPDTSKNQFSLQLNSVTPEDTAVYYCARSGHITVFGVNVDAFDM
WGQGTMVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

Medi8852 HC Reduced Affinity Protein (Expressed)

(SEQ ID NO: 12)
MGWSCIILFLVATATGVHSQVQLQQSGPGLVKPSQTLSLTCAISGDSVSSYNAVWNWI
RQSPSRGLEWLGATAYRSGWYNDYAESVKSRITINPDTSKNQFSLQLNSVTPEDTAVYY
CARSGHITVFGVNVDAFDMWGQGTMVTVSSASTKGPSVFPLAPSSKSTSGGTAALGCL
VKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQK
SLSLSPGK

Signal Sequence Ala Mutation Constant Region

FIG. 2G

H1 HA +9 LYS Protein (Purified)

(SEQ ID NO: 13)
DTICIGYHANNSTDTVDTVLEKNVTVTHSVNLLEDSHNGKLCKLKGIAPLQLGKCSVAG
WILGNPECELLISKESWSYIVETPNPENGTCFPGYFADYEELREQLSSVSSFERFEIFPKES
SWPNHTVKGVSASCSHKGKSSFYKNLLWLTGKNGLYPKLSKSYKNNKEKEVLVLWGV
HHPPNIKNQKALYHTENAYVSVVSSHYSRRFTPEIAKRPKVRDQEGRINYYWTLLEPGD
TIIFEANGNLIAPWYAFALSRGFGSGIITSNAPMDECDAKCQTPQGAINSSLPFQNVHPVTI
GECPKYVRSAKLRMVTGLRNIPQRETGGLFGAIAGFIEGGWTGMVDGWYGYHHQNEQ
GSGYAADQKSTQNAINGITNKVNSVIEKMNTQFTAVGKEFNKLERRMENLNKKVDDGF
LDIWTYNAELLVLLENERTLDFHDSNVKNLYEKVKSQLKNNAKEIGNGCFEFYHKCNN
ECMESVKNGTYDYPKYSEESKLNREKIDGSGYIPEAPRDGQAYVRKDGEWVLLSTFLGS
*GLNDIFEAQKIEWHEG**HHHHHH*

H1 HA +9 LYS Protein (Expressed)

(SEQ ID NO: 14)
MYRMQLLSCIALSLALVTNSDTICIGYHANNSTDTVDTVLEKNVTVTHSVNLLEDSHN
GKLCKLKGIAPLQLGKCSVAGWILGNPECELLISKESWSYIVETPNPENGTCFPGYFADY
EELREQLSSVSSFERFEIFPKESSWPNHTVKGVSASCSHKGKSSFYKNLLWLTGKNGLYP
KLSKSYKNNKEKEVLVLWGVHHPPNIKNQKALYHTENAYVSVVSSHYSRRFTPEIAKRP
KVRDQEGRINYYWTLLEPGDTIIFEANGNLIAPWYAFALSRGFGSGIITSNAPMDECDAK
CQTPQGAINSSLPFQNVHPVTIGECPKYVRSAKLRMVTGLRNIPQRETGGLFGAIAGFIEG
GWTGMVDGWYGYHHQNEQGSGYAADQKSTQNAINGITNKVNSVIEKMNTQFTAVGK
EFNKLERRMENLNKKVDDGFLDIWTYNAELLVLLENERTLDFHDSNVKNLYEKVKSQL
KNNAKEIGNGCFEFYHKCNNECMESVKNGTYDYPKYSEESKLNREKIDGSGYIPEAPRD
GQAYVRKDGEWVLLSTFLGS*GLNDIFEAQKIEWHEG**HHHHHH*

IL2 Signal Sequence *Avi Tag* Foldon Tag *Hexa His-Tag*

FIG. 2H

H5 HA Protein (Purified)

(SEQ ID NO: 15)
DQICIGYHANNSTEQVDTIMEKNVTVTHAQDILEKTHNGKLCDLDGVKPLILRDCSVAG
WLLGNPMCDEFINVPEWSYIVEKANPVNDLCFPGDFNDYEELKHLLSRINHFEKIQIIPKS
SWSSHEASLGVSSACPYQGKSSFFRNVVWLIKKNSTYPTIKRSYNNTNQEDLLVLWGIH
HPNDAAEQTKLYQNPTTYISVGTSTLNQRLVPRIATRSKVNGQSGRMEFFWTILKPNDAI
NFESNGNFIAPEYAYKIVKKGDSTIMKSELEYGNCNTKCQTPMGAINSSMPFHNIHPLTI
GECPKYVKSNRLVLATGLRNSPQRETRGLFGAIAGFIEGGWQGMVDGWYGYHHSNEQ
GSGYAADKESTQKAIDGVTNKVNSIIDKMNTQFEAVGREFNNLERRIENLNKKMEDGFL
DVWTYNAELLVLMENERTLDFHDSNVKNLYDKVRLQLRDNAKELGNGCFEFYHKCDN
ECMESVRNGTYDYPQYSEEARLKREEISGS<u>GYIPEAPRDGQAYVRKDGEWVLLSTFLGS</u>
*GLNDIFEAQKIEWHEG*<u>*HHHHHH*</u>

H5 HA Protein (Expressed)

(SEQ ID NO: 16)
MEKIVLLFAIVSLVKSDQICIGYHANNSTEQVDTIMEKNVTVTHAQDILEKTHNGKLCD
LDGVKPLILRDCSVAGWLLGNPMCDEFINVPEWSYIVEKANPVNDLCFPGDFNDYEELK
HLLSRINHFEKIQIIPKSSWSSHEASLGVSSACPYQGKSSFFRNVVWLIKKNSTYPTIKRSY
NNTNQEDLLVLWGIHHPNDAAEQTKLYQNPTTYISVGTSTLNQRLVPRIATRSKVNGQS
GRMEFFWTILKPNDAINFESNGNFIAPEYAYKIVKKGDSTIMKSELEYGNCNTKCQTPM
GAINSSMPFHNIHPLTIGECPKYVKSNRLVLATGLRNSPQRETRGLFGAIAGFIEGGWQG
MVDGWYGYHHSNEQGSGYAADKESTQKAIDGVTNKVNSIIDKMNTQFEAVGREFNNL
ERRIENLNKKMEDGFLDVWTYNAELLVLMENERTLDFHDSNVKNLYDKVRLQLRDNA
KELGNGCFEFYHKCDNECMESVRNGTYDYPQYSEEARLKREEISGS<u>GYIPEAPRDGQAY</u>
<u>VRKDGEWVLLSTFLGS</u>*GLNDIFEAQKIEWHEG*<u>*HHHHHH*</u>

Signal Sequence <u>Foldon Tag</u> *Avi Tag* <u>*Hexa His-tag*</u>

FIG. 2I

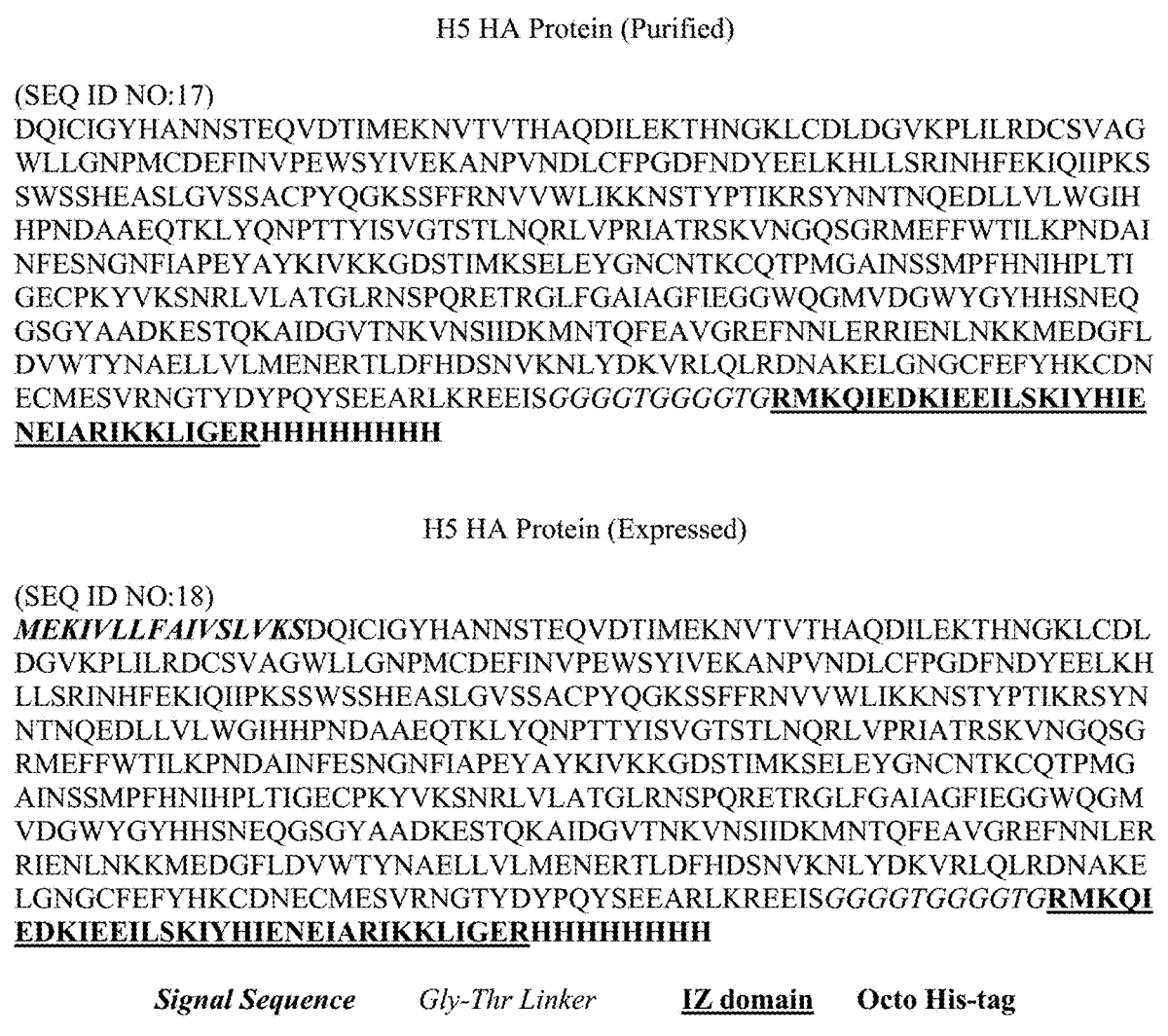

H5 HA Protein (Purified)

(SEQ ID NO:17)
DQICIGYHANNSTEQVDTIMEKNVTVTHAQDILEKTHNGKLCDLDGVKPLILRDCSVAG
WLLGNPMCDEFINVPEWSYIVEKANPVNDLCFPGDFNDYEELKHLLSRINHFEKIQIIPKS
SWSSHEASLGVSSACPYQGKSSFFRNVVWLIKKNSTYPTIKRSYNNTNQEDLLVLWGIH
HPNDAAEQTKLYQNPTTYISVGTSTLNQRLVPRIATRSKVNGQSGRMEFFWTILKPNDAI
NFESNGNFIAPEYAYKIVKKGDSTIMKSELEYGNCNTKCQTPMGAINSSMPFHNIHPLTI
GECPKYVKSNRLVLATGLRNSPQRETRGLFGAIAGFIEGGWQGMVDGWYGYHHSNEQ
GSGYAADKESTQKAIDGVTNKVNSIIDKMNTQFEAVGREFNNLERRIENLNKKMEDGFL
DVWTYNAELLVLMENERTLDFHDSNVKNLYDKVRLQLRDNAKELGNGCFEFYHKCDN
ECMESVRNGTYDYPQYSEEARLKREEIS*GGGGTGGGGTG***RMKQIEDKIEEILSKIYHIE
NEIARIKKLIGER**HHHHHHHH

H5 HA Protein (Expressed)

(SEQ ID NO:18)
*MEKIVLLFAIVSLVKS*DQICIGYHANNSTEQVDTIMEKNVTVTHAQDILEKTHNGKLCDL
DGVKPLILRDCSVAGWLLGNPMCDEFINVPEWSYIVEKANPVNDLCFPGDFNDYEELKH
LLSRINHFEKIQIIPKSSWSSHEASLGVSSACPYQGKSSFFRNVVWLIKKNSTYPTIKRSYN
NTNQEDLLVLWGIHHPNDAAEQTKLYQNPTTYISVGTSTLNQRLVPRIATRSKVNGQSG
RMEFFWTILKPNDAINFESNGNFIAPEYAYKIVKKGDSTIMKSELEYGNCNTKCQTPMG
AINSSMPFHNIHPLTIGECPKYVKSNRLVLATGLRNSPQRETRGLFGAIAGFIEGGWQGM
VDGWYGYHHSNEQGSGYAADKESTQKAIDGVTNKVNSIIDKMNTQFEAVGREFNNLER
RIENLNKKMEDGFLDVWTYNAELLVLMENERTLDFHDSNVKNLYDKVRLQLRDNAKE
LGNGCFEFYHKCDNECMESVRNGTYDYPQYSEEARLKREEIS*GGGGTGGGGTG***RMKQI
EDKIEEILSKIYHIENEIARIKKLIGER**HHHHHHHH

*Signal Sequence* *Gly-Thr Linker* IZ domain Octo His-tag

FIG. 2J

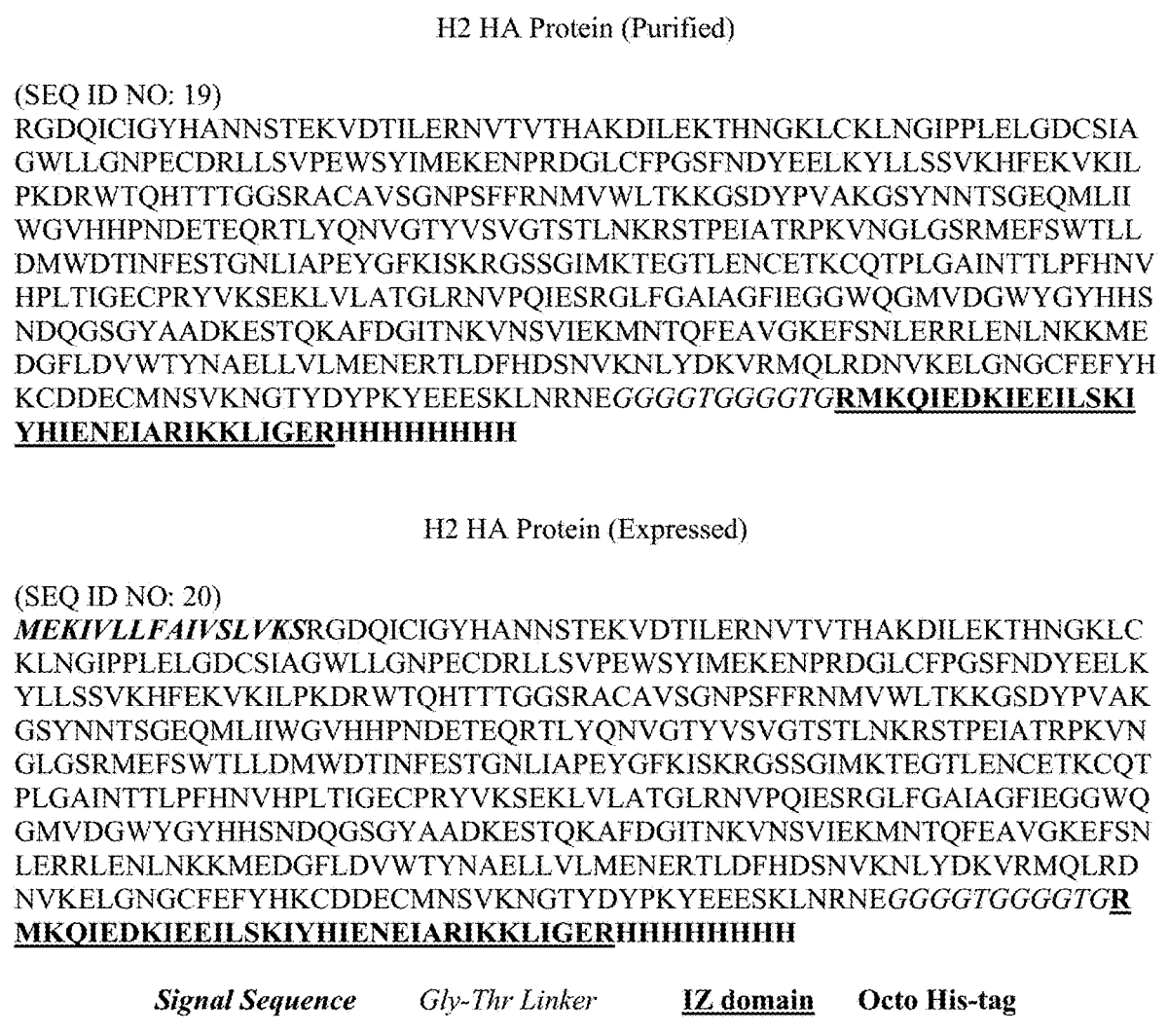

H2 HA Protein (Purified)

(SEQ ID NO: 19)
RGDQICIGYHANNSTEKVDTILERNVTVTHAKDILEKTHNGKLCKLNGIPPLELGDCSIA
GWLLGNPECDRLLSVPEWSYIMEKENPRDGLCFPGSFNDYEELKYLLSSVKHFEKVKIL
PKDRWTQHTTTGGSRACAVSGNPSFFRNMVWLTKKGSDYPVAKGSYNNTSGEQMLII
WGVHHPNDETEQRTLYQNVGTYVSVGTSTLNKRSTPEIATRPKVNGLGSRMEFSWTLL
DMWDTINFESTGNLIAPEYGFKISKRGSSGIMKTEGTLENCETKCQTPLGAINTTLPFHNV
HPLTIGECPRYVKSEKLVLATGLRNVPQIESRGLFGAIAGFIEGGWQGMVDGWYGYHHS
NDQGSGYAADKESTQKAFDGITNKVNSVIEKMNTQFEAVGKEFSNLERRLENLNKKME
DGFLDVWTYNAELLVLMENERTLDFHDSNVKNLYDKVRMQLRDNVKELGNGCFEFYH
KCDDECMNSVKNGTYDYPKYEEESKLNRNE*GGGGTGGGGTG*RMKQIEDKIEEILSKI
YHIENEIARIKKLIGERHHHHHHHH

H2 HA Protein (Expressed)

(SEQ ID NO: 20)
*MEKIVLLFAIVSLVKS*RGDQICIGYHANNSTEKVDTILERNVTVTHAKDILEKTHNGKLC
KLNGIPPLELGDCSIAGWLLGNPECDRLLSVPEWSYIMEKENPRDGLCFPGSFNDYEELK
YLLSSVKHFEKVKILPKDRWTQHTTTGGSRACAVSGNPSFFRNMVWLTKKGSDYPVAK
GSYNNTSGEQMLIIWGVHHPNDETEQRTLYQNVGTYVSVGTSTLNKRSTPEIATRPKVN
GLGSRMEFSWTLLDMWDTINFESTGNLIAPEYGFKISKRGSSGIMKTEGTLENCETKCQT
PLGAINTTLPFHNVHPLTIGECPRYVKSEKLVLATGLRNVPQIESRGLFGAIAGFIEGGWQ
GMVDGWYGYHHSNDQGSGYAADKESTQKAFDGITNKVNSVIEKMNTQFEAVGKEFSN
LERRLENLNKKMEDGFLDVWTYNAELLVLMENERTLDFHDSNVKNLYDKVRMQLRD
NVKELGNGCFEFYHKCDDECMNSVKNGTYDYPKYEEESKLNRNE*GGGGTGGGGTG*R
MKQIEDKIEEILSKIYHIENEIARIKKLIGERHHHHHHHH

*Signal Sequence* *Gly-Thr Linker* IZ domain Octo His-tag

FIG. 2K

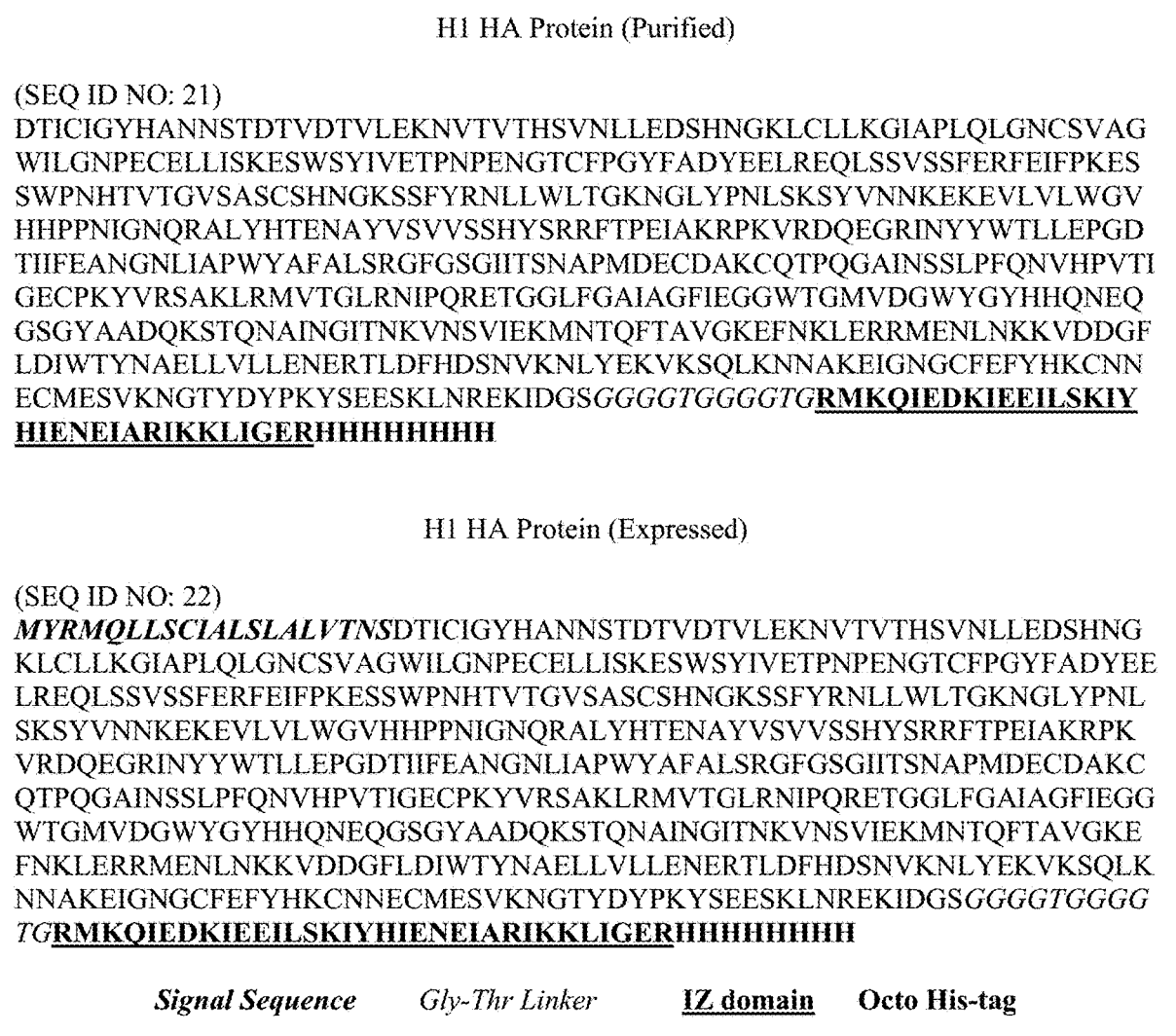

H1 HA Protein (Purified)

(SEQ ID NO: 21)
DTICIGYHANNSTDTVDTVLEKNVTVTHSVNLLEDSHNGKLCLLKGIAPLQLGNCSVAG
WILGNPECELLISKESWSYIVETPNPENGTCFPGYFADYEELREQLSSVSSFERFEIFPKES
SWPNHTVTGVSASCSHNGKSSFYRNLLWLTGKNGLYPNLSKSYVNNKEKEVLVLWGV
HHPPNIGNQRALYHTENAYVSVVSSHYSRRFTPEIAKRPKVRDQEGRINYYWTLLEPGD
TIIFEANGNLIAPWYAFALSRGFGSGIITSNAPMDECDAKCQTPQGAINSSLPFQNVHPVTI
GECPKYVRSAKLRMVTGLRNIPQRETGGLFGAIAGFIEGGWTGMVDGWYGYHHQNEQ
GSGYAADQKSTQNAINGITNKVNSVIEKMNTQFTAVGKEFNKLERRMENLNKKVDDGF
LDIWTYNAELLVLLENERTLDFHDSNVKNLYEKVKSQLKNNAKEIGNGCFEFYHKCNN
ECMESVKNGTYDYPKYSEESKLNREKIDGS*GGGGTGGGGTG*RMKQIEDKIEEILSKIY
HIENEIARIKKLIGERHHHHHHHH

H1 HA Protein (Expressed)

(SEQ ID NO: 22)
*MYRMQLLSCIALSLALVTNS*DTICIGYHANNSTDTVDTVLEKNVTVTHSVNLLEDSHNG
KLCLLKGIAPLQLGNCSVAGWILGNPECELLISKESWSYIVETPNPENGTCFPGYFADYEE
LREQLSSVSSFERFEIFPKESSWPNHTVTGVSASCSHNGKSSFYRNLLWLTGKNGLYPNL
SKSYVNNKEKEVLVLWGVHHPPNIGNQRALYHTENAYVSVVSSHYSRRFTPEIAKRPK
VRDQEGRINYYWTLLEPGDTIIFEANGNLIAPWYAFALSRGFGSGIITSNAPMDECDAKC
QTPQGAINSSLPFQNVHPVTIGECPKYVRSAKLRMVTGLRNIPQRETGGLFGAIAGFIEGG
WTGMVDGWYGYHHQNEQGSGYAADQKSTQNAINGITNKVNSVIEKMNTQFTAVGKE
FNKLERRMENLNKKVDDGFLDIWTYNAELLVLLENERTLDFHDSNVKNLYEKVKSQLK
NNAKEIGNGCFEFYHKCNNECMESVKNGTYDYPKYSEESKLNREKIDGS*GGGGTGGGG*
*TG*RMKQIEDKIEEILSKIYHIENEIARIKKLIGERHHHHHHHH

*Signal Sequence* *Gly-Thr Linker* IZ domain Octo His-tag

FIG. 2L

H1 HA Ectodomain (SEQ ID NO: 23)
DTICIGYHANNSTDTVDTVLEKNVTVTHSVNLLEDSHNGKLCLLKGIAPLQLGNCSVAG
WILGNPECELLISKESWSYIVETPNPENGTCFPGYFADYEELREQLSSVSSFERFEIFPKES
SWPNHTVTGVSASCSHNGKSSFYRNLLWLTGKNGLYPNLSKSYVNNKEKEVLVLWGV
HHPPNIGNQRALYHTENAYVSVVSSHYSRRFTPEIAKRPKVRDQEGRINYYWTLLEPGD
TIIFEANGNLIAPWYAFALSRGFGSGIITSNAPMDECDAKCQTPQGAINSSLPFQNVHPVTI
GECPKYVRSAKLRMVTGLRNIPQRETGGLFGAIAGFIEGGWTGMVDGWYGYHHQNEQ
GSGYAADQKSTQNAINGITNKVNSVIEKMNTQFTAVGKEFNKLERRMENLNKKVDDGF
LDIWTYNAELLVLLENERTLDFHDSNVKNLYEKVKSQLKNNAKEIGNGCFEFYHKCNN
ECMESVKNGTYDYPKYSEESKLNREKIDGS H2 HA Ectodomain (SEQ ID NO: 24)
RGDQICIGYHANNSTEKVDTILERNVTVTHAKDILEKTHNGKLCKLNGIPPLELGDCSIA
GWLLGNPECDRLLSVPEWSYIMEKENPRDGLCFPGSFNDYEELKYLLSSVKHFEKVKIL
PKDRWTQHTTTGGSRACAVSGNPSFFRNMVWLTKKGSDYPVAKGSYNNTSGEQMLII
WGVHHPNDETEQRTLYQNVGTYVSVGTSTLNKRSTPEIATRPKVNGLGSRMEFSWTLL
DMWDTINFESTGNLIAPEYGFKISKRGSSGIMKTEGTLENCETKCQTPLGAINTTLPFHNV
HPLTIGECPRYVKSEKLVLATGLRNVPQIESRGLFGAIAGFIEGGWQGMVDGWYGYHHS
NDQGSGYAADKESTQKAFDGITNKVNSVIEKMNTQFEAVGKEFSNLERRLENLNKKME
DGFLDVWTYNAELLVLMENERTLDFHDSNVKNLYDKVRMQLRDNVKELGNGCFEFYH
KCDDECMNSVKNGTYDYPKYEEESKLNRNE H5 HA Ectodomain (SEQ ID NO: 25)
DQICIGYHANNSTEQVDTIMEKNVTVTHAQDILEKTHNGKLCDLDGVKPLILRDCSVAG
WLLGNPMCDEFINVPEWSYIVEKANPVNDLCFPGDFNDYEELKHLLSRINHFEKIQIIPKS
SWSSHEASLGVSSACPYQGKSSFFRNVVWLIKKNSTYPTIKRSYNNTNQEDLLVLWGIH
HPNDAAEQTKLYQNPTTYISVGTSTLNQRLVPRIATRSKVNGQSGRMEFFWTILKPNDAI
NFESNGNFIAPEYAYKIVKKGDSTIMKSELEYGNCNTKCQTPMGAINSSMPFHNIHPLTI
GECPKYVKSNRLVLATGLRNSPQRETRGLFGAIAGFIEGGWQGMVDGWYGYHHSNEQ
GSGYAADKESTQKAIDGVTNKVNSIIDKMNTQFEAVGREFNNLERRIENLNKKMEDGFL
DVWTYNAELLVLMENERTLDFHDSNVKNLYDKVRLQLRDNAKELGNGCFEFYHKCDN
ECMESVRNGTYDYPQYSEEARLKREEIS

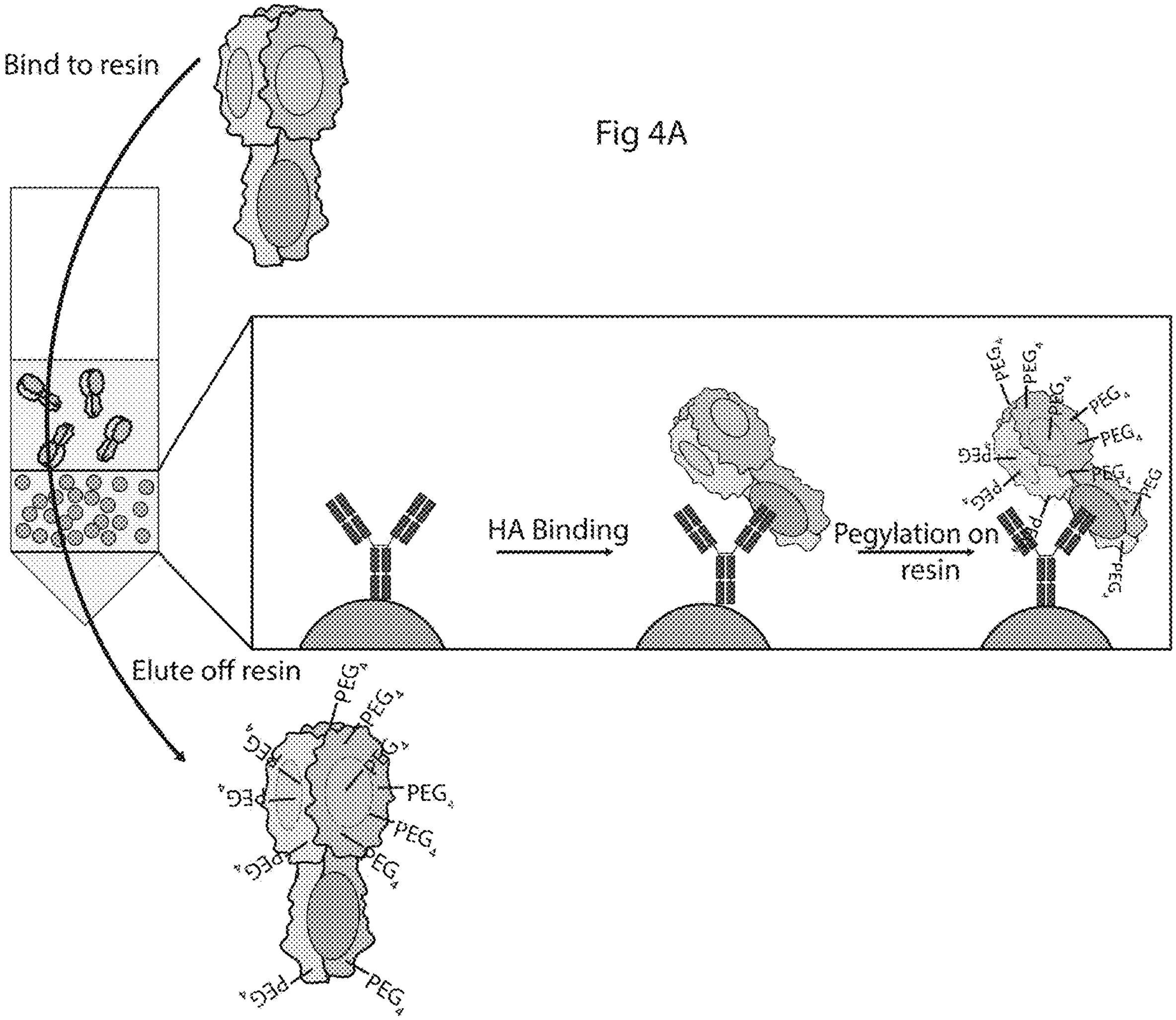
Fig 4A
Fig 4B
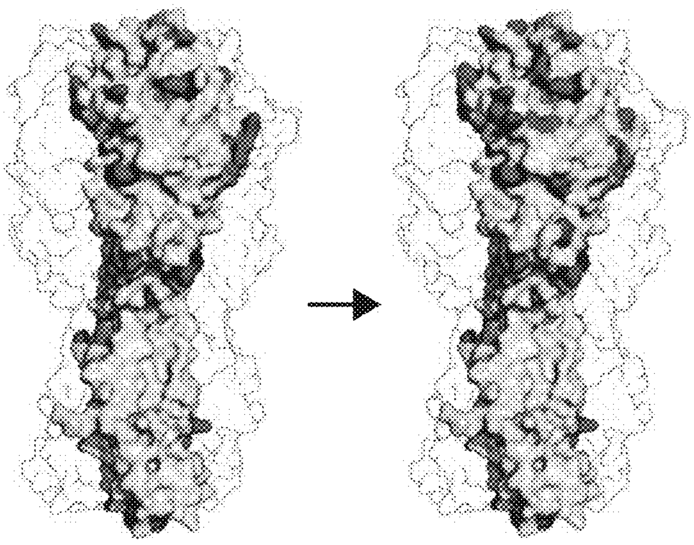

Fig 4C
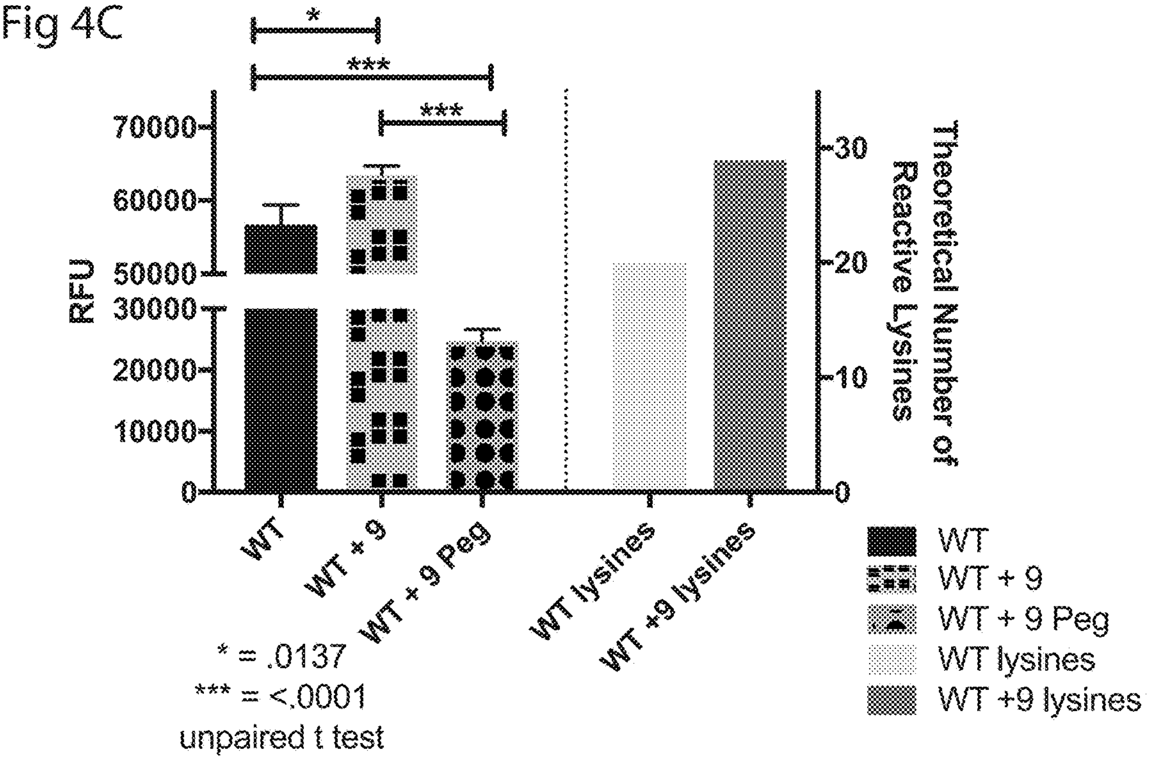
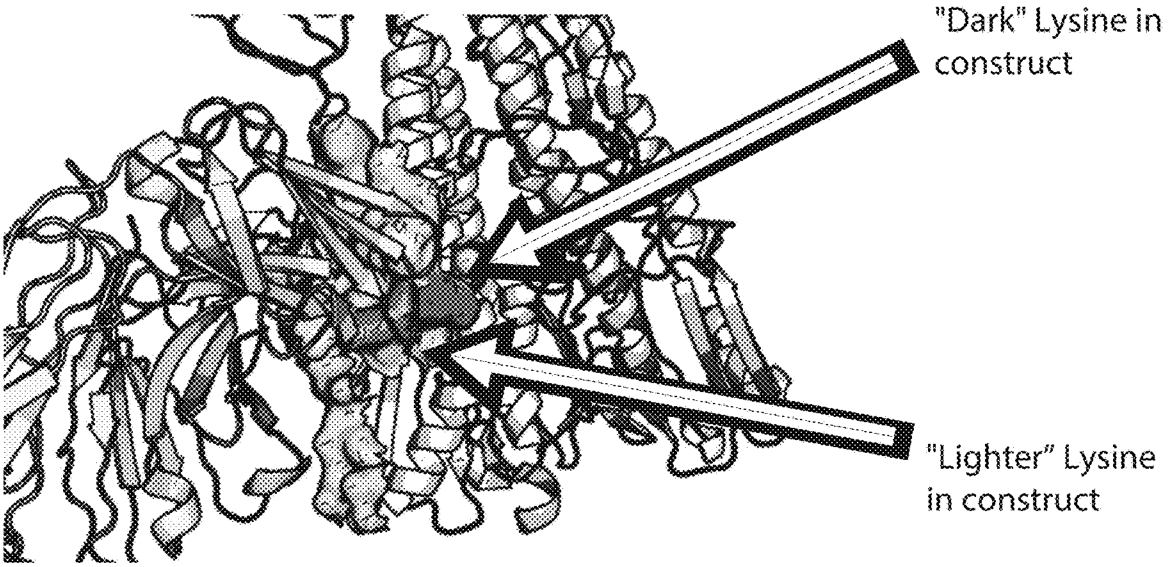
Fig 4D

EPITOPE RESTRICTION FOR ANTIBODY SELECTION

CROSS-REFERENCE TO RELATED APPLICATIONS

This application is a 371 national phase application of PCT Application No. PCT/US2019/032945, filed May 17, 2019, and claims benefit of priority of U.S. Provisional Application No. 62/673,617, filed May 18, 2018, U.S. Provisional Application No. 62/688,939, filed Jun. 22, 2018, and U.S. Provisional Application No. 62/780,595, filed Dec. 17, 2018, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 15, 2019, is named 103182-1134889-000910WO_SL.txt and is 112,726 bytes in size.

BACKGROUND

Creating vaccines against some major infectious agents has been extremely challenging. For example, in spite of over 30 years of hard work and enormous financial resources applied, a vaccine for the Human Immunodeficiency Virus (HIV) remains elusive. As another example, although influenza vaccines have been available for decades, they currently require annual vaccinations, which have limited efficacy against strain variants, including those with pandemic potential. Attempts to create a "universal" flu vaccine that protects against all or even large numbers of circulating influenza subtypes have been largely unsuccessful. These challenges arise in large part because infectious agents, such as influenza and HIV, are constantly evolving by subtle genetic variation, thereby escaping existing immune responses and, in the case of seasonal influenza vaccines, requiring frequent modification of the strains included therein.

"Broadly neutralizing" monoclonal antibodies capable of neutralizing multiple different HIV or influenza viral strains have been identified and some are in clinical development. However, to date there has been little success in creating a vaccine that causes an immunized subject to produce such antibodies and thereby providing protective immunity against heterogeneous and evolving infection agents. In particular, there are challenges in stimulating a subject's immune system to produce antibodies that bind specifically to conserved, less variable regions of viral proteins. As such, there is a need for vaccines that can elicit an immune response that targets a specific region on an immunogen.

BRIEF SUMMARY

In one aspect, provided is a method of making a modified antigenic protein. The method includes the steps of:

(a) providing an antigenic protein comprising a target region and a non-target region;

(b) providing a binding partner, wherein the binding partner binds specifically to the target region of the antigenic protein;

(c) contacting the antigenic protein with the binding partner under conditions in which the binding partner binds specifically to the antigenic protein can occur thereby forming a protein complex comprising the antigenic protein and the binding partner;

(d) contacting amino acid residues of the antigenic protein in the protein complex with a modifying reagent under conditions sufficient to form a modified antigenic protein thereby forming a modified antigenic protein in the protein complex, wherein each of a plurality of amino acid residues in the non-target region of the antigenic protein have a modifying component covalently attached thereto, and wherein amino acid residues of the target region of the antigenic protein do not have a modifying component attached thereto; and (e) separating the modified antigenic protein from the binding partner in the protein complex, thereby providing a modified antigenic protein.

In some embodiments, in step (c), the binding partner or the antigenic protein is attached to a solid support.

In some embodiments, step (d) of modifying the antigenic protein in the protein complex comprises reacting the protein complex with the modifying reagent and a coupling reagent under conditions sufficient to form a modified antigenic protein.

In some embodiments, the modifying component is a polyethylene glycol polymer, a glycopolymer (polysaccharide), a polysialic acid, a hyaluronic acid, a peptide, a protein, a polynucleotide, or a combination of any thereof.

In another aspect, provided is a method of making an antigenic protein complex. The method includes the steps of:

(a) providing an antigenic protein comprising a target region and a non-target region;

(b) providing at least one binding partner, wherein the at least one binding partner binds specifically to the non-target region of the antigenic protein; and (c) contacting the antigenic protein with the at least one binding partner under conditions in which the at least one binding partner binds specifically to the non-target region of the antigenic protein thereby forming the antigenic protein complex, wherein the target region of the antigenic protein is exposed and accessible for interaction with a B cell receptor and the non-target region of the antigenic protein is shielded by the at least one binding partner from interactions with a B cell receptor.

With respect to the provided aspects of the method of making a modified antigenic protein and the method of making an antigenic protein complex, the following embodiments are provided.

In some embodiments, the binding partner comprises at least one of a protein, a peptide, an aptamer, a chemical ligand, a lectin, or a combination of any thereof.

In some embodiments, the binding partner comprises at least one of an antibody or a receptor.

In some embodiments, the binding partner is a recombinant multivalent antibody.

In some embodiments, the at least one binding partner comprises one or more influenza hemagglutinin binding partners as identified in Table 1.

In some embodiments, the at least one binding partner comprises a polypeptide comprising the amino acid sequence of one or more of SEQ ID NOs: 3, 5, 7, 9, or 11.

In some embodiments, the antigenic protein is at least one of a viral protein, a bacterial protein, a fungal protein, or a parasitic protein.

In some embodiments, the viral protein is an influenza virus protein.

In some embodiments, the influenza virus protein is a hemagglutinin protein, a neuraminidase protein, a matrix protein, a nucleoprotein, or a fragment or variant of any thereof.

In some embodiments, the target region of the influenza virus protein is conserved across at least one of influenza A viruses, influenza B viruses, or influenza C viruses.

In some embodiments, the influenza virus protein is a hemagglutinin protein, or fragment or variant thereof, comprising a head region and a stem region, wherein the head region is the non-target region and the target region comprises the stem region or a portion thereof.

In some embodiments, the influenza virus protein is a hemagglutinin protein, or fragment or variant thereof, comprising a head region that comprises a hemagglutinin receptor binding site, wherein the hemagglutinin receptor binding site is the target region and the non-target region comprises other portions of the hemagglutinin protein.

In some embodiments, the influenza hemagglutinin protein, or fragment or variant thereof is a recombinant H1 influenza hemagglutinin protein comprising at least one of the amino acid substitutions L60K, N71K, T146K, N155K, R162K, N176K, V182K, G202K, or R205K.

In some embodiments, the viral antigenic protein comprises a polypeptide having at least 90% identity to the amino acid sequence of one or more of SEQ ID NOs: 21, 23, 13, 19, 24, 15, 17, or 25.

In some embodiments, the viral protein is a human immunodeficiency virus (HIV) protein.

In some embodiments, the target region of the HIV protein is conserved across HIV-1 viruses, HIV-2 viruses, or both HIV-1 viruses and HIV-2 viruses.

In some embodiments, the HIV protein comprises a gp160 protein, a gp120 protein, a gp41 protein, or a fragment or variant of any thereof.

In some embodiments, the HIV protein is a complex comprising a gp120 protein, or a fragment or variant thereof, and gp41, or a fragment or variant thereof.

In some embodiments, the HIV protein comprises a gp120 protein, or variant or fragment thereof, comprising a CD4 receptor binding region, wherein the target region is the CD4 receptor binding region and the non-target region comprises other portions of the gp120 protein.

In some embodiments, the HIV protein comprises a gp120 protein, or variant or fragment thereof, comprising a CXCR4 receptor binding region, wherein the target region is the CXCR4 receptor binding region and the non-target region comprises other portions of the gp120 protein.

In some embodiments, the antigenic protein is an engineered polypeptide having structural similarity to a conserved region of a protein expressed by an infectious agent, wherein the engineered polypeptide is bound specifically by antibodies that bind specifically to the conserved region of the protein expressed by the infectious agent.

In some embodiments, the antigenic protein comprises at least one amino acid substitution in a non-target region, wherein the at least one amino acid substitution incorporates at least one non-native amino acid residue that increases or decreases the affinity of at least one binding partner to the non-target region.

In some embodiments, the antigenic protein comprises at least one amino acid substitution in a non-target region, wherein the at least one amino acid substitution incorporates at least one non-native amino acid residue to which a modifying component is attachable.

In another aspect, provided is a modified antigenic protein. The antigenic protein includes a target region and a non-target region, wherein the non-target region comprises a plurality of amino acid residues each of which having a modifying component attached.

In some embodiments of the modified antigenic protein, the modified antigenic protein is a recombinant antigenic protein comprising at least one amino acid substitution in a non-target region of the antigenic protein, wherein the at least one amino acid substitution incorporates at least one non-native amino acid residue to which the modifying component is attachable.

In some embodiments of the modified antigenic protein, the modifying component is a polyethylene glycol polymer, a glycopolymer (polysaccharide), a polysialic acid, a hyaluronic acid, a peptide, a protein, a polynucleotide, or a combination of any thereof.

In some embodiments of the modified antigenic protein, the modifying component is a polyethylene glycol polymer, a glycopolymer (polysaccharide), a polysialic acid, a hyaluronic acid, a peptide, a protein, a polynucleotide, or a combination of any thereof.

In some embodiments of the modified antigenic protein, the at least one non-native amino acid residue to which the modifying component is attachable is lysine, and wherein the modifying component is a polyethylene glycol polymer.

In some embodiments of the modified antigenic protein, the modified antigenic protein is a modified viral antigenic protein comprising a target region and a non-target region, wherein the non-target region comprises a plurality of amino acid residues each of which having a modifying component attached, wherein the viral antigenic protein is an influenza hemagglutinin protein, or fragment or variant thereof, comprising a head region and a stem region.

In another aspect, provided is an antigenic protein complex. The antigenic protein complex includes (a) an antigenic protein comprising a target region and a non-target region; and (b) at least one binding partner, wherein the at least one binding partner comprises at least one protein binding domain that binds specifically with the non-target region of the antigenic protein, wherein the antigenic protein and the at least one binding partner are bound to each other, and wherein the target region of the antigenic protein is exposed and accessible for interaction with a B cell receptor and the non-target region of the antigenic protein is shielded by the at least one binding partner from interactions with a B cell receptor.

In some embodiments of the antigenic protein complex, the antigenic protein and the at least one binding partner are non-covalently bound to each other.

In some embodiments of the antigenic protein complex, the antigenic protein and the at least one binding partner are covalently bound to each other.

In some embodiments of the antigenic protein complex, the binding partner comprises a protein, a peptide, an aptamer, a chemical ligand, a lectin, or a combination of any thereof.

In some embodiments of the antigenic protein complex, the binding partner comprises at least one of an antibody or a receptor.

In some embodiments of the antigenic protein complex, the binding partner is a recombinant multivalent antibody.

In some embodiments of the antigenic protein complex, the at least one binding partner comprises one or more binding partners as identified in Table 1.

In some embodiments of the antigenic protein complex, the at least one binding partner comprises a polypeptide comprising the amino acid sequence of one or more of SEQ ID NOs: 3, 5, 7, 9, or 11.

In some embodiments of the antigenic protein complex, the antigenic protein comprises at least one amino acid substitution in a non-target region, wherein the at least one amino acid substitution incorporates at least one non-native amino acid residue that increases or decreases the affinity of at least one binding partner to the non-target region.

In some embodiments of the antigenic protein complex, the non-target region comprises one or more amino acid residues having a modifying component attached thereto.

In some embodiments of the antigenic protein complex, the antigenic protein comprises at least one amino acid substitution in a non-target region, wherein the at least one amino acid substitution incorporates at least one non-native amino acid residue to which the modifying component is attachable.

In some embodiments of the antigenic protein complex, the modifying component is a polyethylene glycol polymer, a glycopolymer (polysaccharide), a polysialic acid, a hyaluronic acid, a peptide, a protein, a polynucleotide, or a combination of any thereof.

In some embodiments of the antigenic protein complex, the at least one non-native amino acid residue to which the modifying component is attachable is lysine, and wherein the modifying component is a polyethylene glycol polymer.

With respect to the provided aspects of the modified antigenic protein and the antigenic protein complex, the following embodiments are provided.

In some embodiments, the antigenic protein is at least one of a viral protein, a bacterial protein, a fungal protein, or a parasitic protein.

In some embodiments, the viral protein is an influenza virus protein.

In some embodiments, the influenza virus protein is a hemagglutinin protein, a neuraminidase protein, a matrix protein, a nucleoprotein, or a fragment or variant of any thereof.

In some embodiments, the target region of the influenza virus protein is conserved across at least one of influenza A viruses, influenza B viruses, or influenza C viruses.

In some embodiments, the influenza virus protein is a hemagglutinin protein, or fragment or variant thereof, comprising a head region and a stem region, wherein the non-target region comprises the head region and the target region is the stem region or a portion thereof.

In some embodiments, the influenza virus protein is a hemagglutinin protein, or fragment or variant thereof, comprising a head region that comprises a hemagglutinin receptor binding site, wherein the hemagglutinin receptor binding site is the target region and the non-target region comprises other portions of the hemagglutinin protein.

In some embodiments, the influenza virus protein is a hemagglutinin protein having a head region and a stem region, wherein:

(i) the non-target region comprises the head region and the target region is the stem region or a portion thereof, or (ii) the head region of the influenza hemagglutinin protein, or fragment or variant thereof, comprises a hemagglutinin receptor binding site, and wherein the hemagglutinin receptor binding site is the target region and the non-target region comprises other portions of the influenza hemagglutinin protein.

In some embodiments, the influenza virus protein is a hemagglutinin protein, or fragment or variant thereof, is a recombinant H1 influenza hemagglutinin protein comprising at least one of the amino acid substitutions L60K, N71K, T146K, N155K, R162K, N176K, V182K, G202K, or R205K.

In some embodiments, the antigenic protein comprises a polypeptide having at least 90% identity to the amino acid sequence of one or more of SEQ ID NOs: 21, 23, 13, 19, 24, 15, 17, or 25.

In some embodiments, in the antigenic protein complex, the influenza virus protein is a hemagglutinin protein, wherein the target region is the stem region or a portion thereof and the non-target region is the head region, and wherein the binding partner comprises a multivalent antibody that binds specifically to multiple epitopes of the head region.

In some embodiments, the viral protein is a human immunodeficiency virus (HIV) protein.

In some embodiments, the target region of the HIV protein is conserved across HIV-1 viruses, HIV-2 viruses, or both HIV-1 viruses and HIV-2 viruses.

In some embodiments, the HIV protein comprises at least one of a gp160 protein, a gp120 protein, a sp41 protein, or a fragment or variant of any thereof.

In some embodiments, the HIV protein is a complex comprising a gp120 protein, or a fragment or variant thereof, and gp41, or a fragment or variant thereof.

In some embodiments, the HIV protein comprises a gp120 protein, or variant or fragment thereof, comprising a CD4 receptor binding region, wherein the target region is the CD4 receptor binding region and the non-target region comprises other portions of the gp120 protein.

In some embodiments, the HIV protein is a gp120 protein, or variant or fragment thereof, comprising a CXCR4 receptor binding region, wherein the target region is the CXCR4 receptor binding region and the non-target region comprises other portions of the gp120 protein.

In some embodiments, the influenza virus protein is a hemagglutinin protein comprising a head region and a stem region, wherein the target region is the stem region or a portion thereof, and wherein the head region is the non-target region and comprises a plurality of amino acid residues having a polyethylene glycol polymer attached thereto.

In some embodiments, the influenza virus protein is a hemagglutinin protein comprising a head region and a stem region, wherein the target region is the stem region or a portion thereof and the non-target region is the head region, and wherein the binding partner comprises a multivalent antibody that binds specifically to multiple epitopes of the head region.

In some embodiments, the antigenic protein is an engineered polypeptide having structural similarity to a conserved region of a protein expressed by an infectious agent, wherein the engineered polypeptide is bound specifically by antibodies that bind specifically to the conserved region of the protein expressed by the infectious agent.

In another aspect, provided are pharmaceutical compositions that include the modified antigenic protein or the antigenic protein complex as provided herein and a pharmaceutically acceptable diluent, carrier, or excipient. Also provided are pharmaceutical compositions that include either the antigenic protein or one or more binding partner, and a pharmaceutically acceptable diluent, carrier, or excipient. In some embodiments, the pharmaceutical composition also includes an adjuvant.

In another aspect, provided is a kit that includes the modified antigenic protein or the antigenic protein complex as provided herein and a pharmaceutically acceptable diluent, carrier, or excipient. In some embodiments, the kit also includes an adjuvant. The kit can include instructions for the administration of the modified antigenic protein or the antigenic protein complex.

In another aspect, provided is a kit that includes (a) a first pharmaceutical composition comprising an antigenic protein comprising a target region and a non-target region and a pharmaceutically acceptable diluent, carrier, or excipient, the first pharmaceutical composition packaged in a first container;

(b) a second pharmaceutical composition comprising at least one binding partner and a pharmaceutically acceptable diluent, carrier, or excipient, the second pharmaceutical composition packaged in a second container, wherein the at least one binding partner comprises at least one protein binding domain that binds specifically with the non-target region of the antigenic protein; and (c) instructions for the administration of the first pharmaceutical composition and the second pharmaceutical composition, wherein, when the antigenic protein and the at least one binding partner are bound to each other, the target region of the antigenic protein is exposed and accessible for interaction with a B cell receptor and the non-target region of the antigenic protein is shielded by the at least one binding partner from interactions with a B cell receptor. The antigenic protein and the at least one binding partner are those as described with regarding the methods of making and the compositions as provided herein. In some embodiments, the kit also includes an adjuvant. The kit can include instructions for the administration of the first and second first pharmaceutical compositions.

In another aspect, provided is a kit that includes a first polynucleotide encoding an antigenic protein and a second polynucleotide encoding at least one binding partner of the antigenic protein complexes described herein packaged in a container and instructions for the administration thereof. The polynucleotides may be DNA or RNA polynucleotides. The antigenic protein and the at least one binding partner are those as described with regards to the methods of making and the compositions as provided herein. In some embodiments, the first polynucleotide and the second polynucleotide are the same polynucleotide. In some embodiments, the first polynucleotide and the second polynucleotide are DNA polynucleotides. In some embodiments, the first polynucleotide and the second polynucleotide are RNA polynucleotides. In some embodiments, the first polynucleotide and the second polynucleotide plasmids for the production of virus particles. In some embodiments, the kit further comprises an adjuvant. The kit can include instructions for the administration of the first and second first polynucleotides.

In another aspect, provided is a method of eliciting in a subject an immune response against a target region of the antigenic protein. The method includes the step of administering a pharmaceutically effective amount of the pharmaceutical compositions described herein to a subject in which an immune response against the target region of the antigenic protein is desired.

In another aspect, provided is a method of eliciting in a subject an immune response against the target region of the antigenic protein. The method includes the step of administering:

(a) a pharmaceutically effective amount of a first pharmaceutical composition comprising an antigenic protein comprising a target region and a non-target region and a pharmaceutically acceptable diluent, carrier, or excipient; and (b) a pharmaceutically effective amount of a second pharmaceutical composition comprising at least one binding partner and a pharmaceutically acceptable diluent, carrier, or excipient, the second pharmaceutical composition, wherein the at least one binding partner comprises at least one protein binding domain that binds specifically with the non-target region of the antigenic protein, wherein the antigenic protein and the at least one binding partner bind to each other after administration to the subject such that the target region of the antigenic protein is exposed and accessible for interaction with a B cell receptor and the non-target region of the antigenic protein is shielded by the at least one binding partner from interactions with a B cell receptor. In some embodiments, the first pharmaceutical composition and the second pharmaceutical composition are administered simultaneously. In some embodiments, the first pharmaceutical composition and the second pharmaceutical composition are administered sequentially on the same day or different days. The antigenic protein and the at least one binding partner are those as described with regards to the methods of making and the compositions as provided herein.

In another aspect, provided is a method of eliciting in a subject an immune response against the target region of the antigenic protein that includes the step of administering a pharmaceutically effective amount of a first polynucleotide encoding an antigenic protein and a second polynucleotide encoding at least one binding partner of the antigenic protein complexes described herein to a subject in which an immune response against the target region of the antigenic protein is desired. In some embodiments, the first polynucleotide and the second polynucleotide are the same polynucleotide. In some embodiments, the first polynucleotide and the second polynucleotide are DNA polynucleotides. In some embodiments, the first polynucleotide and the second polynucleotide are RNA polynucleotides. The antigenic protein and the at least one binding partner are those as described with regards to the methods of making and the compositions as provided herein.

In another aspect, provided is a method of identifying genetic sequences encoding an antibody that binds specifically to a target region of an antigenic protein. The method includes the steps of:

(a) obtaining a plurality of antibodies;

(b) contacting the antibodies with a modified antigenic protein or an antigenic protein complex;

(c) separating an antibody that binds specifically to the target region of the antigenic protein from antibodies that do not bind specifically to the target region of the antigenic protein; and (d) determining the genetic sequences encoding the antibody that binds specifically to the target region of the antigenic protein. In some embodiments, the plurality of antibodies are expressed on the surface of a plurality of B cells. In some embodiments, the plurality of antibodies are expressed on a yeast display library, a phage display library, or a ribosome display library. The modified antigenic protein and the antigenic protein complex are those as described with regards to the methods of making and the compositions as provided herein.

In another aspect, provided is a method of identifying genetic sequences encoding an antibody specific for a target region of an antigenic protein. The method includes the steps of:

(a) obtaining a biological sample from a subject containing B cells;

(b) contacting the B cells with a modified antigenic protein or an antigenic protein complex;

(c) separating a B cell expressing an antibody that binds specifically to the target region of the antigenic protein from B cells that do not express an antibody that binds specifically to the target region of the antigenic protein;

(d) obtaining genetic sequences from the B cell expressing an antibody that binds specifically to the target region of the antigenic protein; and (e) sequencing a genetic sequence that encodes the antibody that binds specifically to the target region of the antigenic protein. In some embodiments, the B cells are isolated from the biological sample, and the isolated B cells are contacted with the modified antigenic protein or the antigenic protein complex in step (b). In some embodiments, the subject has been exposed to the antigenic protein. In some embodiments, steps (c) and (d) are performed by flow cytometry. The modified antigenic protein and the antigenic protein complex are those as described with regards to the methods of making and the compositions as provided herein.

BRIEF DESCRIPTION OF THE DRAWINGS

The present disclosure includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. 2A-2L shows recombinant protein sequences of antigenic proteins and binding partners according to some aspects of this disclosure. Shown are the expressed and purified amino acid residue sequences of anti-HEWL bispecific antibody (FIG. 2A); a first H5 HA trispecific (trispec) heavy chain (HC) antibody (FIG. 2B); H5 HA trispec light chain (LC) antibody (FIG. 2C); a second H5 HA trispect HC antibody (FIG. 2D); a Medi8852 LC antibody having an alanine mutation that reduces binding affinity for the antibody's epitope (FIG. 2E); a Medi8852 HC antibody having an alanine mutation that reduces binding affinity for the antibody's epitope (FIG. 2F); a H1 HA ectodomain containing nine lysine substitution mutations and having a C' terminal foldon-avi-his tag (FIG. 2G); a H5 HA ectodomain having a C' terminal foldon-avi-his tag (FIG. 211); a H5 HA ectodomain having a C' terminal GT-IZ-his tag (FIG. 2I); a H2 HA ectodomain having a C' terminal GT-IZ-his tag (FIG. 2J); a H1 HA ectodomain having a C' terminal GT-IZ-his tag (FIG. 2K); and untagged H1 HA, H2 HA, and H5 HA ectodomains (FIG. 2L). FIGS. 2G-2H disclose "Hexa His-Tag" as SEQ ID NO: 26. FIGS. 2I-2K disclose "Octo His-Tag" as SEQ ID NO: 27.

FIG. 3A and FIG. 3B show results with an affinity resin column using mAb HyHEL-5 and demonstrated that HEWL PEGylated with NHS-$PEG_2$-methyl on this resin and eluted off the HyHEL-5 resin retains binding to HyHEL-5 but ablates binding to HyHEL-10. FIG. 3C shows results with an affinity resin made with HyHEL-10 and demonstrates only partial PEGylation when the reaction with NHS-$PEG_8$-methyl is done on resin containing HyHEL-10 and eluted off of this resin. The partial PEGylation is demonstrated by the difference in molecular weight when compared to the fully PEGylated protein as assessed by Coomassie gel. FIG. 3D demonstrates that HyHEL-10 which has lysine residues in its epitope retains binding to the WT protein and the protein eluted off the HyHEL-10 resin but not the fully PEGylated protein as assessed by Western blot analysis with HyHEL-10 (right most lane is a molecular weight ladder—bottom band 10 kDa top band 15 kDa). FIG. 3E shows that a bispecific antibody (di-ScFv) of HyHEL-5 and D11.15 (similar epitope as D1.3) significantly ablates binding to HyHEL-5, D11.15, D1.3 but retains substantial binding to HyHEL-10, which is outside of the epitopes. FIG. 3F-FIG. 3H show competition ELISA results from bleed 2 serum from rabbits immunized with WT HEWL (FIG. 3F), HyHEL-5 PEGylated on resin containing HyHEL-5 with either NHS-$PEG_2$-methyl (FIG. 3G) or NHS-$PEG_4$-methyl (FIG. 3H). In this competition ELISA, a higher absorbance indicates that there is less serum antibody binding at that site. These results demonstrate a shift in epitope preference, from D1.3 (WT) to HyHEL-5 (NHS-$PEG_{2/4}$-methyl).

FIG. 3J shows the three epitopes that are bound by antibodies D1.3, HyHEL10, and HyHEL5 mapped on the lysozyme; they are roughly indicated by dashed lines. FIG. 3K shows a face-on view of two epitopes bound by antibodies HyHEL10 (PDB ID: 3HFM) and F9.13.7 (PDB ID: 1FBI). There is substantial overlap in the epitopes bound by these antibodies. HyHE10 was selected as a proof of concept antibody for the PMD method because it binds over two lysine residues and, therefore, protection of lysozyme with HyHEL10 during NHS ester modification should prevent modification of the two lysine residues in its epitope. FIG. 3L shows a face-on view of two epitopes bound by antibodies D1.3 (PDB ID: 1FDL) and D11.15 (PDB ID: 1JHL). The epitopes bound by these antibodies have some overlap. The D1.3 epitope is adjacent to multiple lysine residues but the antibody does not directly cover any of them. The D11.15 epitope does directly cover a lysine residue. This lysine residue is not within the HyHEL10 epitope (see FIG. 3K) and, therefore, NHS ester modification of lysozyme while it is protected with HyHEL10 should still modify this lysine residue. Thus, it is expected that the binding of D11.15 to a lysozyme that was modified in the presence of HyHEL10 would be ablated but that the D1.3 antibody would still bind its epitope, which does not contain any lysine residues. FIG. 3M shows a face-on view of the epitope bound by antibody HyHEL5 (PDB ID: 1YQV). This epitope does not encompass any lysine residues, nor is it too close to any lysine residues. Thus, NHS modification of lysozyme in the presence of HyHEL10 protection should not impact HyHEL5 binding to the modified lysozyme.

FIGS. 4A-4C show production and testing of H1 HA antigenic proteins using the PMD approach according to aspects of this disclosure. FIG. 4A shows a schematic of the PMD method for H1 HA using a Medi8852 derivative antibody with 2 point mutations as the binding partner on the affinity resin. FIG. 4B shows a space-filling representations of the native H1 HA protein (left) and with an additional 9 lysine residues added to the head to facilitate improved PEGylation (right). All the lysine residues in the protein are shaded dark. FIG. 4C shows the results of a fluorescamine assay conducted to demonstrate the number of exposed (free) amines in the WT and mutated protein, PEGylated and not PEGylated. The WT shows less fluorescence than the +9 lysine mutant, however, upon PEGylation there is a significantly lower signal, demonstrating that the majority of the lysine residues were already modified. This is compared to the expected number of exposed (free) amines per sample (right axis).

FIG. 4D shows a ribbon diagram representation of the interaction between the Medi8852 antibody and H1 HA according to some aspects of this disclosure. Medi8852 binds over the stem lysine residues in this (dark) and other strains (lighter) and, therefore, was selected to protect these residues during modification with amine reactive modification methods. Mutations were made in the sequence of Medi8852 to decrease Medi8852 binding that should not alter its epitope.

FIG. 5C discloses "GGSGG" as SEQ ID NO: 28.

FIG. 6A shows Octet binding of the antibodies against WT H1 HA. FIG. 6B shows Octet binding of the antibodies against H1+9+PEG, which shows ablation of head directed antibodies. FIG. 6C shows Octet binding of the antibodies against H1+9, which shows decreased head antibody binding but did not show ablation. The association step is depicted in the first two minutes of the assay and the dissociation step is shown as minutes 2-3.

FIG. 7A shows Octet binding of the antibodies against WT H5 HA. FIG. 7B shows Octet binding of the antibodies against H5 WT preincubated with a 2 fold molar excess of the trispecific antibody, which shows ablation of head directed antibodies. The association step is depicted in the first two minutes of the assay and the dissociation step is shown as mins 2-3.

FIG. 8A shows the percentage of antigen positive clones for WT H1 HA. In this context of high avidity on the yeast cell surface, significant binding of both H1 head antibody binding and stem antibody to the WT immunogen was observed. Positive gates were set such that ~1% of the streptavidin alone control fell within antigen positive gate. FIG. 8B shows the percentage of antigen positive clones for H1+9 lysine+PEG. Significant ablation of H1 head antibody binding was observed while binding of stem directed antibodies was retained compared to the WT immunogen. This ablation occurs even in the context of high avidity on the yeast cell surface.

FIG. 9A shows the percentage of antigen positive clones for WT H5 HA. In this context of high avidity on the yeast cell surface, significant binding of both head antibody and stem antibody to the WT immunogen was observed. Positive gates were set such that ~1% of the streptavidin alone control fell within antigen positive gate. FIG. 9B shows the percentage of antigen positive clones for H5 preincubated with a 2 fold molar excess of trispecific antibody. Significant ablation of head antibody binding to the modified immunogen while retaining stem antibody binding was observed even in the context of high avidity on the yeast cell surface.

As shown in FIG. 10A, these pooled yeast clones were then subjected to one of the biotinylated baits: H1 WT or H1+9+PEG at 12.5 nM tetramer and an antibody binding to the c-myc tag. The c-myc tag is at the C-terminal end of the scFv and indicates the yeast are expressing full length scFvs. The yeast were then sorted for all antigen positive cells. Positive gates were set such that ~1% of the streptavidin alone control fell within antigen positive gate. The resultant populations from either the whole library (left most bars), the H1 WT (middle bars), or H1+9 PEG (right most bars) were sequenced. This analysis demonstrates enrichment of stem directed antibodies as reflected in the right most bars. The experiment was repeated using the H1 WT, H1+9+PEG, and H1+9 immunogens. The results are shown as circle plots in FIG. 10B-1 and FIG. 10B-2, with the figure legend shown in FIG. 10B-3. When the yeast library was sorted with H1 WT, there was no significant enrichment for either head or stem directed clones. When sorted with H1+9 there was a slight enrichment for stem-directed clones. However, when the library was sorted with H1+9+PEG, there was a profound enrichment for stem-directed clones. These results show that H1+9+PEG is capable of enriching a polyclonal library for stem directed clones.

FIG. 13A shows the relative number of the antibodies (expressed as a percent) that bound to H5-coated plates. Eight of nine of the antibodies identified from the H1+9+PEG sort were able to bind to H5, while only 12 of the 23 antibodies from the H1 WT sort bound to H5. This demonstrates that the antibodies identified based on the H1 WT sort were less cross reactive. This indicates that, in an immunization setting, production of more cross reactive B cells would be stimulated if a patient was immunized with H1+9+PEG compared to H1 WT. FIG. 13B shows the relative number of the antibodies (expressed as a percent) that bound to H2-coated plates. Three of nine antibodies from the H1+9+PEG sorted cells bound to H2, while only five of 23 antibodies from the H1 WT sort bound to H2. This demonstrates that the antibodies identified from the H1 WT sort were less cross reactive. This indicates that, in an immunization setting, production of more cross reactive B cells would be stimulated if a patient was immunized with H1+9+PEG compared to H1 WT. FIG. 13C shows the relative number of the antibodies (expressed as a percent) that bound to plates coated with H1 WT soluble head domain. The head is the immunodominant region that should be masked by PEGylation in the H1+9+PEG protein. It is expected that fewer antibodies from the H1+9+PEG sort would bind at this region as compared to those from the H1 WT sort. Only one of the nine H1+9+PEG sorted antibodies bound to the H1 WT head, while seven of the 23 sorted with H1 WT bound to the H1 WT head. This demonstrates that the PEGylation process masked the head, obscuring it to make it less antigenic.

FIGS. 15A-15C show ELISA analysis assessing binding of serum from guinea pigs immunized with H1 WT or H1+9+PEG to H1, H2, and H5 ectodomains according to aspects of this disclosure. As a negative control, binding to plates coated with no protein was also assessed as shown in FIG. 15D. Serial dilutions of guinea pig serum (7 animals for H1 WT and 6 animals for H1+9+PEG) in PBST were assessed. The readout of this colorimetric assay was determined using a 96 well plate reader (Biotek). $EC_{25}$ was determined determined for the serum from each individual animal for each antigen using a standard curve interpolation (Sigmoidal, 4PL) on Prism GraphPad, the dotted line on the $EC_{25}$ graph shows the limit of detection for this assay. The graph on the left side of each figure shows the plotted average of binding from the pooled serum by ELISA, with standard deviations shown by shaded regions (H1+9+PEG immunized animals, light grey; H1 WT immunized animals, darker grey), the dotted line depicts OD=0.602 which was used to determine the $EC_{25}$. The graph on the right side of each figure shows the $EC_{25}$ determined for the serum from each individual animal (H1 WT immunized animals, black circles; H1+9+PEG immunized animals, white squares), with the $EC_{25}$ cutoff value shown with a dotted line. The data shown in FIG. 15A demonstrates that the H1 WT immunized animals had a better antibody response towards H1 than H1+9+PEG immunized animals. This is not surprising as the PEGylation decreases the immunogenicity of protein. The data shown in FIG. 15B and FIG. 15C demonstrates that the H1 WT immunized animals had a worse antibody response towards H2 and H5, respectively, than H1+9+PEG immunized animals. This indicates that, despite the overall immune response of these animals being lower, the animals produced a more cross reactive immune response and are able to bind to hemagglutinin from other strains better. This suggests that their antibody response is focused on a more conserved region. The data shown in FIG. 15D shows that there was minimal background binding to the control plate. This demonstrates that the binding seen for the antigen-coated plates reflect specific responses.

FIG. 16B shows the entire binding curve over a 1 hour association of pooled serum, and then the dissociation for 1 hour. The data shown in FIGS. 16A-16B is consistent with the ELISA analyses described above, showing that animals immunized with H1+9+PEG produced a more cross reactive immune response, binding better to H2 and H5 than the WT serum, but produced a worse H1 immune response.

FIG. 18A-18B show the results of depletion assays using the H2897 antibody assessing the nature of the observed antigenic 'hole' resulting in residual binding of the H2897 antibody to the H1+9+PEG immunogen (as seen in FIG. 6B) according to aspects of this disclosure. FIG. 18A shows Western blot analysis following H2897 antibody resin pulldowns for H1 WT, H1+9, and H1+9+PEG proteins. There is incomplete depletion of the H1+9+PEG immunogen from the pulldown solution. FIGS. 18B-18C show biolayer interferometry ("Octet binding") analyses of the H1+9+PEG immunogen from the pulldown solution assessing interactions with the MEDI8852 and H2897 antibodies, respectively. The H1+9+PEG protein that was not depleted by the pulldown procedure showed decreased binding to H2897 with retention of binding to MEDI8852.

DETAILED DESCRIPTION

Figure 1A:
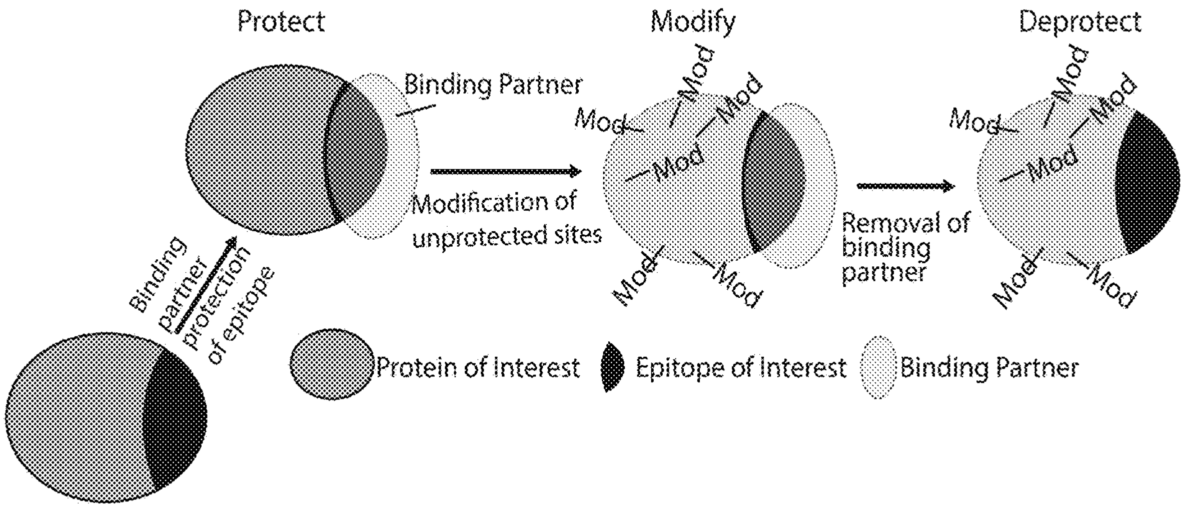
FIG. 1A shows a schematic representation of a method of producing an antigenic protein using the Protect-Modify-Deprotect approach according to aspects of this disclosure.

As used in the disclosure and the appended claims, the singular forms "a," "an," and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

The present invention provides methods of producing antigenic proteins and antigenic protein complexes and compositions and vaccines produced from such methods. Also provided are methods of immunizing a subject using such compositions and vaccines. The antigenic proteins and protein complexes of this disclosure are useful as vaccine immunogens that can direct the immune system of a subject immunized with such vaccine immunogens to generate antibodies against a specific region, or epitope, of a protein that is known to be productive or neutralizing in the case of an infection. This approach is referred to herein as immune-focusing. The proteins of infectious agents, such as viruses, may be highly variable across different types or even isolates. If much of the exposed surface of a protein does not lead to the production of antibodies that serve a protective function because the protein sequence is variable or antibodies against it are not productive to protect against infection, the majority of the immune response against this protein would be unproductive in terms of generating a protective response against multiple infectious agents that express that protein. The provided methods of immunization are able to direct an immune response towards a region of interest (target region) by using modified antigenic proteins or protein complexes in which epitopes in non-target regions, such as in variable regions of the antigenic protein, are sterically occluded, thus reducing antibody formation against such epitopes. Because the regions of the protein that will not lead to a productive/neutralizing immune response (non-target regions) are sterically occluded while the epitope of interest (target region) is not, the immune response may be focused on the epitope of interest (target region). Also provided are methods of screening for B cells expressing antibodies that bind specifically to a particular, desired epitope (target region).

Two general methods for producing antigenic proteins and protein complexes for immune-focusing are described herein. They can be used individually or together to generate specific antigenic proteins and protein complexes for use in vaccines. One method is referred to herein as the Protect-Modify-Deprotect (PMD) method. The other method is referred to the Epitope Shielding (ES) method. Collectively, these methods are referred to as Epitope Restriction for Antibody Selection (ERAS).

I. Methods of Epitope Restriction for Antibody Selection

In one aspect, a method for producing antigenic proteins provided herein is the Protect-Modify-Deprotect (PMD) method. This method is illustrated by example in FIG. 1A. In this method, a target region of the antigenic protein (an epitope of interest) is protected by complexing the antigenic protein with a binding partner that specifically binds to the target region. The target region is protected by the interaction with the binding partner, while the other regions of the antigenic protein (one or more non-target regions) are exposed. The antigenic protein is then modified chemically by the addition of a modifying component that reacts with amino acid residues in the non-target region(s) of the antigenic protein. The modified antigenic protein is then separated from the binding partner, exposing the (unmodified) target region. The modified antigenic protein contains amino acid residues with modifying components attached to them in non-target regions but not does not contain modified amino acid residues in the target region. The modified antigenic protein may be used as an immunogen in a vaccine. The addition of the modifying component to amino acid residues in the non-target region(s) of the antigenic protein should reduce antibody formation to all sites other than the target region when the modified antigenic protein is used as an immunogen.

For example, in one aspect, provided are methods of making a modified antigenic protein. In such methods, an antigenic protein comprising a target region and a non-target region is provided. Also provided is a binding partner, wherein the binding partner binds specifically to the target region of the antigenic protein. The method comprises contacting the antigenic protein with the binding partner under conditions in which the binding partner binds specifically to the antigenic protein thereby forming a protein complex comprising the antigenic protein and the binding partner. Subsequently, the method comprises situations where amino acid residues in the non-target region of the antigenic protein in the protein complex are contacted with a modifying reagent such that amino acid residues in the non-target region of the antigenic protein come into contact with the modifying reagent under conditions sufficient to form a modified antigenic protein thereby forming a modified antigenic protein in the protein complex, wherein each of a plurality of amino acid residues in the non-target region of the antigenic protein have a modifying component covalently attached thereto, and wherein amino acid residues of the target region of the antigenic protein do not have a modifying component attached thereto. Following the modification step, the method comprises separating the modified antigenic protein from the binding partner.

In another aspect, provided are methods of making a modified antigenic protein that do not require protection of the target region of the antigenic protein with a binding partner. In the method described above, the binding partner that binds specifically to the target region of the antigenic protein protects amino acid residues of the target region from reacting with the modifying reagent such that the modification reaction does not result in the amino acids in the target region having a modifying agent attached thereto. In other methods, an antigenic protein is provided in which the target region comprises at least one amino acid residue substitution, wherein the at least one amino acid residue substitution incorporates at least one non-native amino acid residue in the target region of the antigenic protein. The term "non-native amino acid residue" refers herein to an amino acid residue that is not the known amino acid residue(s) encoded at a given position in a protein of interest. In contrast, the term "native amino acid residue" refers herein to the amino acid residue(s) known to be encoded at a given position in a protein of interest. The at least one amino acid residue substitution replaces at least one native amino acid residue that is modifiable by the desired modifying agent with an amino acid residue that is not modifiable by the desired modifying agent. In some instances, the at least one amino acid residue substitution is a conservative amino acid substitution. The target region containing the at least one amino acid residue substitution generally retains similar tertiary structure and antigenicity relative to the native target region of the antigenic protein. In some instances, the target region may also contain at least one amino acid residue substitution that introduces at least one non-native amino acid residue that causes the target region to have increased antigenicity, increased binding affinity with a B cell receptor, or both. The method may then comprise contacting amino acid residues of the antigenic protein with the modifying reagent under conditions sufficient to form a modified antigenic protein, wherein each of a plurality of amino acid residues in the non-target region of the antigenic protein have a modifying component covalently attached thereto, and wherein amino acid residues of the target region of the antigenic protein do not have a modifying component attached thereto.

Figure 1B:
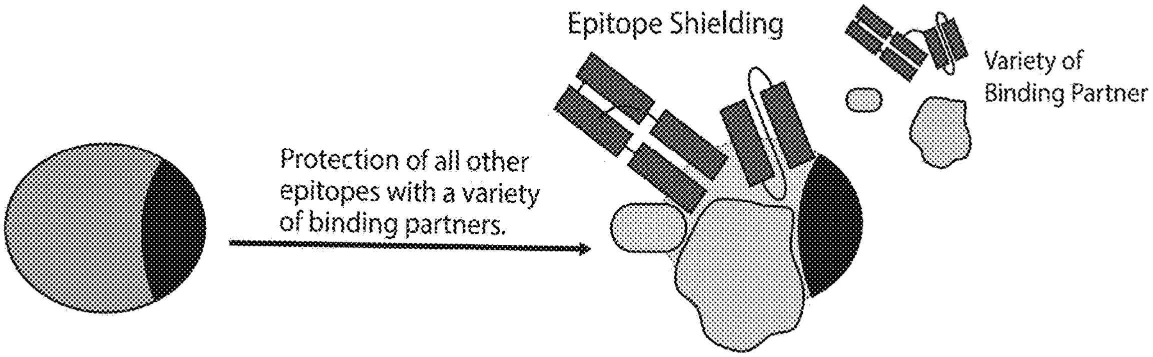
FIG. 1B shows a schematic representation of a method of producing an antigenic protein complex using the Epitope Shielding approach according to aspects of this disclosure.

In another aspect, a method for producing antigenic protein complexes provided herein is the Epitope Shielding (ES) method. This method is illustrated by example in FIG. 1B. In this method, regions of the antigenic protein that do not contain epitopes of interest (one or more non-target regions) for generating an immune response are shielded using one or more binding partners while a target region (the epitope of interest) of the antigenic protein is exposed. A protein complex is formed between the antigenic protein and one or more binding partners that bind to the non-target region(s) of the protein. In the protein complex, the target region is exposed. The binding of the one or more binding partners to the non-target region(s) reduces or ablates antibody formation against epitopes when the protein complex is used as an immunogen. The binding partner used in this method may be one large molecule that binds at multiple epitopes in the non-target region(s) of the antigenic protein. Alternatively, a plurality of binding partners may be used that act to shield epitopes in the non-target region(s) of the antigenic protein but not the target region. When used as an immunogen, the antigenic protein complex can produce a specific immune response targeting the target region (the epitope of interest). In some instances, the one or more binding partners bind specifically but not covalently to the non-target region of the antigenic protein. In other instances, the one or more binding partners may bind specifically to and covalently to the non-target region of the antigenic protein.

For example, in one aspect, provided are methods of making an antigenic protein complex. In such methods, an antigenic protein comprising a target region and a non-target region is provided. Also provided is at least one binding partner, wherein the at least one binding partner binds specifically to the non-target region of the antigenic protein. The method comprises contacting the antigenic protein with the at least one binding partner under conditions in which the at least one binding partner binds specifically to the non-target region of the antigenic protein thereby forming the antigenic protein complex, wherein the target region of the antigenic protein is exposed and accessible for interaction with a B cell receptor and the non-target region of the antigenic protein is shielded by the at least one binding partner from interactions with a B cell receptor.

In another aspect, the above-described methods of making an antigenic protein according to the PMD approach and the methods for producing antigenic protein complexes according to the ES approach may be combined to produce an antigenic protein complex that contains a modified antigenic protein in complex with one or more binding partners that are bound to non-target region(s) of the antigenic protein. This approach may be used where the antigenic protein does not contain a sufficient number of modifiable amino acid residues in non-target region(s) to mask the immunogenicity of the native antigenic protein in such regions. This approach may also be useful where there are insufficient known or readily available binding partners that bind to non-target region(s) of the antigenic protein. In some instances, the method comprises providing an antigenic protein comprising a target region and a non-target region; providing a first binding partner, wherein the first binding partner binds specifically to the target region of the antigenic protein, and providing at least one second binding partner, wherein the at least one second binding partner binds specifically to the non-target region of the antigenic protein.

In some instances, the method may comprise contacting the antigenic protein with the first binding partner under conditions in which the first binding partner binds specifically to the antigenic protein thereby forming a protein complex comprising the antigenic protein and the binding partner. Subsequently, the method may comprise contacting amino acid residues in the protein complex with a modifying reagent under conditions sufficient to form a modified antigenic protein thereby forming a modified antigenic protein in the protein complex. Following the modification reaction, each of a plurality of amino acid residues in the non-target region of the antigenic protein have a modifying component covalently attached thereto. Thus, in some instances, the non-target region of the antigenic protein comprises a plurality of amino acid residues with a modifying component covalently attached thereto and a plurality of amino acids that do not have a modifying component covalently attached thereto (i.e. amino acid residues that are not modified in the modifying reaction). Amino acid residues of the target region of the antigenic protein do not have a modifying component attached thereto. The method may then further comprise separating the modified antigenic protein from the first binding partner. In some instances, there are portions of the non-target region of the modified antigenic protein that do not contain a sufficient number of amino acid residues having a modifying component covalently attached thereto so as to mask the immunogenicity of the native antigenic protein of such portions of the non-target region of the modified antigenic protein. The method then may further comprise contacting the modified antigenic protein with the at least one second binding partner under conditions in which the at least one second binding partner binds specifically to the non-target region of the modified antigenic protein thereby forming the modified antigenic protein complex, wherein the target region of the antigenic protein is exposed and accessible for interaction with a B cell receptor. Some portions of the non-target region(s) of the antigenic protein in the modified antigenic protein complex are shielded through the binding interaction with the at least one second binding partner and other portions of the non-target region(s) contain a plurality of amino acids having a modifying component covalently attached thereto.

In other instances, the method may comprise first contacting the antigenic protein with the at least one second binding partner under conditions in which the at least one second binding partner binds specifically to the non-target region of the antigenic protein thereby forming the antigenic protein complex, wherein the target region of the antigenic protein is exposed and accessible for interaction with a B cell receptor and the non-target region of the antigenic protein is shielded in part by the at least one second binding partner from interactions with a B cell receptor. The antigenic protein complex may then be contacted with the first binding partner under conditions in which the first binding partner binds specifically to the antigenic protein thereby forming a second protein complex comprising the antigenic protein, the first binding partner, and the one or more second binding partners. In some instances, the second protein complex is contacted with a modifying reagent such that amino acid residues in the second protein complex come into contact with the modifying reagent, under conditions sufficient to form a modified antigenic protein thereby forming a modified antigenic protein in the second protein complex. Following the modification reaction, each of a plurality of amino acid residues in the non-target region of the antigenic protein have a modifying component covalently attached thereto. Thus, in some instances, the non-target region of the antigenic protein comprises a plurality of amino acid residues with a modifying component covalently attached thereto and a plurality of amino acids that do not have a modifying component covalently attached thereto (i.e. amino acid residues that are not modified in the modifying reaction). Amino acid residues of the target region of the antigenic protein do not have a modifying component attached thereto. The modified antigenic protein and the at least one second binding partner, referred to as a modified antigenic protein complex, may then be separated from the first binding partner. Separation conditions will be selected such that the binding interaction between the modified antigenic protein and the at least one second binding partner is not disrupted. Some portions of the non-target region(s) of the antigenic protein in the modified antigenic protein complex are shielded through the binding interaction with the at least one second binding partner and other portions of the non-target region(s) contain a plurality of amino acids having a modifying component covalently attached thereto. Because the at least one second binding partner is bound to the antigenic protein during the modification reaction, one or more amino acid residues in the one or more second binding partners may also have a modifying component covalently attached thereto. As such, in some instances, the one or more second binding partners in the modified antigenic protein complex may be one or more modified second binding partners.

It may be desirable to introduce mutations into the target region of the antigenic protein to improve binding of the at least one first binding partner to the target region. In some instances, the method comprises providing an antigenic protein comprising a target region and a non-target region, wherein the target region comprises at least one amino acid residue substitution, the at least one amino acid residue substitution incorporating at least one non-native amino acid residue in the target region of the antigenic protein. In some instances, the at least one non-native amino acid residue may be an amino acid residue that is not modifiable by the selected modifying agent. In some instances, the at least one non-native amino acid residue may have side chain moieties that form stronger non-covalent bonds with one or more chemical moieties in the at least one first binding partner as compared to the the at least one native amino acid residue. Also provided is at least one second binding partner, wherein the at least one second binding partner binds specifically to the non-target region of the antigenic protein. Subsequently, the method may comprise contacting amino acid residues in the protein complex with a modifying reagent under conditions sufficient to form a modified antigenic protein thereby forming a modified antigenic protein in the protein complex. Following the modification reaction, each of a plurality of amino acid residues in the non-target region of the antigenic protein have a modifying component covalently attached thereto. Thus, in some instances, the non-target region of the antigenic protein comprises a plurality of amino acid residues with a modifying component covalently attached thereto and a plurality of amino acids that do not have a modifying component covalently attached thereto (i.e. amino acid residues that are not modified in the modifying reaction). Amino acid residues of the target region of the antigenic protein do not have a modifying component attached thereto. In some instances, there are portions of the non-target region of the modified antigenic protein that do not contain a sufficient number of amino acid residues having a modifying component covalently attached thereto so as to mask the immunogenicity of the native antigenic protein of such portions of the non-target region of the modified antigenic protein. The method then may further comprise contacting the modified antigenic protein with the at least one second binding partner under conditions in which the at least one second binding partner binds specifically to the non-target region of the modified antigenic protein thereby forming the modified antigenic protein complex, wherein the target region of the antigenic protein is exposed and accessible for interaction with a B cell receptor. Some portions of the non-target region(s) of the antigenic protein in the modified antigenic protein complex are shielded through the binding interaction with the at least one second binding partner and other portions of the non-target region(s) contain a plurality of amino acids having a modifying component covalently attached thereto.

In other instances, the method comprises first contacting an antigenic protein having at least one amino acid residue substitution incorporating at least one non-native amino acid residue in the target region as described above with the at least one second binding partner under conditions in which the at least one second binding partner binds specifically to the non-target region of the antigenic protein thereby forming the antigenic protein complex, wherein the target region of the antigenic protein is exposed and accessible for interaction with a B cell receptor and the non-target region of the antigenic protein is shielded in part by the at least one second binding partner from interactions with a B cell receptor. The antigenic protein complex may then be contacted with a modifying reagent such that amino acid residues in the non-target region of the antigenic protein in the antigenic protein complex come into contact with the modifying reagent, under conditions sufficient to form a modified antigenic protein thereby forming a modified antigenic protein in the second protein complex. Following the modification reaction, each of a plurality of amino acid residues in the non-target region of the antigenic protein have a modifying component covalently attached thereto. Thus, in some instances, the non-target region of the antigenic protein comprises a plurality of amino acid residues with a modifying component covalently attached thereto and a plurality of amino acids that do not have a modifying component covalently attached thereto (i.e. amino acid residues that are not modified in the modifying reaction). Amino acid residues of the target region of the antigenic protein do not have a modifying component attached thereto. Some portions of the non-target region(s) of the antigenic protein in the modified antigenic protein complex are shielded through the binding interaction with the at least one second binding partner and other portions of the non-target region(s) contain a plurality of amino acids having a modifying component covalently attached thereto. Because the at least one second binding partner is bound to the antigenic protein during the modification reaction, one or more amino acid residues in the one or more second binding partners may also have a modifying component covalently attached thereto. As such, in some instances, the one or more second binding partners in the modified antigenic protein complex may be one or more modified second binding partners.

It may be desirable to introduce mutations into the non-target region of the antigenic protein adjacent to the target region so as to reduce antigenicity of the non-target region of the protein, as to reduce binding affinity of non-neutralizing B cell receptors, or both. An antigenic protein may contain two or more epitopes that overlap substantially but only one of which is a target region that has the desirable property of being able to elicit a neutralizing immune response against the antigenic protein in a subject following immunization. The other epitope (non-target epitope) elicits the production of non-neutralizing antibodies upon immunization. In some instances, an epitope that is a target region may overlap with an epitope that is also partially in the non-target region of the antigenic protein. In this scenario, it may be desirable to reduce the immunogenicity of the non-target epitope while retaining the ability of the target region epitope of the immunogen to elicit the production of broadly neutralizing antibodies through its interaction with BCRs in the subject. In some instances, this may be achieved by mutating one or more amino acid residues of the non-target epitope in the non-target region of the antigenic protein that are not shared with the target region epitope. Such one or more amino acid residues may be mutated by replacing them with non-native amino acids that are modifiable by the selected modification chemistry used in a PMD based method of making an antigenic protein. In other instances, the amino acid residues may be mutated by replacing them with non-native amino acids that reduce the binding affinity of a non-neutralizing antibody, and by extension its BCR, to the non-target epitope.

In some instances, the antigenic protein comprises a target region and a non-target region. In some instances, the antigenic protein is a protein expressed by an infectious agent. The antigenic protein is typically expressed such that at least a portion of the protein is expressed on the surface of the infectious agent. For example, the antigenic protein may be a transmembrane protein or membrane-associated protein such as, for example, a receptor or other surface protein. In some instances, the antigenic protein is a viral protein, a bacterial protein, a fungal protein, or a parasite protein. The target region of the antigenic protein may be a conserved domain, region, or portion of a protein expressed by an infectious agent. In the context of this disclosure, a target region may be referred to as "broadly neutralizing", meaning that the region has high conservation through isolates of the infectious agent, and that antibodies targeting these sites are protective against many strains of an infectious agent. In some instances, the target region may be the binding site of a characterized broadly neutralizing antibody that binds specifically to a highly conserved region of a protein expressed by an infectious agent. Target regions may include regions that have been characterized as, or are assumed to be, required for infection or function of the infectious agent.

Viruses are infectious agents for which the methods of this disclosure are particularly useful. Exemplary viruses include HIV, influenza, Respiratory Syncytial Virus (RSV), Zika Virus, West Nile Virus, Dengue Virus, Ebola Virus, and coronaviruses such as Severe acute respiratory syndrome coronavirus (SARS) and Human Coronavirus Erasmus Medical Center/2012 (hCoV-EMC), amongst other viruses. Several antibodies have been identified that bind to broadly neutralizing epitopes of proteins in these infectious agents, including the influenza hemagglutinin protein and the HIV envelope protein. In some instances, the viral proteins, or fragments thereof, form trimeric complexes that can be antigenic proteins within the context of the methods and compositions provided in this disclosure. The trimeric complexes may be homotrimeric (three of the same proteins) or a trimeric complex of three heterodimers. In some instances, the trimeric complexes comprises trimers of protein fragments as described below.

In one example, the viral protein may be an influenza virus protein. Influenza circulates in three serotypes (types) A, B, and C. The target region of the influenza virus protein may be conserved across at least one of influenza A viruses, influenza B viruses, or influenza C viruses. In some instances, the target region of the influenza virus protein may be conserved across one or more of influenza A serotypes H1, H2, H3, H5, H9, or others. The influenza protein may include, but is not limited to, any of a hemagglutinin protein, a neuraminidase protein, a matrix protein, or a nucleoprotein, or a fragment or variant of any thereof.

HA is a glycoprotein found on the surface of influenza viruses. It is responsible for binding the virus to cell membranes, such as cells in the upper respiratory tract or erythrocytes. HA is also responsible for the fusion of the viral envelope with the endosomal membrane, after the pH drops in the endosome. HA is a homotrimeric integral membrane glycoprotein. HA is expressed as a precursor protein (referred to as HA0) that trimerizes and then is cleaved into two smaller polypeptides—the HA1 and HA2 subunits, which remain complexed. The mature form of HA is thus a trimer of HA1-HA2 heterodimers. The HA1 subunit includes a globular head region containing the hemagglutinin receptor binding site that interacts with sialic acid on the surface of eukaryotic cells. The HA2 subunit includes a long, helical chain, a transmembrane region, and a cytoplasmic region. A portion of the HA1 subunit and the helical chain portion of the HA2 subunit are referred to as the stem region of the HA protein. The head region of HA appears to be immunodominant, meaning that during viral infection or during vaccination, subjects often produce antibodies predominantly against the head region. The head region, however, has significantly higher sequence variability when compared to the stem region, and antibodies against it are often not protective against challenges with other viral isolates. The HA stem domain is highly conserved and appears to contain broadly neutralizing epitopes. As such, antibodies directed against the HA stem domain may protect against many strains of the virus.

In some instances, the influenza virus protein is a hemagglutinin protein, or fragment or variant thereof, comprising a head region and a stem region, wherein the head region is the non-target region and the target region comprises the stem region or a portion thereof. In other instances, the influenza virus protein is a hemagglutinin protein, or fragment or variant thereof, wherein the target region is a hemagglutinin receptor binding site in the head region and the non-target region comprises other portions of the hemagglutinin protein. In another instance, the influenza virus protein is a hemagglutinin protein fragment or variant thereof comprising the stem region or a portion thereof and lacking all or a substantial portion of the head region (for example, at least 25%, 30%, 40%, 35%, 50%, 55%, 60%, 65%, 70%, 75%, 80%, 85%, 90%, 95%, 99% of the amino acid residues of the head region). In some instances, the influenza virus protein is a hemagglutinin protein fragment or variant thereof comprising the stem region or a portion thereof and lacking all of the head region. In some instances, the influenza virus protein is an HA protein fragment comprising the ectodomain of the HA protein or a variant thereof. In some instances, the hemagglutinin protein may be a trimeric complex of HA1-HA2 heterodimers. In one example, the hemagglutinin protein is a trimeric complex of HA1-HA2 heterodimers, wherein the HA2 subunit is a C'-terminally truncated variant lacking the transmembrane region and the cytoplasmic region of the protein, such trimeric complex referred to as the ectodomain of the hemagglutinin protein. In some instances, the hemagglutinin protein may be a trimeric complex of HA0 monomoers. In one example, the hemagglutinin protein is a trimeric complex of HA0 monomers, wherein the HA0 protein is a C'-terminally truncated variant lacking the transmembrane region and the cytoplasmic region of the protein, such trimeric complex referred to as the HA0 ectodomain.

In some instances, the viral protein may be a human immunodeficiency virus (HIV) protein. Two types of HIV have been characterized: HIV-1 and HIV-2. HIV-1 is the initially-identified virus and termed both LAV (Lymphadenopathy Associated Virus) and HTLV-III (Human T cell Lymphotropic Virus III). HIV-1 is more virulent and more infective than HIV-2, and is the cause of the majority of HIV infections globally. Where the viral protein is an HIV protein, the target region of the HIV protein may be conserved across HIV-1 viruses, HIV-2 viruses, or both HIV-1 viruses and HIV-2 viruses.

Envelope glycoprotein gp120 is a glycoprotein expressed on the surface of the HIV envelope. gp120 is coded by the HIV env gene, which is around 2.5 kb long and codes a precursor polypeptide of approximately 850 amino acid residues. The primary env product is the precursor protein gp160, which is proteolytically cleaved to gp120 (about 480 amino acid residues) and gp41 (about 345 amino acid residues). The gp120 protein contains a CD4 receptor binding region and a CXCR4 receptor binding region. The gp41 protein contains a transmembrane region and cytoplasmic region. Gp120 is anchored to the viral membrane, or envelope, via interactions with gp41. Three gp120s and gp41s combine in a trimer of heterodimers to form the envelope spike, which mediates attachment to and entry into the host cell.

The HIV protein may comprise one or more of a gp120 protein, a gp41 protein, a gp160 protein, or a fragment or variant of any thereof. In some instances, the HIV protein may be a gp120-gp41 complex comprising (i) a gp120 protein, or a fragment or variant thereof, and (ii) gp41, or a fragment or variant thereof. For example, the HIV protein may include a gp120 protein, or variant or fragment thereof, comprising a CD4 receptor binding region, wherein the target region is the CD4 receptor binding region and the non-target region comprises other portions of the HIV protein. In another example, the HIV protein may include a gp120 protein, or variant or fragment thereof, comprising a CXCR4 receptor binding region, wherein the target region is the CXCR4 receptor binding region and the non-target region comprises other portions of the HIV protein. In some instances, the HIV protein is a gp120 protein, or fragment or a variant thereof, alone or complexed with the ectodomain of gp41, or a fragment or variant thereof. The ectodomain of gp41 is a C' terminally truncated variant lacking the the transmembrane region and the cytoplasmic region of the protein. In some instances the HIV protein is a gp160 protein ectomain fragment comprising the amino acid sequence of the gp120 protein, or a fragment or variant thereof, and the amino acid sequence of the ectodomain portion gp41 protein, or variant thereof, wherein the ectodomain portion gp41 protein, or variant thereof, comprises a C' terminally truncated variant lacking the transmembrane region and the cytoplasmic region of the protein.

As used herein, the terms "protein," "peptide," and "polypeptide" are used interchangeably herein to refer to a polymer of amino acid residues. All three terms apply to naturally occurring amino acid polymers and non-natural amino acid polymers, as well as to amino acid polymers in which one (or more) amino acid residue is an artificial chemical mimetic of a corresponding naturally occurring amino acid. As used herein, the terms encompass amino acid chains of any length, including full-length proteins, wherein the amino acid residues are linked by covalent peptide bonds.

An "isolated" or "purified" polypeptide or protein, or biologically active portion thereof, is substantially or essentially free from components that normally accompany or interact with the polypeptide or protein as found in its naturally occurring environment. Thus, an isolated or purified polypeptide or protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, 1%, 0.5%, or 0.1% (total protein) of contaminating protein. When the protein of the invention or biologically active portion thereof is recombinantly produced, optimally culture medium represents less than about 30%, 20%, 10%, 5%, 1%, 0.5%, or 0.1% (by concentration) of chemical precursors or non-protein-of-interest chemicals.

The term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

In some instances, the antigenic protein is a fragment or variant of a protein expressed by an infectious agent. The term "fragment" refers to a portion of a polypeptide sequence of the invention. "Fragments" or "biologically active portions" include polypeptides comprising a sufficient number of contiguous amino acid residues to retain the biological activity, i.e., contains a target region. Fragments of the antigenic proteins include those that are shorter than the full-length sequences, either due to the use of an alternate downstream start site, or due to processing that produces a shorter protein retaining the target region. Processing may occur in the organism the protein is expressed in or to which the antigenic protein is administered. Such biologically active portions can be prepared by recombinant techniques and evaluated for the ability of a binding partner to bind specifically to the target region.

In some instances, a fragment of an antigenic protein may include the ectodomain or extracellular domain of a transmembrane protein. Proteins expressed by infectious agents against which a protective immune response could be induced may comprise an ectodomain (extracellular portion) and a transmembrane region. They may also comprise a cytoplasmic domain that is usually positioned C' terminal to the transmembrane domain. In some instances, the antigenic protein that may be used in the methods and compositions provided in this disclosure may be an ectodomain of an infectious agent protein, wherein the transmembrane region and, if present, the cytoplasmic region of the protein are not expressed (i.e. deleted). In some instances, such ectodomains can trimerize to form trimeric complexes that, as mentioned above, can be used as antigenic proteins within the context of the methods and compositions provided in this disclosure. Non-limiting examples of such fragments are the ectodomain of the influenza hemagglutinin protein or the ectodomain of the HIV gp160 protein or the gp120/gp41 complex, both of which are described above.

In some instances, the antigenic protein may be a fusion protein in which the antigenic protein is fused to a scaffold protein that forms spherical nanoparticles. The scaffold protein may self-assemble into spherical nanoparticles and the antigenic protein is presented externally on the nanoparticles. Exemplary scaffold proteins include ferritin (mammalian, insect, *H. pylori*, etc.) and lumazine synthase. Exemplary antigenic fusion proteins include those described in Kanekiyo, M., et al., 2013, Nature 499(7456):102-106, U.S. Pat. No. 9,441,019, and PCT Application No. PCT/US2012/056822.

In some instances, the antigenic protein is an engineered polypeptide having structural similarity to a conserved region of a protein expressed by an infectious agent, wherein the engineered polypeptide can be bound specifically by antibodies that bind specifically to the conserved region of the protein expressed by the infectious agent. As used herein, the term "engineered polypeptide" refers to a recombinant polypeptide designed and expressed or synthesized to have particular characteristics, such as, for example, an antigenic epitope of an antigenic protein. In some instances, the engineered polypeptide may comprise a conserved polypeptide sequence, the conserved polypeptide sequence comprising 10 to 100 amino acid residues that have been determined to be conserved in an antigenic protein of an infectious agent. For example, the conserved polypeptide sequence may comprise 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In some instances, the conserved polypeptide sequence may comprise 10-20 amino acid residues, 25-30 amino acid residues, 30-50 amino acid residues, 40-60 amino acid residues, or 75-100 amino acid residues. The conserved polypeptide sequence may be at least 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid residues that have been determined to be conserved in an antigenic protein of an infectious agent. Exemplary engineered polypeptides may be based on the sequence of influenza hemagglutinin proteins as described in Sutton, T. C., et al., 2017, NPJ Vaccines, Vol. 2, Article 35, doi: 10.1038/s41541-017-0036-2; Impagliazzo, A., et al., 2015, Science 349(6254):1301-1306; Lee, P. S., et al., 2015, J. of Virology 89(14):7417-7420; Mallajosyula, V. V. A., et al., 2015, Front. Immunol., Vol. 6, Article 329, doi: 10.3389/fimmu.2015.00329, and Yassine et al., 2015, Nature Medicine 21:1065-1070. Exemplary engineered polypeptides may also be based on the sequence of the HIV gp160/gp120 protein as described in Jardine, J. et al., 2013, Science 340(6133): 711-716 and International PCT Appl. No. PCT/US2016/038162, both of which are incorporated herein by reference. Other exemplary proteins may be based on the sequence of the HIV Env trimer such as, for example, BG505 SOSIP (as described, for example, in Sanders, R. W., et al., 2013, PLoS Pathology 9(9): e1003618 and Georgiev, I. S., et al., 2015, J. of Virology 89(10):5318-5329); BG505 DS-SOSIP (as described, for example, in Kwon, Y. D., et al., Nature Struct. Mol. Biol. 22(7):522-531); Chuang, G. Y., et al., 2017, J. Virol. 91(10): e02268-16; and Joyce, M. G., et al., 2017, Cell Reports 21(10):2992-3002); and as described in Rutten, L., et al., 2018, Cell Reports 23(2):584-595. Other exemplary engineered polypeptides are based on the sequence of RSV proteins such as, for example, CA-Cav1 protein, such as described in McLellan, J. S., et al., 2013, Science 342(6158): 592-598.

In some instances, the antigenic protein may comprise a bacterial capsular polysaccharide-protein conjugate. Many bacteria express chains of distinct polysaccharide subunits anchored to the cell wall surface. For example, capsular polysaccharide antigens decorate many bacterial pathogens, such as *Pneumococcus, Meningococcus, Haemophilus, Neisseria*, and *Streptococcus* bacteria. One or more capsular polysaccharide haptens may be covalently conjugated to a protein carrier. Exemplary capsular polysaccharides include *Haemophilus* influenza saccharides such as type b polysaccharide and type b saccharide. Other exemplary capsular polysaccharides include *Neisseria meningitides* saccharides such as group C saccharide, group C saccharide 0-acetylated, and group C polysaccharide deO-acetylated. Other exemplary capsular polysaccharides include *Streptococcus pneumoniae* saccharides such as Serotypes 4, 9V, 14, 19F and 23F polysaccharides; 6B saccharide, types 1 and 5 polysaccharides, 1, 4, 5, 7F, 9V, 19F and 23F polysaccharides, types 3, 14 18C and 6B polysaccharides, 1, 3, 4, 5, 6B, 7F, 9V, 14, 18C, 19F and 23F polysaccharides. Exemplary protein carriers include diphtheria toxin/toxoid, mutant non-toxic diphtheria toxin CRM197, tetanus toxin/toxoid, *Neisseria meningitidis* outer membrane protein, non-typeable *H. influenzae* outer membrane protein. Other exemplary capsular polysaccharides and protein carriers are described in Finn, A., 2004, British Medical Bulletin 70(1):1-14, which is incorporated herein in its entirety for all purposes. Such polysaccharide-protein conjugates can then induce humoral immune responses when administered to a subject with the characteristics of T cell dependent antigens: responses with memory, affinity maturation, and immunogenicity.

In some instances, the antigenic protein may comprise a bacterial toxin or toxoid. A toxoid is an inactivated bacterial toxin. Toxoids may be produced, for example, by chemical treatment (e.g., with formalin) or heat treatment). Exemplary toxins (and toxoids) are those produced by the *Corynebacterium* diphtherias bacterium, which causes diphtheria, and *Clostridium tetani*, which causes tetanus.

It is recognized that modifications may be made to a known antigenic protein to create variant proteins. Changes designed by man may be introduced through the application of site-directed mutagenesis techniques. Alternatively, native, as yet-unknown or as yet unidentified polynucleotides and/or polypeptides structurally and/or functionally-related to known antigenic proteins may also be identified that fall within the scope of the present invention. Conservative amino acid residue substitutions may be made in nonconserved regions that do not alter the antigenicity or accessibility of the target region of the antigenic proteins. Alternatively, modifications may be made in the target region that improve its immunogenicity, it binding affinity to a binding partner, or both. As indicated, fragments and variants of antigenic proteins as described herein will retain a target region, the target region comprising an epitope of interest.

Polypeptide variants of this disclosure include polypeptides having an amino acid sequence that is at least 60%, 65%, 70%, 75%, 80%, 85%, 86%, 87%, 88%, 89%, 90%, 91%, 92%, 93%, 94%, 95%, 96%, 97%, 98%, or 99% identical to a known antigenic protein as described herein as a whole or, in the context of variants comprising deletions, with respect to the expressed polypeptide sequence. In some instances, a biologically active variant of the contemplated antigenic proteins may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N'-terminal, a C'-terminal truncation, or an internal deletion. As discussed elsewhere in this disclosure, variants include antigenic proteins comprising truncated antigenic proteins in which only the extracellular portions of the protein are expressed, while a transmembrane region, an intracellular (cytoplasmic) region, or both, are deleted.

Variants of the antigenic proteins described herein may include various genetic modifications. For example, genetic modifications may increase the number of amino acid residues having functional groups to which a modifying component may be attached. In another example, genetic modifications may introduce post-translational modification sites into the antigenic protein such as glycosylation sites. In another example, genetic modifications may introduce sequences to which specific chemical or peptide tags may be added. Examples of this include biotinylation sequences such as an Avitag™ sequence. They may include amino acid sequences to optimize expression in a particular organism. In some instances, they include amino acid sequences that facilitate purification such as sequences that cause secretion (signal sequences) or tags useful for affinity or chemical isolation.

In some instances, the antigenic protein is a recombinant antigenic protein comprising at least one amino acid residue substitution in the non-target region of the antigenic protein, wherein the at least one amino acid residue substitution incorporates at least one non-native amino acid to which the modifying component is attachable. For example, amino acid sequence of the antigenic protein may be modified to increase the number of amino acid residues that can be modified by the chemical reaction selected for the modification reaction. This may be done by introducing substitution mutations to incorporate the desired non-native amino into one or more non-target regions of the antigenic protein. In some instances, conservative amino acid substitutions are made. In some instances, one or more non-native amino acid residues may be added by insertion mutation into one or more non-target regions of the antigenic protein. Selection of native amino acid residues for mutagenesis, or selection of sites for insertion mutations, may be directed by analysis of the native antigenic protein sequence to determine non-target regions in which few of the native amino acid residues will be modified in the modification step.

As used herein, the term "binding partner" refers to a molecule that can bind specifically to (selectively interact with) a feature of an antigenic protein, that feature being a target region or a non-target region depending on the method being employed. A "binding partner" may be a protein, a peptide, an aptamer, a chemical ligand, a lectin, or a combination of any thereof. Exemplary binding partners include, but are not limited to, receptors and antibodies. In one example, a binding partner is monoclonal antibody. In some instances, the binding partner may be a chemical ligand. As used herein, the term "chemical ligand" refers to a chemical molecule that binds specifically to the antigenic protein. The chemical ligand may be fully or partially synthetic. The chemical ligand may include a portion thereof that is a synthetic polypeptide designed to bind to the target region of the antigenic protein. The chemical ligand may be a carbohydrate. One example, where hemagglutinin is the antigenic protein, is a chemical ligand comprising sialic acid and other chemical moieties, wherein the sialic acid can interact with the hemagglutinin receptor binding region and the other chemical moieties interact with portions of the hemagglutinin protein around the hemagglutinin receptor binding region. Another example of a chemical ligand is a chemical molecule that comprises one or more polypeptide sequences that mimics the CDR configuration of an antibody known to bind to the target region of an antigenic protein. In some instances, the chemical ligand may be a small molecule designed to interact with the target site of an antigenic protein. Such chemical ligands may be designed computationally or based on the interaction of a known drug, antibody, receptor, or other chemical to the desired target site of the antigenic protein such as described, for example, in Kadam, R. U. & Wilson, I. A. A., 2018, Proc. Natl. Acad. Sci. U.S.A. 1-6 (2018). doi:10.1073/pnas.1801999115. In other instances, the chemical ligand may be identified through screening of chemical molecule libraries. In some instances, the binding partner may be a lectin, which is particularly useful in the context of ES methods for shielding the non-target region of the antigenic protein, specifically where the antigenic protein is a glycoprotein. For example, lectin binding partners may be useful in shielding the non-target region of the HIV gp160, gp120/gp41 complex, or gp120, or fragments or variants of any thereof, which are glycosylated and known to be immunogenic.

In some instances, binding partners useful in the context of this disclosure are recombinant or engineered proteins or peptides. They may include amino acid sequences to optimize expression in a particular organism. In some instances, they include amino acid sequences that facilitate purification such as sequences that cause secretion (signal sequences) or tags useful for affinity or chemical isolation. The binding partner may include a plurality of epitope binding domains from different antibodies known to bind a particular antigenic protein. Such epitope binding domains may be separate by various loops or linker sequences to facilitate proper folding of the domains and overall tertiary structure of the binding partner upon expression.

"Antibody" refers to an immunoglobulin or fragment thereof that binds to, and is thereby defined as complementary with, a particular spatial and polar organization of another molecule. The antibody can be monoclonal or recombinant and can be prepared by techniques that are well known in the art such as by preparing continuous hybrid cell lines and collecting the secreted protein (monoclonal) or by cloning and expressing nucleotide sequences or mutagenized versions thereof coding at least for the amino acid sequences required for binding. Antibodies may include a complete immunoglobulin or fragment thereof, such immunoglobulins include the various classes and isotypes, such as IgA, IgD, IgE, IgG1, IgG2a, IgG2b and IgG3, IgG4, IgM, etc., derived from human or other cell lines, including natural or genetically modified forms such as humanized, human, single-chain, chimeric, synthetic, recombinant, hybrid, mutated, grafted, and in vitro generated antibodies and fragments thereof. The term "antibody" also includes composite forms including but not limited to fusion proteins containing an immunoglobulin moiety. "Antibody" also refers to non-quaternary antibody structures (such as camelids and camelid derivatives). Antibody fragments may include Fab, Fv and F(ab')2, Fab', scFv, Fd, dAb, Fc, and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained.

The term "complementarity determining region" or "CDR" (also known as "hypervariable region" or "HVR") refers to an immunoglobulin hypervariable domain that determines specific binding of an immunoglobulin to an epitope. The variable regions of both the heavy and light chains of an antibody each generally contain three CDRs. Antibodies with different specificities have different CDRs.

A "constant region" refers to a region in the heavy and light chains of an antibody having relatively less variability compared to the N' terminal variable region of the heavy and light chains of an antibody. On the heavy chains, the constant region is generally the same in all antibodies of the same isotype and differs in antibodies of different isotypes. There are two primary types of light chains (kappa and lambda), each with a distinct constant region.

The term "variable region" refers to an N' terminal region of each of the heavy and light chains of an antibody that has relatively more variability compared to the constant region(s) of the heavy and light chains of an antibody. The variable region contains the CDRs.

An array of isolated antibodies that bind specifically to antigenic proteins of interest (such as certain viral proteins) are known. In some instances, where such proteins (or variants thereof) are used as an antigenic protein in the context of this disclosure, such known, isolated antibodies may be used as a binding agent in the context of this disclosure. For example, there are many known antibodies that target broadly neutralizing target regions of certain viral proteins. While antibodies are an attractive option, the binding partner could readily be another type of molecule that binds at the epitope of interest, for example the viral receptor (CD4 in the case of HIV) as discussed above. Recombinant and engineered polypeptides may also be used as binding partners. In some instances, such recombinant or engineered polypeptides may comprise multiple epitope binding domains incorporated from different known binding partners such as antibodies and receptors. For example, a binding partner may be a recombinant multivalent antibody as described in Examples 1 and 2. Known binding proteins, such as known monoclonal antibodies, may have point mutations introduced to alter binding kinetics, either to increasing binding affinity or decrease binding affinity as desired, for example, to facilitate epitope binding or aid in elution or separation.

An exemplary, non-exhaustive list of antigenic proteins, epitopes therein, and binding partners are shown in Table 1.

TABLE 1

Infectious Agent Antigenic Proteins and Binding Partners

| Epitope | Binding Partner |
|---|---|
| Influenza<br>Antigenic Protein: Influenza Hemagglutinin, or derivatives of hemagglutinin | |
| Targeting the stem: Group 1 or Group 2 or Type B | Medi8852 |
| | CR8020 |
| | CR6261 |
| | FI6v3 |
| | CR9114 |
| | MAb 3.1 |
| Targeting the receptor binding site (sialic acid binding site) | C05 |
| | F045-092 |
| | 8M2 |
| | CH65 |
| | 5J8 |
| | S139/1 |
| | 2G1 |
| Targeting the lateral patch | CL6649 |
| Targeting the esterase domain | H5M9 |
| Antigenic Protein: Neuraminidase | |
| N1 domain | 1000-3B06 |
| | 1000-1D05 |
| | 294-A-1C02 |
| | 294-A-1D05 |
| N2 domain | 229-1D05 |
| | 235-1C02 |
| | 235-1E06 |
| HIV<br>Antigenic Protein: HIV gp 120 or Env Trimer, or derivatives of Env ectodomain | |
| CD4-Binding Site | CD4 |
| | b12 |
| | HJ16 |
| | CH103-106 |
| | VRCO1-03 |
| | VRCO7-523 |
| | VRC-PG04, VRC-PG04b |
| | VRC-CH30-34 |
| | 3BNC117 |
| | 3BNC60 |
| | NIH45-46 |
| | 12A12 |
| | 12A21 |
| | 8ANC131, 8ANC134 |
| | 1NC9 |
| | 1B2530 |
| MPER gp41 | 2F5 |
| | 4E10 |
| | M66.6 |
| | CAP206-CH12 |
| | 10E8 |
| | DH511 |
| | Z13e1 |
| | VRC42 |
| Fusion peptide (15 to 20 hydrophobic residues at the N' terminus of the Env-gp41 subunit) | PGT151 |
| | VRC24 |
| | ACS202 |
| | CH07 |
| | vFP16 |
| VlV2-Glycan | PG9, PG16 |
| | CH01-04 |
| | PGT 141-145 |
| V3-Glycan | PGT121-123 |
| | PGT 125-131 |
| | PGT 135-137 |
| | 2G12 |
| RSV | |
| RSV fusion glycoprotein (RSV F) ectodomain | Medi8897 |
| | REGN2222 |
| | ALX-0171 |
| | palivizumab |

TABLE 1-continued

| Infectious Agent Antigenic Proteins and Binding Partners | |
|---|---|
| Epitope | Binding Partner |
| Zika Virus<br>Antigenic Protein: Envelope glycoprotein | |
| Fusion Loop Epitopes | |
| Quaternary Epitopes | |
| West Nile Virus<br>Antigenic Protein: Envelope glycoprotein | |
| Antigenic Site II | |
| Antigenic Site IV | |
| SARS<br>Antigenic Protein: Envelope glycoprotein | |
| Receptor Binding Region | ACE2 |
| hCoV-EMC<br>Antigenic Protein: Envelope glycoprotein | |
| Receptor Binding Region | DPP4 (CD26) |
| Dengue Virus<br>Antigenic Protein: Envelope protein | |
| Envelope dimer epitope 1 (EDE1) | 652-2 C8 |
| | 753(3) C10 |
| Envelope dimer epitope 2 (EDE2) | 747(4) A11 |
| | 747(4) B7 |
| Ebola Virus | |
| Glycoprotein Nieman-Pick disease type C1 (NPC-1) protein binding site | mAb114 |
| Malaria (*Plasmodium falciparum*) | |
| PfCSP | COS43 |
| circumsporozoite protein (CSP) | mAb311 |
| | mAb317 |

There are various binding partner selection criteria that may be considered for the PMD and ES approaches described herein.

For example, criteria for a binding partner for use in the PMD method include, but are not limited to, the following. The binding domain of the binding partner must cover (sterically block access to) the target region (site of interest) of the antigenic protein and preferably covers as many reactive residues as possible within the target region. In some instances, the binding domain of the binding partner covers no or a minimal number of reactive residues in the non-target region of the antigenic protein. Here, the term reactive residues means the amino acid residues or, more specifically, the chemical moiety or functional group in the amino acid residues within the antigenic protein that is reacted with the modifying reagent and modified by addition of the modifying component. In some instances, if a single binding partner does not meet this criteria, a plurality of binding partners may be used simultaneously. Where multiple binding partners are to be used to protect multiple epitopes simultaneously, the amino acid residues to which these binding partners bind should not overlap. Generally, with respect to the affinity of the binding partner(s), the binding partner(s) should have a slow enough off rate that the binding partner(s) can remain bound to the antigenic protein during the modification reaction. The affinity of the binding partner(s) should also be sufficiently low such that separation of the modified antigenic protein from the binding partner(s) may occur. This may be under a condition that could be different from the conditions used during the modification reaction. The affinity of a binding partner may be optimized through mutations to increase or decrease affinity as desired based on one or more of the known characteristics of the binding interaction with the antigenic protein, the structure of either or both of the binding partner or the antigenic protein. In some instances, the binding partner permits facile elution of the modified antigenic protein complex under desirable elution conditions as discussed below. These features and details are also readily applicable to the first binding partner in the context of the methods of making a modified antigenic protein complex.

In another example, criteria for the one or more binding partners used in the ES method include, but are not limited to the following. The binding domain(s) of the one or more binding partners must cover (sterically block access to) the non-target region(s) of the antigenic protein and preferably cover as many amino acid residues as possible in the non-target region(s). In some instances, the binding domain(s) of the one or more binding partners preferably covers epitopes of the antigenic protein that are considered immunodominant (they preferentially elicit an immune response over the course of infection or vaccination). Where multiple binding partners bound to the antigenic protein at multiple epitopes in the non-target regions simultaneously, the amino acid residues to which these binding partners bind should not overlap. Even if the epitopes to which the binding partners bind do not overlap, preferably other components of the binding partners (such as the constant regions of Fabs or IgGs for example) would not sterically clash with other binding partners. In some instances, the binding partners do not sterically impede, or do so only minimally, the accessibility of the target site such that B cell receptors may interact with the target site is specific therefore. Generally, with respect to the affinity of the binding partner(s), the binding partner(s) should have a sufficiently slow off rate such that the binding partner(s) remain bound to the antigenic protein during routine manipulation, storage, and administration. The affinity of a binding partner may be optimized through mutations to increase affinity based on one or more of the known characteristics of the binding interaction with the antigenic protein, the structure of either or both of the binding partner or the antigenic protein. In some instances, multiple binding partners may be covalently linked in such a way that their affinity for the antigenic protein is increased. These features and details are also readily applicable to the at least one second binding partner in the context of the methods of making a modified antigenic protein complex.

In the above described methods, a mixture of the antigenic protein and the binding partner(s) is formed. The antigenic protein and the binding partner(s) are contacted under conditions in which the binding partner(s) bind specifically to their specific epitopes. In methods of making a modified antigenic protein, the binding partner binds specifically to the target region of the antigenic protein, thereby forming a protein complex in which the target region contains an epitope of interest that is to be protected. In method of making an antigenic protein complex, the one or more binding partners bind specific to one or more non-target regions of the antigenic protein, thereby forming the antigenic protein complex. In the antigenic protein complex, the target region of the antigenic protein may be exposed and accessible for interaction with a B cell receptor (for example, after immunization of a subject) and the non-target region(s) of the antigenic protein may be shielded by the at least one binding partner from interactions with a B cell receptor (for example, after immunization of a subject). The features and details are also readily applicable to the methods of making a modified antigenic protein complex.

In some instances, the one or more binding partners used in the ES method can be provided attached to a nanoparticle.

Thus, a mixture of the antigenic protein and the nanoparticle comprising one or more binding partners attached thereto is formed. In some embodiments, a plurality of a binding partner is attached to the nanoparticle. In some embodiments, a plurality of more than one type of binding partner is attached to the nanoparticle. In some instances, where more than one type of binding partner is required for adequate shielding of the non-target regions of the antigenic protein, the mixture comprising the antigenic protein and the nanoparticle comprising one or more binding partners attached thereto can also comprise one or more other binding partners that are not bound to the nanoparticle. When the ES method is performed using a nanoparticle comprising one or more binding partners attached thereto, the method produces a nanoparticles comprising one or more antigenic protein complexes attached thereto, produced from the specific binding between the one or more binding partners and the antigenic proteins in the mixture. In some instances, where the nanoparticle used in the method comprises a plurality of binding partners attached thereto, the method produces a nanoparticle comprising a plurality of antigenic protein complexes attached thereto.

In the PMD method, a binding partner in the antigenic protein complex protects the target region of an antigenic protein (i.e. an epitope of interest) during a chemical modification reaction that is performed to modify amino acid residues in the non-target region(s) of the antigenic protein in the complex. In some instances, a binding partner may also stabilize the overall fold the antigenic protein, even regions of the distant from the protected target region. Antibody fragments are often used in crystallography to stabilize whole protein conformations and, thereby, facilitate protein crystallisation. Similarly, a binding partner used in the PMD protocol can stabilize the overall conformation of the antigenic protein (secondary structure, tertiary structure, or both) so that the antigenic protein folding structure is not perturbed by the chemical modification. This is valuable in the case of immunogen development as use of a misfolded protein during immunization would elicit off-target or non-productive antibodies. In some instances, binding partner selection can be based on the extent to which the binding partner stabilizes the overall fold/structure of the antigenic protein.

In the methods of making modified antigenic proteins provided herein, once the protein complex of the antigenic protein and the binding partner is formed, a chemical modification reaction may be performed to modify amino acid residues in the non-target region(s) of the antigenic protein in the complex. A reaction mixture is formed in which one or more amino acid residues in the non-target region of the antigenic protein in the protein complex may be contacted with a modifying reagent under conditions sufficient to form a modified antigenic protein, thereby forming a modified antigenic protein in the protein complex. The modified antigenic protein is also referred to herein as a "protein conjugate". In the modified antigenic protein, each of a plurality of amino acid residues in the non-target region thereof have a modifying component covalently attached thereto, while amino acid residues of the target region of the antigenic protein do not have a modifying component attached thereto. In some instances, the non-target region of the antigenic protein also comprises a plurality of amino acids that do not have a modifying component covalently attached thereto (i.e. amino acid residues that are not modified in the modifying reaction). Once the modification reaction is complete, the modified antigenic protein and the binding partner are separated. The features and details and those set forth below are also readily applicable to the methods of making a modified antigenic protein complex.

As used herein, the terms "bind" and "binding" generally refer to the non-covalent interaction between a pair of partner molecules or portions thereof (e.g., antigenic protein-binding partner complexes) that exhibit mutual affinity or binding capacity. Binding can occur such that the partners are able to interact with each other to a substantially higher degree than with other, similar substances. This specificity can result in stable complexes (e.g., antigenic protein-binding partner complexes) that remain bound during handling steps such as chromatography, centrifugation, filtration, and other techniques typically used for separations and other processes. As described herein, the interaction between a target region of an antigenic protein and a binding partner that binds specifically thereto is a non-covalent interaction. In some instances, the interaction between a binding partner and a non-target region of an antigenic protein is a non-covalent interaction. However, in other instances, the interaction between a binding partner and a non-target region of an antigenic protein may be a covalent interaction. For example, the binding partner and the antigenic protein could be expressed as a single contiguous polypeptide. In some instances, the binding partner may be expressed at the N' terminal end or at the C' terminal end of the contiguous polypeptide. The contiguous polypeptide may comprise a linker between the amino acid sequence of the antigenic protein and the coding sequence of the binding partner. Exemplary linkers are the YolTag ScFv Linker and the ScFv-Fab Linker as described in SEQ ID NO:6. In some instances, a protein complex comprising the antigenic protein and the binding partner may be contacted with a chemical crosslinking reagent that causes covalent bonds between the antigenic protein and the binding partner to be formed. In another example, the antigenic protein may contain a first reactive chemical moiety (handle) and the one or more binding partners may each contain a second reactive chemical moiety (handle), wherein the first and second chemical reactive moieties can react with each other to form a covalent bond. Exemplary reactive chemical moieties include those useable in "click" chemistry, which is a class of biocompatible small molecule reactions commonly used in bioconjugation, allowing the joining of substrates of choice with specific biomolecules. Click chemistry is not a single specific reaction, but refers to a way of generating products that follow examples in nature, which also generates substances by joining small modular units. In one example, the antigenic protein may have a first reactive chemical moiety such as a clickable handle like an azide, and the binding partner(s) could have a complementary reactive handle such as, for example a strained cyclooctyne, or vice versa. When these reactive chemical moieties come into proximity when the antigenic protein and the one or binding partners interact to form a protein complex, they can react with each other to form a covalently bond between the proteins.

The terms "elute" and "eluting" refer to the disruption of non-covalent interactions between partner molecules (e.g., a modified antigenic protein and a binding partner) such that the partners become unbound from one another. The disruption can be effected via introduction of a competitive binding species, or via a change in environmental conditions (e.g., ionic strength, pH, or other conditions).

As used herein, the term "forming a mixture" refers to the process of bringing into contact at least two distinct species such that they mix together and interact. "Forming a reaction mixture" and "contacting" refer to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture. "Conversion" and "converting" refer to a process including one or more steps wherein a species is transformed into a distinct product.

The methods provided herein include contacting a protein complex with a modifying reagent, so as to covalently bond modifying components to amino acid residues in the non-target region of the antigenic protein in the complex. As used herein, the term "modifying reagent" refers to a substance comprising one or more modifying components and capable of reacting with a protein so as to covalently bond the one or more modifying components to the protein, thereby forming a modified protein. At least one molar equivalent of the modifying reagent (e.g., 1.1-100 molar equivalents) with respect to the reactive groups on the antigenic protein is employed. Where the antigenic protein is itself a protein complex, such as a trimeric protein complex, the molar equivalent is in relation to the reactive groups in the entire protein complex. In some instances, the modifying reagent may be contacted to the protein complex all at once. In other instances, the modifying reagent may be contacted to the protein complex in batches (fractions). For example, if a certain number of molar equivalents of modifying reagent (e.g., 10) are to be contacted to the protein complex of the antigenic protein and the binding partner, the modifying reagent may be contacted to the protein complex in a series of batches over time, wherein each batch is a portion of the total amount of molar equivalents of modifying reagent to be used (e.g., 10 batches of 1 molar equivalents, 5 batches of 2 molar equivalents, 4 batches of 2.5 molar equivalents, or 2 batches of 5 molar equivalents). As used herein, the term "modifying component" refers to a prosthetic moiety that is or can be covalently bonded to a protein. By "prosthetic," it is meant that the modifying component is not present in the antigenic protein following expression of the protein in an organism from which the protein is derived (i.e., after translation and/or post-translational modification in the organism or a heterologous expression system). Rather, the modifying component is appended to the antigenic protein via reaction with one or more modifying reagents so as to modify the protein—i.e., to covalently bond the modifying component to the protein. A number of modifying components can be used in the methods. Exemplary modifying components include, but are not limited to, a polyethylene glycol polymer, a glycopolymer (polysaccharide), a polysialic acid, a hyaluronic acid, a peptide, a protein, a polynucleotide, or a combination of any thereof. In some instances, the modifying component may be an adjuvant. Exemplary adjuvants include glycopolymers and CpG DNA polynucleotides.

The modified antigenic protein contains one or more amino acid residues having a modifying component covalently bonded thereto in a non-target region. Modifying components can be covalently bonded to the antigenic protein at one or more amino acid residue sidechains (e.g., at a terminal amino group in a lysine sidechain or a thiol group in a cysteine sidechain). In some instances, modifying components can be covalently bonded to the antigenic protein at one or more positions in the peptide backbone of the protein (e.g., at the N-terminus or C-terminus of the protein), or at other locations in the protein (e.g., in a sugar moiety of a glycosylated protein). In some instances, one type of amino acid residue in the antigenic protein may be covalently bonded with one type of modifying component using a single reaction chemistry. In other instances, different types of amino acid residues in the antigenic protein may be covalently bonded with one type of modifying component using a single reaction chemistry. In some instances, one type of amino acid residue in the antigenic protein may be covalently bonded with one type of modifying component using different reaction chemistries. In other instances, different types of amino acid residues in the antigenic protein may be covalently bonded with different types of modifying components using different reaction chemistries. In some instances, different types of amino acid residues in the antigenic protein may be covalently bonded with one type of modifying components using different reaction chemistries.

In some embodiments, the modifying component, e.g., a polymer such as poly(ethylene glycol), is covalently linked to the antigenic protein via a linking moiety. As used herein, the term "linking moiety" refers to a functional group that covalently bonds two or more moieties in a compound or material. For example, the linking moiety can serve to covalently bond a modifying component to an antigenic protein or to covalently bond a binding partner to a solid support. Useful bonds for connecting modifying components and/or binding partners to antigenic proteins and other materials include, but are not limited to, amides, amines, esters, carbamates, ureas, thioethers, thiocarbamates, thiocarbonates, and thioureas. A "divalent" linking moiety contains two points of attachment for linking two functional groups; polyvalent linking moieties can have additional points of attachment for linking further functional groups. For example, divalent linking moieties include divalent polymer moieties such as divalent poly(ethylene glycol), divalent poly(propylene glycol), and divalent poly(vinyl alcohol).

In some embodiments, the structure of the linking moiety is selected from:

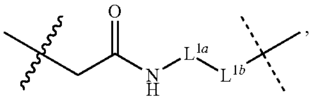,
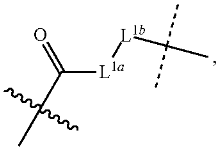,
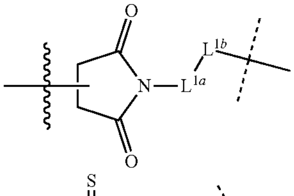,
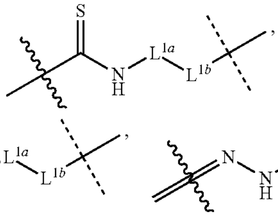,
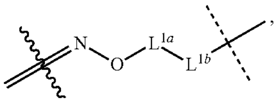,
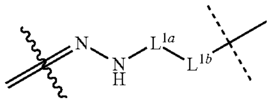,
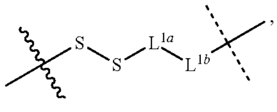, -continued

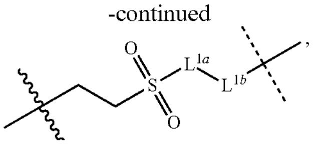

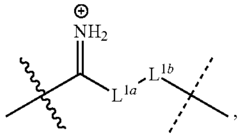

and

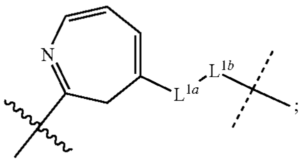

wherein $L^{1a}$ and $L^{1b}$ are independently selected from a bond, a divalent polymer moiety, and linear or branched, saturated or unsaturated $C_{1-30}$ alkyl; wherein one or more carbon atoms in the $C_{1-30}$ alkyl is optionally and independently replaced by O, S, $NR^a$; wherein one or more groupings of adjacent carbon atoms in the $C_{1-30}$ alkyl are optionally and independently replaced by —$NR^a$(CO)— or —(CO)$NR^a$—; and wherein one or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from 0, S, and N;

each $R^a$ is independently selected from H and $C_{1-6}$ alkyl;

the wavy line represents the point of connection to the antigenic protein; and the dashed line represents the point of connection to the modifying component.

Antigenic proteins can be modified with modifying components using various chemistries for protein modification, and linking moieties described above can result from the reaction of protein functional groups (e.g., amino acid residue side chains or protein termini) with a number of modifying reagents having reactive linker groups. Examples of such reagents include, but are not limited to, N-hydroxysuccinimidyl (NETS) esters and N-hydroxysulfosuccinimidyl (sulfo-NHS) esters (amine reactive); carboxylic acid anhydrides (amine reactive); carbodiimides (amine and carboxyl reactive); hydroxymethyl phosphines (amine reactive); maleimides (sulfhydryl reactive); haloacetamides, including iodoacetamides (sulfhydryl reactive); acyl and aryl azides (amine reactive); fluorinated aryl azides (reactive via carbon-hydrogen (C—H) insertion); sulfonyl chlorides (amine reactive); aryl halides (amine reactive); pentafluorophenyl (PFP) esters (amine reactive); imidoesters (amine reactive); isocyanates and isothiocyanates (amine and hydroxyl reactive); vinyl sulfones (sulfhydryl, amine, and hydroxyl reactive); pyridyl disulfides (sulfhydryl reactive); benzophenone derivatives (reactive via C—H bond insertion); glyoxals (amine reactive); epoxides/oxiranes (amine reactive); rhodium carbenoids (tryptophan reactive); diazonium salts (tyrosine reactive); and ketones and aldehydes (amine reactive, e.g., via reductive amination).

Further reagents and methods include, but are not limited, to those described by Hermanson (*Bioconjugate Techniques* 2nd Edition, Academic Press, 2008) and Bernard and Francis (*Frontiers in Microbiology,* 2014, Vol 5, Article 734, pp. 1-7).

In some embodiments, the modifying components are installed using a modifying reagent selected from:

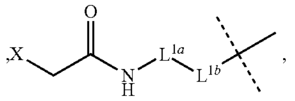

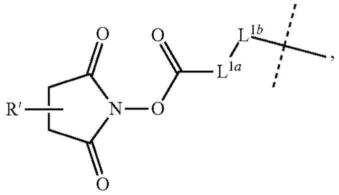

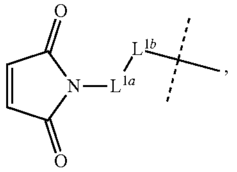

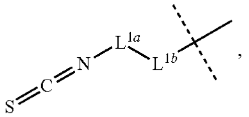

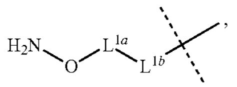

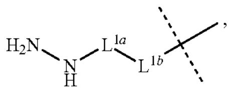

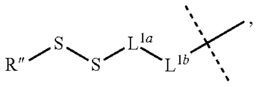

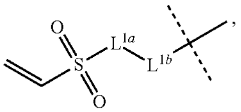

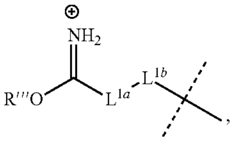

and

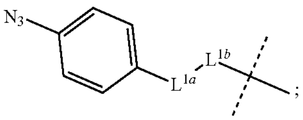

wherein X is halogen (e.g., iodo or chloro); R' is H or sulfo; R" is optionally substituted aryl (e.g., 3-carboxy-4-nitrophenyl) or optionally substituted heteroaryl (e.g., pyridin-2-yl); R''' is optionally substituted alkyl (e.g., methoxy); $L^{1a}$ and $L^{1b}$ are as described above; and the dashed line represents the point of connection to the modifying component, e.g., a polymer such as poly(ethylene glycol).

In some embodiments, modifying components are installed in the antigenic protein using a modifying reagent and a coupling reagent. For example, a modifying reagent having a carboxylate reactive group (e.g., a carboxylate-terminated poly(ethylene glycol) can be used in conjunction with a coupling reagent such as 1-ethyl-3-(3-dimethylaminopropyl)carbodiimide hydrochloride (EDC) or another carbodiimide coupling reagent so as to install the modifying component via amide bond formation with an amine (e.g., a lysine residue sidechain) on the antigenic protein. In such cases, at least one molar equivalent of the coupling reagent (e.g., 1.1-100 molar equivalents) with respect to the antigenic protein is employed. As discussed above, the modifying reagent can be contacted to the protein complex comprising the antigenic protein and the binding partner all at once or in batches over time. The coupling reagent may also be contacted to the protein complex comprising the antigenic protein and the binding partner all at once or in batches over time. In some instances, the step of modifying the protein complex comprises reacting the protein complex with the modifying reagent and a coupling reagent under conditions sufficient to form a modified antigenic protein.

Functional groups in naturally occurring amino acids and non-naturally occurring amino acids can be used as handles for the incorporation of modifying components in the antigenic proteins. For example, the primary amine of the lysine sidechains can be modified via reaction with NHS esters or carboxylic acids in the presence of EDC while the sulfhydryl moiety of cysteine sidechains can be modified via reaction with maleimides or iodoacetamides. Cysteine residues, which occur relatively infrequently on solvent-accessible protein surfaces, can be introduced into the antigenic proteins via site-directed mutagenesis and related techniques to provide for selective protein modification in certain instances. The N-terminus of the antigenic protein can be modified by using pyridoxal phosphate (PLP) to oxidize the N-terminal amine to form a ketone or aldehyde, which can be further elaborated via reaction with aminooxy-compounds or hydrazines to form oximes or hydrazones (see, e.g., Gilmore et al. *Angew. Chem. Int. Ed.* 2006, 45, 5307-5311). Uniquely reactive functional groups (e.g., azides, alkynes, ketones, etc.) can also be introduced into antigenic proteins as genetically-encoded non-naturally occurring amino acid residues as described, for example, by Liu & Schultz (*Annu. Rev. Biochem.* 2010, 79, 413-444).

Reactions are conducted under conditions sufficient to modify the antigenic protein with the modifying component. In general, the reactions are conducted in aqueous reaction mixtures. Typically, at least one molar equivalent of the modifying reagent with respect to the the number of moles of amino acid residues in the antigenic protein that are chemically modifiable by the modifying reagent will be employed. Frequently, an excess of the modifying reagent is used. For example, a reaction mixture for modifying the antigenic protein can include anywhere between 1.1 molar equivalents and 100 equivalents of the modifying reagent with respect to the antigenic protein. The reaction mixture can contain 2-50 molar equivalents of the modifying reagent, or 2-20 molar equivalents of the modifying reagent, or 5-15 molar equivalents of the modifying reagent. The reactions can be conducted at any suitable temperature. In general, the reactions are conducted at a temperature of from about 4° C. to about 40° C. The reactions can be conducted, for example, at about 20° C. or about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of the antigenic protein and the modifying reagent used for installing the modifying component.

Reaction mixtures for installing modifying components can contain additional reagents of the sort typically used in bioconjugation reactions. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[bis(carboxymethyl)amino]ethyl} (carboxymethyl)amino)acetic acid (EDTA), and 1,2-bis(o-aminophenoxy)ethane-N,N,N',N'-tetraacetic acid (BAP TA)), and reducing agents (e.g., dithiothreitol (DTT), β-mercaptoethanol (BME), and tris(2-carboxyethyl)phosphine (TCEP)). Buffers, cosolvents, salts, detergents/surfactants, chelators, and reducing agents can be used at any suitable concentration, which can be readily determined by one of skill in the art. In general, buffers, cosolvents, salts, detergents/surfactants, chelators, and reducing agents are included in reaction mixtures at concentrations ranging from about 1 μM to about 1 M. For example, a buffer, a cosolvent, a salt, a detergent/surfactant, a chelator, or a reducing agent can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M.

In some instances, a modification reaction will result in a product mixture containing antigenic proteins having different numbers of modifying components. In typical modification reactions, product mixtures can contain unmodified protein or modified proteins with one, two, three, five, eight, ten, 12, 15, 18, 20, or more modifying components. In the provided methods, protein mixtures can contain unmodified protein as well as modified proteins with one, two, three, four, five, or more modifying components. The distribution of modifying components in the product mixture may vary, depending on the particular protein and modifying reagents used for installing the modifying components.

In some instances, in the method of forming an antigenic protein, the binding partner is attached to a solid support when the binding partner and the antigenic protein are brought into contact. In other instances, the antigenic protein may be attached to a solid support when the binding partner and the antigenic protein are brought into contact.

The term "solid support" is used herein to denote a solid inert surface or body to which an agent, such as a binding partner, that is reactive in any of the binding reactions described herein can be immobilized. The term "immobilized" as used herein denotes a molecularly-based coupling that is not dislodged or de-coupled under any of the conditions imposed during any of the steps of the assays described herein. Such immobilization can be achieved through a covalent bond, an ionic bond, an affinity-type bond, or any other covalent or non-covalent bond. Exemplary solid supports include chromatography resins and multi-well plates.

The solid support may be a macrocyclic matrix material. As used herein, the term "macrocyclic matrix material" refers to a material containing an insoluble support and a plurality of macrocyclic host moieties. By "insoluble," it is meant that the matrix material does not dissolve when contacted with liquid media of the sort typically used for handling proteins and other biomolecules (e.g., aqueous buffers and aqueous mixtures containing organic co-solvents). Examples of support materials include, but are not limited to, crosslinked polysaccharides; porous silica gels; silica and mineral oxides modified with hydrogel-forming polymers; crosslinked polyacrylamides (e.g., bis-acrylamide copolymers and acrylamide-poly(ethylene glycol) copolymers); and monolithic materials. A "monolith" refers to a porous, three-dimensional material having a continuous interconnected pore structure in a single body. The term monolith is meant to be distinguished from a collection of individual particles packed into a bed formation.

In some embodiments, the matrix material may be a crosslinked polysaccharide, a porous silica gel, a mineral oxide hydrogel composite, a silica hydrogel composite, a bis-acrylamide copolymer, an acrylamide-poly(ethylene glycol) copolymer, or combinations thereof. In some embodiments, the support includes crosslinked agarose, crosslinked dextran, or a combination thereof.

As used herein, the term "crosslinked polysaccharide" refers to a beaded resin formed from carbohydrate polymers (e.g., dextrose, agarose, and combinations thereof) that are rendered insoluble in liquid media (e.g., aqueous solutions and aqueous mixtures containing organic co-solvents) by reaction with crosslinking reagents such as epihalohydrin, bis-epoxides, divinyl sulfone, and the like. A number of crosslinked polysaccharides are commercially available under tradenames including SEPHADEX™, SEPHAROSE™, SEPHACRYL™ (GE Healthcare Life Sciences), and others.

As used herein, the terms "separating," "isolating," and "recovering" refer to the process of removing at least a portion (i.e., a fraction) of a first substance from a mixture containing the first substance, a second substance, and other optional substances. Separation can be conducted such that the separated substance is substantially free of at least one of the other substances present in the original mixture. For example, when the separated first substance is substantially free of the second substance, it is meant that at least about 50% of the second substance is removed from the isolated first substance. For example, at least about 55, 60, 65, 70, 75, 80, 85, 86, 87, 88, 89, 90, 91, 92, 93, 94, 95, 96, 97, 98, or 99% (w/w) of the second substance is removed from the isolated first substance. A "separated protein fraction" refers to a mixture containing a protein and optional excipients (e.g., buffers, detergents, and the like), wherein the protein molecules in the fraction are substantially identical. By "substantially identical," is it meant that at least about 50% of the protein molecules have the same polypeptide sequence and the same level of modification with a modifying component. For example, at least about 55, 60, 65, 70, 75, 80, 85, 86, 87, 88, 89, 90, 91, 92, 93, 94, 95, 96, 97, 98, or 99% (w/w) of the protein molecules may have the same polypeptide sequence and the same level of modification with a modifying component.

In some instances, in the provided methods of making a modified antigenic protein, the step of separating the modified antigenic protein from the binding part may include eluting the modified antigenic protein from the binding partner, when then binding partner is attached to a solid support (such as a macrocyclic matrix material). In other instances, the step of separating the modified antigenic protein from the binding part may include eluting the binding partner from the modified antigenic protein, when the modified antigenic protein is attached to a solid support (such as a macrocyclic matrix material). Where the modified antigenic protein is attached to the solid support, the modified antigenic protein is subsequently eluted or cleaved from the solid support after the binding partner is separated therefrom. Conditions may be selected where the binding partner may be eluted from the modified antigenic protein using a first elution condition while the modified antigenic protein remains attached to the solid support, and then eluting the modified antigenic protein from the solid support using a second elution condition. In some instances, the modified antigenic protein may be cleaved from the solid support chemically or enzymatically. In practice, eluting the proteins from the matrix material can include collecting a single fraction number of fractions (e.g., 5, 10, 25, or more fractions) or can include collecting a single elution batch or multiple elution batches (e.g., 2, 3, 4, 5, or more batches).

Preferably, the separation steps in the methods of making an antigenic protein may be conducted using conventional equipment and instrumentation for column chromatography. Such instrumentation is described, for example, in U.S. Pat. Nos. 8,986,543; 7,208,087; and 4,563,275. Typically, around 1 gram of the macrocyclic matrix material will be used for separation mixtures of modified protein in amounts ranging from micrograms to milligrams. For example, a chromatography column can be loaded with 1 μg-100 mg protein per gram of the macrocyclic matrix material. The loading capacity of the matrix will depend on factors such as the identity of the proteins in the mixture, the level of modification, and the identity of the modifying component(s). After loading, the protein can be eluted from the macrocyclic matrix material by passing an aqueous buffer (or another fluid mobile phase) through the column. Any suitable flow-rate for separating the modified proteins can be used, and flow-rates ranging from 0.1-5 mL/min can be employed depending on factors such as the quantity of protein and the dimensions of the column and ancillary equipment. Any buffer compatible with the protein and the macrocyclic matrix material can be used in the methods of the invention. Examples of suitable buffers include 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate. Such buffers will typically be used at concentrations ranging from around 1 mM to about 250 mM, and the pH of the buffers will typically range between around 5.5 and 8. One of skill in the art will appreciate that the concentration and/or pH of the buffer can be adjusted depending on the properties of the protein being separated. The buffer used in the separation step can also include cosolvents, detergents/surfactants, chelators, and reducing agents, as described above.

Typically, the buffer used in the separation step will also include an elution compound that promotes unbinding of the modified protein from the matrix material. For example, the elution compound can be a salt (e.g., NaCl, KCl, $CaCl_2$, $MgSO_4$, $(NH_4)_2SO_4$) or a competitive guest substance that binds to the matrix or modified protein (e.g., adamantane carboxylic acid, soluble cyclodextrin). The separation steps will typically be conducted at or below room temperature. For example, the separation can be conducted at around 25° C., or around 20° C., or around 8° C., or around 4° C.

There are various elution condition selection criteria that may be considered for the PMD approach described herein.

For example, the elution conditions preferably do not denature the protein. Conditions should be selected such that protein integrity is not compromised and that regions of the protein that are typically unexposed regions due to tertiary structure of the protein do not become exposed due to protein unfolding. Elution conditions that do not cause or result in conformational changes in the protein may also be selected. For example, if the antigenic protein is known to undergo conformational changes under particular conditions such as, for example low pH or high pH, elution conditions should be selected to avoid the particular condition and the resulting conformational change. One example of this is the influenza hemagglutinin protein, which undergoes a conformational change at low pH and, as such, should be eluted using conditions where the pH is sufficiently high to avoid causing a conformational change in the protein. In some instances, elution conditions may be selected that permit rapid buffer exchange to eliminate the eluent. This means conditions should be selected under which the modified antigenic protein is not covalently or otherwise irreversibly bound to the eluent. Preferably, the eluent can be removed by buffer exchange using dialysis, desalting column, progressive concentration and dilution, etc. In some instances, elution conditions may be selected such that the modified antigenic protein elicits an expected response upon buffer exchange, which would validate the selection of the eluent conditions from points discussed above.

The above-described methods of producing modified antigenic proteins, antigenic protein complexes, and modified antigenic protein complexes may also be conducted iteratively to develop an immunogen in which the target region of the antigenic protein is antigenic and the non-target region is not. A modified antigenic protein, antigenic protein complex, or modified antigenic protein complex may be screened against a screening library comprising a plurality of binding partners that bind specifically to non-target region(s) of the antigenic protein. The protein/complex may be screened against the screening library to assess if any binding is detected between said proteins/complexes and a binding partner that binds specifically to a non-target region of the antigenic protein. If binding is detected, this indicates that the non-target region of the antigenic protein is insufficiently shielded or masked by one or both of modification of amino acids with a modifying component or protein interaction with one or more binding partners. This may be referred to as the protein/complex having antigenic "holes" in the non-target region of the antigenic protein. If binding is detected between the protein/complex and a binding partner in the screening library, a revised version of the protein/complex may be produced in which the protein/complex is designed to further ablate the antigenicity of the non-target region of the antigenic protein (i.e. fill the "holes"). For example, a variant of the antigenic protein may be produced that includes one or more amino acid residue substitutions in the portion of the non-target region of the antigenic protein to which the binding partner from the screening library was bound, such one or more amino acid residue substitutions comprising amino acid residues being modifiable by the chemical reaction selected for the modification reaction. In this manner, the antigenic "hole" in the non-target region of the antigenic protein may be "filled" by masking the native antigenic configuration of the region using modifying components attached to the amino acid residues therein. In another example, a new binding partner, such as the one from the screening library that was found to bind to the non-target region, could be complexed with the antigenic protein to shield that portion of the non-target region (i.e. fill the antigenic hole). This step of screening the protein/complex against a screening library may be performed for each new version of the protein/complex until a protein/complex is obtained that has the desired antigenicity. The screening library may comprise, for example, a plurality of known antibodies, known antibody fragments, or isolated peripheral blood mononuclear cells. In some instances, the protein/complex may be screened against more than one screening library.

As discussed in more detail below, an intended purpose for the provided modified antigenic proteins, antigenic protein complexes, and modified antigenic protein complexes is as immunogens capable of stimulating an immune response against the target region of the antigenic protein in a subject to which they are administered. In some instances, to stimulate an immune response in a subject, particularly human and animal subjects, an immunogen must bind specifically to B cells in the subject such that the B cell may be activated. B cells express B cell receptors (BCRs) that are immunoglobulin molecules that form a type 1 transmembrane receptor protein located on the outer surface of the B cells. The BCR binding moiety is composed of a membrane-bound antibody that has a unique and randomly determined antigen-binding site. Without being held to any particular theory, a B cell is activated by its first encounter with an antigen that binds to its receptor (its "cognate antigen"), and the cell proliferates and differentiates to generate a population of antibody-secreting plasma B cells and memory B cells. And without being held to any particular theory, in the activation process, B cells undergo somatic hypermutation of the variable regions of precursor immunoglobulin genes in the cell genome that results in affinity maturation and the production of high affinity, secreted antibody molecules. As such, the BCR expressed by a B cell may have relatively weak binding affinity for its cognate antigen relative to the binding affinity of a mature antibody to the same cognate antigen produced by the activated B cell. In some instances, an immunogen should have sufficient affinity for a BCR in order to result in B cell activation and the production of high affinity antibodies that bind specifically to the immunogen in the subject.

In some instances, provided are methods of screening the modified antigenic proteins, antigenic protein complexes, and modified antigenic protein complexes, and components thereof, (collectively, "putative immunogens") to determine if they can be bound specifically by B cell receptors. The B cell receptors may be germline BCRs or non-germline BCRs. To do so, the putative immunogen may be screened against one or more BCRs.

In some instances, the putative immunogen may be screened against a single BCR. Such screening may be performed to determine whether a specific interaction occurs between the putative immunogen and a specific BCR sequence. For example, the immunoglobulin coding sequence may be cloned and expressed in a eukaryotic cell, such as a human cell. The full length immunoglobulin gene coding sequence or, alternatively, portions of the immunoglobulin gene coding sequence encoding the variable domains of the BCR, may be cloned and expressed. For example, the heavy chain and light chain regions of the immunoglobulin gene may be cloned and expressed. In another example, the variable domains of the immunoglobulin may be cloned and expressed as a single chain variable fragment (scFv). The soluble recombinant antibody can be purified from cells and assayed for specific protein-protein interaction with the target region of the putative immunogen. Where the BCR is a germline or precursor immunoglobulin, the coding sequences modified so as to produce a soluble immunoglobulin protein. For example, the heavy chain and light chain regions of the precursor immunoglobulin gene may be cloned into the full length sequence of an immunoglobulin G coding sequence. The resulting recombinant immunoglobulin G protein expressed by the eukaryotic cells is a soluble recombinant antibody containing the heavy chain and light chain regions of the precursor immunoglobulin gene. Soluble scFv fragments of such may also be generated. In some instances, the soluble recombinant antibodies described above, or other soluble recombinant antibodies containing the variable domains of BCRs, are commercially available.

Exemplary assays for assessing such protein-protein interactions include but are not limited to enzyme-linked immunosorbent assays (ELISA), co-immunoprecipitation and pull down assays, and biolayer interferometry binding assays such as, for example, those described in the examples using the ForteBio Octet® biosensors. In some instances, the BCR, or fragment thereof containing the variable domains, may be expressed as a fusion protein with a membrane protein on the surface of a eukaryotic cell. For example, the fusion protein may comprise an scFv covalently linked to a membrane protein on the surface of a eukaryotic cell. In some instances, the eukaryotic cell may be a yeast cell or a mammalian cell such as a human cell. The putative immunogen can be assayed for specific protein-protein interaction with the BCR, or fragment thereof containing the variable domains, on the surface of the eukaryotic cell. Exemplary assays for assessing such protein-protein interactions include but are not limited to cell-based ELISAs and flow cytometry. Where the protein-protein interactions are assessed by flow cytometry, the immunoglobulin, or fragment thereof, on the surface of the eukaryotic cell may be labeled with a fluorescent tag. For example, the immunoglobulin, or fragment thereof, may comprise a biotinylation sequence, such as an AviTag™, that is then bound to a fluorescently labeled streptavidin protein.

In other instances, a putative immunogen may be screened against a plurality of BCRs, such as a pool of BCRs. In some instances, the plurality of BCR may be a pool of germline sequence BCRs. In other instances, it may be a pool of mature BCRs. Such screening may be performed to assess if any of a diverse array of BCR have the ability to bind specifically to the target region of the putative immunogen. Similar to as described above with respect to assessing the binding of a putative immunogen to a single BCR, a putative immunogen can be screened against a panel comprising a plurality of soluble recombinant antibodies, each soluble recombinant antibody in the panel comprising variable domains from a different immunoglobulin gene. In some instances, such soluble recombinant antibodies are commercially available. Protein-protein interactions can be assessed as described above for the single BCR assessment.

In some instances, the putative immunogen can be screened against a binding pool, the binding pool comprising a plurality of eukaryotic cells or phage that express BCRs, or fragments thereof containing the variable domains, on the surface of the eukaryotic cells or phage. For example, the BCRs, or fragments thereof, may be expressed as fusion proteins with a membrane protein on the surface of the eukaryotic cells or phage. Each cell or phage in the binding pool expresses a BCR or fragment thereof comprising variable domains from a different immunoglobulin gene. In some instances, the fusion proteins may comprise a plurality of scFv covalently linked to a membrane protein on the surface of eukaryotic cells or phage. In some instances, the eukaryotic cell may be a yeast cell or a mammalian cell such as a human cell. The putative immunogen can be assayed to detect whether there is specific protein-protein interaction with any of the BCRs, or fragments thereof containing the variable domains, expressed on the surface of the eukaryotic cells or phage. Methods of detecting protein-protein interactions using phage display are well-known in the art. For example, the putative immunogen may be bound to a solid support and the pool of phage applied thereto. After washing the solid support, any phage that remain bound to the solid support may express a BCR, or fragment thereof, that can binding specifically to the putative immunogen. The phage DNA is isolated (after bacterial amplification) and sequenced to identify the sequence of the BCR, or fragments thereof comprising the variable domains, expressed by the phage. Such BCRs, or fragments thereof, may then be further assessed individually as described above for specific binding to the putative immunogen. In some instances, where the binding pool comprises eukaryotic cells, specific protein-protein interaction with any of the BCRs, or fragments thereof, may be assessed by flow cytometry. In some instances, the eukaryotic cells of the binding pool may be yeast cells. In such instances, the yeast cells in the binding pool may express membrane-bound scFv fragments of BCRs or Fab fragments. In some instances, the eukaryotic cells of the binding pool may be mammalian cells such as human cells. In some instances, the mammalian cells in the binding pool may express the full length BCR or a membrane-bound Fab fragment. As discussed above, the BCRs, or fragments thereof, that are expressed on the cells of the binding pool may be fluorescently labeled. The putative immunogen and the binding pool may be combined, and FACS analysis performed to identify cells that expressed BCRs, or fragments thereof, that bound specifically to the putative immunogen. In some instances, the identified cells may then be expanded in vitro, and the DNA or the RNA analyzed, such as by next generation sequencing. In some instances, single cell PCR may be performed followed by RNA and/or DNA sequence analysis. Other exemplary methods for assessing protein-protein interactions between a putative immunogen and a binding pool include those described in Jardine, J., et al., 2013, Science 340(6133):711-716 and McGuire, A. T., et al., 2014, J. of Virology 88(5): 2645-2657, both of which are incorporated by reference in their entireties herein.

In some instances, the putative immunogens may be screened against a biological sample from a subject comprising antibodies. For example, a putative immunogen may be screened against a plurality of peripheral blood mononuclear cells (PBMCs) isolated from a subject. Such screening may be performed to identify one or B cells that express a BCR that binds specifically to the target region of the antigenic protein. In some instances, the subject may have been vaccinated against the infectious agent. In other instances, the subject may have been exposed to the infectious agent. In other instances, the subject may have been neither vaccinated against or exposed to the infectious agent.

II. Compositions, Formulations, and Kits

Provided in this disclosure are modified antigenic proteins and antigenic protein complexes made using the methods described in Section I. The features and embodiments as provided in Section I with respect to the modified antigenic protein and the antigenic protein complex are also features and embodiments of the compositions and formulations described in this section. The compositions, formulations, and kit of this disclosure may include any of antigenic proteins, modified antigenic proteins, antigenic protein complexes, binding partners, modifying components described in Section 1 and combinations thereof.

In one aspect, provided is a modified antigenic protein comprising a target region and a non-target region, wherein the non-target region comprises a plurality of amino acid residues each of which having a modifying component attached. In some instances, the non-target region of the antigenic protein also comprises a plurality of amino acid residues that do not have a modifying component covalently attached thereto (i.e. amino acid residues that are not modified in the modifying reaction). In another aspect, the target region of the modified antigenic protein may further comprise at least one amino acid residue substitution that replaces at least one native amino acid residue with at least one non-native amino acid residue. In some instances, the at least one non-native amino acid residue has a side chain that cannot be covalently linked to the modifying agent in the same manner that the modifying agent is covalently linked to the plurality of amino acids in the non-target region of the antigenic protein, while the at least one native amino acid residue that has been substituted had a side chain that could be covalently linked to the modifying agent in the same manner that the modifying agent is covalently linked to the plurality of amino acids in the non-target region of the antigenic protein. In some instances, the at least one amino acid residue substitution is a conservative amino acid substitution. In some instances, the target region containing the at least one amino acid residue substitution generally retains similar tertiary structure and antigenicity relative to the native target region of the antigenic protein. In some instances, the target region may also contain at least one amino acid residue substitution that introduces at least one non-native amino acid residue that causes the target region to have increased antigenicity, increased binding affinity with a B cell receptor, or both.

The modified antigenic protein may comprise any of the modifying components described in Section I. As discussed in Section I, a variety of modifying components may be covalently linked to amino acid residues in the non-target region of the antigenic protein in the complex. Exemplary modifying components include, but are not limited to, a polyethylene glycol polymer, a glycopolymer (polysaccharide), a polysialic acid, a hyaluronic acid, a peptide, a protein, a polynucleotide, or a combination of any thereof. In some instances, the modifying component may be an adjuvant. Exemplary adjuvants include glyopolymers and CpG DNA polynucleotides.

The modified antigenic protein contains one or more amino acid residues having a modifying component covalently bonded thereto in the non-target region. Modifying components can be covalently bonded to the antigenic protein at one or more amino acid residue sidechains (e.g., at a terminal amino group in a lysine sidechain or a thiol group in a cysteine sidechain). In some instances, modifying components can be covalently bonded to the antigenic protein at one or positions in the peptide backbone of the protein (e.g., at the N-terminus or C-terminus of the protein), or at other locations in the protein (e.g., in a sugar moiety of a glycosylated protein). In some instances, one type of amino acid residue in the antigenic protein may be covalently bonded with one type of modifying component using a single reaction chemistry. In other instances, different types of amino acid residues in the antigenic protein may be covalently bonded with one type of modifying component using a single reaction chemistry. In some instances, one type of amino acid residue in the antigenic protein may be covalently bonded with one type of modifying component using different reaction chemistries. In other instances, different types of amino acid residues in the antigenic protein may be covalently bonded with different types of modifying components using different reaction chemistries. In some instances, different types of amino acid residues in the antigenic protein may be covalently bonded with one type of modifying components using different reaction chemistries.

In some embodiments, the modifying component, e.g., a polymer such as poly(ethylene glycol), is covalently to the antigenic protein via a linking moiety. As discussed in Section I, useful bonds for connecting modifying components and/or binding partners to antigenic proteins and other materials include, but are not limited to, amides, amines, esters, carbamates, ureas, thioethers, thiocarbamates, thiocarbonates, and thioureas. The modified antigenic proteins provided herein may comprise one or more modifying components covalently linked to one or more amino acid residues of the non-target region(s) via any of the linking moieties described in Section I.

In some instances, a modified antigenic protein may comprise a mixture of modified antigenic proteins comprising different numbers of modifying components. For example, the mixtures can contain unmodified protein or modified proteins with one, two, three, five, eight, ten, 12, 15, 18, 20, or more modifying components. In the provided methods, protein mixtures can contain unmodified protein as well as modified proteins with one, two, three, four, five, or more modifying components. The distribution of modifying components in the product mixture may vary, depending on the particular protein and modifying reagents used for installing the modifying components.

In another aspect, provided are antigenic protein complexes comprising an antigenic protein comprising a target region and a non-target region; and at least one binding partner, wherein the at least one binding partner comprises at least one protein binding domain that binds specifically with the non-target region of the antigenic protein. In some instances, the antigenic protein and the at least one binding partner may be non-covalently bound to each other via specific interaction between the at least one protein binding domain and the non-target region of the antigenic protein. In other instances, the antigenic protein and the at least one binding partner may be covalently bound to each other as described above. In the antigenic protein complex, the target region of the antigenic protein is exposed and accessible for interaction with a B cell receptor. In certain instances, in the antigenic protein complex, the non-target region of the antigenic protein is shielded by the at least one binding partner from interactions with a B cell receptor.

In another aspect, provided are modified antigenic protein complexes comprising an antigenic protein comprising a target region and a non-target region; and at least one binding partner, wherein the at least one binding partner comprises at least one protein binding domain that binds specifically with the non-target region of the antigenic protein, and wherein the non-target region comprises one or more amino acid residues having a modifying component covalently bonded thereto. The portion(s) of the non-target region to which the one or more binding partners is bound may be different than the portions of the non-target region containing the one or more amino acids having a modifying component bonded thereto. Thus, in some instances, some portions of the non-target region(s) of the antigenic protein in the modified antigenic protein complex are shielded through the binding interaction with the at least one second binding partner and other portions of the non-target region (s) contain a plurality of amino acids having a modifying component covalently attached thereto. The features and details described above with respect to the modified antigenic protein are also applicable to the modified antigenic protein complexes. In some instances, the one or more binding partners may comprise one or more amino acid residues having a modifying component covalently attached thereto.

The antigenic protein, modified or not, is a protein expressed by an infectious agent as described above. The antigenic protein may be a viral protein, a bacterial protein, a fungal protein, or a parasite protein. Exemplary viral proteins include, but are not limited to, HIV proteins, influenza proteins, RSV proteins, Zika Virus proteins, West Nile Virus proteins, Dengue Virus proteins, Ebola Virus proteins, and coronavirus proteins such as those expressed by SARS and hCoV-EMC. Specific exemplary viral proteins are listed in Table 1. In one example, the viral protein is an influenza virus protein. In another example, the viral protein is an HIV protein. Exemplary bacterial proteins include proteins expressed by *Virbio* bacterial species and *Staphylococcus* bacterial species, amongst other bacteria. For example, the bacterial protein may be a *Virbrio* cholera protein such as Toxin B, TcpA, or combinations thereof. In another example, the bacterial protein may be a *Staphylococcus aureus* protein such as enterotoxin-B, IsdB, or MA. Exemplary fungal proteins include proteins expressed by any of *Candida* species, *Aspergillus* species, and *Cryptococcus* species. For example, the fungal protein may be a *Candida albicans* protein such as Alsip, A1s3p, or combinations thereof. In another example, the fungal protein may be a *Aspergillus fumigatus* protein such as Asp 16 f. In another example, the fungal protein may be a *Cryptococcus neoformans* protein such as glucuronoxylomannann. Exemplary parasite proteins include proteins expressed by *Plasmodium* species and *Toxoplasma* species. For example, the parasite protein may be a *Plasmodium falciparum* protein such as circumsporozoite. In another example, the parasite protein may be a *Toxoplasma gondii* protein such as SAG1, GRA2, or combinations thereof. While specific examples are provided herein, it is understood that the any antigenic protein of an infectious agent may be used in the methods and compositions described in this disclosure.

As discussed above, the antigenic protein comprises a target region and a non-target region. The target region of the antigenic protein may be a conserved domain, region, or portion of a protein expressed by an infectious agent. In the context of this disclosure, a target region may be referred to as “broadly neutralizing”, meaning that the region has high conservation through isolates of the infectious agent, and that antibodies targeting these sites are protective against many strains of an infectious agent. In some instances, the target region may be the binding site of a characterized broadly neutralizing antibody that binds specifically to a highly conserved region of a protein expressed by an infectious agent. Target regions may include regions that have been characterized as, or are assumed to be, required for function of the infectious agent. In some embodiments, the antigenic protein is a polypeptide having the sequence of one or more of SEQ ID NO: 23, 24, or 25, or antigenic variants thereof. These sequences may be modified as described in Section I. For example, the polypeptide may have a linker or tag/moiety. For example, the antigenic protein may comprise a polypeptide having the sequence of any of SEQ ID NO: 13, 15, 17, 19, or 21.

In some instances, the antigenic protein, modified or not, may be an influenza virus protein, wherein the influenza virus protein may be a hemagglutinin protein comprising a head region and a stem region, wherein the target region is the stem region or a portion thereof, and wherein the head region is the non-target region and comprises a plurality of amino acid residues having a polyethylene glycol polymer attached thereto. In some instances, the non-target region of the hemagglutinin protein also comprises a plurality of amino acid residues that do not have a modifying component covalently attached thereto (i.e. amino acid residues that are not modified in the modifying reaction). In some instances, the hemagglutinin protein is a portion of the full length protein comprising the protein ectodomain and lacking all or a substantial portion of the other amino acid residues of the protein. In some instances, the hemagglutinin protein may be a trimeric complex of HA1-HA2 heterodimers. In one example, the hemagglutinin protein is a trimeric complex of HA1-HA2 heterodimers, wherein the HA2 subunit is a C' terminally truncated variant lacking the transmembrane region and the cytoplasmic region of the protein, such trimeric complex referred to as the ectodomain of the hemagglutinin protein. In some instances, the hemagglutinin protein may be a trimeric complex of HA0 monomoers. In one example, the hemagglutinin protein is a trimeric complex of HA0 monomers, wherein the HA0 protein is a C'-terminally truncated variant lacking the transmembrane region and the cytoplasmic region of the protein, such trimeric complex referred to as the HA0 ectodomain.

In some instances, the antigenic protein, modified or not, may be an influenza virus protein, wherein the influenza virus protein may be hemagglutinin protein comprising a head region and a stem region, wherein the target region is the stem region or a portion thereof and the non-target region is the head region, and wherein the binding partner comprises a multivalent antibody that binds specifically to multiple epitopes of the head region. In another instance, the influenza virus protein is a hemagglutinin protein fragment or variant thereof comprising the stem region or a portion thereof and lacking all or a substantial portion of the head region (for example, at least 25%, 30%, 40%, 35%, 50%, 55%, 60%, 65%, 70%, 75%, 80%, 85%, 90%, 95%, 99% of the amino acid residues of the head region). In some instances, the influenza virus protein is a hemagglutinin protein fragment or variant thereof comprising the stem region or a portion thereof and lacking all of the head region. In some instances, the hemagglutinin protein is a portion of the full length protein comprising the protein ectodomain and lacking all or a substantial portion of the other amino acid residues of the protein. In some instances, the hemagglutinin protein may be a trimeric complex of HA1-HA2 heterodimers. In one example, the hemagglutinin protein is a trimeric complex of HA1-HA2 heterodimers, wherein the HA2 subunit is a C' terminally truncated variant lacking the transmembrane region and the cytoplasmic region of the protein, such trimeric complex referred to as the ectodomain of the hemagglutinin protein. In some instances, the hemagglutinin protein may be a trimeric complex of HA0 monomoers. In one example, the hemagglutinin protein is a trimeric complex of HA0 monomers, wherein the HA0 protein is a C'-terminally truncated variant lacking the transmembrane region and the cytoplasmic region of the protein, such trimeric complex referred to as the HA0 ectodomain.

Figure 3A:
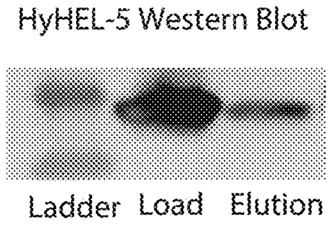
FIGS. 3A-3H show production and testing of HEWL antigenic proteins and protein complexes according to aspects of this disclosure.
Figure 3B:
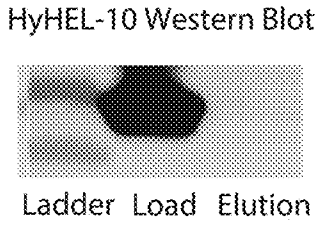
Figure 3C:
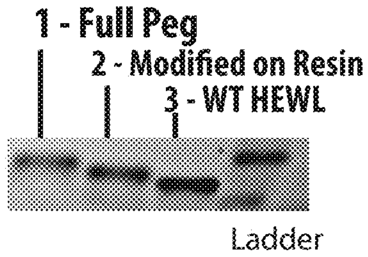
Figure 3D:
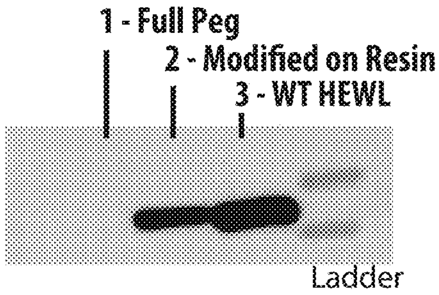
Figure 3E:
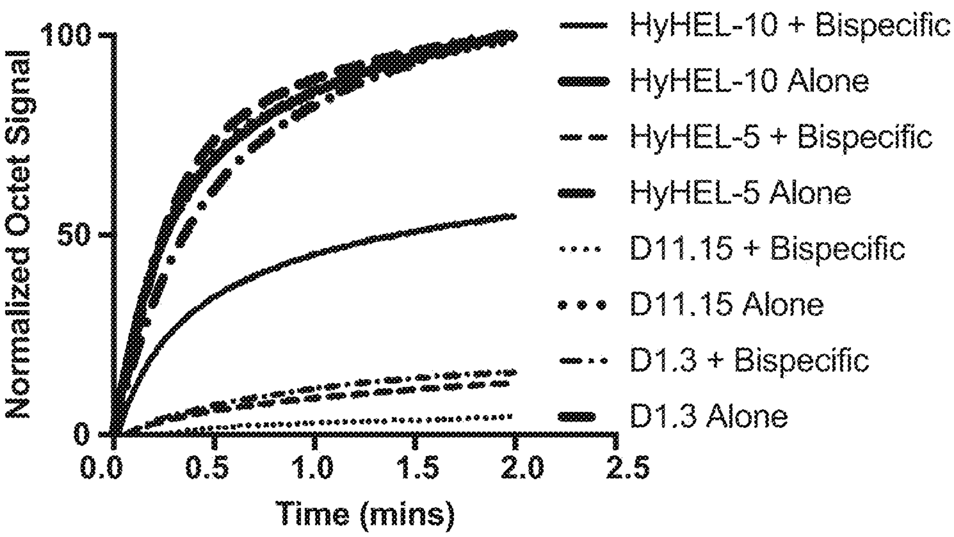
Figure 3F:
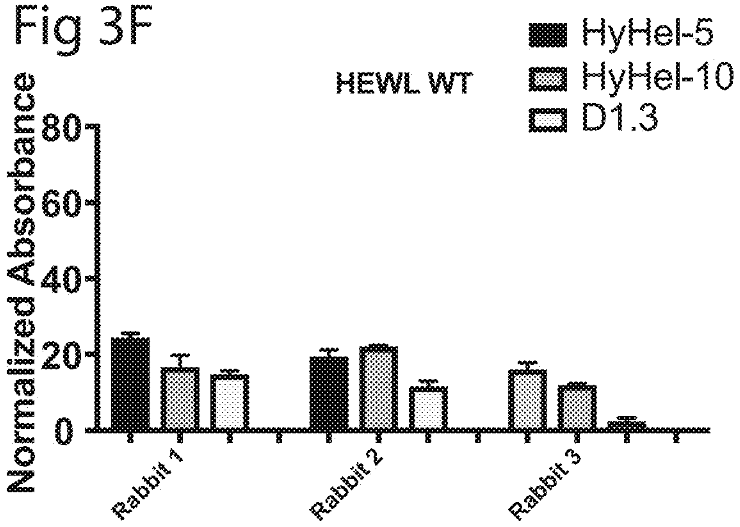
Figure 3G:
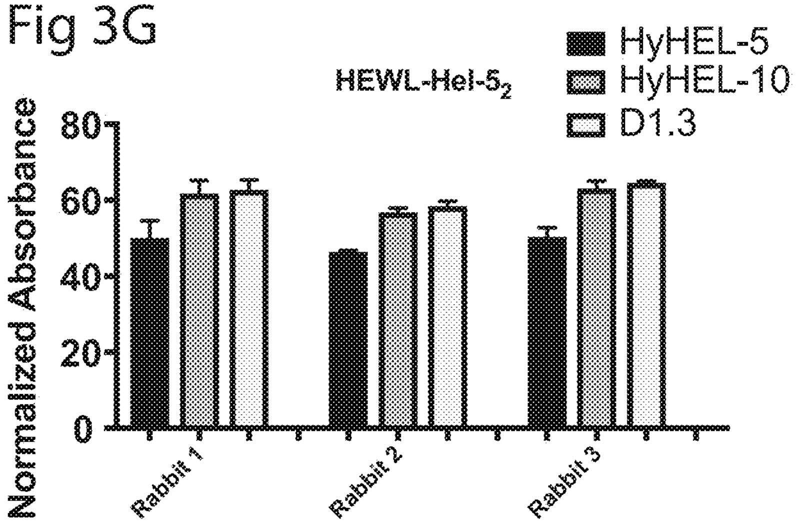
Figure 3H:
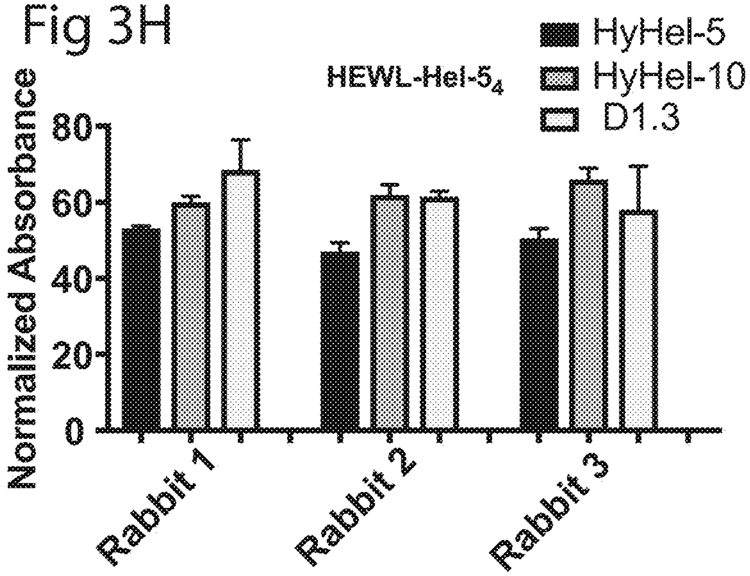
Figure 3I:
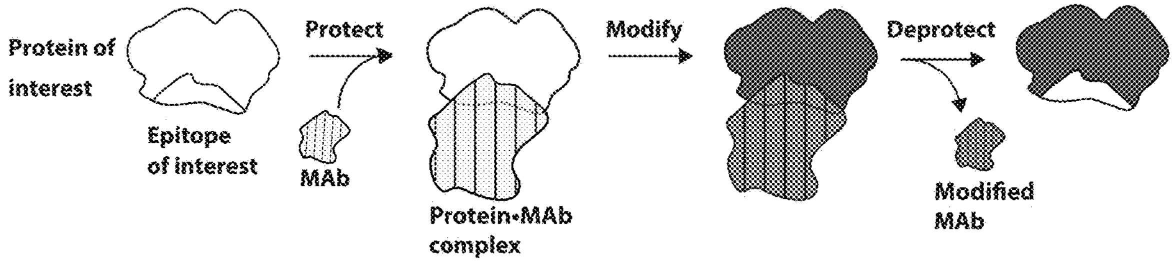
FIG. 3I is a general schematic of the PMD protocol is outlined for lysozyme using HyHEL10 according to aspects of this disclosure. First, associating an antibody (MAb) with a protein of interest (white so that the antibody binds to its specific epitope on the protein; second, modifying the amino acid residues of the protein of interest to render uncovered/unprotected epitopes non-immunogenic (shown darker); and, third, deprotection of the protein of interest by disassociating the antibody to expose the antibody's epitope, which remains unmodified.
Figure 3J:
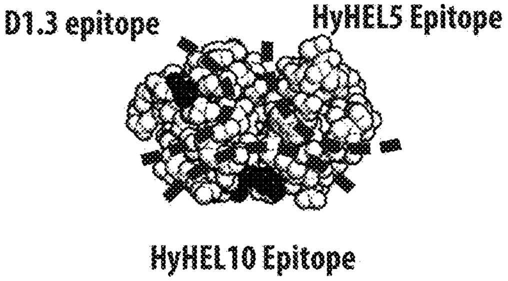
FIGS. 3J-3M show packing spheres illustrations of various views of the lysozyme crystal structure (1LYZ) and monoclonal antibody epitopes mapped thereon according to aspects of this disclosure. The amino acid residues of the epitopes are shown in grey, and the lysine residues are shown in black.
Figure 3K:
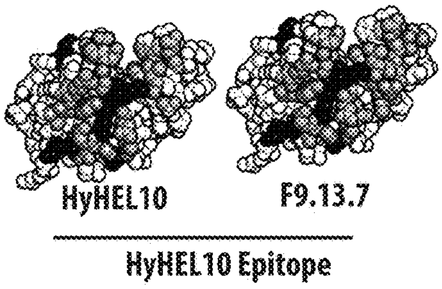
Figure 3L:
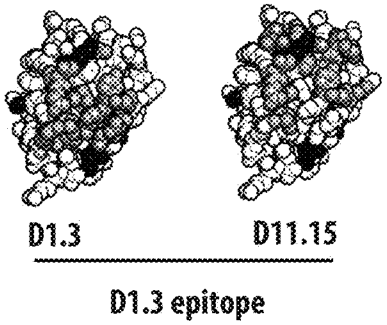
Figure 3M:
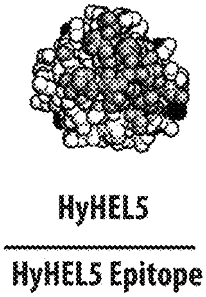
Figure 3N:
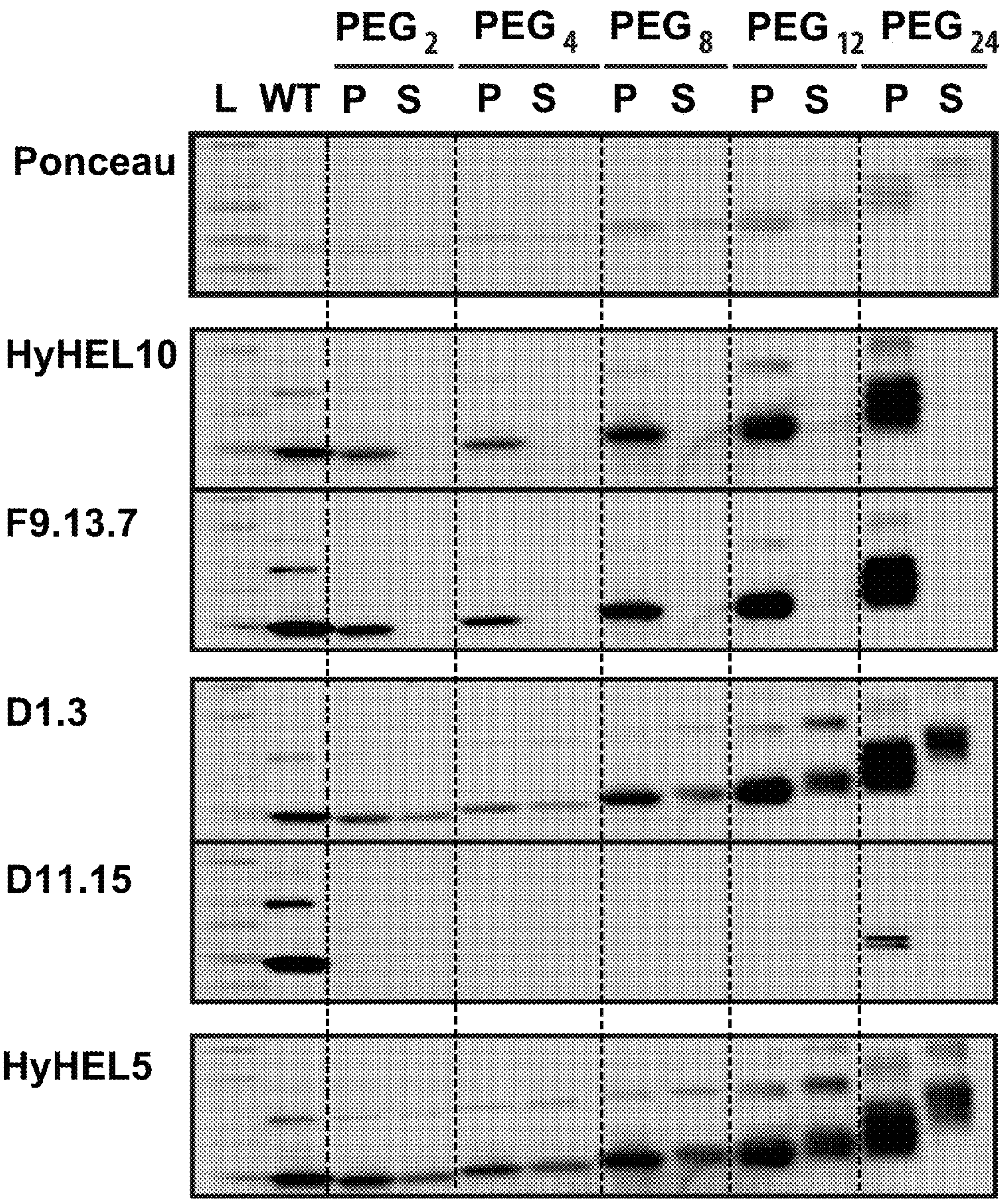
FIG. 3N shows a blot analysis of HEWL derivatives that were modified on a resin made with HyHEL10 protected using the PMD procedure illustrated in FIG. 3I (P) or modified in solution (fully unprotected) (S), according to aspects of this disclosure). The first lane is a standard ladder (dual color, Bio-Rad). Lane two is WT HEWL. The experiment included HEWL protein PEGylated with different sized PEG molecules ($PEG_x$, where x=2, 4, 8, 12, 24). The top blot is a Ponceau S stain, and the remaining are Western blots stained with the five antibodies discussed in FIGS. 3K-FIG. 3M. The Ponceau S stain shows that all 11 of these proteins are on the blot. The Western blots with antibodies HyHEL10 and F9.13.7, which both bind over the protected site of HyHEL10, show that the antibodies can bind to the WT protein and all of the proteins modified using the PMD method (P), indicating that the epitope was protected from modification on the resin. The Western blot using antibody D1.3 shows that the antibody can bind to all the modified proteins as its epitope does not contain lysines. The Western blot with antibody D11.15, the epitope of which contains a lysine residue, shows that the antibody binds only to the WT protein and to a small extent to the protein modified with $PEG_{24}$. (likely due to steric impact from modified lysine residues adjacent to the epitope). The Western blot with the HyHEL5 antibody, the epitope of which does not contain any lysine residues binds to all the proteins.
Figures 1, 3O:
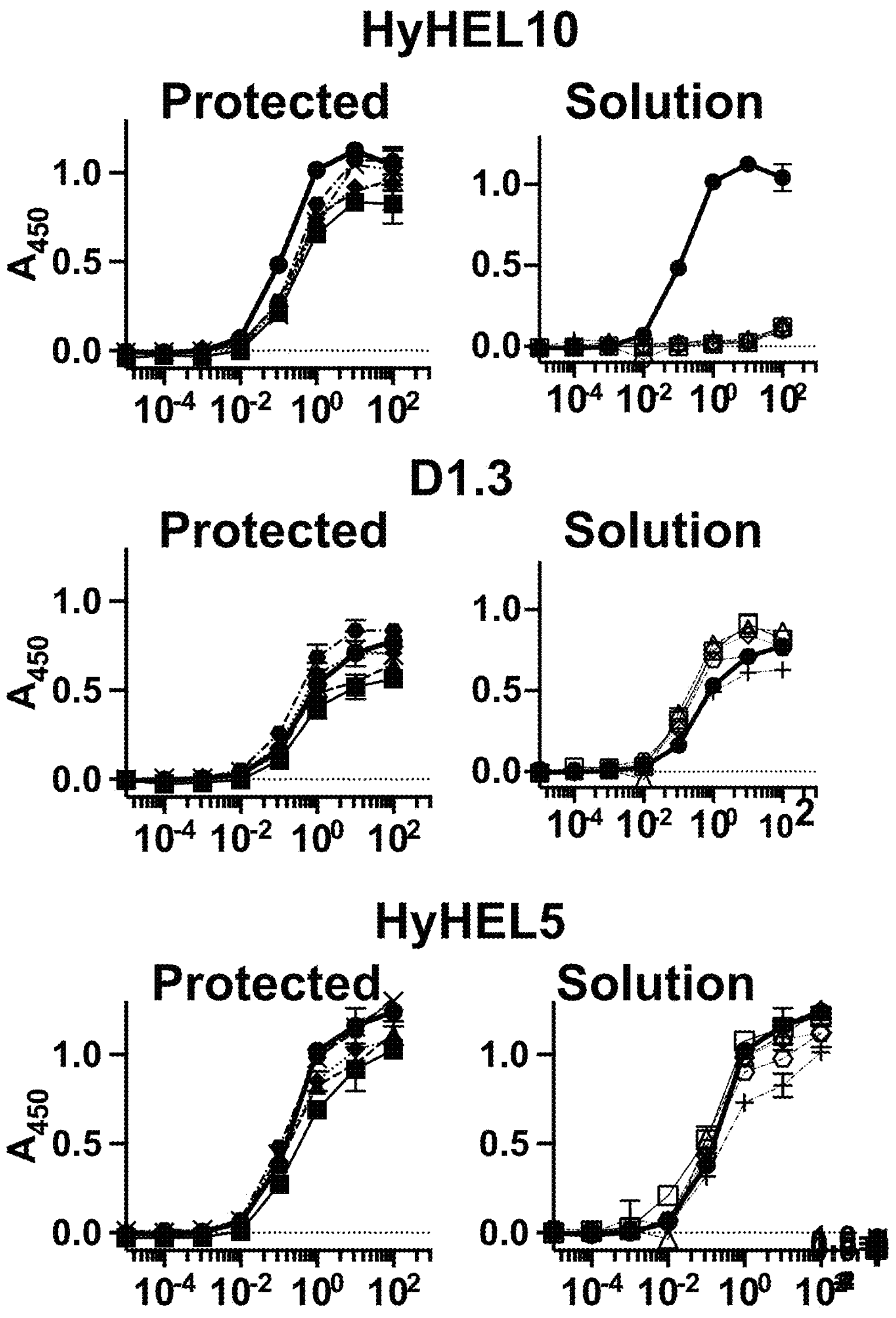
FIG. 3O-1 and FIG. 3O-2 shows graphs illustrating data from Enzyme Linked Immunosorbent assay (ELISA) experiments assessing binding of the antibodies described in FIGS. 3K-3M to (1) WT HEWL, (2) HEWL modified on an HYHEL10 resin, (3) HEWL modified in solution. The experiment included HEWL protein PEGylated with different sized PEG molecules ($PEG_x$, where x=2, 4, 8, 12, 24), according to aspects of this disclosure. ELISAs with each of the antibodies were conducted using a 10× serial dilution of monoclonal antibody starting at 100 nM on plates made by coating either of these 11 proteins. A symbol legend is shown in the figure. The top row of graphs is for ELISAs done with antibodies HyHEL10 and F9.13.7, which have overlapping epitopes. These antibodies were found to bind to the WT HEWL and the HEWL PEGylated on the HyHEL10 resin, but not to the HEWL PEGylated in solution. The second row of graphs is for ELISAs done with antibodies D1.3 and D11.15, which have partially overlapping epitopes with each other but do not overlap with the HyHEL10 epitope. The D11.15 antibody shows markedly reduced binding to all modified proteins, as its epitope contains a lysine residue and was not protected during the modification reactions. The bottom row of graphs is for ELISAs done with HyHEL5 and shows that the antibody binds to all derivatives, which was expected based on the fact that there are no lysines in its epitope.
Figures 2, 3O:
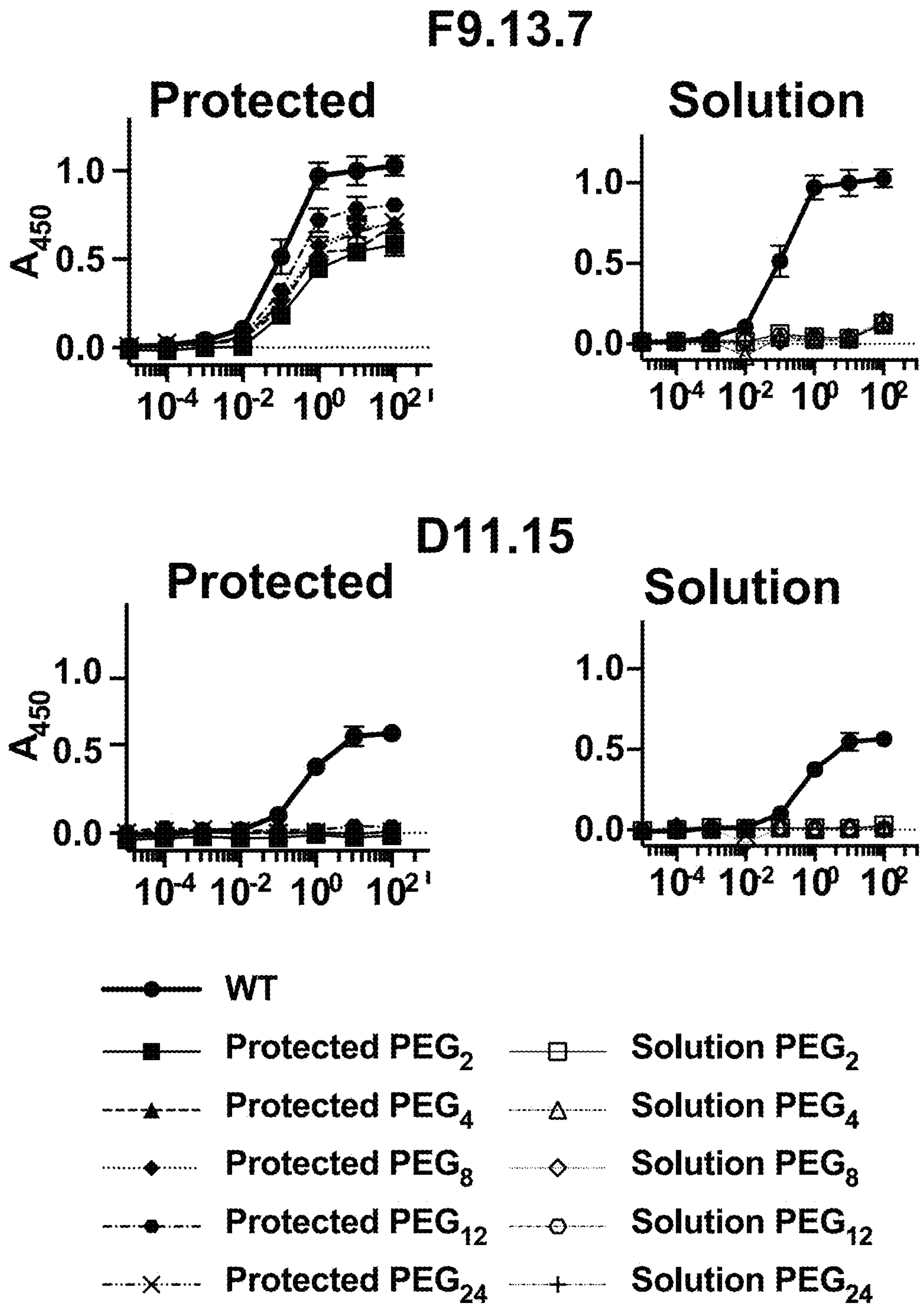

As provided herein, the antigenic proteins, modified antigenic proteins, antigenic protein complexes, and binding partners may include proteins comprising the sequences set forth in FIG. 2. The signal sequences, linkers, tags, and domains of the proteins set forth in FIG. 2 may be modified, altered, or substituted for other signal sequences, linkers, tags, and domains.

In one embodiment, provided is a binding partner comprising the polypeptide sequence as set forth in any one of SEQ ID NOs: 1, 3, 5, 7, 9, or 11. The signal sequences, linkers, tags, and domains of the proteins set forth in SEQ ID NOs: 1, 3, 5, 7, 9, and 11 may be modified, altered, or substituted for other signal sequences, linkers, tags, and domains.

In another aspect, provided are pharmaceutical compositions comprising any of the antigenic proteins, modified antigenic proteins, antigenic protein complexes, and binding partners described herein, and a pharmaceutically acceptable diluent, carrier, or excipient. The pharmaceutical compositions include a pharmaceutically effective amount of the antigenic proteins, modified antigenic proteins, antigenic protein complexes, and binding partners described herein, or derivatives thereof, in combination with a pharmaceutically acceptable carrier. In particular, the pharmaceutically effective amount may be an immunogenically effective amount. As used herein, an "immunogenically effective amount" refers to an amount that induces an immune response, e.g., antibodies (humoral) against the target region when administered to a subject. In addition, the pharmaceutical compositions may include other medicinal agents, pharmaceutical agents, carriers, or diluents. The term pharmaceutically acceptable refers to a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, for example, Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, orimmunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, New Jersey), polyethylene glycol (PEG), and PLURONICS™ (BASF; Florham Park, NJ).

Pharmaceutical compositions containing proteins and complexes described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. Also contemplated are the proteins and complexes described herein formulated to permit mist, gas-liquid suspension or liquid nebulized, dry powder aerosol administration, or metered-dose aerosol administration to supply pharmaceutically effective concentrations conferring desired immunogen levels to the subject.

The provided pharmaceutical compositions may also contain adjuvants, such as preserving, wetting, emulsifying, and dispensing agents. Prevention of the action of microorganisms can be promoted by various anti-viral agents, antibacterial, antifungal agents, and anti-parasitic agents, for example, parabens, chlorobutanol, phenol, sorbic acid, and the like. Isotonic agents, for example, sugars, sodium chloride, and the like, may also be included. Prolonged absorption of the injectable pharmaceutical form can be brought about by the use of agents delaying absorption, for example, aluminum monostearate and gelatin. Exemplary adjuvants include glyopolymers and CpG DNA polynucleotides. In another example, the pharmaceutical composition may comprise the adjuvant system AS01, which contains liposomes and two immunostimulants, 3-O-desacyl-4'-monophosphoryl lipid A and the purified saponin, QS-21. In some instances, the adjuvant may be an aluminum-containing adjuvant such as Alum adjuvant, which contains aluminum hydroxide and magnesium hydroxide.

The pharmaceutical compositions can include a pharmaceutically acceptable salt of any of the proteins described above. The term pharmaceutically acceptable salt refers to those salts of the peptides described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Barge et al., *J. Pharm. Sci.* 66:1-19 (1977), which is incorporated herein by reference in its entirety.)

Administration of the proteins, complexes, and compositions described herein, or pharmaceutically acceptable salts thereof, can be carried out using a pharmaceutically effective amount thereof for one or more periods of time to be effective to treat a disease or condition. The effective amount of the proteins, complexes, and compositions described herein, or pharmaceutically acceptable salts thereof as described herein, may be determined by one of ordinary skill in the art.

The modified antigenic protein and antigenic protein complexes (and components thereof) described herein can be provided in a pharmaceutical composition. Depending on the intended mode of administration, the pharmaceutical composition can be in the form of solid, semi-solid, liquid dosage forms, or combinations thereof, such as, for example, tablets, suppositories, pills, capsules, powders, liquids, or suspensions, preferably in unit dosage form suitable for single administration of a precise dosage. The compositions include a pharmaceutically effective amount of the proteins and complexes described herein in combination with a pharmaceutically acceptable carrier and, in addition, may include other medicinal agents, pharmaceutical agents, carriers, or diluents. The term pharmaceutically acceptable refers to a material that is not biologically or otherwise undesirable, which can be administered to an individual along with the selected compound without causing unacceptable biological effects or interacting in a deleterious manner with the other components of the pharmaceutical composition in which it is contained.

The pharmaceutical composition may comprise an amount of antigenic protein or antigenic protein complex (or component thereof) that induces an immunoprotective response without significant, adverse side effects in a typical subject. Such amount will vary depending on which specific antigens are employed. The pharmaceutical compositions may be packaged in dosage forms. Generally it is expected that each dose will comprise 1-10,000 μg of total antigenic protein. For example, the total amount of antigenic protein may be any of 1-100 μg, 1-250 μg, 1-300 μg, 1-350 μg, 1-400 μg, 1-450 μg, 1-500 μg, 1-550 μg, 1-600 μg, 1-650 μg, 1-700 μg, 1-750 μg, 1-1000 μg, 1-1500 μg, 1-1750 μg, 1-2000 μg, 1-2500 μg, 1-3000 μg, 1-3500 μg, 1-4000 μg, 1-4500 μg, 1-5000 μg, 1-5500 μg, 1-6000 μg, 1-6500 μg, 1-7000 μg, 1-7500 μg, 1-8000 μg, 1-8500 μg, 1-9000 μg, 1-9500 μg, 10-100 μg, 10-200 μg, 10-300 μg, 10-600 μg, 10-700 μg, 10-800 μg, 10-900 μg, 10-1000 μg, 50-100 μg, 50-200 μg, 50-300 μg, 50-600 μg, 50-700 μg, 50-800 μg, 50-900 μg, 50-1000 μg, 100-200 μg, 100-300 μg, 100-600 μg, 100-700 μg, 100-800 μg, 100-900 μg, 100-1000 μg, 100-1100 μg, 100-1200 μg, 100-1300 μg, 100-1400 μg, 100-1500 μg, 100-1600 μg, 100-1700 μg, 100-1800 μg, 100-1900 μg, 100-2000 μg, 200-300 μg, 200-600 μg, 200-700 μg, 200-800 μg, 200-900 μg, 200-1000 μg, 500-1000 μg, 500-1500 μg, 500-2000 μg, 500-2500 μg, 500-3000 μg, 500-3500 μg, 500-4000 μg, 500-4500 μg, 500-5000 μg, 500-5500 μg, 500-6000 μg, 500-6500 μg, 500-7000 μg, 500-7500 μg, 500-8000 μg, 500-8500 μg, 500-9000 μg, 500-10000 μg, 1000-2000 μg, 1000-3000 μg, 1000-4000 μg, 1000-5000 μg, 1000-6000 μg, 1000-7000 μg, 1000-8000 μg, 1000-9000 μg, 1000-10000 μg, 2000-3000 μg, 2000-4000 μg, 2000-5000 μg, 2000-6000 μg, 2000-8000 μg, 2000-9000 μg, 2000-10000 μg, 3000-4000 μg, 3000-5000 μg, 3000-6000 μg, 3000-7000 μg, 3000-8000 μg, 3000-9000 μg, 3000-10000 μg, 4000-5000 μg, 4000-6000, 4000-7000 μg, 4000-8000 μg, 4000-9000 μg, 4000-10000 μg, 5000-6000 μg, 5000-7000 μg, 5000-8000 μg, 5000-9000 μg, 5000-10000 μg, 6000-7000 μg, 6000-8000 μg, 6000-9000 μg, 6000-10000 μg, 7000-8000 μg, 7000-8000 μg, 7000-9000 μg, 7000-10000 μg, 8000-9000 μg, 8000-10000 μg, or 9000-10000 μg.

Also provided in this disclosure are kits comprising the compositions described herein.

In one aspect, provided are kits comprising any of the pharmaceutical compositions comprising modified antigenic proteins or antigenic protein complexes as described herein packaged in a container and instructions for the administration thereof.

In one aspect, provided are kits comprising any of the modified antigenic proteins or antigenic protein complexes as described herein packaged in a container and instructions for laboratory use thereof.

In another aspect, provided are kits comprising a first pharmaceutical composition comprising an antigenic protein comprising a target region and a non-target region as described herein and a pharmaceutically acceptable diluent, carrier, or excipient; a second pharmaceutical composition comprising at least one binding partner as described herein and a pharmaceutically acceptable diluent, carrier, or excipient; and instructions for the administration of the first pharmaceutical composition and the second pharmaceutical composition. The first and second pharmaceutical compositions are packaged separately in first and second containers, respectively. The at least one binding partner comprises at least one protein binding domain that binds specifically with one or more non-target regions of the antigenic protein. In some instances, such as upon mixture of the antigenic protein and the at least one binding partner (such as after administration to a subject), the antigenic protein and the at least one binding partner may bind to each other thereby forming an antigenic protein complex. The proteins may be bound covalently or non-covalently. When the antigenic protein and the at least one binding partner are specifically bound to each other, the target region of the antigenic protein is exposed and accessible for interaction with a B cell receptor (e.g., within a subject) and the non-target region of the antigenic protein is shielded by the at least one binding partner from interactions with a B cell receptor (e.g., within a subject).

In another aspect, provided are kits comprising a first composition comprising an antigenic protein comprising a target region and a non-target region as described herein; a second composition comprising at least one binding partner as described herein; and instructions for the laboratory use of the first composition and the second composition. The first and second compositions are packaged separately in first and second containers, respectively. The at least one binding partner comprises at least one protein binding domain that binds specifically with one or more non-target regions of the antigenic protein. In some instances, such as upon mixture of the antigenic protein and the at least one binding partner (such as after addition into a mixture in vitro), the antigenic protein and the at least one binding partner may bind to each other thereby forming an antigenic protein complex. The proteins may be bound non-covalently or covalently. When the antigenic protein and the at least one binding partner are specifically bound to each other, the target region of the antigenic protein is exposed and accessible for interaction with a B cell receptor (e.g., in vitro) and the non-target region of the antigenic protein is shielded by the at least one binding partner from interactions with a B cell (e.g., in vitro).

In some instances, the provided kits may include an adjuvant as discussed above. Kits may also include a means for administering the proteins or compositions described herein, and/or a carrier. Kits can include single doses or multiple doses (such as, for example, in a blister pack or a multi-dose volume vial). Kits can include means for administration (such as a delivery device like a syringe, a nebulizer, or an inhaler), or the like.

The instructions provided in the kits may include instructions regarding combination of components of the kits, dosage, safety, indication, and storage, amongst other information.

In another aspect, provided herein are polynucleotides that encode the antigenic proteins or binding partners as discussed throughout this disclosure. The polynucleotides are recombinant or synthetic and may be DNA or RNA. In many instances, the polynucleotides comprise non-heterologous sequences such as, for example, mutations or other modifications to native coding sequences. In some instances, the polynucleotide sequences are optimized for expression in humans or animals. In some instances, the polynucleotides comprise a non-heterologous promoter sequence and may include other regulatory elements. Generally, the promoter sequence can drive expression of the polynucleotide sequence when the polynucleotide sequence is introduced into a subject. In some instances, the polynucleotides may contain one or more non-native nucleotide or non-native codon. In some instances, the polynucleotides may contain one or more chemically modified nucleotides. Also provided are plasmids comprising any of these polynucleotides alone or in combination. DNA and RNA vaccine approaches useful in the context of this disclosure are described in McClements, 1996, Proc. Natl. Acad. Sci. USA, 93:11414-11420 and Lutz, et al., 2017, NJP Vaccines 2:29; doi: 10.1038/s41541-017-0032-6.

In some instances, the polynucleotides encoding the antigenic proteins or binding partners as described herein may be encapsulated in a liposome, a lipid-based nanoparticle, or a polymer-based nanoparticle. In some instances, the polynucleotides may be packaged into a viral vector such as a virus particle or virus-like particle. The viral vector may be a retrovirus, lentivirus, adenovirus, adeno-associated virus, a modified version of any thereof, and hybrids thereof. In some instances, the polynucleotides may be packaged into a synthetic delivery vehicle such as, but not limited to, an amphiphile-based nanoparticles. Agents that aid in delivery of nucleic acids for vaccines range from physical devices to chemical compositions. An exemplary physical device is a nanopatch comprising a microprojection array that has the DNA polynucleotide coated on its surface. The nanopatch is then applied directly to the skin of a subject to be vaccinated, and the DNA is transmitted into the cells of the subject where it leads to protein expression. Another example of physical facilitation of immunization by nucleic acid uptake is electroporation, in which an electrical pulse(s) is applied to the skin of a subject to which the DNA polynucleotide has been applied thereby increasing uptake, expression, and immunogenicity. Chemical compositions are more common in the case of RNA-based vaccines, but can also be used in DNA vaccines. Chemical compositions that facilitate delivery can include cationic polymers that complex with the polynucleotide and aid in cellular uptake and lipid nanoparticles that can encapsulate the nucleic acid. An example of such chemical compositions is lipofectamine, which is commercially available and can be used to complex with polynucleotides for delivery into cells. Another example of a chemical compound that facilitates nucleic acid uptake is polyethylenimine (PEI).

Of particular interest are nucleic acid sequences that have been designed for expression, purification, or both. A "recombinant polynucleotide" or "recombinant nucleic acid" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or a variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides include chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide or nucleic acid" comprises at least one of a combination of two or more chemically linked nucleotides which are not found directly joined in nature.

Also provided herein are kits comprising the contemplated polynucleotide sequences as described above.

III. Method of Use

Provided herein are methods of using the antigenic proteins, modified antigenic proteins, antigenic protein complexes, and binding partners, and compositions comprising these any of these proteins.

In one aspect, provided are methods of eliciting in a subject an immune response against the target region of the antigenic protein, the method comprising administering a pharmaceutically effective amount of a pharmaceutical composition comprising a modified antigenic protein, an antigenic protein complex, a modified antigenic protein complex, components of any thereof, or polynucleotides encoding any thereof as described above to a subject in which an immune response against the target region of the antigenic protein is desired.

In another aspect, provided are methods of eliciting in a subject an immune response against the target region of the antigenic protein, the method comprising administering a pharmaceutically effective amount of a first pharmaceutical composition comprising an antigenic protein comprising a target region and a non-target region, or a polynucleotide encoding said antigenic protein, and a pharmaceutically acceptable diluent, carrier, or excipient; and a pharmaceutically effective amount of a second pharmaceutical composition comprising at least one binding partner, or at least one polynucleotide sequence encoding said at least one binding partner, and a pharmaceutically acceptable diluent, carrier, or excipient, wherein the at least one binding partner comprises at least one protein binding domain that binds specifically with the non-target region of the antigenic protein. The antigenic protein and the at least one binding partner may bind to each other after administration to the subject such that the target region of the antigenic protein is exposed and accessible for interaction with a B cell receptor and the non-target region of the antigenic protein is shielded by the at least one binding partner from interactions with a B cell receptor. The proteins may be bound non-covalently or non-covalently.

In some instances, the first pharmaceutical composition and the second pharmaceutical composition are administered simultaneously. In other instances, the first pharmaceutical composition and the second pharmaceutical composition are administered sequentially on the same day or different days. Combinations are administered either concomitantly (such as an admixture), separately but simultaneously (such as via separate injections the same subject), or sequentially (such as one of the pharmaceutical composition is given first followed by the second pharmaceutical composition). Thus, the term combination is used to refer to concomitant, simultaneous, or sequential administration of two or more pharmaceutical compositions.

As used herein, subject means both mammals and non-mammals. Mammals include, for example, humans; non-human primates, such as apes and monkeys; cattle; horses; sheep; rats; dogs; cats; mice; pigs; and goats. Non-mammals include, for example, fish, amphibians, reptiles, birds, and insects. In some embodiments, the subject is a human. In some embodiments, the subject is a non-human animal, such as rodents and non-human primates, which may or may not be laboratory test animals. In some embodiments, the subject is a transgenic animal. For example, the transgenic animal may comprise genomic alterations. For example, the transgenic animal can be a mouse comprising human immunoglobulin genes. or segments thereof, instead of murine immunoglobulin genes, or segments thereof. In some embodiments, the subject is a human. In some embodiments, the subject is at risk of being exposed to one or more infectious agents.

The provided modified antigenic proteins, protein complexes, components thereof, and polynucleotides encoding any thereof, and pharmaceutical compositions of the same may be administered to a subject to induce the production of antibodies against the target region of the antigenic protein. Administration of the proteins, complexes, and compositions may be carried out by any suitable means, including parenteral injection, using methods known in the art. For example the proteins, complexes, and compositions of the disclosure may be administered intravenously, intramuscular, intraperitoneally, nasally, or orally. In some instances, proteins, complexes, and compositions may be administered intramuscularly. The compositions may be administered in an immunogenically effective amount to a subject who is susceptible to or otherwise at risk of infection by or exposure to an infectious agent that contains the target region of the antigenic protein. In particular, the pharmaceutically effective amount may be an immunogenically effective amount. As used herein, an "immunogenically effective amount" refers to an amount that induces an immune response, e.g., antibodies (humoral) against the target region when administered to a subject. The immunogen(s) in the compositions may also induce cellular (non-humoral) immune responses. Such immunogenically effective amounts can be readily determined using methods known in the art and depend on the subject's state of health and weight, the mode of administration, the nature of the formulation, etc.

Single or multiple administration of the modified antigenic proteins, protein complexes, components thereof, and polynucleotides encoding any thereof, and compositions of any thereof as provided in this disclosure may be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

"Eliciting an immune response" refers to an adaptive immune system response in a subject to which an immunogen has been administered in which antibodies that bind specifically to the immunogen are produced by the cells of the immune system. In some instances, the immune response elicited by the provided methods comprises preferential generation of antibodies specific for the target region of the antigenic protein relative to the non-target region of the antigenic protein. In some instances, the immune response elicited by the provided methods comprises preferential generation of B cells that express antibodies specific for the target region of the antigenic protein relative to memory B cells that express antibodies specific for the non-target region of the antigenic protein. The immune response elicited may provide protective immunity against infectious agents comprising proteins containing the target region. For example, where the antigenic protein is an influenza protein, the immune response elicited may provide protective immunity against at least one of influenza A viruses, influenza B viruses, or influenza C viruses. In another example, where the antigenic protein is an HIV protein, the immune response elicited may provide protective immunity against HIV-1 viruses, HIV-2 viruses, or both HIV-1 viruses and HIV-2 viruses.

In some instances, the proteins, complexes, and compositions, or polynucleotides encoding any thereof, as provided in this disclosure may be administered prophylactically. In certain instances, the proteins, complexes, and compositions as described in this disclosure may be administered prophylactically. When administered prophylactically, the proteins, complexes, and compositions are administered prior to the onset of symptoms of an infection. Prophylactically, the methods prevent the onset of an infection, disease, disorder, or condition caused by an infectious agent that expresses a protein containing the target region of the antigenic protein, or ameliorate or reduce one or more symptoms of the infectious, disease, disorder, or condition caused by an infectious agent following infection. When administered therapeutically, the proteins, complexes, and compositions may treat an infection, disease, disorder, or condition caused by an infectious agent. In treating the subject, the methods ameliorate or reduce one or more symptoms of a disease, disorder, or condition caused by an infectious agent. Therapeutic administration may occur at about the same time or after a subject begins to show one or more symptoms of the disease, disorder, or condition. Therapeutic administration inhibits or delays onset or severity of one or more symptoms of the infection, disease, disorder, or condition. Treatment can refer to a 10%, 20%, 30%, 40%, 50%, 60%, 70%, 80%, 90%, or 100% reduction in the severity of one or more symptoms of the infection, disease, disorder, or condition.

In some instances, the modified antigenic protein, antigenic protein complex, modified antigenic protein complex, components of any thereof, and polynucleotides encoding any thereof, or compositions of any thereof as provided in this disclosure may be administered in one or more primary immunizations over a period of time. The method may comprise 1, 2, 3, 4, 5, or 6 primary immunizations over a period of time. The period of time for primary immunizations may be a period of weeks over the course of a few months, a period of months over the course of a year, or a period of years. In some instances, each primary immunization may be the same protein, complex, polynucleotide, or composition. In some instances, when the method comprises a plurality of primary immunizations, one or more of the primary immunizations may be the same protein, complex, or composition with at least one primary immunization comprising a different protein, complex, polynucleotide, or composition. In other instances, when the method comprises a plurality of primary immunizations, each primary immunization may be a different protein, complex, polynucleotide, or composition. In some instances, when the method comprises a plurality of primary immunizations, one or more of the primary immunizations may be a unmodified antigenic protein or a polynucleotide encoding an unmodified antigenic protein. For example, a first primary immunization may comprise an unmodified antigenic protein, or polynucleotide encoding thereof, and one or more subsequent primary immunizations may comprise a modified protein or modified complex (or component thereof), or composition thereof as provided in this disclosure.

Booster administrations may be required in order to achieve protection, maintain protection, alleviating, reducing or delaying symptoms or improving clinical markers of infection. The booster administrations may be administered to the subject at a period of time after the primary immunization. The period of time for the booster may be a period of years such as 2 years, 4 years, 5, years, 10 years, 12 years, 15 years, or 20 years. In some instances, the booster may be the same protein, complex, or composition administered to the subject for primary immunization, generally referred to as a homologous boost. In some instances, the booster is a different protein, complex, or composition that administered to the subject for primary immunization. In some instances, the booster may be a different type of pharmaceutical composition than the pharmaceutical composition administered for the primary immunization. For example, if the pharmaceutical composition administered for the primary immunization is a modified antigenic protein, the booster pharmaceutical composition may be an antigenic protein complex or a nucleic acid vaccine comprising a polynucleotide described herein. In another example, if the pharmaceutical composition administered for the primary immunization is an antigenic protein complex, the booster pharmaceutical composition may be a modified antigenic protein or a nucleic acid vaccine comprising a polynucleotide described herein. In some instances, the booster pharmaceutical composition may have a different mode of administration than the primary immunization pharmaceutical composition.

Those of skill in the art will understand that the specific dose level and frequency of dosage for any particular subject may be varied and will depend upon a variety of factors including, for example, the antigenicity of the specific modified antigenic protein or antigenic protein complex (or components thereof) employed; the physical and chemical characteristics of the composition/formulation employed; the physical stability of the modified antigenic protein or antigenic protein complex (or components thereof) or polynucleotides encoding components thereof; the mode and time of administration; rate of excretion; and, in some instances, the species, age, body weight, general health, sex and diet of the subject. In some instances, the dose level and dosage frequency may also depend on the nature of the disease or condition experienced by the subject and/or severity of the particular disease or condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. An optimal amount for a particular pharmaceutical composition can be ascertained by standard studies involving observation of antibody titers and other responses in a reference population of subjects. Further, depending on the route of administration, one of skill in the art would know how to determine doses that result in a plasma concentration for a desired level of response in the cells, tissues and/or organs of a subject. In particular, the amount of antigen administered to the subject is selected as an amount that induces an immunoprotective response without significant, adverse side effects in a typical subject. Such amount will vary depending on which specific antigens are employed and the form in which they are administered to the subject.

For example, for formulations containing antigenic protein (modified or not), a dose may comprise 1-10,000 μg of total antigenic protein. For example, the total amount of antigenic protein may be any of 1-100 μg, 1-250 μg, 1-300 μg, 1-350 μg, 1-400 μg, 1-450 μg, 1-500 μg, 1-550 μg, 1-600 μg, 1-650 μg, 1-700 μg, 1-750 μg, 1-1000 μg, 1-1500 μg, 1-1750 μg, 1-2000 μg, 1-2500 μg, 1-3000 μg, 1-3500 μg, 1-4000 μg, 1-4500 μg, 1-5000 μg, 1-5500 μg, 1-6000 μg, 1-6500 μg, 1-7000 μg, 1-7500 μg, 1-8000 μg, 1-8500 μg, 1-9000 μg, 1-9500 μg, 10-100 μg, 10-200 μg, 10-300 μg, 10-600 μg, 10-700 μg, 10-800 μg, 10-900 μg, 10-1000 μg, 50-100 μg, 50-200 μg, 50-300 μg, 50-600 μg, 50-700 μg, 50-800 μg, 50-900 μg, 50-1000 μg, 100-200 μg, 100-300 μg, 100-600 μg, 100-700 μg, 100-800 μg, 100-900 μg, 100-1000 μg, 100-1100 μg, 100-1200 μg, 100-1300 μg, 100-1400 μg, 100-1500 μg, 100-1600 μg, 100-1700 μg, 100-1800 μg, 100-1900 μg, 100-2000 μg, 200-300 μg, 200-600 μg, 200-700 μg, 200-800 μg, 200-900 μg, 200-1000 μg, 500-1000 μg, 500-1500 μg, 500-2000 μg, 500-2500 μg, 500-3000 μg, 500-3500 μg, 500-4000 μg, 500-4500 μg, 500-5000 μg, 500-5500 μg, 500-6000 μg, 500-6500 μg, 500-7000 μg, 500-7500 μg, 500-8000 μg, 500-8500 μg, 500-9000 μg, 500-10000 μg, 1000-2000 μg, 1000-3000 μg, 1000-4000 μg, 1000-5000 μg, 1000-6000 μg, 1000-7000 μg, 1000-8000 μg, 1000-9000 μg, 1000-10000 μg, 2000-3000 μg, 2000-4000 μg, 2000-5000 μg, 2000-6000 μg, 2000-8000 μg, 2000-9000 μg, 2000-10000 μg, 3000-4000 μg, 3000-5000 μg, 3000-6000 μg, 3000-7000 μg, 3000-8000 μg, 3000-9000 μg, 3000-10000 μg, 4000-5000 μg, 4000-6000, 4000-7000 μg, 4000-8000 μg, 4000-9000 μg, 4000-10000 μg, 5000-6000 μg, 5000-7000 μg, 5000-8000 μg, 5000-9000 μg, 5000-10000 μg, 6000-7000 μg, 6000-8000 μg, 6000-9000 μg, 6000-10000 μg, 7000-8000 μg, 7000-8000 μg, 7000-9000 μg, 7000-10000 μg, 8000-9000 μg, 8000-10000 μg, or 9000-10000 μg.

The immune response elicited by the above-described methods may be characterized in different ways.

For example, the production of antibodies reflecting a neutralizing response/broadly neutralizing response may be determined. For example, the subject may be demonstrated to be protected from lethal challenge with the infectious agent. In some instances, passive transfer of serum from the immunized subject to a non-immunized subject may result in the non-immunized subject also being protected from lethal challenge with the infectious agent. In some instances, the serum can be tested in vitro to show neutralization in assays that are understood to be surrogates for in vivo protection. Also, for example, determining if the target region in the immunogen confers broad reactivity may be assessed by conducting in vitro tests with a panel of infectious agents.

In another example, the presence of target region-specific antibodies in the serum of a subject may be determined. Enzyme-linked immunosorbent assays (ELISA) assessing binding against the whole protein can be done. In some instances, an ELISA may be performed assess the target region (epitope of interest) displayed on another protein. For these ELISA assay readout, high levels of such antibodies, may imply a high affinity antibody response. In other instances, ELISA assays assessing the full length antigenic protein (or domain thereof) where the target region (epitope of interest) has been removed, the expected readout may be a lower readout than in the prior two assay formats. In some instances, ELISA assays assessing peptides contained within the target region may be performed. The expected readout would likely imply some antibody response. In some instances, ELISAs assessing peptides contained within the non-target region may be performed. This expected readout implies a lower antibody response than the previous method. Competition ELISAs using antibodies or binding partners that bind within the epitope may be performed. Binding assays with the serum can be used to determine competition with known monoclonal antibodies that binding to the target region or the non-target region. In some instances, serum may compete more strongly at the target region. In some instances, these experiments can also be conducted on other devices that can produce similar read outs (biolayer interferometry, surface plasmon resonance, etc.).

In some instances, antibodies can be isolated using WT antigenic protein or modified antigen, or portions thereof comprising the target region, as bait and used for analysis of prevalence and affinity of isolated fractions of antibodies (binding at different epitopes on the protein). These can also be analyzed using mass-spec to compare the serum antibody response generally. These assays may be conducted with the WT protein immunization control and compared to this immune response.

In some instances, B cells in an immunized animal may be assessed for BCRs that bind specifically to the target region. B cells can be sorted from subjects after immunization based on their binding to either WT antigen or modified antigen, and their binding screened towards the site of interest. The frequency and prevalence of B cells that target the region of interest to other regions may be assessed in all immunizations. The affinity of B cells that target the region of interest can be compared to other regions in all immunizations. The prevalence of sorted B cells can be compared to serum antibodies.

In some instances, upon re-exposure, subjects may have altered immune responses. Animals can be given another dose of immunogen (with or without modifications to the epitope/site of interest) and the serum response to the immunogen or the physical immunogen can be followed within the animal. As a readout, change in the immune response after this dose using the above mentioned methods may be assessed. Also, the presence or loss of an antigenic protein over time may be assessed. Loss of the antigen may be due to antigen opsonization into phagocytes, complement dependent lysis if antigen is bound to membrane (virion, whole virus, bacteria, liposome, etc.), etc. Changes in antigen localization over time can also be assessed to determine if the antigenic protein is being translocated to the lymphoid tissue, or elsewhere.

IV. Methods of Identifying New Broadly Neutralizing Antibodies

In another aspect, provided are method of identifying new antibodies that are broadly neutralizing against different species or strains of an infectious agent. The immunogen (e.g., modified antigenic proteins, antigenic protein complexes, and modified antigenic protein complexes) may be used to screen biological samples for antibodies that bind specifically to the target region of an antigenic protein of an infectious agent and, thus, may bind specifically to the target region of antigenic proteins expressed by species or strains related to the infectious agent.

In another aspect, provided are methods of identifying genetic sequences encoding an antibody specific for a target region of an antigenic protein. In some instances, such sequences can be identified using a biological sample from a subject containing B cells. In other instances, such sequences may be identified from other sources such as, but not limited to, yeast-display libraries of antibodies, phage-display libraries of antibodies, and ribosome-display libraries of antibodies. In the provided method, B cells, yeast, phage, or otherwise expressed antibodies are contacted with any of the modified antigenic proteins or the antigenic protein complexes described in this disclosure. Subsequently, antibodies that bind specifically to the target region of the antigenic protein are identified and then separated or selected from antibodies that do not bind specifically to the target region of the antigenic protein. Upon identification of such antibodies, the coding sequences of the antibody may be identified through routine cloning and sequence analysis.

In some instances, provided are methods of identifying genetic sequences encoding an antibody specific for a target region of an antigenic protein from B cells. The methods include obtaining a biological sample from a subject containing B cells. In some instances, the subject has been exposed to the antigenic protein comprising the target region of an antigenic protein. In some instances, the subject has not been exposed to the antigenic protein. The B cells are contacted with any of the modified antigenic proteins or the antigenic protein complexes described in this disclosure. In some instances, the B cells are in the biological sample when they are contacted with the modified antigenic proteins or the antigenic protein complexes. In other instances, the B cells may be isolated from the biological sample before being contacted with the modified antigenic proteins or the antigenic protein complexes. Subsequently, B cells expressing an antibody that binds specifically to the target region of the antigenic protein are separated from B cells that do not express an antibody that binds specifically to the target region of the antigenic protein. The steps of contacting and separating (sorting) the B cells may be performed by flow cytometry. Upon identification of B cells that express an antibody that binds specifically to the target region of the antigenic protein, the coding sequences of the antibody may be identified through routine cloning and sequence analysis.

In some instances, a putative immunogen may be screened against a plurality of peripheral blood mononuclear cells (PBMCs) isolated from a subject. Such screening may be performed to isolate B cells that express BCRs that bind specifically to the target region of the antigenic protein. In some instances, the subject may have been vaccinated against the infectious agent. In other instances, the subject may have been exposed to the infectious agent. In other instances, the subject may have been neither vaccinated against or exposed to the infectious agent.

In some instances, monoclonal antibodies that bind specifically to the target region of the antigenic protein may be produced using such isolated B cells. The gene encoding a BCR that binds specifically to the target region of the antigenic protein, or a nucleotide sequence encoding all or a portion thereof, from such an isolated B cell may be cloned, and a soluble antibody may be purified. Methods of cloning and protein purification are well-known in the art. In some instances, such purified antibodies may be used as prophylactic agents, therapeutic agents, or both. In some instances, such an antibody or fragment or variant thereof (defined above) may be administered as a purified protein in a pharmaceutical composition in a pharmaceutically effective amount to a subject who has been exposed to the infectious agent or a related species or strain, or who is at risk of exposure. In other instances, DNA or mRNA vectors encoding such an antibody or fragment or variant thereof may be administered in a pharmaceutically effective amount to a subject who has been exposed to the infectious agent or a related species or strain, or who is at risk of exposure.

In some instances, the antibodies identified using these methods may be assayed for broadly neutralizing activity. The antibodies can be passively transferred to a non-immunized subject and the subject assessed to determine if they are protected from lethal challenge with the infectious agent. In some instances, the antibodies can be tested in vitro to show neutralization in assays that are understood to be surrogates for in vivo protection. Also, for example, determining if the target region in the immunogen confers broad reactivity may be assessed by conducting in vitro tests with a panel of infectious agents.

ELISAs assessing binding of the antibodies against the whole protein can be done. In some instances, an ELISA may be performed assess the target region (epitope of interest) displayed on another protein. For these ELISA assay readout, high levels of such antibodies, may imply a high affinity antibody response. In other instances, ELISA assays assessing the full length antigenic protein (or domain thereof) where the target region (epitope of interest) has been removed, the expected readout may be a lower readout than in the prior two assay formats. In some instances, ELISA assays assessing peptides contained within the target region may be performed. The expected readout would likely imply some antibody response. In some instances, ELISA assays assessing peptides contained within the non-target region may be performed. This expected readout implies a lower antibody response than the previous method. Competition ELISAs using antibodies or binding partners that bind within the target region may be performed. Such antibodies can also be used in ELISAs to assess competition binding with known monoclonal antibodies that binding to the target region or non-target region. Desirable antibodies competes more strongly at the target region. In some instances, these experiments can also be conducted on other devices that can produce similar read outs (biolayer interferometry, surface plasmon resonance, etc.).

In this disclosure, the terms "about" and "around," as used to modify a numerical value, indicate a close range surrounding that explicit value. If "X" were the value, "about X" or "around X" would indicate a value from 0.8X to 1.2X, preferably a value from 0.9X to 1.1X, and, more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X." As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

In the foregoing description, numerous specific details are set forth to provide a more thorough understanding of the present invention. However, it will be apparent to one of skill in the art that the invention described in this disclosure may be practiced without one or more of these specific details. In other instances, well-known features and procedures well known to those skilled in the art have not been described in order to avoid obscuring the invention. Embodiments of the disclosure have been described for illustrative and not restrictive purposes. Although the present invention is described primarily with reference to specific embodiments, it is also envisioned that other embodiments will become apparent to those skilled in the art upon reading the present disclosure, and it is intended that such embodiments be contained within the present inventive methods. Accordingly, the present disclosure is not limited to the embodiments described above or depicted in the drawings, and various embodiments and modifications can be made without departing from the scope of the claims below.

EXAMPLES

Example 1. ERAS Using Hen Egg White Lysozyme (HEWL) Antigen

Hen Egg White Lysozyme (HEWL) is useful immunogen for assessing the methods of this disclosure because it is a very stable, well-studied immunogen that is readily available. Lysozyme immunology focuses around three main regions that are targeted by multiple, previously crystalized, monoclonal antibodies. The main antibodies that target these three regions are HyHEL-10, which binds over two surface exposed lysines; D1.3, which binds adjacent to two surface exposed lysine; and HyHEL-5, which binds within a few angstroms of the N-terminus and the N-terminal residue, which happens to be a lysine. There are other antibodies that bind at, or near, these sites. For example, D11.15 shares the majority of its epitope with D1.3, and F9.13.7 shares a majority of its epitope with HyHEL-10. For HyHEL-10, HyHEL-5, D1.3, the epitope of these three antibodies are all distinct, meaning they could all bind to HEWL simultaneously.

A. Materials and Methods

HEWL Biotinylation: HEWL was purchased from Alfa Aesar, and for all experiments not requiring biontinylation was used unmodified. For all reaction in which the protein needed to first be biotinylated we reacted the protein at 1 mg/mL in 1×PBS with a 1:1 molar equivalent of NHS-$PEG_{12}$-Biotin (EZ-LINK, ThermoFisher scientific). This reaction was let to run for 2 hours at room temperature and was then purified into 1×PBS from hydrolyzed and unreacted NHS-PEG-$_{12}$-Biotin using a PD-10 desalting column as per the manufacturers recommendation, pre-equilibrated in 1×PBS. The resulting protein concentration was judged using a NANODROP™ 2000 (ThermoFisher Scientific).

HEWL Monoclonal Antibody Cloning, Expression, and Purification: Antibody protein sequences for HyHEL-10, HyHEL-5, D1.3, D11.15, and F9.13.7 were obtained from the Protein Data Bank database (PDB ID numbers: 3HFM, 1YQV, 1FDL, 1JHL, and 1FBI, respectively). These protein sequences were codon optimized (using the IDT Codon Opt tool) for human protein expression. The heavy chain and light chain were then cloned into pFUSE-CHIg-HG1 vector and pFUSE2-CLIg-hK vector (InvivoGen), respectively, after the IL-2 signal sequence. These vectors, one containing the heavy chain and one containing the light chain of each antibody, were cotransfected. This was conducted by incubating 20 µg of each plasmid (40 µg total) in 1.5 mL opti-MEM (ThermoFisher) and mixing this with 1.5 mL of opti-MEM containing 108 µl of expifectamine. This was incubated for 20-30 mins and added to 25.5 mL of Expi-cells at 3 million cells/mL. These cells were then boosted 18-24 hours later with 150 µl of boost 1 and 1.5 mL boost 2. Cells were harvested by centrifugation at day 4 and the supernatant was diluted 1:1 into 1×PBS. This diluted supernatant was then flowed over a column containing protein A resin (ThermoFisher) at least two times, washed with 10 column volumes of PBS and eluted with 100 mM glycine pH 2.8 directly into 1/10th volume of 1M tris pH 8.0.

HEWL Bispecific Antibody Cloning, Expression, and Purification: A bispecific antibody encoding the scFv regions of both HyHEL-5 and D11.15 was produced by conducting a stitching PCR reaction from their above stated vectors. Primers were designed to prepare a construct in which the HyHEL-5 variable region HC sequence was linked through a Yol-tag to the N-terminus of the HyHEL-5 variable region LC sequence, which itself was linked though the human muscle aldolase linker to the N-terminus of the D11.15 variable region HC, which was linked through a Yol-tag to the D11.15 variable region LC, which was followed by a short linker and a C-terminal his tag. This entire construct was stitched using PCR (HIFI PCR premix, Clontech) and then cloned using the In-Fusion® HD Cloning Kit (Clontech) into the pET-22b vector after the PelB signal peptide to enable periplasmic expression. The expressed and purified sequences of the bispecific antibody are shown in FIG. 2A.

Protect, Modify, Deprotect—Anti-HEWL HyHEL-5 and HyHEL-10 Column Resin Coupling: To produce the antibody-affinity resins, HyHel-5 and HyHEL-10 were expressed in Expi cells at ~45 mg/L-100 mg/L. 7 mg of HyHel-5 was coupled to a AminoLink® Plus Coupling Resin (ThermoFisher) using the pH 7.4 coupling protocol. Briefly, 7 mg of HyHEL-5 in 3 mL of 1×PBS was added to 1 mL of AminoLink® Plus Coupling Resin pre-equilibrated in 1×PBS. To this mixture, 40 µl of 5M $NaCNBH_3$ in 1M NaOH, and the reaction was let to react overnight at 4° C., rotating. The resin was then washed with 1M Tris pH 8.0 and reactive sites were quenched with 3 mL of 1 M Tris pH 8.0 incubated with resin and 40 µl of $NaCNBH_3$ for 30 mins at room temperature. This resin was finally washed with 1 M NaCl to wash away all unconjugated protein. The theoretical binding capacity of the resin should have been ~1.5 mg of HEWL per reaction. The actual binding capacity was deduced to be ~200 µg indicating that much of the coupled antibody was in a nonproductive form. The same reaction was conducted for coupling HyHEL-10 to the Amino Link® Plus Coupling Resin.

HEWL Pegylation: HEWL, 1 mg/mL in PBS, was flowed over either the HyHEL-5 or HyHEL-10 affinity resins until saturating. The resins were subsequently washed three times with 1×PBS. The resin was then incubated with NHS-$PEG_x$-Methyl at 3 mM such that there were 10 molar equivalents of NHS ester per theoretical exposed (free) amine (2 h at room temperature, rotating). Fluid was eluted from the resin and another incubation with NHS-$PEG_x$-Methyl at 3 mM was added to the resin and incubated for 2 hours rotating. The NHS-$PEG_x$-Methyl used were x=2, 4, 8, 12, and 24 (x referring to the PEG length). The resin was then washed 2× with 100 mM Tris pH 8 to quench any unreacted NHS esters and eluted three times with pH 1.5 glycine directly into 1/5th volume equivalent of 1 M Tris pH 8 to neutralize the pH. The pH was tested and further adjusted with 1 M Tris pH 8 if needed until a near neutral pH was obtained. In certain experiments, the extent of PEGylation on resin was compared to PEGylation in solution. To do this, the HEWL protein was PEGylated in solution in the absence of the protecting antibody. This was done by taking a known amount of HEWL and adding 10 molar equivalents of NHS-$PEG_x$-Methyl per number of theoretical exposed (free) amine (to a final concentration of 3 mM). This reaction was incubated for 2 hours at room temperature and then an additional 10 molar equivalents of NHS-$PEG_x$-Methyl was added and incubated for an additional 2 hours. Organic solvent was removed using a Zeba™ Spin Desalting Column 7k MWCO, as per the manufacturers recommendation, pre-equilibrated in 1×PBS.

Western Blots—HEWL Analysis: After SDS-PAGE analysis, Western blots were conducted by transferring the SDS-PAGE minigel (BioRad) using the mixed molecular weight setting on a Transblot Turbo™ (BioRad) to a nitrocellulose membrane (blot). In some experiments, the Western blot was first Ponceau S stained. This is done by taking the nitrocellulose blot and submerging it in Ponceau S Solution (Sigma Aldrich) for 3 mins rocking, and washing the resulting blot in deionized water until protein bands were apparent. The Ponseau S stain was then washed off with continuous rounds of PBST until all the stain was removed from the blot. For the Western blot, blots were blocked using 2.5% milk for 30 mins at room temperature, or overnight at 4° C. To the blocking solution was added 3 µl of 1 mg/mL HyHEL-5, HyHEL-10, D1.3, D11.15, or F9.13.7, which was then incubated for 1 h at room temperature rocking. This was washed 3× with 1×PBST and goat-antihuman horseradish peroxidase (HRP) secondary (GenScript) antibody was added as per the manufacturers' recommendation and left to rock for 1 h at room temperature. This was washed 3× with 1×PBST and developed using Pierce ECL Western Blotting Substrate or Pierce ECL Plus Western Blotting Substrate (ThermoFisher). Western blots were read on a GE AI600 RGB Gel Imaging System. In experiments where the Western blot was screened against multiple antibodies, the blot was stripped after imaging. This was done by first washing the blot 2× in deionized water, and then 7 mL of 1× Restore™ Western Blot Stripping Buffer (ThermoFisher) was added and let incubate for 7 mins rocking at room temperature. The blot was then washed 2× with PBST and 2.5% milk was added for 10 mins before another primary antibody was added. The same procedure was then followed for further development of the Western blot.

Biolayer Interferometry (Octet) Binding Experiments—HEWL Analysis: All reactions were run in PBS with 0.1% BSA and 0.05% Tween 20. For the experiments described in Example 1(B)(1), nonspecifically biotinylated HEWL, unmodified or PEGylated in solution, was loaded onto eight streptavidin (SA) biosensors (4 each). This is done by incubating the SA biosensors directly into a 100 nM solution of biotinylated HEWL for 2 mins. Four of these biosensors were then loaded with bispecific antibody (approx . . . 10 nM) for 10 mins, while the remaining 4 tips were simply immersed in the PBS with 0.1% BSA and 0.05% TWEEN 20 buffer during this stage (two tips per antigen). Monoclonal antibody binding (HyHEL-10, HyHEL-5, D1.3, D11.15, and F9.13.7 was then probed by immersing these loaded octet biosensor tips in six concentrations of antibodies (starting at 100 nM and decreasing 3 fold in concentration). These were left to associate for 2 mins and then dissociate for 5 mins so that a Kd could be determined using the Forte Bio Octet Analysis Software. For the experiments described in Example 1 (B)(2)(d), monoclonal antibodies HyHEL-10, HyHEL-5, D1.3, D11.15, and F9.13.7 were loaded onto the anti-IgG Fc Capture (AHC) Biosensors at 100 nM and the load threshold was set at 1 nm. After loading, the tips were washed and then were associated, immersed, in 100 nM of unbiotinylated HEWL WT, HEWL PEGylated on resin with $PEG_x$ (as described above) or HEWL PEGylated in solution with $PEG_x$ (as described above). This step was left to run for 90 sec and then the biosensors were moved to PBST BSA to dissociate for 10 mins. The resulting tips were then regenerated in pH 1.5 glycine and neutralized in PBST BSA 3 times before reloading monoclonal antibodies. All samples in all experiments were baseline subtracted to a buffer control well that had a loaded tip but was not contacted with a sample, reflecting any buffer trends within the experiment. The resulting binding curves were fit in GraphPad Prism to determine the Kds of the interactions. For the experiments described in Example 1(E)(1) nonspecifically biotinylated HEWL was loaded onto eight SA biosensors as described above. These eight tips were then associated in 100 nM of each of the four antibodies (HyHEL-10, HyHEL-5, D1.3, D11.15) and each antibody was associated onto both a tip that had only been preloaded with HEWL or onto a tip that had been preloaded with HEWL and with bispecific antibody. All binding to preloaded bispecific HEWL signals were normalized such that each antibody binding to WT HEWL was set as 100. These curves were exported and plotted on GraphPad (Prism 7). Only the association step is shown.

HEWL PEGylated ELISAs: HEWL either WT or PEGylated on resin or PEGylated in solution was plated at 50 µL onto a microtiter plate at 1 µg/mL in 50 mM sodium bicarbonate pH 8.75. This was incubated overnight at 4° C., then washed 3× with PBST, and then blocked with 300 µL of PBST+0.5% BSA overnight at 4° C. The blocking solution was removed and serial dilution of monoclonal antibodies (HyHEL-10, HyHEL-5, D1.3, D11.15, or F9.13.7) were added, starting at 100 nM and undergoing 10-fold serial dilutions. These were incubated for 1 hour at room temperature and then washed 3× with PBST using an ELx 405 Bio-Tex plate washer. Goat anti-human HRP (Abcam ab7153) was added at a 1:50,000 dilution in PBST. This was incubated at room temperature for 1 hour and then washed 6× with PBST. Plates were developed using 50 µL of 1-Step™ Turbo-TMB-ELISA Substrate Solution (ThermoFisher) added to each well and quenched with 50 µL of 2M $H_2SO_4$. Plates were read at 450 nM and normalized for path length using a BioTek Synergy™ HT Microplate Reader. Lastly, the samples were baseline subtracted by subtracting the average of wells containing only secondary antibody (i.e. normalized for secondary antibody non-specific binding).

HEWL Serum Competition ELISA Using HyHEL-5, HyHEL-10, or D1.3: HEWL was plated at 5 µg/mL on NUNC MAXISORP flat-bottom 96 well plates (50 mM sodium bicarb) 50 µL per well. This was incubated at least 1 hour at room temperature. Plates were then washed 3× in 1×PBST 300 µL per well and blocked with 300 µL of 1×PBST with 0.5% BSA for at least 2 hours at room temperature. Plates were stored in 1×PBST with 0.5% BSA and 0.02% $NaN_3$ at 4° C. for later use. Plates were washed with 1×PBST 2 times and 50 µL of rabbit serum from bleed 2 (1:32 fold dilution) was added to each well in triplicate and incubated for 1 hour. To some wells, no serum was added to allow for a no serum control and a no antibody control. After 1 hour 50 µL of 50 µg/mL solution of each human monoclonal antibody in PBS was added directly to the wells containing rabbit serum. This solution was also added to half of the "no serum" controls to all for an antibody alone control. This was incubated for 20 mins at room temperature and then washed 3× with 1×PBST. 50 µL of a 1:100,000 dilution into 1×PBST of rabbit anti-human HRP (Abcam) as per the manufacturer's recommendation was added to each well for 1 hour. This was washed 4× with 1×PBST and 50 µL of 1-Step™ Turbo-TMB-ELISA Substrate Solution (ThermoFisher) was added to each well and quenched with 50 µL of 2M $H_2SO_4$. Plates were read at 450 nM and normalized for path length using a BioTek Synergy™ HT Microplate Reader. Absorbance values were normalized to the average of the human antibody alone control as 100 and no human antibody as 0.

B. Protect-Modify-Deprotect Method—Proof of Concept

1. Epitope Modification Ablates Antibody Binding

A proof of concept study for the Protect-Modify-Deprotect (PMD) method was conducted using the HyHEL-10 antibody and the HyHEL-5 antibody. The aim of the study was to generate a pegylated HEWL protein having PEG molecules added to lysine residues in the unprotected regions of the protein. These antibodies were chosen because the HyHEL-10 antibody binds directly over 2 lysine residues in the HEWL protein, while the HyHEL-5 antibody does not bind directly over any lysine residues or exposed (free) amines in the HEWL protein. Thus, it was expected that the HyHEL-10 antibody would only bind to WT HEWL and HEWL that has been protected on a HyHEL-10 resin, whereas the HyHEL-5 antibody would bind to HEWL regardless of the amount of amine modification. Importantly, HyHEL-10 antibody, should not bind to HEWL upon amine modification on the HyHEL-5 resin or in solution due to the fact that its epitope contains two lysine residues centrally, giving confidence about the level of modification of the immunogen.

To test the hypothesis that HyHEL-5 should bind to a "fully" PEGylated immunogen while HyHEL-10 should not, HEWL was first reacted in solution with a vast excess NHS-$PEG_8$-Me. This created an immunogen that contained primarily 6-7 modifications (pegylated lysine residues) as determined by MALDI analysis (data not shown). This immunogen is referred to throughout this example as HEWL-$Full_8$. Little to no difference in binding of HyHel-5 to HEWL-$Full_8$ when compared to HyHel-5 binding to HEWL WT as determined by its on/off rate measured on the Octet® RED96 System (ForteBio) as shown in Table 2. However, HyHel-10 showed complete ablation of binding to HEWL-$Full_8$. This was expected because, as described above, the epitope, as determined by X-ray crystallography (RCSB Protein Data Bank (PDB) ID:3HFM) showed that this epitope contained two lysine residues. The dissociation step was not long enough to determine an accurate off rate for these high affinity antibodies.

TABLE 2

Binding Affinity Assessment of HyHel-5 and HyHEL-10 Antibodies to Unmodified and Pegylated HEWL

| Antigen | Antibody | $k_{on}$ (1/Ms) | $k_{off}$ (1/s) | $K_D$ (M) |
|---|---|---|---|---|
| WT HEWL | HyHEL-5 | $9.11 \times 10^5$ | $<1 \times 10^{-7}$ | $<1 \times 10^{-12}$ |
| | HyHEL-10 | $5.4 \times 10^5$ | $<1 \times 10^{-7}$ | $<1 \times 10^{-12}$ |
| HEWL-$Full_8$ | HyHEL-5 | $9.22 \times 10^5$ | $<1 \times 10^{-7}$ | $<1 \times 10^{-12}$ |
| | HyHEL-10 | NA | NA | NA |

This proof of concept demonstrated it is possible to quickly and easily produce an immunogen that was selective in binding to affinity-matured antibodies and, by continuation, germline antibodies by chemical modification of the immunogen. Moreover, this selectivity could be predicted based on the contacts from the crystal structure or their expected epitopes.

2. PEGylation Studies of Antibody Binding

Questions from these studies was whether a resin made of HyHEL-10 could sufficiently protect its HEWL epitope from PEG modification and what role, if any, PEG length played in either extent of modification or ability to ablate antibody binding. To answer these questions, a resin from HyHEL-10 was prepared as described and used to bind to HEWL. This complex was then PEGylated with a set of different NHS-$PEG_x$-Methyl where x is different PEG lengths (x=2, 4, 8, 12, and 24). Following PEGylation, the resin was washed and the modified HEWL was eluted off of the resin. Fully PEGylated HEWL derivatives were also prepared by incubating HEWL in solution (without any antibodies present) with the same number of molar equivalents per exposed (free) amine of the NHS-$PEG_x$-Methyl. The resin-produced (protected) PEGylated HEWL derivatives are referred to as HEWL-Hel-$10_2$ (i.e. made using NHS-$PEG_2$-Methyl), HEWL-Hel-$10_4$, HEWL-Hel-$10_8$, HEWL-Hel-$10_{12}$, and HEWL-Hel-$10_{24}$. The solution-produced (unprotected, fully PEGylated) HEWL derivatives are referred to as HEWL-Fully (i.e. made using NHS-$PEG_2$-Methyl), HEWL-$Full_4$, HEWL-Fully, HEWL-$Full_{12}$, HEWL-$Full_{24}$. These ten HEWL derivatives and the WT HEWL were used to assess the extent of PEGylation with different PEG groups and their binding to a range of monoclonal antibodies. In addition to the HyHEL-10 antibody and the HyHEL-5 antibody, three other antibodies were tested in the context of these antigens: F9.13.7, D1.3, and D11.15. Antibody F9.13.7 shares an epitope with the HyHEL-10 antibody and should only bind to WT and HEWL PEGylated on an HyHEL-10 resin but should not bind to HEWL PEGylated in solution. Antibody D1.3 should bind to all version of HEWL but, as its epitope is close to lysine residues, it is expected that its affinity will decrease upon PEGylation. Antibody D11.15 shares part of its epitope with D1.3 and binds directly over a lysine residue and, as such, is expected to bind to WT HEWL but not to HEWL PEGylated on HyHEL-10 resin or in solution because both of these PEGylated at the lysine within its epitope (epitopes shown in FIG. 3J).

a. Gel Electrophoresis

The initial analysis was performed by gel electrophoresis. The proteins were run on an SDS page gel, transferred to nitrocellulose, and then Ponceau S stained to assess the extent of PEGylation. The results are shown in FIG. 3N, top panel. The resin-produced PEGylated HEWL derivatives generally ran faster than the solution PEGylated derivatives, indicating that the HyHEL-10 epitope was protected by the resin such that the two reactive lysine residues in its epitope were unmodified. It was also observed that the HEWL derivatives made using NHS-$PEG_{12}$-Methyl and NHS-$PEG_{24}$-Methyl showed a bit of 'laddering', indicating that there were different forms of the protein in the solution, which is most likely due to different extents of PEGylation. For the HEWL derivatives made using smaller molecular weight PEGs (NHS-$PEG_2$-Methyl and NHS-$PEG_4$-Methyl), the gel shift was less apparent, and a Western blot was used to assess the level of modification as described below.

b. Western Blots

Western blots were performed on the blots using the following primary antibodies: HyHEL-10, F9.13.7, D1.3, D11.15, HyHEL-5, as shown in FIG. 3N.

HyHEL-10 and F9.13.7 bound to the WT protein, HEWL-Hel-$10_2$, HEWL-Hel-$10_4$, HEWL-Hel-$10_8$, HEWL-Hel-$10_{12}$, and HEWL-Hel-$10_{24}$ but did not bind at all to HEWL-$Full_2$, HEWL-$Full_4$, HEWL-$Full_8$, HEWL-$Full_{12}$, or HEWL-$Full_{24}$ (FIG. 3N, second and third panels). This demonstrated HEWL required protection during PEGylation on the HyHEL-10 resin to preserve binding by HyHEL-10 and F9.13.7.

D1.3 and HyHEL-5 were observed to bind to all the proteins as shown in FIG. 3N, fourth and sixth panels. This was expected given that their epitopes do not bind over any lysine residues and so PEGylation should not impact their binding. D11.15, which despite sharing a significant amount of its epitope with D1.3, is shifted such that it does bind over a lysine residue, was shown to bind to the WT protein and to a diminished extent to the HEWL-Hel-$10_{24}$ derivative as shown in FIG. 3N, fifth panel. This demonstrated that PEGylating HEWL on the HyHEL-10 on resin was able to specifically ablate an off-target antibody (D11.15) while retaining binding of antibodies at the site of interest. As the HEWL-Hel-$10_{24}$ derivative was still bound by the D11.15 antibody, indicating that the reduced extent of modification reflected by the observed laddering, led to insufficient protection of the epitope. It is likely that this PEG length would be too long to use in this current method, due to insufficient modification. This demonstrates that, generally, the size of the modifying component should be considered to discourage off-target antibody binding while still successfully modifying and shielding a significant portion of the protein.

c. ELISA

ELISA experiments were also used to further interrogate the binding of these 5 antibodies towards WT HEWL and these HEWL derivatives. The proteins were each coated on ELISA plates, the plates were blocked, and then incubated with serial dilutions of the monoclonal antibodies followed by secondary antibody. The results are shown in FIG. 3O-1 and FIG. 3O-2. The same trends as seen by Western blot were observed.

HyHEL-10 and F9.13.7 bound to the WT protein and HEWL-Hel-10$_2$, HEWL-Hel-10$_4$, HEWL-Hel-10$_8$, HEWL-Hel-10$_{12}$, and HEWL-Hel-10$_{24}$ but did not bind to the HEWL-Full$_2$, HEWL-Full$_4$, HEWL-Full$_8$, HEWL-Full$_{12}$, HEWL-Full$_{24}$ fully PEGylated proteins (except for a small amount of binding observed at the highest antibody concentration (100 nM)). This demonstrated again the necessity of PEGylating in the presence of the protecting antibody of the resin in order to preserve the integrity of the epitope for HyHEL-10 and F9.13.7. There was a small decrease in binding of HyHEL-10 and F9.13.7 to the antigens that were PEGylated on resin (HEWL-HEL-10$_x$). This result could be due to effects in plating the antigens on the ELISA plates or because there is another lysine close in proximity that could have an impact on their binding.

D1.3 and HyHEL-5 bound to all the proteins to varying degrees but all quite significantly. D11.15 only bound to an appreciable amount to the WT protein. This again demonstrates that PEGylating HEWL on the HyHEL-10 resin was sufficient to ablate D11.15 binding but retain on-target binding by HyHEL-10 and F9.13.7.

d. Biolayer Interferometry

Biolayer Interferometry experiments using the Octet Red 96 (Forte Bio) were also used to assess the solution kinetics of the proteins in solution binding to the antibodies. As described above, AHC octet biosensors were loaded with one of monoclonal antibodies HyHEL-10, F9.13.7, D1.3, D11.15, or HyHEL-5, and then these tips were submerged in 100 nM solution of HEWL WT or one of the 10 HEWL derivatives for 90 seconds. The tips were then allowed to disassociate for 10 mins. These binding curves were exported and plotted on GraphPad Prism and the Kds are shown in Table 3 below.

The same trends are observed as seen with the gel electrophoresis and ELISA experiments. HyHEL-10 and F9.13.7 only bind to WT HEWL and the resin-produced PEGylated derivatives. D1.3 and HyHEL-5 bind to all the protein antigens. D11.15 only binds to WT. In addition, more subtle trends can be seen. For example HyHEL-10 appears to still bind slightly to HEWL-Full$_2$ although >10,000 fold more weakly compared to HEWL WT. In addition, increasing PEG length appeared to decrease the affinity of D1.3 towards the immunogen, suggesting that even when there is not a lysine directly in the epitope (i.e. when a lysine is merely adjacent to the epitope), this method can still decrease antibody binding, likely by steric occlusion of the antibody. Finally, increasing PEG length appeared to decrease the affinity of HyHEL-10 towards the resin-produced (protected) antigens.

These results together indicate the following: 1) the presence of the HyHEL-10 antibody during PEGylation was necessary to protect the epitope of interest and retain its integrity as demonstrated by the lack of binding of HyHEL-10 and F9.13.7 to the solution-produced (unprotected) antigen (FIG. 3N, FIG. 3O-1, FIG. 3O-2, Table 3). 2) The size of the modifying component impacts epitope protection—too small and the epitope is not sufficiently blocked; too large and the modification reaction can be impaired. This is seen by HyHEL-10 retaining a small amount of binding to HEWL-Full$_2$ (Octet study; Table 3) and by D11.15 retaining binding to HEWL-Hel-10$_{24}$ (Western blot; FIG. 3N). 3) As the modifying component increases in size, it can impact binding of both on-target and off-target antibodies. This is seen in the case of HyHEL-10 affinity decreasing slightly as one compares HEWL-HEL-10$_4$ to HEWL-HEL-10$_{24}$ (Table 3).

TABLE 3

Biolayer interferometry binding curves

|  | WT | PEG$_2$ | | PEG$_4$ | | PEG$_8$ | |
|---|---|---|---|---|---|---|---|
|  |  | P | S | P | S | P | S |
| Hy HEL10 | <1.0E−11$^a$ | 6.8E−11$^b$ | 1.5E−07$^f$ | 9.1E−11$^b$ | 1.0E−06$^g$ | 9.2E−11$^b$ | 1.0E−06$^g$ |
| F9.13.7 | 7.0E−11$^b$ | 3.4E−10$^c$ | 1.0E−06$^g$ | 4.2E−10$^c$ | >1.0E−06$^g$ | 3.8E−10$^c$ | >1.0E−06$^g$ |
| D1.3 | 5.8E−10$^c$ | 1.7E−09$^d$ | >2.9E−09$^d$ | 4.7E−09$^d$ | >7.9E−09$^d$ | 5.7E−09$^d$ | >1.2E−08$^e$ |
| D11.15 | 2.3E−09$^d$ | 1.0E−06$^g$ | 1.0E−06$^g$ | 1.0E−06$^g$ | 1.0E−06$^g$ | 1.0E−06$^g$ | 1.0E−06$^g$ |
| Hy HEL5 | 1.8E−11$^b$ | >1.2E−10$^c$ | >1.4E−10$^c$ | >1.4E−10$^c$ | >1.5E−10$^c$ | >1.4E−10$^c$ | >1.8E−10$^c$ |

|  | PEG$_{12}$ | | PEG$_{24}$ | |
|---|---|---|---|---|
|  | P | S | P | S |
| Hy HEL10 | 5.5E−11$^b$ | 1.0E−06$^g$ | 2.6E−10$^c$ | 1.0E−06$^g$ |
| F9.13.7 | 4.0E−10$^c$ | >1.0E−06$^g$ | 7.8E−10$^c$ | >1.0E−06$^g$ |
| D1.3 | 4.7E−09$^d$ | >2.7E−08$^e$ | 1.1E−08$^e$ | >1.1E−08$^e$ |
| D11.15 | 1.0E−06$^g$ | 1.0E−06$^g$ | 1.0E−06$^g$ | 1.0E−06$^g$ |
| Hy HEL5 | >1.1E−10$^c$ | >3.6E−10$^c$ | >2.0E−10$^c$ | >1.7E−10$^c$ |

Measurement "x":
$^a$x < 1.0E−11;
$^b$1.0E−11 < x < 1.0E−10;
$^c$1.0E−10 < x < 1.0E−9;
$^d$1.0E−9 < x < 1.0E−8;
$^e$1.0E−8 < x < 1.0E−7;
$^f$1.0E−7 < x < 1.0E−6;
$^g$1.0E−6 < x C. Protect-Modify-De Protect Method—Modified Antigen Production The next aim was to produce an immunogen using the PMD method that mirror the antibody binding profile seen in the proof of concept study and would also produce a directed immune response in vivo. This experiment used a HyHEL-5 affinity resin because the epitope bound by the HyHEL-5 antibody is not directly covering any lysine residues and would allow for a good and simple demonstration of the ability to modify an antigen whilst bound to an affinity resin. HEWL was modified by pegylation.

Two modified immunogens were produced through an on-resin amine reaction, one reaction carried out with NHS-$PEG_2$-Me and another reaction carried out with NHS-$PEG_4$-Me. The modified antigens made from these reactions are referred to in this disclosure as HEWL-Hel-$5_2$ and HEWL-Hel-$5_4$, respectively. By using two different sized modifying components ($PEG_2$ and $PEG_4$), we aimed to demonstrate the versatility of this method. The on-resin reactions produced derivatives of HEWL with >6 modifications per HEWL as determined by MALDI analysis, as shown in Table 4 below. HEWL-Hel-$5_2$ and HEWL-Hel-$5_4$ showed ablation of binding of HyHEL-10, which binds over two lysine residues (FIG. 3B ($PEG_2$) and data not shown for $PEG_4$). However, both of these modified immunogens retained binding to HyHEL-5, the antibody used to protect them on resin (FIG. 3A ($PEG_2$) and data not shown for $PEG_4$). This indicated that the reaction of HEWL on the solid support conjugated HyHEL-5 reproduced the results from the solution phase experiment.

TABLE 4

MALDI Analysis of Pegylated HEWL

| Antigen | Maldi Peaks | Corresponding number of PEG additions |
|---|---|---|
| HEWL-HEL-$5_2$ | 15069 | 6 PEG |
| | 15200 | 7 PEG |
| HEWL-HEL-$5_4$ | 15610 | 6 PEG |
| | 15828 | 7 PEG |

It is important that this method is also applicable to target sites where the antibody's or protecting protein's epitope contain reactive residues and that these residues, due to the fact that the binding partner shields them from the modifying group, are resistant to modification. This was demonstrated by production of a second resin containing HyHEL-10 and modification of HEWL on this resin following the same procedure as above with the sole exception that the modifying reagent was NHS-$PEG_8$-Me. NHS-$PEG_8$-Me was selected because, due to its larger molecular weight than the NHS-$PEG_{214}$-Me, a gel shift could be used to determine extent of conjugation. The on-resin PEGylation reaction with HyHEL-10 on the resin produced a less PEGylated derivative than the in solution amine reaction, which generated a fully PEGylated HEWL. This is apparent from gel analysis as shown in FIG. 3C. This was the expected result as two lysine residues are theoretically shielded by the HyHEL-10 binding and the on resin reaction should, therefore, result in less modification than the in-solution reaction. Further, the WT HEWL and the resin modified immunogen retained binding to HyHEL-10, while HyHEL-10 did not bind to the fully PEGylated HEWL as shown in FIG. 3D. This result implies that the epitope for HyHEL-10 is retained during the on resin PEGylation, but not during the in-solution reaction. The on-resin lysine modification reaction was optimized by conducting the on resin reactions (described above) while changing the incubation times as well as the number of molar equivalents of NHS-$PEG_x$-Me added. The reaction conditions were optimized (testing, for example, room temperature stationary, room temperature rotating, 37° C. shaking, etc.), and room temperature rotating was found to produce the most uniform and reacted product.

Elution conditions were optimized by testing different elution conditions of the modified HEWL bound to resin. This is to say that we would conduct the reaction and then flow different potential elution conditions over the resin and then run this eluent on a gel to determine if any protein was present.

Optimization of the modification and elution steps allowed for production of highly modified antigens (similar to that produced in the solution phase reaction) and also complete elution of the modified antigens off the affinity resin.

These modified immunogens retained robust binding to HyHel-5 but showed complete ablation of binding to HyHel-10 (FIG. 3A) indicating that the immunogen had been successfully protected by the HyHel-5 affinity resin during the amine reaction and that the modifications introduced by the amine reaction had proceeded as expected to block binding of HyHel-10 to HEWL.

D. Protect-Modify-Deprotect Method—In Vivo Proof of Concept

The next focus was to assess the in vivo immune response to the HEWL-Hel-$5_2$ and HEWL-Hel-$5_4$ immunogens to see if they could stimulate a specific immune response towards a particular epitope (the epitope bound by HyHel-5). Three rabbits were immunized with either HEWL WT, HEWL-Hel-$5_2$, or HEWL-Hel-$5_4$. The immunization schedule was such that the rabbits received 250 μg of immunogen per immunization with Freund's complete and were bled on week 2 and week 4 following the initial immunization and week 6 following a boost on week 4 with Freund's incomplete adjuvant. Serum obtained from the rabbits was then analyzed to detect preferential binding towards an individual site through a variety of competition based enzyme linked immunosorbent assays (ELISAs).

In brief, the ELISAs were performed as follows: (1) rabbit serum was incubated on a plate coated with HEWL WT, (2) monoclonal humanized versions of either HyHel-5, HyHel-10, or D1.3, produced using Expi293 cells as described above, were added and incubated for 20 mins, (3) the plate was washed and a rabbit anti-human-horseradish peroxidase (HRP) secondary (abcam) antibody was added, (4) the plate was washed again and ELISA substrate (1-Step™ Turbo TMB-ELISA Substrate, ThermoFisher) was added, and (5) the plate was quenched and read.

In this experiment, the secondary antibody should only bind to the monoclonal humanized antibodies. As such, the assay readout is dependent on the amount of monoclonal humanized antibody bound to the HEWL WT on the plate, reflecting a qualitative inverse of the amount rabbit antibodies in the serum capable of binding to HEWL WT. It was expected that a lower signal would be observed for an epitope for which the polyclonal serum contained more or higher affinity antibodies towards. As such, if the immune response was skewed in a particular direction by the immunogen used, a lower signal for the protected epitope would be observed because less of the human monoclonal antibody would be bound to the plate (because rabbit antibodies from the serum would be bound to the epitope already).

As shown in FIG. 3F, the polyclonal serum from the group immunized with HEWL WT immunogen showed a preference for the epitope bound specifically by the D1.3 antibody because the lowest relative signal was observed for the humanized D1.3 antibody condition. In contrast, as shown in FIG. 3G and FIG. 3H, the polyclonal serum from the groups immunized with either HEWL-Hel-$5_2$ or HEWL-Hel-$5_4$ (respectively) showed a preference for the site mapped by HyHel-5—the protecting antibody (affinity resin antibody)—because the lowest relative signal was observed for the humanized HyHel-5 antibody condition.

The immune response was also assessed by an ELISA $IC_{50}$. The immune response for the groups immunized with HEWL-Hel-$5_2$ or HEWL-Hel-$5_4$ was weaker (data not shown). This is not surprising because these proteins are highly pegylated.

E. Epitope Shielding Method

A proof of concept for the Epitope Shielding (ES) method was conducted. A bispecific di-ScFv of D11.15 and HyHEL-10 was produced. This di-ScFv was expected to block the epitopes bound by the D11.15 and HyHEL-10 antibodies while not blocking the epitope for HyHEL-5 The di-ScFv was expressed and purified from the periplasmic space of *E. coli* cells.

Binding of the di-ScFv to HEWL (biotinylated) was assessed using the Octet RED96 system (ForteBio). A protein complex was formed between HEWL and the di-ScFv by progressive incubations of the streptavidin-coated Octet biosensors—first, in a solution of biotinylated HEWL and, second, in a solution of bispecific antibody. The first incubation should coat the biosensors with HEWL. The second incubation coats the HEWL on the biosensors in bispecific antibody. The incubation in bispecific antibody was left for 10 mins such that the solution reached equilibrium. This complex, conjugated on the surface of the biosensors, was added to solutions containing 100 nM of either HyHEL-10, HyHEL-5, D11.15, or D1.3 in 1×PBS with 0.1% BSA and 0.05% Tween. Biosensors coated in only HEWL were simultaneously incubated in solutions containing these antibodies. This produces data simultaneously for antibodies binding to the complex and antibodies binding to the protein without the complex present. As shown in FIG. 3E, the only antibody that retains significant binding is HyHEL-5, indicating that the epitopes for the HyHEL-10, D1.3, D11.15 antibodies were shielded by the di-ScFv, only the association step is shown.

Example 2. ERAS Using Influenza Hemagglutinin Antigens

Having completed the proof of concept studies with HEWL, the PMD and ES ERAS methods were used to generate immunogens based on the ectodomain of the influenza hemagglutinin (HA) protein.

A. Materials and Methods

HA Protein Cloning: Hemagglutinin ectodomains constructs of H1 (AHJ09883.1) and H5 (AII30339.1) were developed as previously described by Whittle, J. R. et al., *J Virol* 88:4047-4057 (2014) and cloned into the pADD2 backbone as described by Han, P. et al., *Nature* 514:102-106 (2014). Both constructs contained only the ectodomain of the respective HA proteins (i.e. lacked the transmembrane domain and C' terminal cytoplasmic domain). The H1 construct is derived from HAASA, which has an R343G mutation that discourages cleavage, and an IL-2 leader sequence was added to the N-terminus to result in protein secretion. The H5 construct is derived from Viet Nam/1194/2004 x Puerto Rico/8/1934, and the native leader sequence was used to result in protein secretion. To the C' terminal end of the H1 and H5 ectodomains, a foldon domain, an AviTag™, and hexa-HIS tag (SEQ ID NO: 26) (in this order) were added to enable purification and biotinylation (together referred to as "foldon-avi-his tag"). A Y108F mutation was made in all HA ectodomains to ablate sialic acid binding and reduce binding affinity, permitting easier protein purification. The foldon domain constitutes the C-terminal 30 amino acid residues of the trimeric protein fibritin from bacteriophage T4, and it is added to the HA ectodomains to cause the expressed proteins to trimerize. The AviTag™ is a 15 amino acid peptide tag that is site specifically biotinylated (at a lysine residue there) by *E. coli* biotin ligase (BirA). The expressed and purified H5 HA protein sequences are shown in FIG. 211. Hemagglutinin ectodomains constructs of H2 and H3 were prepared in a similar fashion. The H3 ectodomain sequence was obtained from A/Victoria/3/1975(H3N2) (NCBI: txid392809; Accession number: CY113181), and the H2 ectodomain sequence was obtained from A/Japan/305/1957(H2N2) (NCBI: txid387161; Accession number: CY045804). Both constructs contained only the ectodomain of the respective HA proteins (i.e. lacked the transmembrane domain and C' terminal cytoplasmic domain). The H3 and H2 ectodomain constructs were cloned in the same way as the H5 and H1 ectodomain constructs, with the foldon-avi-his tag at the C' terminus. In addition, H1, H2 and H5 ectodomain constructs were prepared in which the foldon-avi-his tag was replaced with an gly-thr linker, IZ domain (a coiled-coil trimerization domain), and an octo-HIS tag (SEQ ID NO: 27) (in this order; referred to as a "GT-IZ-his tag"). These constructs are shown in FIGS. 2I-2K (showing expressed protein sequences and purified protein sequences). Constructs of H1, H2, and H5 ectodomains without either the foldon-avi-his tag or the GT-IZ-his tag were also prepared.

HA Antibody Cloning: All antibodies described in this this portion were cloned into the CMV/R plasmid backbone under a CMV promoter. The antibodies variable HC and variable LC were cloned between the CMV promoter and the bGH poly(A) signal sequence of the CMV/R plasmid to facilitate improved protein expression. This vector also contained the HVM06_Mouse (P01750) Ig heavy chain V region 102 signal peptide to allow for protein secretion and purification from the supernatant. The antibody sequences were either taken from the protein sequence (obtained from RCFB Protein Databank) from the crystal structure and codon optimized (IDT CodonOpt tool) or from the reported NCBA Accession number as provided below in Table 5. Cloning of scFvs is described below. Both of the trispecific HC and LC were inserted into the same CMV/R vector at the same position preceded by the same signal sequence. This construct did not contain the constant region (Fc region) of the H5M9 antibody. The HC of the trispecific construct was produced by expressing the scFv of H5.3 on the N terminus of the HC of the Fab of H5M9. The LC of the trispecific was produced by expressing the scFv of 65C6 on the N terminus of the LC of the H5M9 FAb. All constructs were designed such that there was a 12-15 base pair overlap with the open vector. Cloning was performed using the In-Fusion® HD Cloning Kit master mix (Clontech). A mutated Medi8852 antibody was generated that had decreased binding affinity towards its HA stem epitope and allow for elution off of an affinity resin made of this modified antibody. Two mutations were identified by examining the crystal structure that should decrease the binding affinity upon alanine mutation. Both residues were within the HC of the known Medi8852 antibody. Residues 52 and 54 were both mutated to alanine residues (HC R52A, HC Y54A). The clone was generated by mutational PCR using primers that overlapped the codons of the amino acid residue to mutated and contained the desired point mutation followed by stitching PCR using the HIFI PCR premix (Clontech) to stitch together the amplification products. The constructs were then cloned into the CMV/R plasmid backbone using the In-Fusion Cloning Kit (Clontech). The expressed and purified protein sequences for the H5 HA Trispec HC are shown in FIG. 2B. The expressed and purified protein sequences for the H5 HA Trispec LC are shown in FIG. 2C. In addition, the expressed and purified protein sequences for an alternate H5 HA Trispec HC in which the H5.3 scFv was replaced with a F045-092 scFv are shown in are shown in FIG. 2D. The expressed and purified protein sequences for the Medi8852 LC having a single Alanine mutation (Y32A) as used in the elution condition study described below in Subsection C of this Example are shown in FIG. 2E. The expressed and purified protein sequences for the Medi8852 HC have a the two Alanine substitution mutations (HC R52A, HC Y54A) are shown in FIG. 2F.

TABLE 5

Monoclonal antibody sequences used in Examples.

| Antibody Name | Crystal Structure | Accession Number HC | Accession Number LC | Target | Produced as MAb or scFv on yeast |
|---|---|---|---|---|---|
| Medi8852 | 5JW4 | KX398437.1 | KX398446.1 | HA Stem | Both |
| 65C6 | 5DUM | JF274050.1 | JF274051.1 | H5 Head | Both |
| H5M9 | 4MHH | KF500000.1 | KF499999.1 | H5 Head | Both |
| 3C11 | NA | JF274048.1 | JF274049.1 | H5 Head | ScFv on yeast |
| AvifluIgG03 | 5DUP | NA | NA | H5 Head | ScFv on yeast |
| 100F4 | 5DUR | JF274052.1 | JF274053.1 | H5 Head | Both |
| H5.3 | 4XNM | NA | NA | H5 Head | Both |
| BH151 | 1EO8 | AJ251890.1 | AJ251891.1 | H3 Head | ScFv on yeast |
| F045 | 4O58 | AB649270.1 | AB649271.1 | H3 Head | ScFv on yeast |
| CO5 | 4FP8 | JX206996.1 | JX206997.1 | H3 Head | ScFv on yeast |
| 2G1 | 4HG4 | JN130392.1 | JN130393.1 | H2 Head | ScFv on yeast |
| 8F8 | 4HF5 | JN130388.1 | JN130389.1 | H2 Head | ScFv on yeast |
| 8M2 | 4HFU | JN130390.1 | JN130391.1 | H2 Head | ScFv on yeast |
| CH65 | 5UGY | NA | NA | H1 Head | Both |
| H2987 | 5UG0 | NA | NA | H1 Head | Both |
| 6649 | 5W6G | NA | NA | H1 Head | Both |
| 2DI | 3LZF | EU825949.1 | EU825950.1 | H1 Head | ScFv on yeast |
| CR9114 | 4FQI | JX213639.1 | JX213640.1 | HA Stem | Both |
| F10 | 3FKU | NA | NA | HA Stem | ScFv on yeast |
| CR8020 | 3SDY | NA | NA | HA Stem | ScFv on yeast |
| MAb3.1 | 4PY8 | NA | NA | HA Stem | Both |
| FI6v3 | 3ZTN | NA | NA | HA Stem | Both |

Protein Expression and Purification: All proteins produced in the following examples were produced in Expi HEK293 cells as per the manufacturer's recommendation. Briefly, the cells were maintained in Expi293 expression media (ThermoFisher) and passaged every 3-4 days. The day before transfection Expi HEK293 cells were resuspended to a density of 3 million cells/mL and left to grow overnight. The following day the cells were diluted back to 3 million cells/mL and transfected. These vectors, one containing the heavy chain and one containing the light chain of each antibody, were cotransfected. This was conducted by incubating 20 μg of each plasmid (40 μg total) in 1.5 mL opti-MEM (Thermofisher) and mixing this with 1.5 mL of opti-MEM containing 108 μl of expifectamine. This was incubated for 20-30 mins and added to 25.5 mL of Expi-cells at 3 million cells/mL. These cells were then boosted 18-24 hours later with 150 μl of serum from boost 1 and 1.5 mL of serum from boost 2. Cells were harvested by centrifugation at day 4 and the supernatant was diluted 1:1 into 1×PBS. This diluted supernatant was then flowed over a column containing protein A resin (ThermoFisher) at least two times, washed with 10 column volumes of PBS and eluted with 100 mM glycine pH 2.8 directly into $1/10^{th}$ volume of 1 M Tris pH 8.0. Hemagglutinin constructs were transfected at 30 μg plasmid DNA in 1.5 mL Opti-MEM and 80 μl of expifectamine per 25.5 mL of Expi cells. Cells were harvested by centrifugation and supernatant from cells expressing HA was diluted 1:1 in 1×PBS and purified using nickel affinity chromatography using Ni-NTA agarose (ThermoFisher). In some instances, the hemagglutinin constructs were then further purified using fast protein liquid chromatography (FPLC) on an ÄKTA Pure Chromatography System using a Superdex™ 200 increase column. Briefly, 1 mL of protein solution at a concentration of approximately 2-3 mg/mL was injected into a 2 mL loop and flowed over the column in 1×PBS, samples were collected in a deep well block, and samples containing protein (after a small, obvious shoulder) were pooled. The trispecific conjugate was expressed essentially as per the antibody expression and was purified using protein G affinity chromatography. The purified HA ectodomain proteins are trimeric complexes (trimers of HA1-HA2 heterodimers, HA0 monomers, or a combination thereof).

Lysine Substitution Mutations into H1 HA: To determine amino acid residues that could potentially be mutated into lysine residues, available data on BLAST was used together with data from a previously described single point mutation library as described by Doud, M. B. & Bloom, J. D., *Viruses* 8:1-17 (2016). A clone was generated containing nine additional lysine at sites L60K, N71K, T146K, N155K, R162K, N176K, V182K, G202K, R205K of the H1 HA protein. The clone was generated by mutational PCR using primers that overlapped the amino acid residue to mutated and contained the desired point mutation followed by stitching PCR using the HIFI PCR premix (Clontech) to stitch together the amplification products. The construct was then cloned into the pADD2 vector using the In-Fusion® Cloning Kit (Clontech). The final clone was sequence verified (Sequetech, Mountain View, CA). The protein expressed from this clone is referred to as "H1+9" in this disclosure. The expressed and purified H1+9 protein sequences are shown in FIG. 2G.

Protect, Modify, Deprotect—Anti-H1 Medi8852 Column Resin Coupling: Four milligrams of Medi8852 with 2 point mutations in the heavy chain (R52A, Y54A) was coupled to AminoLink® Plus Coupling Resin (ThermoFisher) as per the manufacturer's recommendation (pH 7.4 protocol). Briefly, 4 mg of Medi8852 R52A Y54A in 2 mL, was incubated with 500 μl of AminoLink® Plus Coupling Resin (ThermoFisher) that had previously been washed with 1×PBS pH 7.4. To this mixture 40 μl of 5M $NaCNBH_3$ was added and left to react overnight, rotating at 4° C. The resin was subsequently washed with 1×PBS and quenched with 2 mL of 1 M Tris pH 8 with 40 μl of 5M $NaCNBH_3$. Finally, the resin was washed with 1×PBS and at least 10 resin bed volumes of 1 M NaCl until no protein was detected in the wash out. This resin was stored in 1×PBS with $NaN_3$ (0.02%).

Protect, Modify, Deprotect—HA Head Protection: H1+9 (1 mg/mL in 1×PBS) was batch incubated with the Medi8852 R52A, Y54A resin for 15 min rotating. This was washed 2× with 1×PBS and then 1×PBS with 3 mM NHS-$PEG_4$-Methyl was added such that there were 5 molar equivalents per theoretical exposed (free) lysine residues. This was incubated for 45 min rotating, let drain after 45 min, and then a second equivalent of this was added for another 45 min rotating. Finally, the resin was washed 1× with 100 mM Tris pH 8 to quench any unreacted NHS ester and wash out hydrolyzed NHS ester. The modified H1+9 was eluted in 2 M KSCN dissolved in 1×PBS, directly into 3 equivalents of 1×PBS. This was immediately put into overnight dialysis in 1×PBS. The subsequent solution was concentrated and buffer exchanged into 1×PBS. The resulting antigen where the H1+9 was PEGylated with NHS-$PEG_4$-Me on a resin of Medi8852 HC R52A, HC Y54A is henceforth referred to as H1+9+PEG in this disclosure.

H1+9 Solution PEGylation: A 'fully' PEGylated version of the H1+9 derivative was prepared by PEGylating H1 in solution. Five molar equivalents of NHS-$PEG_4$-Methyl was added to H1+9 (FPLC purified as described above) at a concentration of 1 mg/mL in 1×PBS. This was left to react for 45 mins at room temperature rotating. An additional 5 molar equivalents of NHS-$PEG_4$-Methyl (as above) was then added, and the reaction was incubated for an additional 45 mins at room temperature rotating. The resulting protein is referred to herein as H1+9 Full.

Hemagglutinin Melt Curve Analysis: H1 WT, H1+9, and H1+9+PEG were purified by FPLC using the ÄKTA Pure Chromatography System with a Superdex™ 200 increase column in 1×PBS as described above. 200 μL of H1 HA, H1+9, H1+9+PEG, or H1+9 Full were dialyzed against 4 L of 0.25×PBS, with one buffer change at 2 hours and then incubated overnight at 4° C. 10 μL of the dialyzed samples were loaded into Prometheus NT.Plex nanoDSF Grade High Sensitivity Capillary Chips using capillary action. These samples were then loaded into the Prometheus NT.48 Protein Stability Instrument (NanoTemper Technologies). The NT.48 instrument progressively increases the temperature of the samples and records the fluorescence due to the tryptophan residues. As the proteins unfold, the detected fluorescence will increase as tryptophan residues hidden in the folded proteins are exposed to water.

Hemagglutinin Circular Dichroism (CD) Analysis: H1 HA, H1+9, H1+9+PEG, and H1+9 Full were dialyzed into 0.25×PBS as described above. The dialyzed samples (200 μL) were loaded into 1 mM quartz cuvettes, which were in turn loaded into a J-815 CD Spectrophotometer (Jasco, Inc.). The dialysis buffer was used as a baseline control. Nitrogen was flowed into the instrument constantly during measurement of the samples to keep the bulb cool. Measurements were recorded every 0.5 nm. Measurements were recorded for nm values only where the voltage of baseline control was below 400 V. Five accumulations were recorded for each sample. The measurements of the negative control were subtracted in a processing step using the Jasco instrument software. Values were converted to Molar Ellipticity using the molecular weight as measured using a NanoDrop 2000C (ThermoFisher), which uses A280 absorbance to determine the molecular weight. The average of five independent measurements was used. The resulting molar ellipticity values were exported and plotted using GraphPad Prism.

BirA Biotinylation: BirA, expressed in *E. coli*, was used to biotinylated-purified hemagglutinin derivatives. 1 mL of the HA at 1 mg/mL in PBS was mixed with 100 μl of 10× reaction buffer (0.5M Bicine pH 8.3, 500 uM biotin final concentrations 50 mM, pH 8.3, 5004 respectively) and 100 μl of 100 mM ATP stored separately (final concentration 10 mM). 2.5 μl of 1 mg/mL BirA stock solution was added and the reaction was incubated at 37° C. for 1 hour. A PD-10 column (SEPHADEX) was used to buffer exchange the HA derivatives.

Fluorescamine Assay: Protein concentration was measured in biological triplicate using A280 on a NanoDrop Microvolume Spectrophotomer (ThermoFisher). Protein was then diluted into 1×PBS to a final concentration of 50 μg/mL. 30 μl of a 3 mg/mL solution of fluorescamine in DMSO was added to 90 μl of protein to produce a final volume of 120 μl. This reaction was left to sit at room temperature in a black bottom 96 well plate for 15 mins. RFU was measured with an excitation at 400 nm 15 nm bandwidth, and a 460 nm 15 nm bandwidth emission filter using a plate reader (Biotek). Data was normalized to the buffer alone control. Fluorescamine reactivity with pegylated protein was measured using the same reaction conditions and the RFU was normalized using an H1+9 control and a buffer alone. A single biological replicate of the two is shown.

Epitope Shielding—HA Head Protection: H5 HA was added in a half (½) molar excess (per monomer) to a solution containing trispecific antibody at ~100 nM. This incubation was conducted in 1×PBS and the solution, containing the mixture of H5 HA and trispecific, was left on ice for at least 2 hours to allow for full protection of the head. This complex of H5 HA and trispecific antibody is henceforth referred to as H5 Trispec for this disclosure.

H1 and H5 Biolayer interferometry (Octet) Binding Experiments: All reactions were run in PBS with 0.1% BSA and 0.05% Tween 20. To determine binding of the trispecific antibody towards the H5 HA, streptavidin (SA) biosensors (ForteBio) were loaded for 2 min with 100 nM BirA biotinylated H5 HA. This was then immersed in buffer containing 30 nM trispecific antibody for 2 mins and then left to dissociate in the original buffer well for 60 seconds. These curves were baseline corrected and exported and plotted on GraphPad (Prism 7). To assess Head vs Stem H1 antibody binding to immunogens, binding was determined by using streptavidin (SA) biosensors (ForteBio) loaded for 5 min with 18 nM biotinylated antigens. Tips were then associated in 100 nM of each antibody and left to dissociate in the original buffer wells for 60 seconds. These curves were baseline corrected and exported and plotted on GraphPad (Prism 7). In experiments in which H1+9+PEG and H1+9 Full were directly compared, it was ensured that the same amount of protein was on the octet biosensor tips by applying a threshold to the load. Briefly, tips with Anti-Penta-HIS HIS1K antibody were immersed in H1+9+PEG and H1+9 Full solutions and loaded at 50 nM until a value of 0.3 nM was reached. The tips were then washed one time and then immersed in 100 nM of HA stem directed monoclonal antibodies. The tips were regenerated by dipping them in 100 mM glycine pH 1.5 (5 sec each) followed by dipping into buffer (5 sec each) for a total three rounds. The tips were then reused to conduct the experiment in triplicate for each protein.

H2897 Depletion of H1+9+PEG: 50 μL of 1.5 μM H1 WT, H1+9, or H1+9+PEG were added to either 50 μL of 1×PBS or 50 μL of 10 μM H2897 and left to incubate for 1 hour at room temperature. The resulting solutions were incubated with 50 μL of protein A resin (ThermoFisher) for 4 hours at 4° C. Resin was isolated by spinning through an ultrafree-MC centrifugal filter (Milipore Sigma), and the resulting solution was incubated again with another 50 μL of protein A resin for 1 hour at 4° C. The final solutions were isolated by spinning through another ultrafree-MC centrifugal filter to remove the resin.

Western Blots—H2897 Depletion Analysis: After SDS-PAGE analysis, Western blots were conducted by transferring the SDS-PAGE minigel (BioRad) using the mixed molecular weight setting on a Transblot® Turbo™ (BioRad). The blot was then blocked using 15 mL of 3% BSA for 30 mins at room temperature. To this 3 μl of streptavidin HRP (BD ELISPOT) was added and left to incubate for at least 1 h at room temperature rocking. This was washed 3× with 1×PBST and developed using Pierce ECL Western Blotting Substrate or Pierce ECL Plus Western Blotting Substrate (ThermoFisher). Western blots were read on a GE AI600 RGB Gel Imaging System.

Yeast Cloning: Yeast clones were produced by cloning the scFv of the antibodies set forth in Table 5 into a pPNL6 backbone. ScFvs were designed using the yol tag as the linker between the HC and the LC of the antibodies. All scFvs were designed in the order HC-yol tag-LC. Clones were sequence confirmed and transformed as previously described. Briefly, yeast were grown on a YPAD plate and then a single colony was inoculated in 5 mL of YPAD overnight shaking at 30° C. Carrier DNA (salmon sperm DNA (Sigma)) was boiled for 5 min, and the aliquots were stored frozen. 200 μl of YPAD culture as harvested per clone and pelleted. 24 μl PEG 3350 (50% w/v), 3.6 μl lithium acetate (1 M), 5 μl boiled carrier DNA (2 mg/mL), plasmid DNA (0.01-0.1 μg), and water (up to 36 μl) was added to each pellet. This was incubated at 42° C. for 2 hours. Cells were harvested by centrifugation and resuspended in 100 μl of water. 10 μl of each clone was plated on selective agar plates lacking tryptophan and grown at 30° C. for 3 days until colonies were visible. Yeast were picked and grown in SD-CAA media overnight (30° C. shaking) and then induced by doing a 1:100 dilution into SG-CAA media and grown at 20° C. shaking for 2 days.

Yeast Binding Experiments—Individual Clone Binding: Following induction in SG-CAA shaking for 2 days at 20° C., yeast clones, each expressing a different scFv on their surface, were separately incubated for 15 mins with 12.5 nM tetrameric bait in 50 μl PBSM. Tetrameric baits were preformed with 50 nM biotinylated antigens and 12.5 nM streptavidin 647 (Jackson Immunoresearch) for each of the respective antigens. Cells were then washed 1× with PBSM and then incubated with 1 μl of anti-c-myc FITC (Miltenyi) in 50 μl PBSM for 15 mins. These samples were flowed (Accuri C6 flow cytometer) and the percent antigen positive was determined as the ratio of antigen positive cells divided by all cells expressing (c-myc positive). Gates were set such that ~1% of yeast were positive in the streptavidin alone control (data not shown).

Yeast Binding Experiments—Polyclonal Sorts: Yeast clones were pooled based on their concentration such that an equimolar ratio of each clone was added to the 'library'. This library was made independently twice, producing a biological duplicate of the yeast library. Both biological duplicate libraries were treated as above, such that an aliquot of the entire yeast library was incubated with 12.5 nM of each of the different tetrameric baits, produced as above. As such, there were 8 independent yeast incubations, one per biological duplicate, for each of the four antigens, H1 WT, H1+9+PEG, H5 WT, and H5 Trispec. These were incubated for 15 mins with the tetrameric baits, after which the yeast libraries were washed once with 1×PBSM and incubated with 1 μl of anti-c-myc FITC (Miltenyi) per 50 μl of yeast in PBSM. These libraries were washed twice with 1×PBSM and the samples were then sorted on a FACS machine (SH800S Sony). The samples were gated such that all antigen positive cells were collected (gates set such that ~1% streptavidin alone controls fell within the gate). 50,000 cells were sorted in each case, except H5 trispec in which only 10,000 cells were sorted due to overall decreased binding. These libraries were grown for 2 days at 30° C. shaking in SD CAA media and then 100 μl of the cultures were miniprepped (Zymo Research) and transformed into STELLAR Competent Cells (Clontech) and plated on carbenicillin LB agar plates (as per pPNL6's resistance marker). *E. coli* cells that grow should, theoretically, contain only a single sequence from each of the yeast that were sorted above. Fifty *E. coli* colonies from each sort (a total of 100 sequence per antigen due to the fact that the experiment was run in biological duplicate) were sent for sequencing (Sequetech, Mountain View CA). The sequences were then analyzed by sequence alignment using SnapGene software.

B. Overview of ERAS Methods

The H1 hemagglutinin was used as the antigenic protein for the PMD method because it is common for patients to already have antibodies against this antigen. The general breakdown for this method can be seen in FIG. 1A and an exemplary schematic is also shown in FIG. 4A. Essentially, an affinity resin containing a binding partner that binds to the site of interest in the antigenic protein is generated. The binding partner selected for the affinity resin allows for control of the epitope that is protected during the future reaction steps. The antigenic protein and the binding partner are allowed to interact so that the binding partner may bind to the antigenic protein. Next, a modifying reagent, such as a solution of amine reactive PEG, is added and incubated. This reaction should selectively PEGylate (or in other ways modify) exposed portions of the antigen at amino acid residues that the chemistry is intended to target, while retaining the integrity of the binding interface between the binding partner and the antigenic protein. Next the sample is quenched, such that the reactive modifying reagents are removed or neutralized from the solution. The modified antigenic protein is then eluted off the resin. The resulting antigenic protein is a modified immunogen in which the binding site (the site of interest) of the binding partner should remain unmodified while regions exposed, meaning uncovered by the binding partner, should be modified. It is worth noting that this method could have been readily performed by attaching the antigenic protein to the affinity resin instead of the binding partner. The binding partner and the antigenic protein are allowed to interact, and then the modification step would be performed. The binding partner would then be eluted and, the modified antigenic protein would need to be separated from the resin (e.g., by proteolytic cleavage) to produce the soluble modified antigenic protein.

Figure 5A:
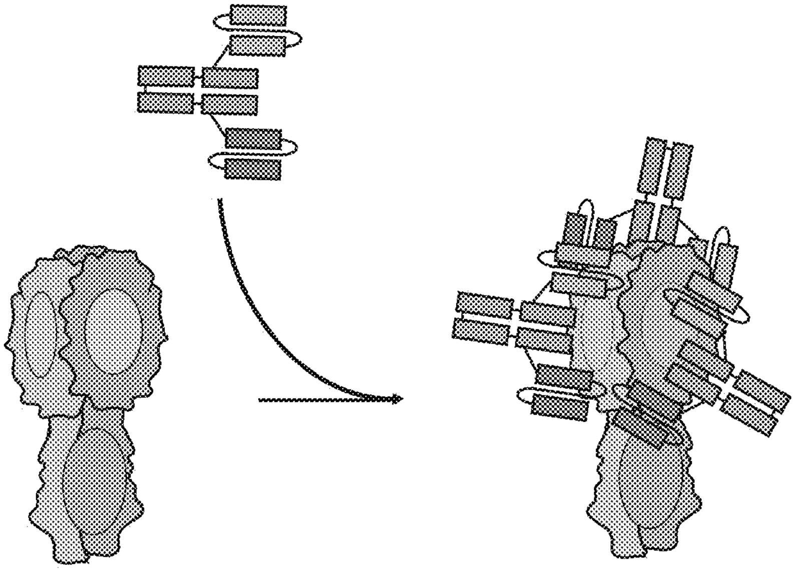
FIG. 5A shows a schematic for production and testing of antigenic protein complexes containing H5 HA using the ES approach according to aspects of this disclosure. The head region of H5 HA was protected using a trispecific antibody (tribody) containing two ScFvs on the N terminus of each half of an Fab.

The H5 hemagglutinin was used as the antigenic protein for the ES method. The general breakdown for this method can be seen in FIG. 1B and an exemplary schematic is also shown in FIG. 5A. In this method, a single linked molecule, a pool of unlinked molecules, or a combination of both types of molecules that can bind specifically to the antigenic protein simultaneously (one or more binding partners) are used to occlude the portion of the antigenic protein that one wishes not to form antibodies against. To assess this method, a tribody antibody (also referred to as a trispecific antibody or a di-scFv-Fab) was created that binds to three sites on the head domain of H5 hemagglutinin. This binding partner was complexed with the antigenic protein H5 HA. When the complex is used to immunize subjects, it should reduce or ablate antibody binding and formation against the head domain of the H5 HA protein but not against the stem domain of the H5 HA protein.

A similar, but more robust, validation path was used for both methods compared to the HEWL case above: (1) solution binding of a variety of different antibodies to the immunogens to demonstrate an ability to regulate binding, (2) a recapitulation of this data via yeast surface display showing that, in the high avidity of the yeast cell surface these results could be maintained, and (3) selecting from a polyclonal yeast library (representative of a simplified immune repertoire) to demonstrate specific enrichment of yeast expressing antibodies that target the site of interest. The final step of the validation process is to immunize subjects with these immunogens and assess whether there is an improved immune response towards the site of interest—in this case, the stem domain of hemagglutinin. Optionally, the B cells from subjects may be sorted to identify which B cells would be stimulated during immunogen delivery and verify their epitope is the target of interest.

C. Production of Modified Antigenic Proteins and Antigenic Protein Complexes

As mentioned, the H1 hemagglutinin protein was used as the antigenic protein for the PMD method. Looking at the sequence of the H1 hemagglutinin, there is an inherent preference for lysine residues on the head compared to the stem. Despite this, there was concern that this number of lysine residues would be insufficient to sufficiently reduce or ablate antibody binding upon modification (in this example, PEGylation). To circumvent this problem, a mutated H1 HA was created containing substitution mutations to add an additional 9 lysine residues on the head of the protein (FIG. 4B, see also FIG. 2G for H1+9 protein sequences). Residues that were mutated were selected based on trying to fill 'holes' (regions of the protein that did not have any lysine residues) and residues that were highly variable and could accommodate a mutation to a lysine residue. Finally, after production of the immunogen, to demonstrate that this new immunogen did have additional conjugatable lysine residues, a fluorescamine assay was conducted. Fluorescamine is a nonfluorescent dye that, upon reaction with exposed (free) amines, becomes fluorescent. Moreover, its reactions with water also produces a nonfluorescent derivative. As shown in FIG. 4C (left most bars), after the addition of the lysine residues to the head there is increased fluorescence upon reaction with fluorescamine. This derivative was therefore selected to be pushed forward.

The resin selected for on-resin PEGylation was derived from Medi8852, a stem directed antibody that covers one of the major lysine residues on the stem for this strain (FIG. 4D). Medi8852 bound with too high affinity to this H1 HA protein, and the antigen could not be eluted off of the resin at any reasonable elution condition. To reduce the binding affinity, multiple Medi8852 derivatives were produced containing alanine substitution mutations in either the heavy chain (HC) or light chain (LC) as described above. These derivatives were screened for improved elution conditions as shown in Table 6 below. A derivative containing two alanine mutations (R52A, Y54A) in the HC was sufficient to improve the elution conditions, permitting removal of the majority of the binding during incubation with 2M potassium thiocyanate (KSCN) (data not shown).

TABLE 6

Results from Elution Condition Screen

| Antibody | 3.5M $MgCl_2$ | 1M KSCN | 2M KSCN | 3M KSCN pH 10.4 | 100 mM trimethylamine pH 10.4 | 25% MeOH pH 10.2 | 100 mM Glycine pH 1.5 |
|---|---|---|---|---|---|---|---|
| WT Medi8852 | − | − | − | − | − | − | ++ |
| 2 Ala Mutant HC Medi 8852 | − | + | +++ | +++ | +++ | +++ | +++ |
| 1 Ala Mutant LC Medi 8852 | − | + | ++ | ++ | ++ | +++ | +++ |
| 2 Ala Mutant HC 1 Ala mutant LC Medi 8852 | + | +++ | +++ | +++ | +++ | +++ | +++ |

Figure 4E:
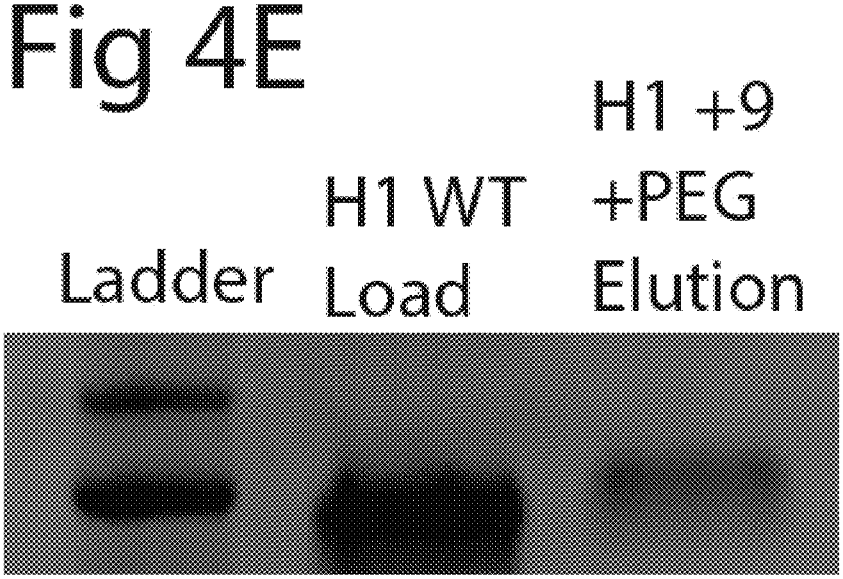
FIG. 4E shows gel analysis of WT H1 HA and H1+9+PEG H1 HA proteins according to some aspects of this disclosure. Upon on resin modification, the H1+9+PEG H1 HA protein has an increased molecular weight compared to the WT protein. This demonstrates that the on-resin modification of lysine residues produced a modified antigen with more PEG residues relative to the WT protein.
Figure 4F:
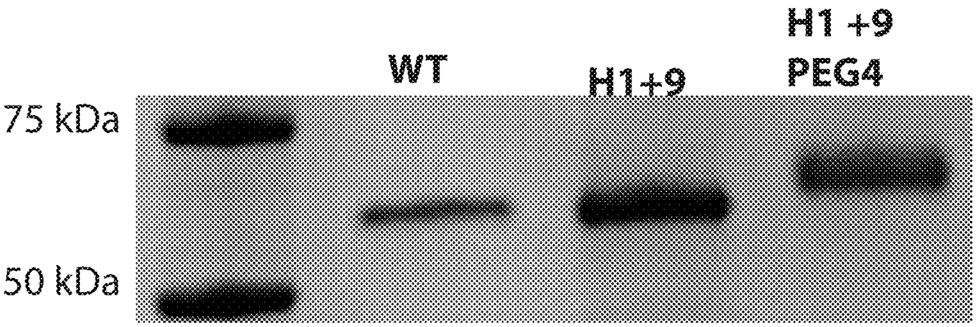
FIG. 4F shows a gel electrophoresis analysis of H1 WT (lane 2), H1+9 (lane 3), and H1+9+PEG (lane 4) proteins according to aspects of this disclosure. H1+9 is a construct in which 9 residues on the head of the hemagglutinin protein of influenza (H1) have been substituted to lysine resides. This substitution was shown not to alter the molecular weight. H1+9+PEG is a modified H1+9 protein that has been PEGylated using NHS-$PEG_4$-Me while bound to a mutated MEDI8852 antibody-resin. H1+9+PEG was shown to have a significant gel shift, implying that the lysine residues of the protein were modified during this process. The first lane is a standard ladder (dual color, Bio-Rad).

− = No elution detected
+ = Some elution upon 30 second exposure to this condition. Screen run by incubating bound complex in condition on biosensor and assessing dissociation.
++ = More than 50% of H1 + 9 eluted off
+++ = Substantially all H1 + 9 eluted off On resin pegylation of the lysine rich H1 derivative (H1+9) using NHS-$PEG_4$-methyl was performed, and the modified antigen (H1+9+PEG) eluted from the resin. A fluorescamine assay was performed to confirm that the majority of the lysine residues were pegylated in the reaction. The H1+9+PEG derivative produced a significantly less fluorescent product (FIG. 4C, middle bar). This was further confirmed by a gel shift observed by SDS-PAGE analysis, indicating that the molecular weight of the protein had increased due to the addition of $PEG_4$-methyl as shown in FIG. 4E. This experiment was repeated comparing all three proteins: H1 HA, H1+9, and H1+9+PEG. As shown in FIG. 4F, H1 HA and H1+9 have an almost identical molecular weight on a gel (electrophoretic pattern) but that H1+9+

PEG has a higher shift. This demonstrates that the lysine substitution did not alter the molecular weight or H1+9+PEG but that the protein was modified with $PEG_4$ on the modification reaction on the resin.

It is important to be sure that the antigenic protein eluted off of the resin maintains its correct three dimensional conformation. This was assessed in three ways: FPLC analysis, melt curve analysis, and circular dichroism (CD) analysis.

Figure 4G:
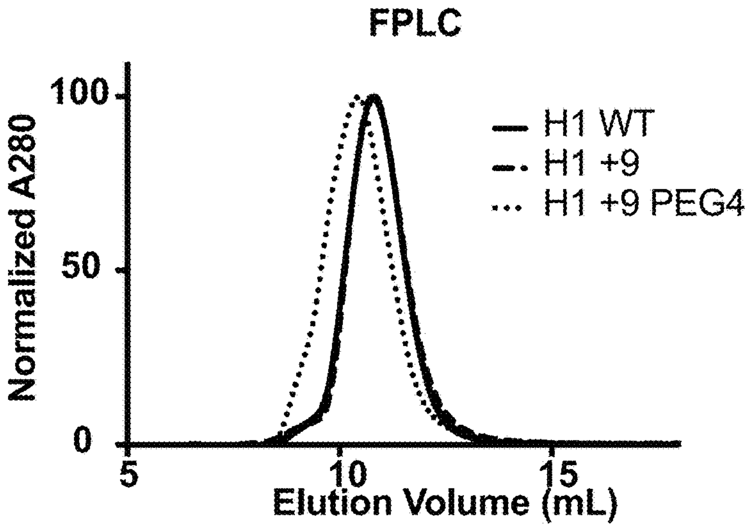
FIG. 4G shows an overlay of FPLC traces of the H1 WT (solid line), H1+9 (dashed line), and H1+9+PEG (dotted line) proteins according to aspects of this disclosure. Samples were run on an ÄKTA Pure Chromatography System using a Superdex™ 200 increase column. Normalization was done using Prism GraphPad. All of the proteins elute at a similar volume (around 12 mL), which implies that they are all trimeric. The shift observed in the elution of the H1+9+PEG protein is expected given that the protein is highly PEGylated as seen in FIG. 4F.
Figure 4H:
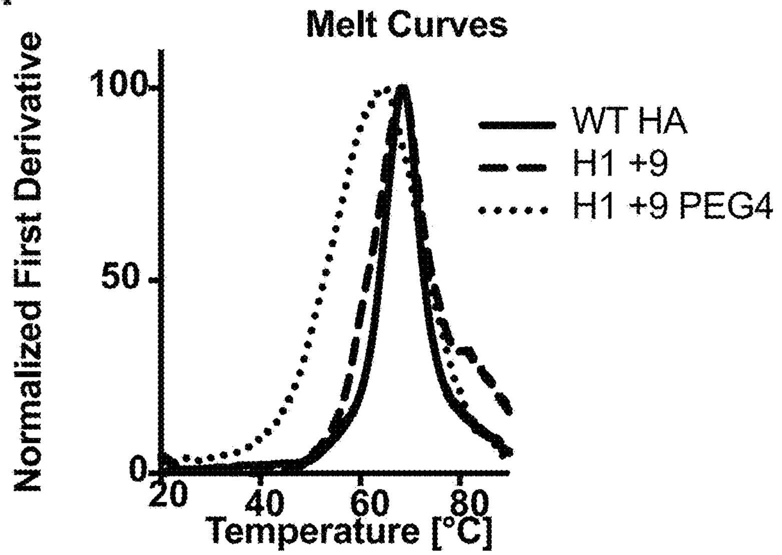
FIG. 4H shows melt curve analysis of H1 WT (solid line), H1+9 (dashed line), and H1+9+PEG (dotted line) according to aspects of this disclosure. The melt curves were determined using the Prometheus NT.48 made by Nanotemper. Samples (~0.1 mg/mL in 0.25×PBS) were loaded into Prometheus NT.Plex nanoDSF Grade High Sensitivity Capillary Chips and the laser intensity was set to 100%. Normalization was done using Prism GraphPad, and the melt curves generated. This data shows that the proteins are all folded and that H1+9+PEG protein melted at a slightly lower temperature, likely because the PEG groups on the protein do a moderate job solubilizing the unfolded state.

FPLC analysis of H1 HA, H1+9, and H1+9+PEG was performed as described above in Section A. As shown in FIG. 4G, looking at the normalized A280 trace, H1 HA and H1+9 have substantially identical elution profiles and they both have a low elution volume (~11-12 mL), suggesting that both proteins are trimeric and that their conformation is not significantly different from each other. This demonstrates that the addition of nine lysine residues in the H1+9 derivative did not impact the ability of the protein to remain a trimer. Also as shown in FIG. 4G, the trace for H1+9+PEG is slightly shifted to a lower elution volume, corresponding to a higher molecular weight. This is expected given that this protein has been modified with the addition of nine $PEG_4$ modifying groups. However, the elution profile is similar to H1 HA and H1+9, suggesting that H1+9+PEG is also a trimer and, thus, PEGylation did not alter the ability to form a trimeric complex.

Figure 4I:
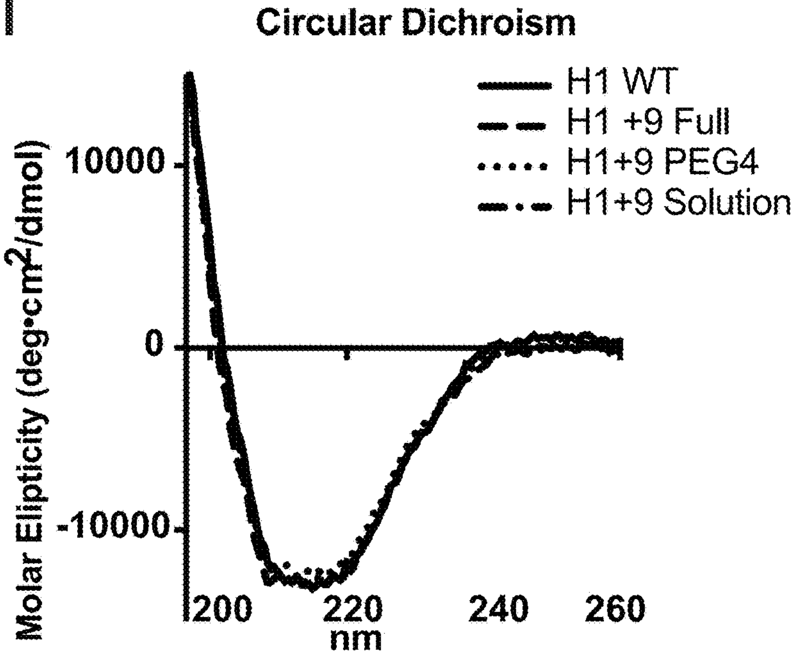
FIG. 4I shows circular dichroism spectroscopy analysis of H1 WT (solid line), H1+9 (dashed line), and H1+9+PEG (dotted line) according to aspects of this disclosure. Proteins (~0.2 mg/mL in 0.25×PBS) were run in on the Jasco J-815 CD spectrometer. Samples were measured every 0.5 nM between 260 nM and 180 nM and run with 5 accumulations. Values were baseline subtracted with the negative control (dialysis buffer alone). Values were then converted to molar ellipticity. The overlay of the spectra indicates that all three proteins are nearly identically folded.
Figure 4J:
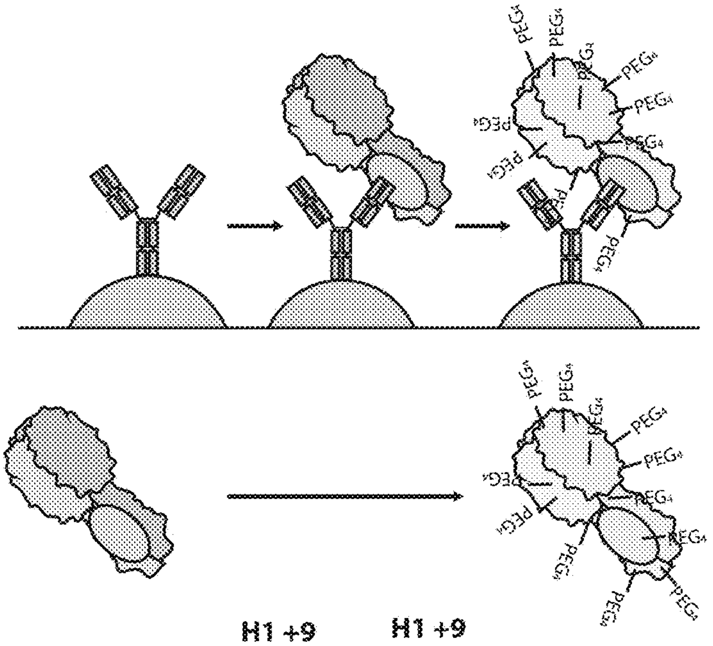
FIG. 4J shows a schematic comparing of a modification reaction (e.g., PEGylation) performed by the PMD method (e.g., producing H1+9+PEG) and a modification reaction (e.g., PEGylation) performed in solution (e.g., producing H1+9 Full) according to aspects of this disclosure.
Figure 4K:
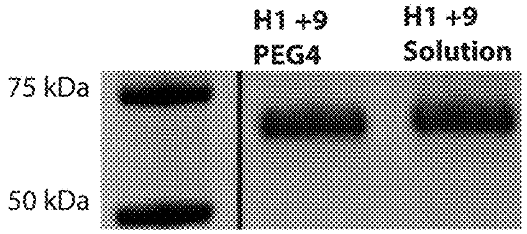
FIG. 4K shows an SDS page gel comparing the sizes of H1+9+PEG (lane 2) and H1+9 Full (lane 3). The first lane is a standard ladder (dual color; Bio-Rad). The migration patterns indicate a slight increase in molecular weight of H1+9 Full compared to H1+9+PEG, reflecting that the protein is PEGylated more extensively than the H1+9+PEG. This indicates that protection of the MEDI8852 epitope when the protein is bound to the MEDI8852 mutant-resin shields some lysine residues from modification.
Figure 4L:
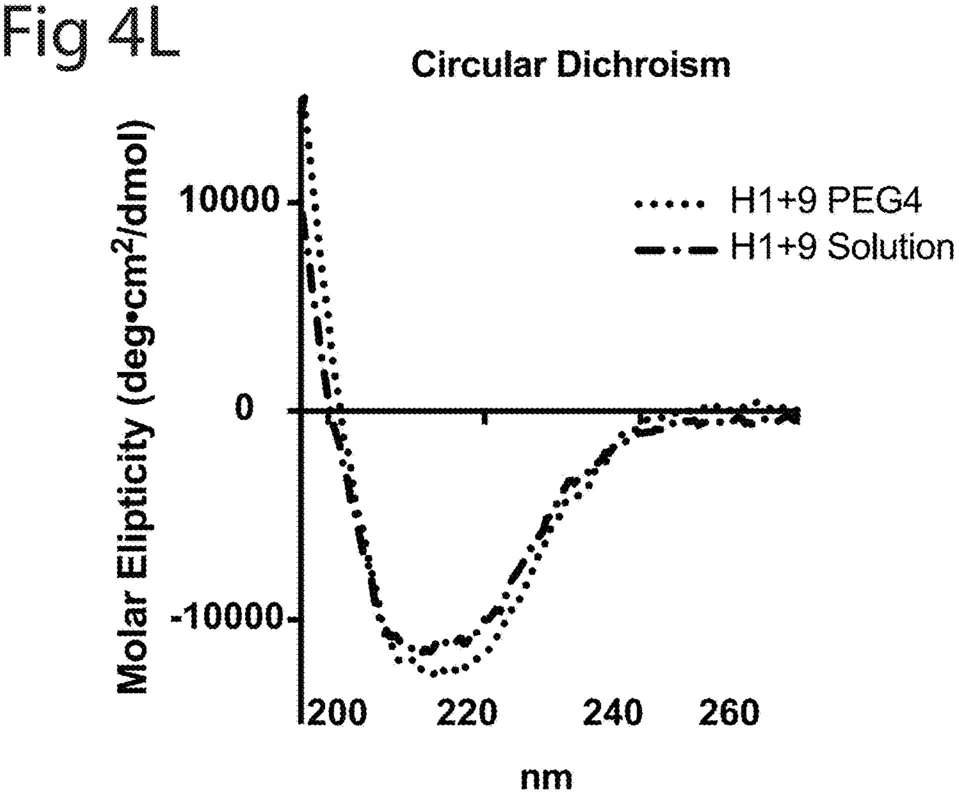
FIG. 4L shows circular dichroism spectroscopy analysis of H1+9+PEG (dotted) and H1+9 Full (dash-dotted) according to aspects of this disclosure. Values are plotted as molar ellipticity, conducted as described above for FIG. 4I. There is a slight discrepancy between the two spectra, implying that the H1+9 Full protein is in a different conformation than the H1+9+PEG protein. This demonstrates the need for the protecting antibody to retain the protein conformation.
Figure 4M:
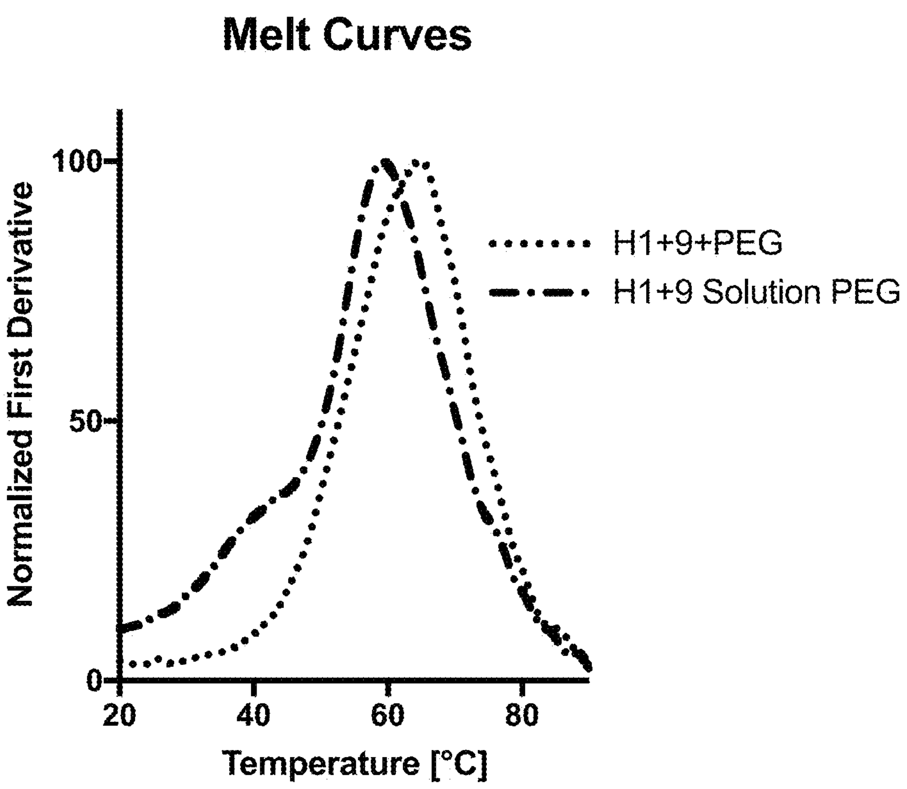
FIG. 4M shows melt curve analysis of H1+9+PEG (dotted) and H1+9 Full (dash-dotted) according to aspects of this disclosure. Melt curves were determined as described for FIG. 4H. The melt curve of H1+9+PEG is clearly shifted to a lower temperature as compared to the melt curve for H1+9 Full. This suggests that H1+9 Full could be in a more unfolded state or is less stable. Moreover, there is an evident shoulder suggesting the H1+9 Full sample is nonhomogeneous.

Melt curve analysis was performed using the Prometheus NT.48 Protein Stability Instrument (NanoTemper Technologies). The melting profiles of H1 HA, H1+9, H1+9+PEG, and H1+9 Full were analyzed. H1+9 Full is simply H1+9 PEGylated in solution (in the absence of protecting antibody) see schematic comparing the preparation of these two proteins in FIG. 4J. Interestingly, as shown in FIG. 4K, there is a subtle but apparent gel shift when comparing H1+9+PEG to H1+9 Full. In the melt curve analysis, it is expected that, as proteins unfold with increased temperature, tryptophan residues hidden in the folded protein become more exposed as the protein denatures, thereby changing the fluorescence (A280). As shown in FIG. 411, each of H1 HA, H1+9, and H1+9+PEG all melt at approximately the same temperature but there is a clear shift to a lower melting temperature for H1+9+PEG (dotted line). This observation can be explained in that the unfolded protein of the modified protein would likely be stabilized given the solubility of PEG chains. Interestingly, here a further shift is seen between H1+9+PEG and H1+9 Full as shown in FIG. 4M. The H1+9 Full derivative has both a lower melting temperature and also a clear shoulder, suggesting that the protein may be less stable than the resin-produced H1+9+PEG.

The FPLC and melt curve experiments demonstrated that all of the proteins are trimeric and that they are folded to some extent. However, these experiments do not demonstrate that the proteins are folded in the same way. To analyze this, circular dichroism spectroscopy was used. The proteins were assessed using a J-815 CD spectrophotometer. Samples were baseline subtracted with a buffer alone sample and converted to molar ellipticity using their concentration and molecular weight. As shown in FIG. 4I, the CD curves for H1 HA, H1+9, and H1+9+PEG overlay almost exactly, indicating that the proteins are in substantially the same conformation. Interestingly, however, the CD curves for H1+9+PEG and H1+9 Full do not align as well. The curve for H1+9 Full has a slightly different shape and slope as compared to H1+9+PEG. This suggests that the modification of H1+9 Full in solution altered the folding structure of the protein relative to the resin-produced H1+9+PEG for which the epitope of interest was protected. Thus, this analysis also demonstrates the importance of the protecting antibody in production of modified antigenic proteins produced using the PMD method.

Figure 5B:
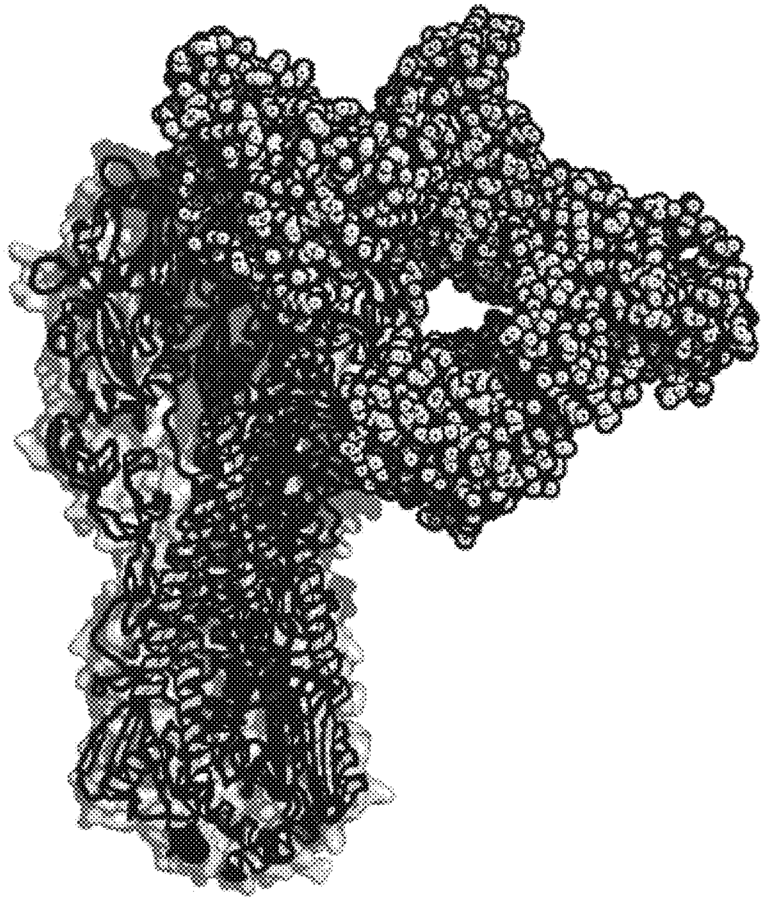
FIG. 5B shows Pymol modeling of these three binding partners bound at the same time according to aspects of this disclosure. The binding is depicted for only one of the HA subunits in the trimer.
Figure 5C:
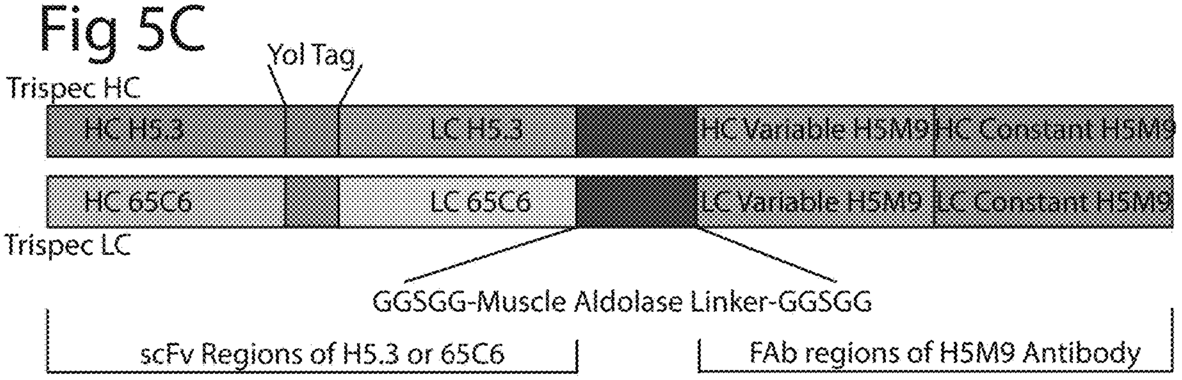
FIG. 5C shows a schematic representation of the H5 HA tribody according to aspects of this disclosure.
Figure 5D:
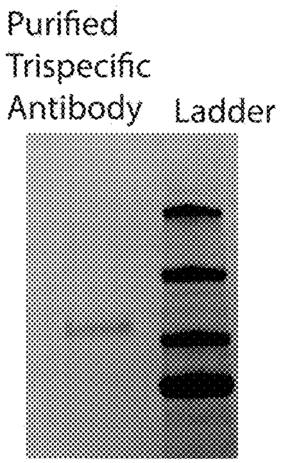
FIG. 5D shows gel analysis demonstrating the purified tribody protein used in subsequent analyses.
Figure 5E:
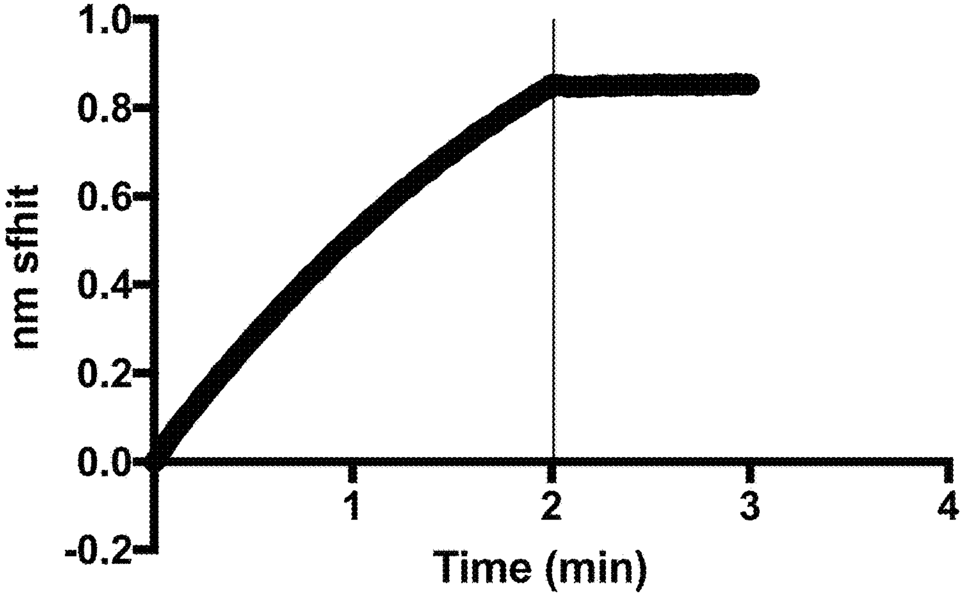
FIG. 5E shows binding of this trispecific antibody (30 nM) to biotinylated H5 HA as assessed in a biolayer interferometry binding assay using a ForteBio Octet® biosensor.

As mentioned, the H5 hemagglutinin protein was used as the antigenic protein for the ES method (scheme in FIG. 5A). A trispecific antibody (tribody) against the head of H5 hemagglutinin was created. This trispecific antibody binds at three distinct epitopes and should be able to ablate binding of head directed antibodies as shown in FIG. 5B. This trispecific antibody was made by putting a different scFv on the N terminus of each of the arms of the FAb of H5M9 (construct design in shown in FIG. 5C). This tribody conjugate was cloned, expressed, and purified (as shown in FIG. 5D) and demonstrated to have high affinity binding for H5 HA (as shown in FIG. 5E).

D. In Vitro Antibody Binding to Modified H1 HA and H5 HA-Tribody Complex

Figure 6A:
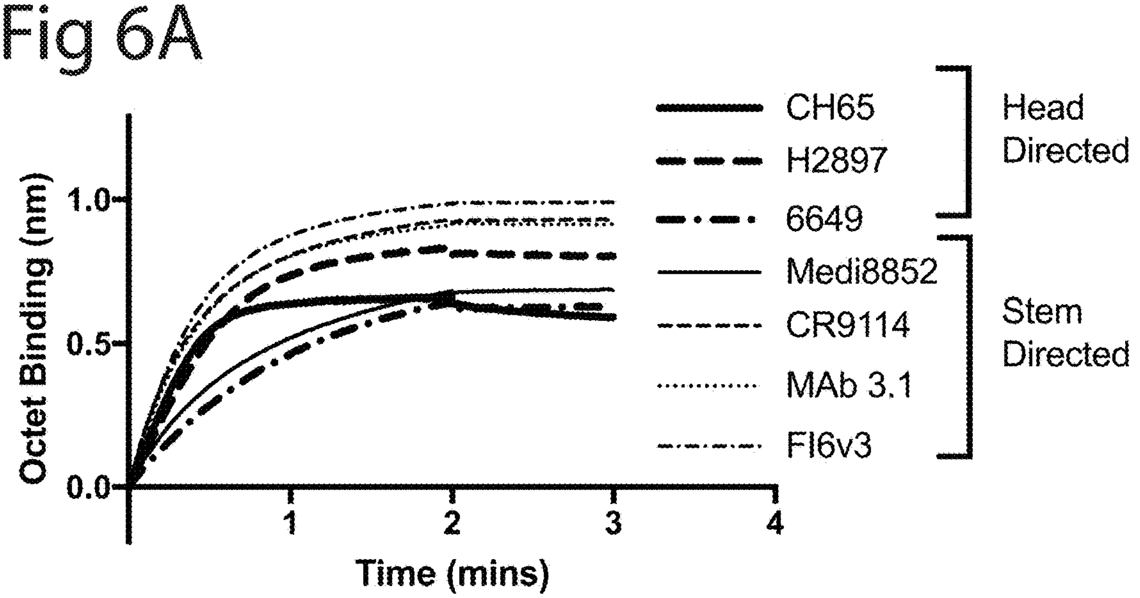
FIGS. 6A-6C show competition binding analysis of H1 HA antigenic proteins generated using the PMD approach in biolayer interferometry binding assays using a ForteBio Octet® biosensor according to aspects of this disclosure. Four stem directed antibodies and three head directed antibodies were assessed for each of WT H1 HA and H1+9+PEG.
Figure 6B:
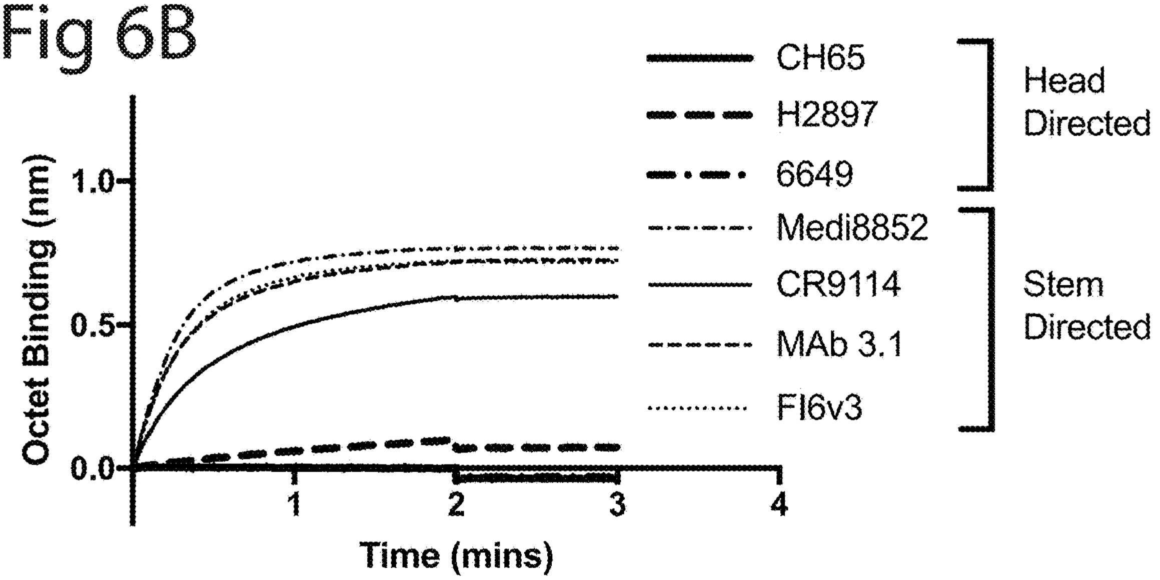
Figure 6C:
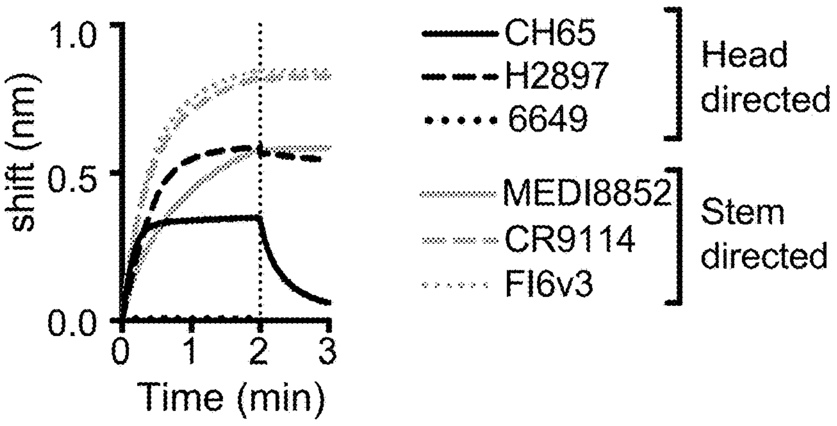
Figure 7A:
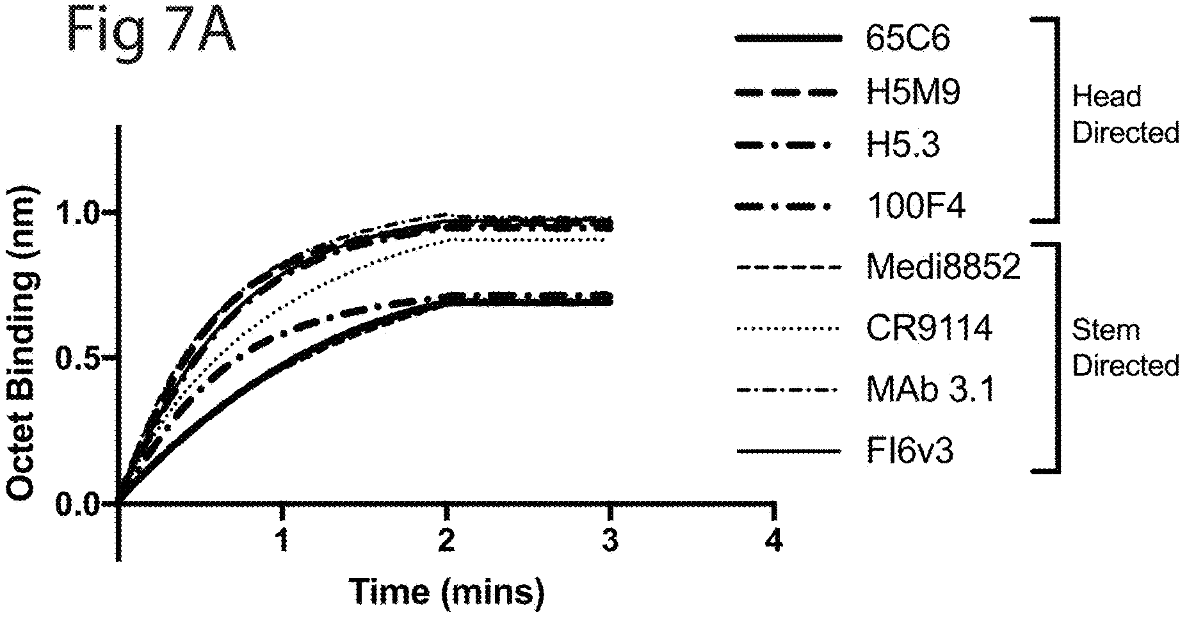
FIGS. 7A-7B show competition binding analysis of H5 HA antigenic protein complexes generated using the ES approach in a biolayer interferometry binding assay using a ForteBio Octet® biosensor according to aspects of this disclosure. Four stem directed antibodies and four head directed antibodies were assessed for each of WT H5 HA and H5 HA-trispecifc complex.
Figure 7B:
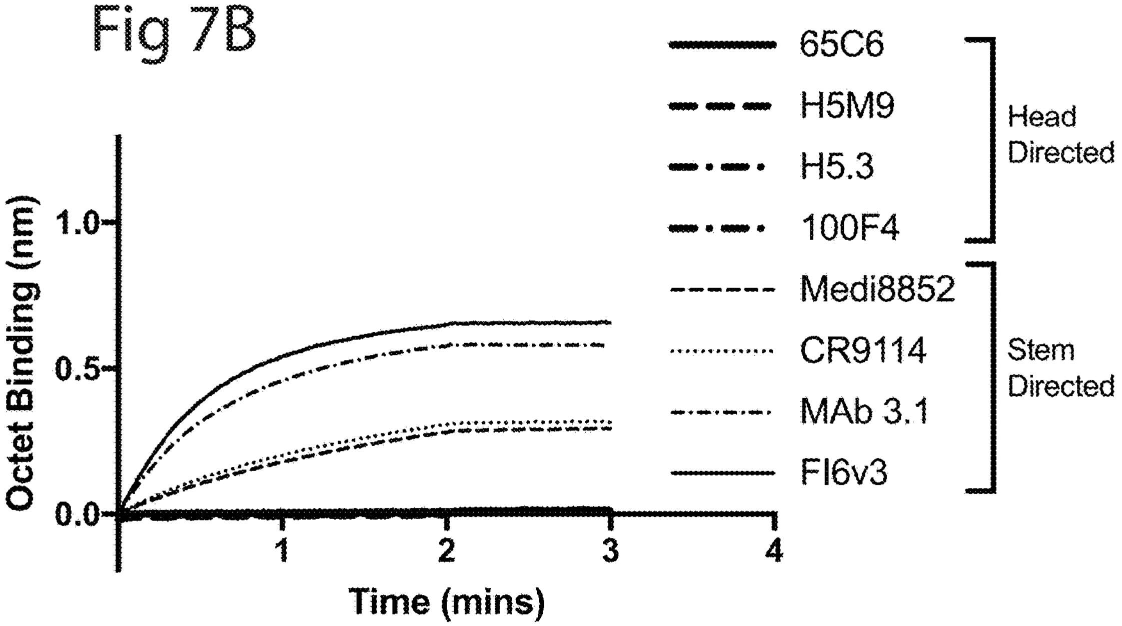

These two constructs, H1 hemagglutinin with 9 additional lysine residues that was PEGylated on resin (H1+9+PEG) and trispecific protected H5 hemagglutinin (H5 Trispec) were tested to determine if they could ablate antibody binding towards the head of HA and retain binding of stem directed antibodies. To test this, the binding of antibodies that targeted either the head or the stem to either the WT immunogens (H1WT and H5 WT), the H1+9 immunogen, or to the modified immunogens (H1+9+PEG and H5 Trispec) was compared using biolayer interferometry binding assays using ForteBio Octet® biosensors. As shown in FIGS. 6A-6C and FIGS. 7A-7B, clear ablation of antibodies binding the head was observed for modified immunogens but all the stem directed antibodies retained their binding in the case of both immunogens. The H1+9 immunogen decreased head antibody binding but did not show ablation, as shown in FIG. 6C. For the ES antigen (H5 Trispec). a moderate decrease in binding of stem directed antibodies was observed, which may be due to the additional steric occlusion of the trispecific towards antibody approach angles. This experiment clearly demonstrated that both of these antigens, meaning H1+9+PEG and H5 Trispec, block binding of head directed antibodies but retain binding to stem directed antibodies.

Figure 18A:
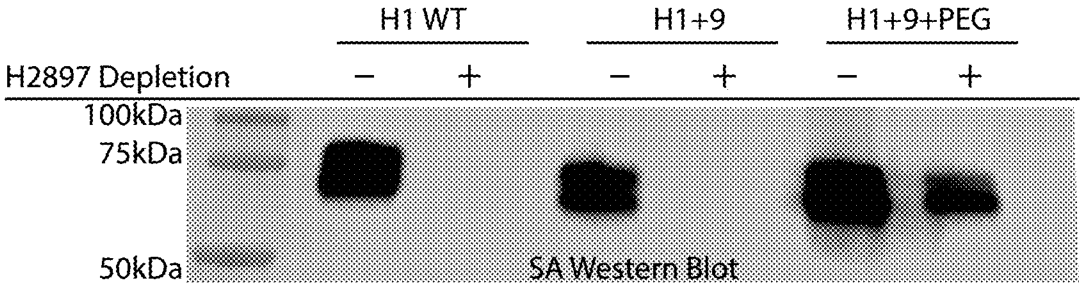
FIGS. 18A-18C.
Figure 18B:
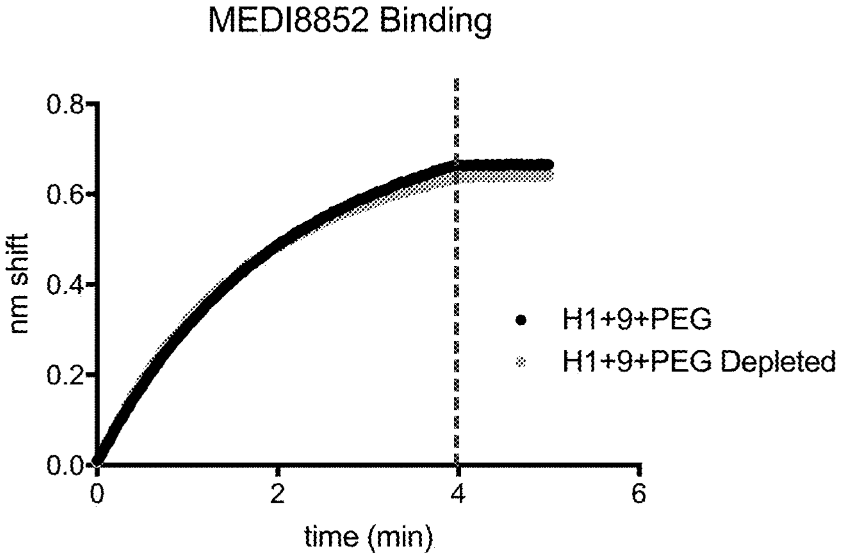
Figure 18C:
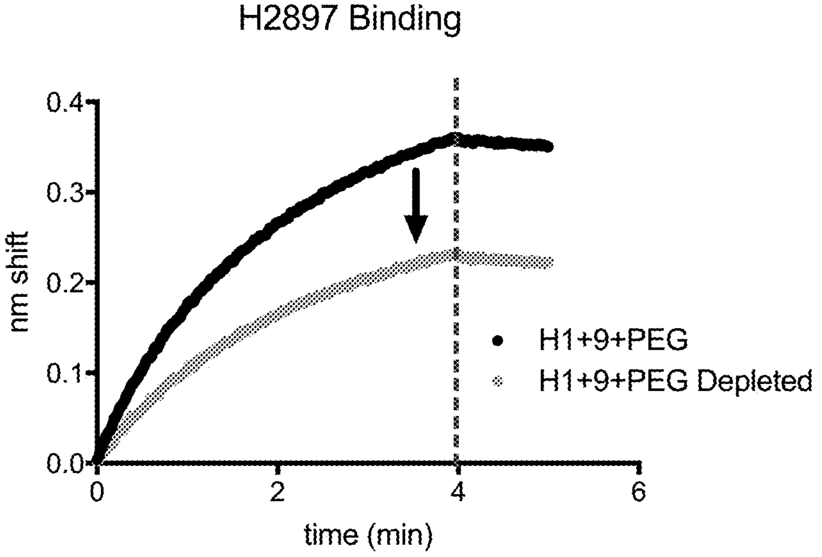

In the case of the H1+9+PEG immunogen, one head directed antibody (H2897) still showed a slight binding after PEGylation. This antigenic site is considered a ‘hole’ in that H2897 retains its antigenicity even after modification. It is expected that ‘holes’ can occur in two different ways. In one case, the hole can be a result of incomplete PEGylation at a site such that, of the proteins in solution following modification, some of the proteins are modified and others are not. This would be comparable to mixing a fully modified solution with a solution in which one site is unmodified. In another case, an antigenic hole may arise when a protein is fully PEGylated (PEGylation is complete) but the PEG moiety does not decrease affinity of the probing antibody or decreases the affinity to only a limited extent. To investigate which of these phenomena may be at issue with respect to the observed slight binding of H2897 antibody to H1+9+PEG, a further experiment was performed. The H2897 antibody was used to deplete protein solution samples of either H1 WT, H1+9, and H1+9+PEG, which should remove proteins from solution that bind with high affinity to H2897. As shown in FIG. 18A, the samples of H1 WT and H1+9 were depleted of all protein by the H2897 antibody but there was only partial depletion of the H1+9+PEG sample. This H1+9+PEG protein solution was then further probed for binding to H2897 or MEDI885 and was found to have decreased affinity for H2897 (FIG. 18B) but retention of binding to MEDI8852 (FIG. 18C). Thus, the 'hole' observed for H2897 antibody binding to the H1+9+PEG immunogen is likely a combination of the two causes outlined above.

Figure 4N:
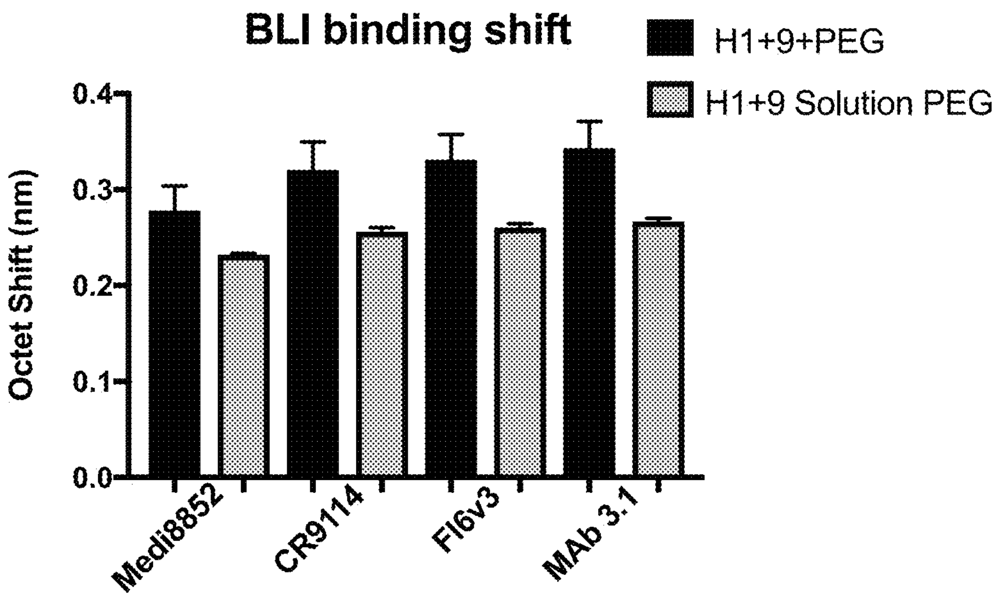
FIG. 4N shows biolayer interferometry binding analysis of four stem-directed antibodies to H1+9+PEG (black) and H1+9 Full (grey). The antibodies tested were Medi8852, CR9114, FI6v3, and MaB3.1. The graphs show the wavelength shift at the final time point in the association step. HIS1K octet biosensors (tips) were loaded in PBST BSA with either H1+9+PEG or H1+9 Full to a shift of 0.2 nM. The resulting tips were associated for 2 mins in PBST BSA in 100 nM of the antibodies (individually), and the values were baseline subtracted using the control tip value (tip loaded with protein but not incubated with antibody). The lower shift observed for the H1+9 Full for each of the antibodies indicates that the antibodies bound more weakly or there was less folded protein in the sample. This is consistent with the data shown in FIGS. 4K-4N, which shows that H1+9+PEG is properly folded and H1+9 Full is misfolded. This demonstrates the importance of utilising the protecting antibody (MEDI8852 mutant) during the modification step of the PMD protocol in retaining antigen conformation.

The above experiment was also performed using H1+9 Full (PEGylated in solution). Interestingly, and consistent with the results described above that the protein has an altered conformation (CD analysis) and had a lower melt temperature, H1+9 Full decreased stem antibody binding more than H1+9+PEG as shown in FIG. 4N. Combined, these results indicate that H1+9 Full is in a slightly different conformation that H1+9+PEG, which further demonstrates the importance of the protecting antibody in retaining antigen protein conformation during the PMD process.

E. Cell-Based Antibody Binding to Modified H1 HA and H5 HA-Tribody Complex

Figure 8A:
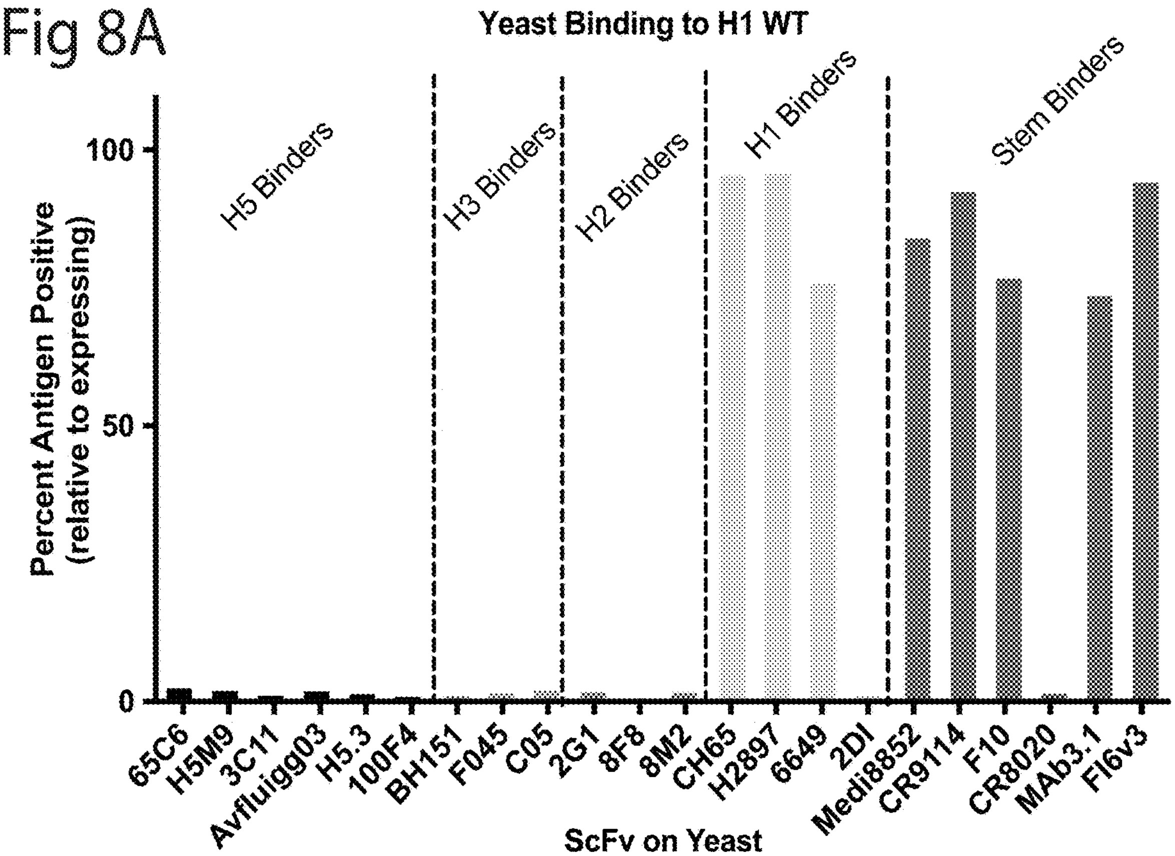
FIGS. 8A-8B shows scFv Yeast Surface Display Competition analysis of H1 HA following the PMD approach according to aspects of this disclosure. 22 yeast clones expressing scFvs to either the head of H5, H3, H2, or H1, or the stem of hemagglutinin were subject to flow cytometry with either antigen.
Figure 8B:
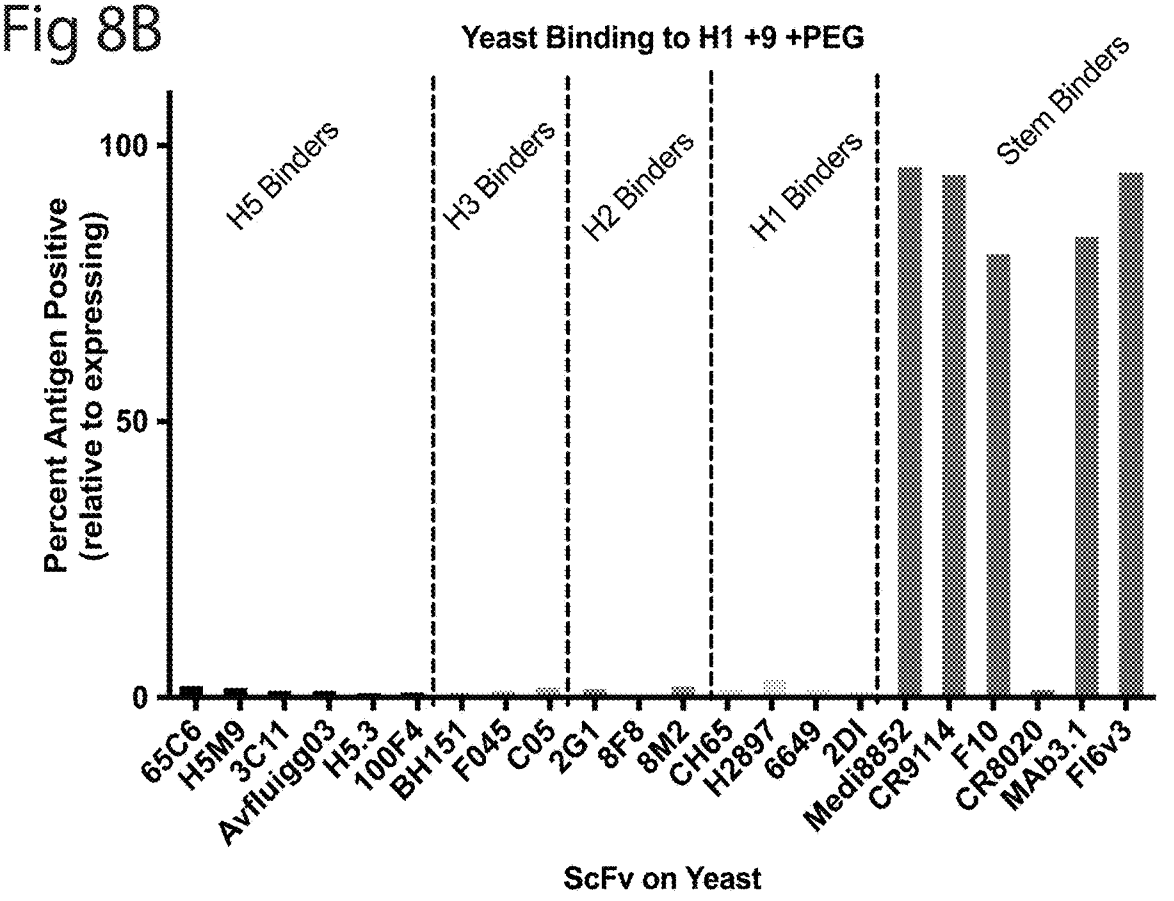
Figure 9A:
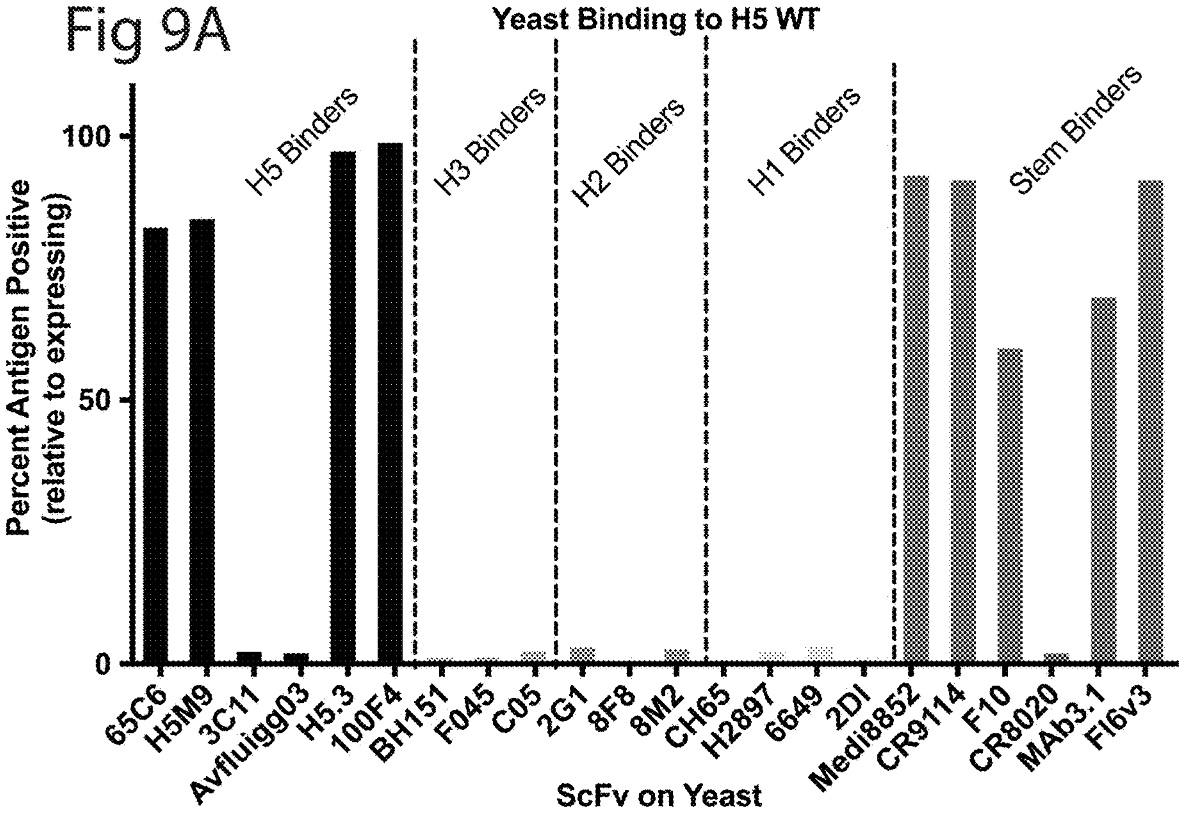
FIGS. 9A-9B shows scFv Yeast Surface Display Competition analysis of H5 HA following the ES approach using the tribody described in FIG. 5C-5D according to aspects of this disclosure. Twenty-22 yeast clones expressing scFvs to either the head of H5, H3, H2, or H1, or the stem of hemagglutinin were subject to flow cytometry with either antigen.
Figure 9B:
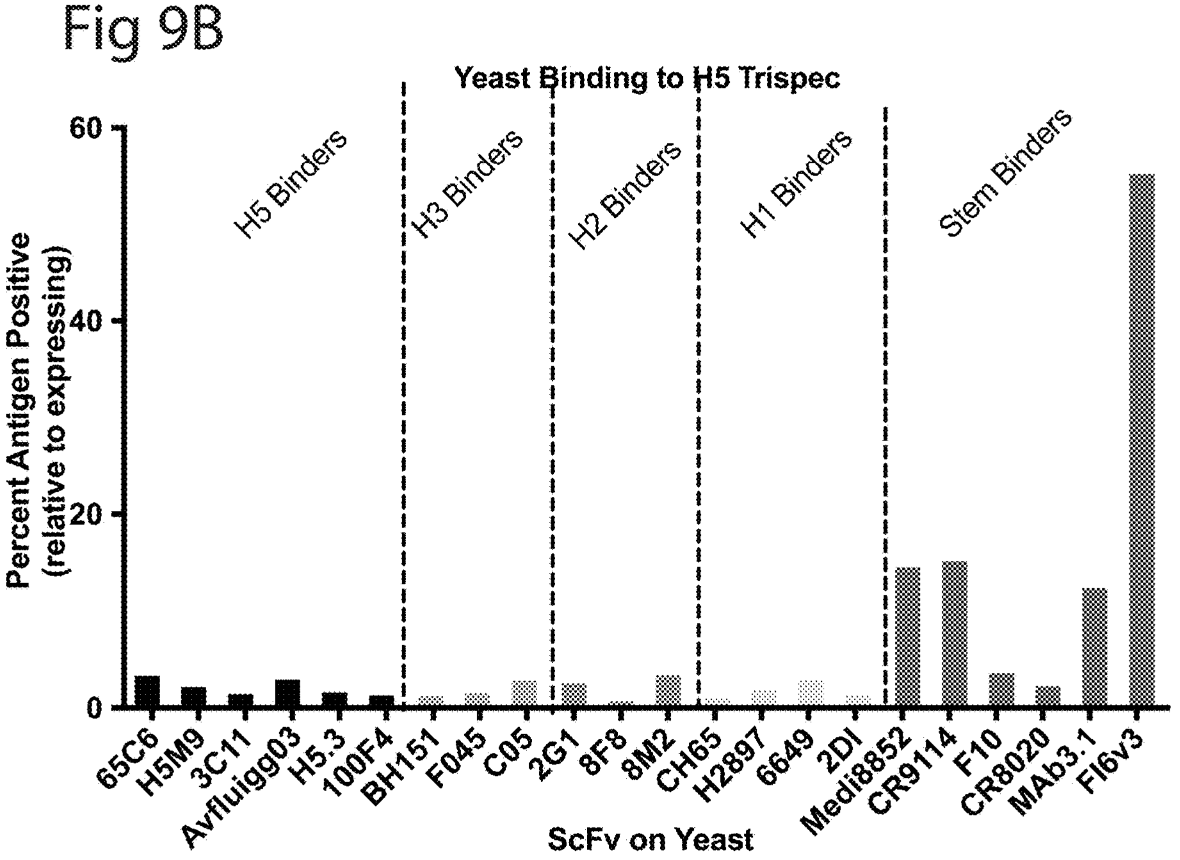

Given that B cells express many copies of their BCRs on their cell surface, an experiment was designed to assess whether in such a higher avidity setting, the same level of selectivity between head and stem directed antibodies could be observed as was seen in the Octet® biolayer interferometry experiments. For this experiment, an attempt was made to simulate the human memory B cell repertoire by producing twenty-two different yeast clones expressing different scFvs on their surface. This repertoire contains a range of scFvs targeting hemagglutinin heads of H5, H3, H2, and H1 as well as stem directed scFv. These clones are described in Table 5. These clones were used to assess whether the level of selectivity observed in vitro could be obtained on a living cell surface. The 22 clones were each individually incubated with each of the four antigens (H1 WT, H1+9+PEG, H5 WT, and H5 Trispec), and flow cytometry was used to determine the percentage of cells that bound the antigen. A distinct separation between head directed and stem directed clones was observed. While many of the head directed scFvs bound with high efficiency to their respective WT antigens as shown in FIG. 8A and FIG. 9A, none of them bound above background to the modified immunogens as shown in FIG. 8B and FIG. 9B. In contrast, the yeast expressing stem directed scFvs retained binding to the modified immunogens. Again, the trispecific antibody appeared to moderately decrease binding of the stem directed clones, likely due to steric occlusion. We suspect that some of the head directed clones didn't bind to their WT antigens due to the high sequence diversity of the head region and it is likely that the epitopes of these scFvs is not conserved within the antigen selected.

Figure 10A:
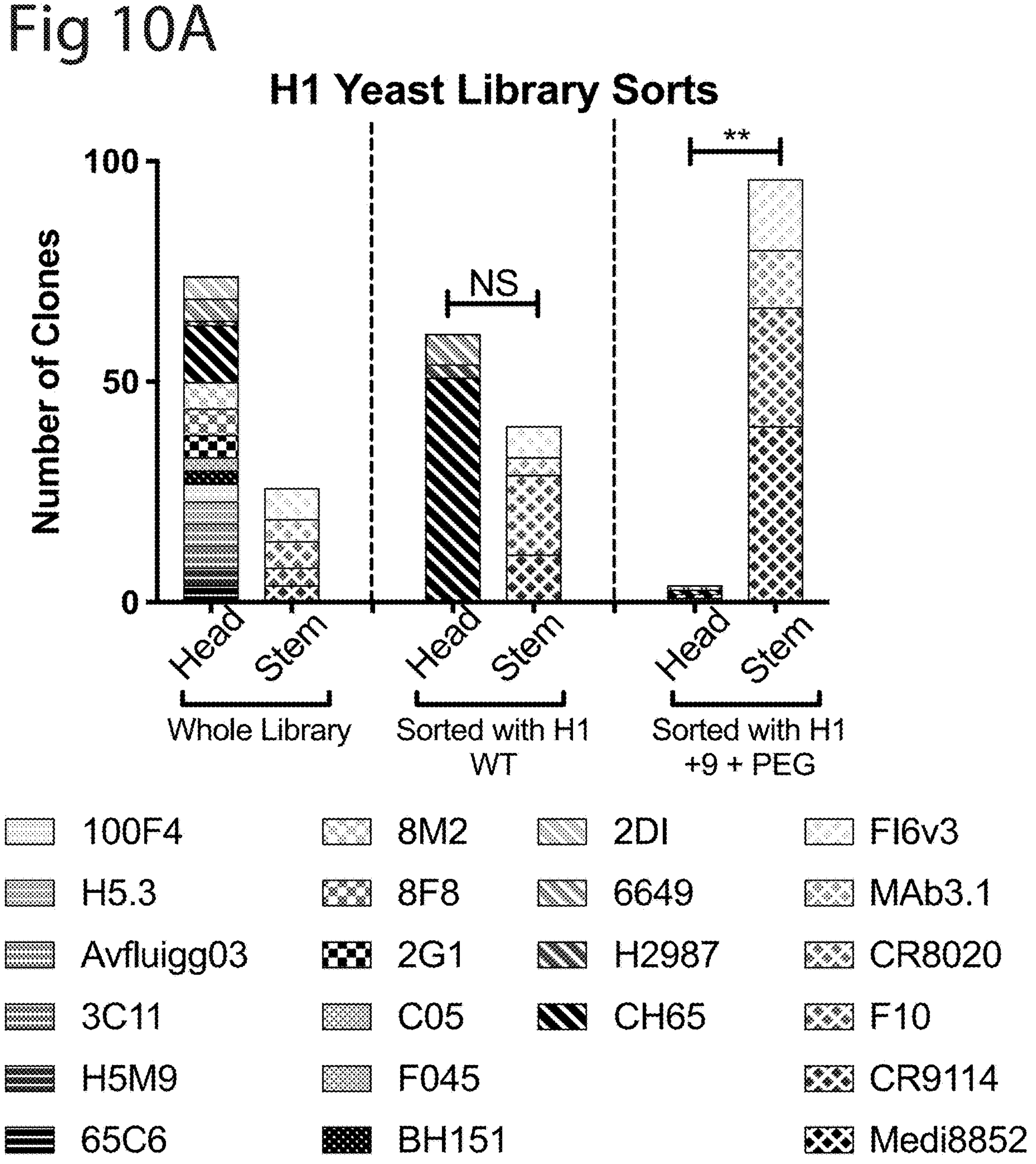
FIGS. 10A-10B-3 shows scFv Yeast Surface Display Competition of a polyclonal yeast library using an antigenic protein generated using the PMD approach according to some aspects of this disclosure. The 22 yeast clones expressing scFvs to either the head of H5, H3, H2, or H1, or the stem of hemagglutinin were combined at near equimolar ratio, as demonstrated by the sequencing (two left most bars).
Figures 1, 10B:
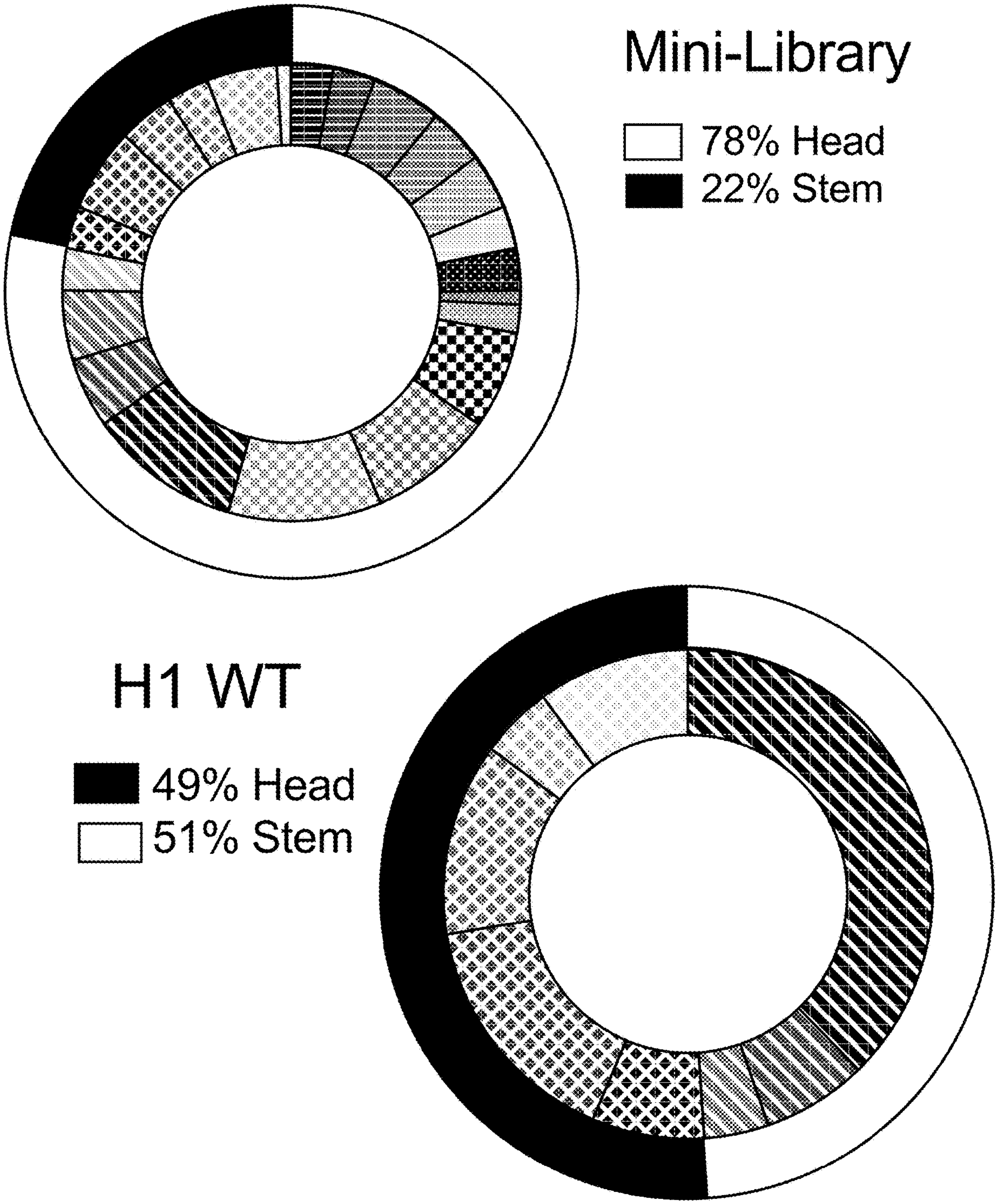
Figures 2, 10B:
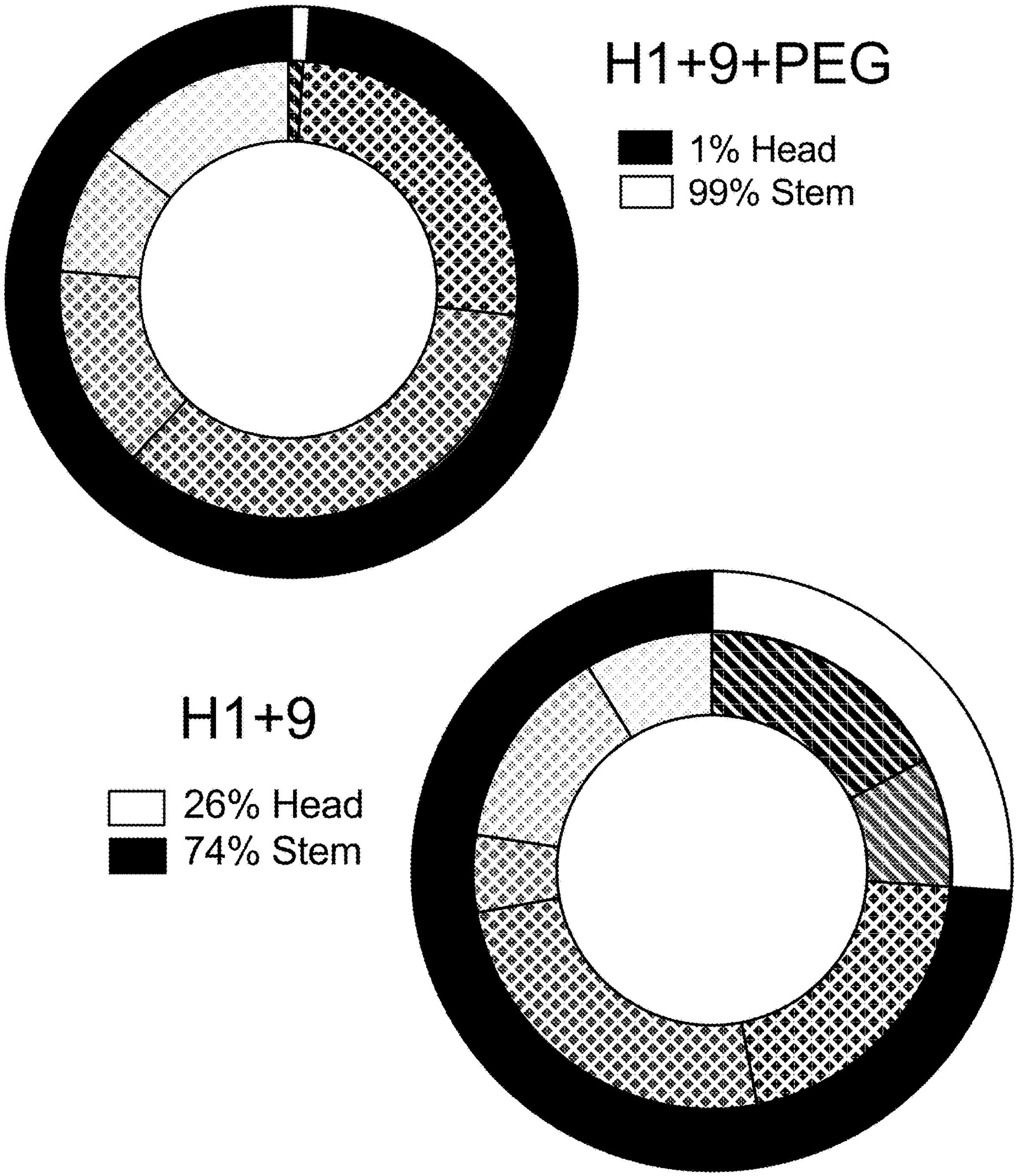
Figures 3, 10B:
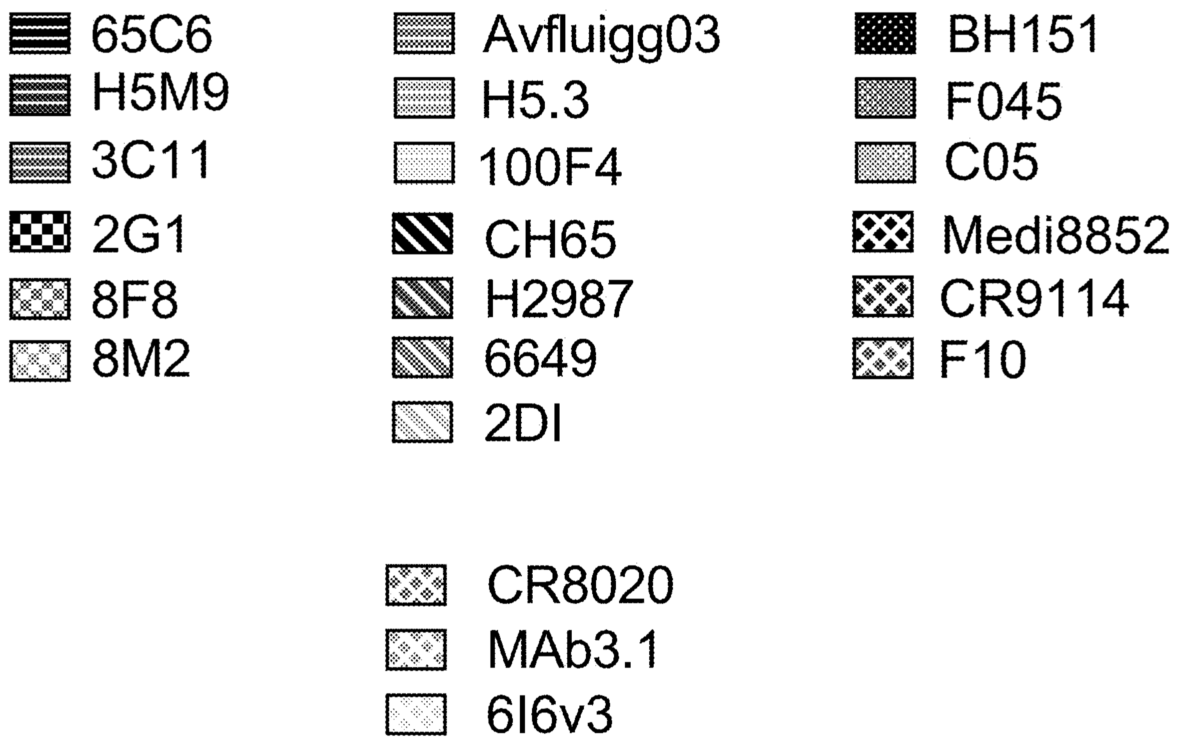
Figure 11:
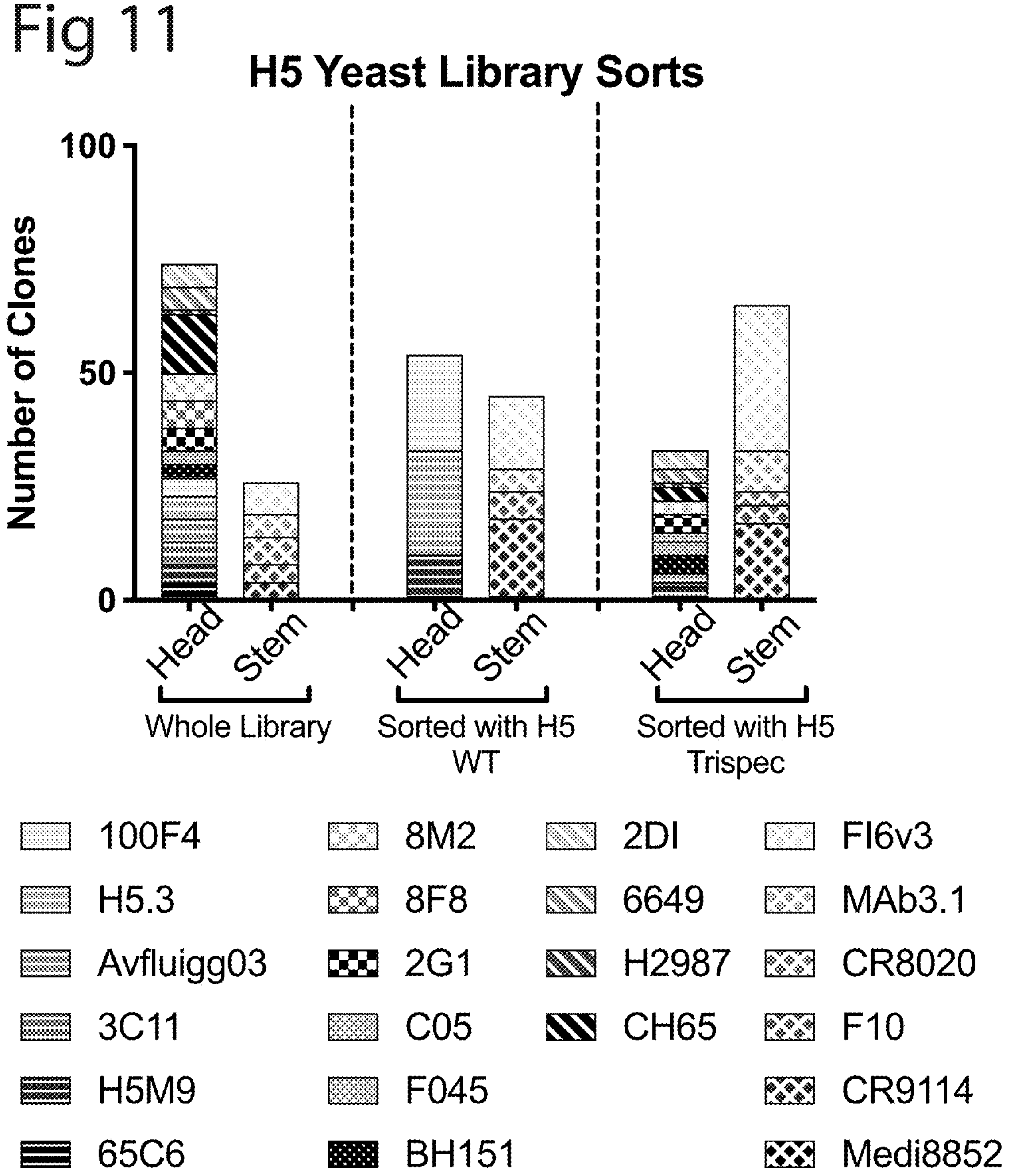
FIG. 11 shows scFv Yeast Surface Display Competition of a polyclonal yeast library using an antigenic protein complex generated using the ES approach according to some aspects of this disclosure. 22 yeast clones expressing scFvs to either the head of H5, H3, H2, or H1, or the stem of hemagglutinin were combined at near equimolar ratio, as demonstrated by the sequencing (two left most bars). These pooled yeast clones were then subjected to one of the biotinylated baits: H5 WT or H5 Trispec at 12.5 nM tetramer and an antibody binding to the c-myc tag. The c-myc tag is at the C-terminal end of the scFv and indicates the yeast are expressing full length scFvs. The yeast were then sorted for all antigen positive cells. Positive gates were set such that ~1% of the streptavidin alone control fell within antigen positive gate. The resultant populations from either the whole library (left most bars), the H5 WT (middle bars), or H5 Trispec (right most bars) were sequenced. This analysis demonstrates enrichment of stem directed antibodies as reflected in the right most bars.

Another experiment was designed to more closely resemble the native immune repertoire. All twenty-two clones were combined to create a pooled library of all 22 yeast clones. This pooled repertoire permitted assessing the binding of clones to antigens in the presence of clones binding at other sites. This pooled repertoire resembles a native immune system where patients would have B cells targeting all of these epitopes, and a stem-directed immunogen would need to preferentially stimulate stem directed clones over head-directed clones. Binding in this assay conceptually could act a surrogate for stimulation of stem directed B cells in an actual patient repertoire. To conduct this experiment, all the yeast clones were pooled at a near equimolar ratio as shown in FIGS. 10A-10B-3 and FIG. 11 (left most bars of each). The library production and antigen dilution portion of this experiment was conducted in biological duplicate. Such that the experiment was run twice to ensure the results weren't due to any error in library production. These pools of clones were then incubated with each of the four antigens, in biological duplicate. The pooled yeast were then sorted, collecting all antigen positive cells. Gates were set as before, such that ~1% of yeast fell into the antigen positive gate for the streptavidin alone control. The yeast that fell into the antigen positive gate were grown in SD-CAA for 2 days at 30° C. and miniprepped (Zymo Research) and resulting DNA was transformed into *E. coli* to allow for an understanding of the quantity of each clone that was isolated from the sort. 50 clones from each of the biological duplicates was sequenced such that 100 total sequences from each antigen sort were produced. The entire library showed no specificity for either head or stem directed clones and showed a good diversity of clones represented. Upon sorting with either of the WT antigens (H1 WT or H5 WT) there was enrichment for both head directed antibodies against these antigens (head directed clones against H1 or H5 respectively) as shown in FIGS. 10A-10B-3 and FIG. 11 (middle bars of each). Upon sorting with either of the modified immunogens, however, there was enrichment of stem directed clones compared to head directed clones as shown in FIGS. 10A-10B-3 and FIG. 11 (right most bars of each). This data demonstrates that both of these immunogens were able to specifically enrich for stem directed yeast clones in a pooled yeast library, suggesting that in an immunization setting they could specifically stimulate stem directed B cells while not stimulating head directed B cells. An additional replicate of this experiment was performed for the H1 WT and H1+9+PEG immunogens and further included the H1+9 immunogen. As shown in FIGS. 10B-1-10B-3, the results are functionally the same as the prior analysis but it is clear that there is slightly decreased binding of head binding clones to the H1+9 immunogen but some slight binding is still retained, while the H1+9+PEG immunogen shows almost complete removal of head directed clones.

F. B Cell Sorting with H1 WT, H1+9+PEG, 115 WT, 115 Trispec

Human PBMCs Isolation: Human PBMCs were isolated by taking whole human blood (~30 mL) and gently layering it on top of Ficoll (Sigma Aldrich). The sample was centrifuged at 400 g for 30-40 mins at 18-22° C. This produced a layer of human peripheral blood mononuclear cells (PBMCs) which was isolated, washed 1× in RPMI, and resuspended at 20 million cells per mL in RPMI with 10% DMSO. Cells were kept as a single donor, meaning cells from multiple donors were not pooled. Cells were be slowly frozen down (1° C. per minute until the temperatures is −80° C. using a Mr. Frosty™, ThermoFisher) and then stored in liquid nitrogen.

On the day of the experiment, tubes containing harvested PBMCs were thawed, cells were washed with PBSM and resuspended in PBSM containing 12.5 nM tetrameric bait of either H1 HA (the WT protein) or H1+9+PEG (the PMD antigen) as described above for yeast binding experiments. In each tube, cells were also stained with an assortment of antibody fluorophore conjugates so that the cells could be gated on the Sony cell sorter (SH800S) for antigen positive memory B cells. Cells were incubated in this cocktail for 1 hour, washed 2× in PBSM, and resuspended in 400 μL PBSM with 40 μL SYTOX™ dead cell stain. The cells were sorted on the SH800S and antigen positive B cells were single cell sorted directly into lysis buffer containing Triton X200 and RNAse inhibitor.

The isolated human memory B cells that bound to the antigen of interest (either H1 WT or H1+9+PEG) were single cell sequenced using the (MiSeq) protocol as per the manufacturer's recommendation, which first requires RT PCR using an oligo dT primer and a template swapping primer to produce double stranded cDNA with known ends.

This cDNA is then amplified with either a cocktail of primers to amplify the HC, or a cocktail of primers to amplify the light chain, and these individual PCR products are then sent for sequencing. Sequences of the antibodies from these isolated B cells were then cloned into the CMV/R plasmid backbone as previously described and expressed in Expi 293 cells and purified as previously described.

The isolated monoclonal antibodies from the above mentioned B cell sort were analyzed for antigen binding using ELISA. Plates were prepared by coating them with 50 μL of 5 μg/mL antigen (WT H1, WT H5, WT H2, or H1 Head) in 50 mM sodium bicarb pH 8.75 in each well. These were washed 3× with PBST and blocked with 1×PBST with 0.5% BSA. Following blocking, monoclonal antibody samples were added as a dilution from Expi 293 media and incubated for 1 hour at room temperature. The plates were then washed 3× with 1×PBST, and a secondary, goat anti-human HRP (Abcam) antibody was added for 1 hour at room temperature. The plates were then washed 6× with 1×PBST, developed using 1-Step Turbo TMB ELISA substrate solution (ThermoFisher), and quenched using 2 M $H_2SO_4$. The readout of this colormetric assay was determined using a 96 well plate reader (Biotek). The cutoff to determine binding was set as 1.3 times background.

Figure 13A:
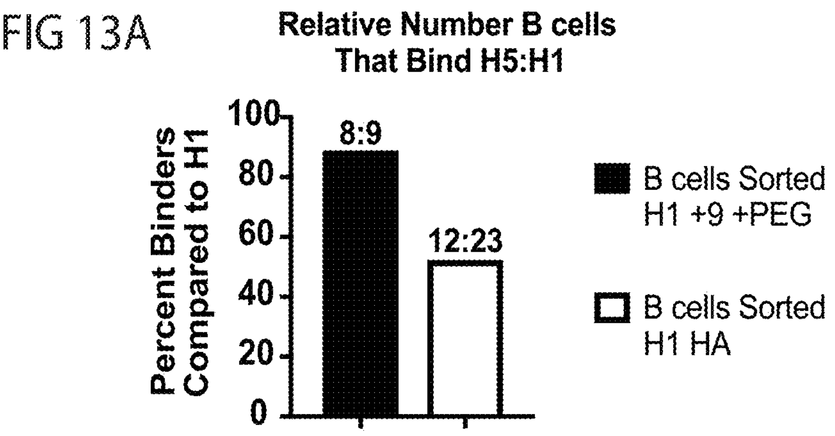
FIGS. 13A-13C show ELISA assay results assessing the hemagglutinin binding ability of antibody sequences identified from human memory B cells sorted from a pool of human peripheral blood mononuclear cells (PBMCs) based on antigen positive binding using either H1 WT or H1+9+PEG. The antibodies were generated from the B cell receptor heavy and light chain sequences from the isolated single cells (9 from H1+9+PEG sort and 23 from H1 WT bind to H1 WT).
Figure 13B:
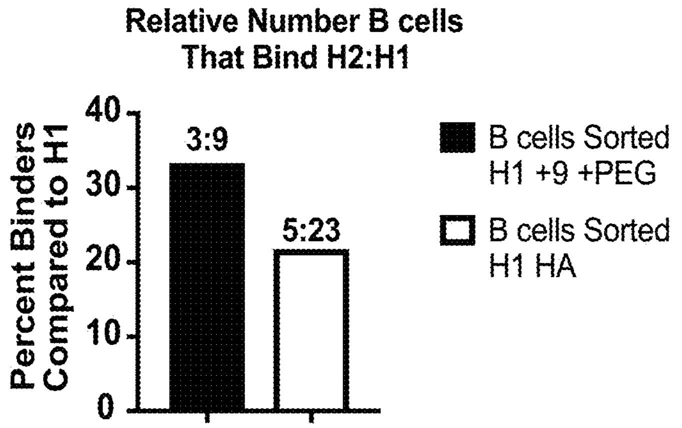
Figure 13C:
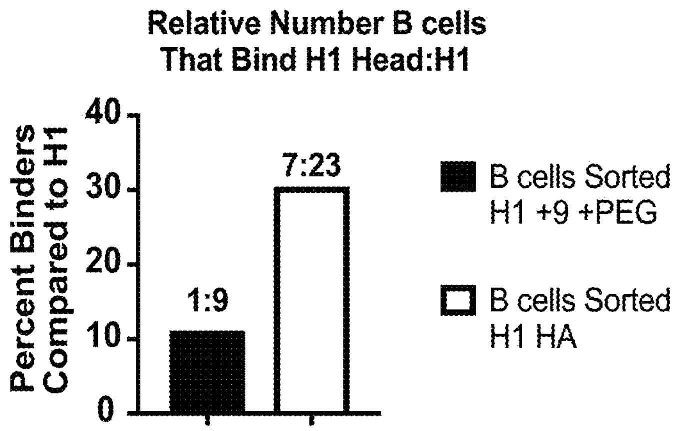

As shown in FIGS. 13A-13C, PBMCs sorted with H1+9+PEG (the modified bait) isolated more B cells that bind to the conserved stem region of HA, as determined by their binding across strains (H5 and H2) and only a single cell bound to the head of H1 HA, while PBMCs sorted with the WT bait H1 HA isolated B cells that bound to either the head or the stem region of the baits. Specifically, B cells sorted with H1+9+PEG showed a higher frequency of cross reactivity as shown by the fact that a higher percentage bound to H5 and H2 compared to B cells sorted with H1 HA (FIG. 13A and FIG. 13B). However, a lower percentage bound to the head when sorted with H1+9+PEG compared to those sorted with H1 HA (FIG. 13C). These results demonstrate that PMD antigens can be used as sorting baits to isolate B cells of interest because they target the region of interest. These results suggest that, if this PMD antigen was used to immunize a human, it would preferentially stimulate B cells that bind to highly conserved regions of HA, in contrast to H1 HA which would be expected to stimulate both head-directed and stem-directed B cells.

G. Immunization with H1 WT, H1+9+PEG, 115 WT, 115 Trispec

1. Immunizations

Four groups of guinea pigs (3 each) were immunized, each group immunized with one of the following immunogens: H1 WT, H1+9+PEG, H5 WT, or H5 Trispec. Each of the immunogens contained C' terminal foldon-avi-his tags. Samples were supplied in 1×PBS with 5% glycerol and were stored at <−80° C. before immunizations. Before the primary immunization, approximately 1 mL serum samples were taken from each guinea pig to act as a preimmune control. For primary immunization, immunogens were used at the following concentrations: H1 WT (50 μg), H1+9+PEG (50 μg), H5 WT (25 μg), or H5 (25 μg)+trispecific antibody (75 μg). The trispecific immunization was based on a 3:1 w/w ratio (2:1 molarity ratio) of tribody to H5 WT monomer. For the primary immunization, guinea pigs were immunized intramuscularly with one of the immunogens and Alum adjuvant (ThermoFisher) mixed 1:1 by volume. All immunizations were conducted at Josman LLC (Napa, CA, USA). The H1 WT and H1+9+PEG immunizations were done at 100 μL mixed 1:1 with Alum adjuvant. The H5 immunizations (H5 WT and HT Trispec) were done at 250 μL of immunogen in 1×PBS with 5% glycerol mixed 1:1 with Alum adjuvant. These two groups (H5 WT and HT Trispec) were immunized at two muscular locations due to the volume of sample. Serum was then isolated from the guinea pigs on day 14 post-immunization. The H1 WT and H1+9+PEG groups were boosted on day 20. The boost contained the same amount of immunogen as the primary immunization. Serum was harvested again on day 30 for all animals, including the H5 WT and H5 Trispec groups, which did not undergo a boost.

A second immunization experiment with the H1 WT and H1+9+PEG antigens was conducted (n=4 per group). As compared to the original immunization experiment, all conditions were the same except that the immunogens were FPLC-purified prior to being used for immunization. All animals were immunized with immunogens containing the foldon-avi-his tag.

2. ELISA Analysis of Immune Serum

Serum from the immunized animals was tested by ELISAs for binding to HA antigens. Two sets of antigens were used for the ELISAs. The first set of antigens used were H1, H2, H3, or H5 ectodomains with the foldon-avi-his tag. As the proteins used for immunization included the foldon-avi-his tag, the animals were expected to generate non-productive antibodies against the tag. As such, for ELISAs performed using the first set of antigens, serum was first depleted as described below so that only HA specific binding would be detected. ELISAs were also performed with a second set of antigens: H1, H2, or H5 ectodomains with the GT-IZ-his tag. The second set of antigens were expected to only be bound by HA specific antibodies in the serum. No serum depletion was required.

First, 96-well plates (Nunc Maxisorp™ flat-bottom, Thermo Fisher Scientific) were prepared by coating them with 50 μL/well of 5 μg/mL antigen in 50 mM sodium bicarbonate (pH 8.75) for at least one hour. The antigens used were each of H1, H2, H3, or H5 ectodomains with the foldon-avi-his tag and each of H1, H2, or H5 ectodomains with the GT-IZ-his tag. Negative controls with no protein antigen (blocking agent only) were also included. For the plates coated with the antigens containing the foldon-avi-his tag, the plates were washed three times with either 300 μL 1×PBST and blocked with 300 μL of NPBST with 0.5% BSA for at least one hour. For plates coated with antigens containing the GT-IZ-his tag or no protein, the plates were washed 3× with 300 μL of double distilled $H_2O$ and blocked with 100 μL Chonblock (Chondrex) for at least one hour.

For the ELISAs using the first set of antigens (containing the foldon-avi-his tag), serum was depleted to remove non-productive antibodies produced against the foldon-avi-his tag during the immunization. This was done by taking NeutrAvidin™ agarose beads (ThermoFisher Scientific) and coating them with non-specifically biotinylated sfGFP that contained a C' terminal foldon-avi-his tag. The sfGFP was biotinylated in the same manner as the HEWL protein as described in Example 1A above. The serum was depleted by incubation of the serum with the coated beads for one hour, and the resulting depleted serum was used for the ELISA experiments on the plates coated with an antigen containing the foldon-avi-his tag. Dilutions of serum samples were added in 1×PBST and let incubate for 1 hour at room temperature. The plates were then washed 3× with 300 μL of 1×PBST and a 1:20,000 in PBST of an anti-guinea pig HRP secondary antibody (Abcam) was added for 1 hour at room temperature. The plates were then washed 6× with 300 μL of 1×PBST and developed using 1-Step™ Turbo TMB ELISA substrate solution (ThermoFisher) for 6 mins and quenched using 2M $H_2SO_4$.

For ELISAs performed using the second set of antigens (containing the GT-IZ-his tag), serum was assessed directly. Following blocking with Chonblock, serum samples were added at a 1:100 dilution and a 10-fold serial dilution in NPBST and let incubate for 1 hour at room temperature. The plates were then washed 3× with 300 μL of 1×PBST and an anti-guinea pig HRP secondary antibody (Abcam) was added for 1 hour at room temperature. The plates were then washed 6× with 300 μL of 1×PBST and developed using 1-Step™ Turbo TMB ELISA substrate solution (ThermoFisher) for 12 mins and quenched using 2M $H_2SO_4$.

The readout of the ELISA assays is colorimetric. The absorbance was determined using a 96 well plate reader (Biotek). The colorimetric readout of the ELISAs was read as absorbance at wavelength 450 nm ("$A_{450}$") using a 96 well plate reader (Biotek). The amount of absorbance reflects the amount of antigen specific binding of antibodies in animal serum to the antigen on the plate. As a final step, the normalized values from the ELISAs were baseline subtracted (subtracting the average of the background signal from secondary antibody only control wells). To determine relative binding, the baseline-subtracted absorbance values for immunogens H2, H3, and H5 (each with a C' terminal foldon-avi-his tag) were then divided by the respective baseline-subtracted absorbance value from the immunogen H1 WT.

Figure 12A:
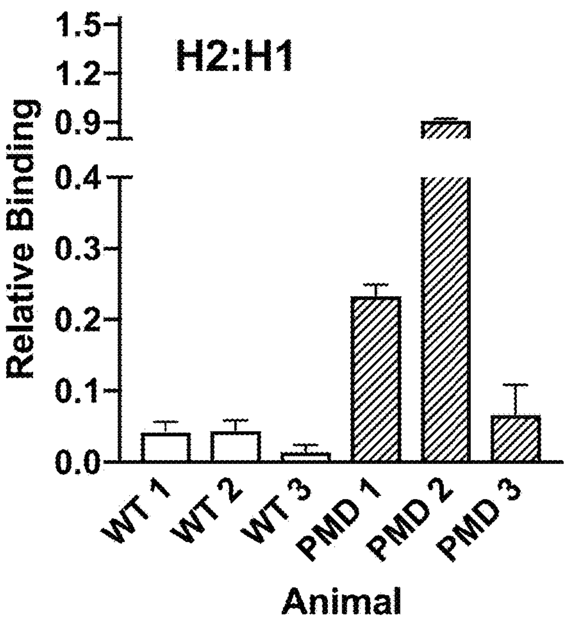
FIGS. 12A-12C show assessment of antibody production in guinea pigs immunized with H1 WT or H1+9+PEG immunogens according to aspects of this disclosure. Guinea pigs were immunized with either immunogen and boosted on day 20 with the same immunogen as the primary injection. Alum was used as an adjuvant. The animal serum, taken 10 days after the boost, was depleted of antibodies that bind to the foldon-avi-his tags. The resulting depleted serum was then tested at a 1:1000 dilution against either H1, H2, H3, or H5 using an enzyme linked immunosorbent assay (ELISA). The serum was incubated with plates precoated with the antigen of interest (H1, H2, H3, or H5). The intensity of the absorbance (measured at 450 nM) was measured as an indication of the amount of antibodies in the serum that bound to the plate. After baseline-subtraction, the baseline-subtracted absorbance values for immunogens H2, H3, and H5 were divided by the respective baseline-subtracted absorbance value from the immunogen H1 WT to determine the relative amount of binding. The relative binding for each of the other three HA strains is plotted in FIG. 12A (H2), FIG. 12B (H3), and FIG. 12C (H5). Three animals were tested for each condition (H1 WT immunized: WT 1, 2, 3; H1+9+PEG immunized: PMD 1, 2, 3).
Figure 12B:
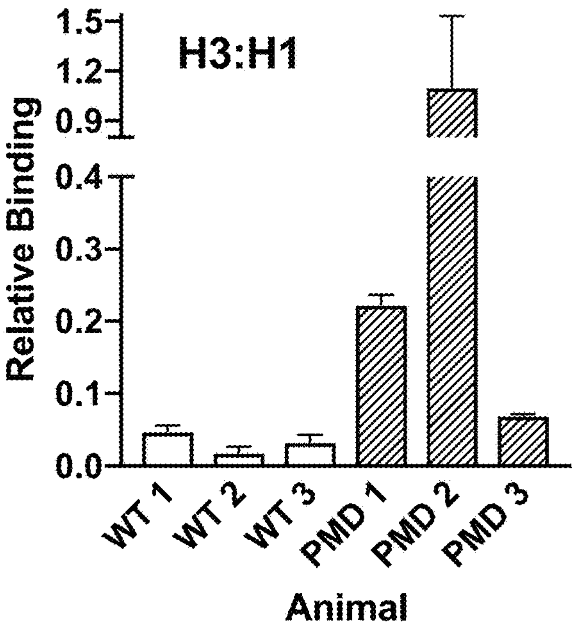
Figure 12C:
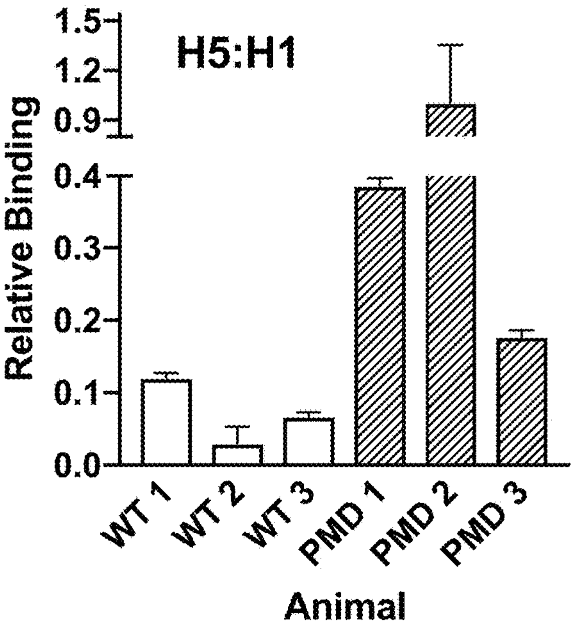

The relative binding of the serum for each animal in the first immunization for each of H2, H3, and H5 ectodomains with the foldon-avi-his tag as compared to H1 ectodomain with the foldon-avi-his tag is shown plotted, respectively, in FIG. 12A, FIG. 12B, and FIG. 12C. The white bars show the cross reactivity of the H1 WT immunized animals, and the hashed bars are the H1+9+PEG immunized animals. The height of the bar is indicative of the amount of cross reactivity where a higher bar means that more of the serum is cross reactive to that antigen relative to its binding to H1 WT. Taken collectively, these graphs show that the animals immunized with the PMD modified antigen H1+9+PEG produced a better relative cross reactive response towards H2, H3, and H5. This cross reactivity reflects that animals immunized with this immunogen generated HA stem-directed antibodies as this is the most highly conserved region on the protein. The highest bars shown by the H1+9+PEG immunized animals demonstrate that these animals are producing a more HA stem-directed polyclonal immune response.

Figure 14:
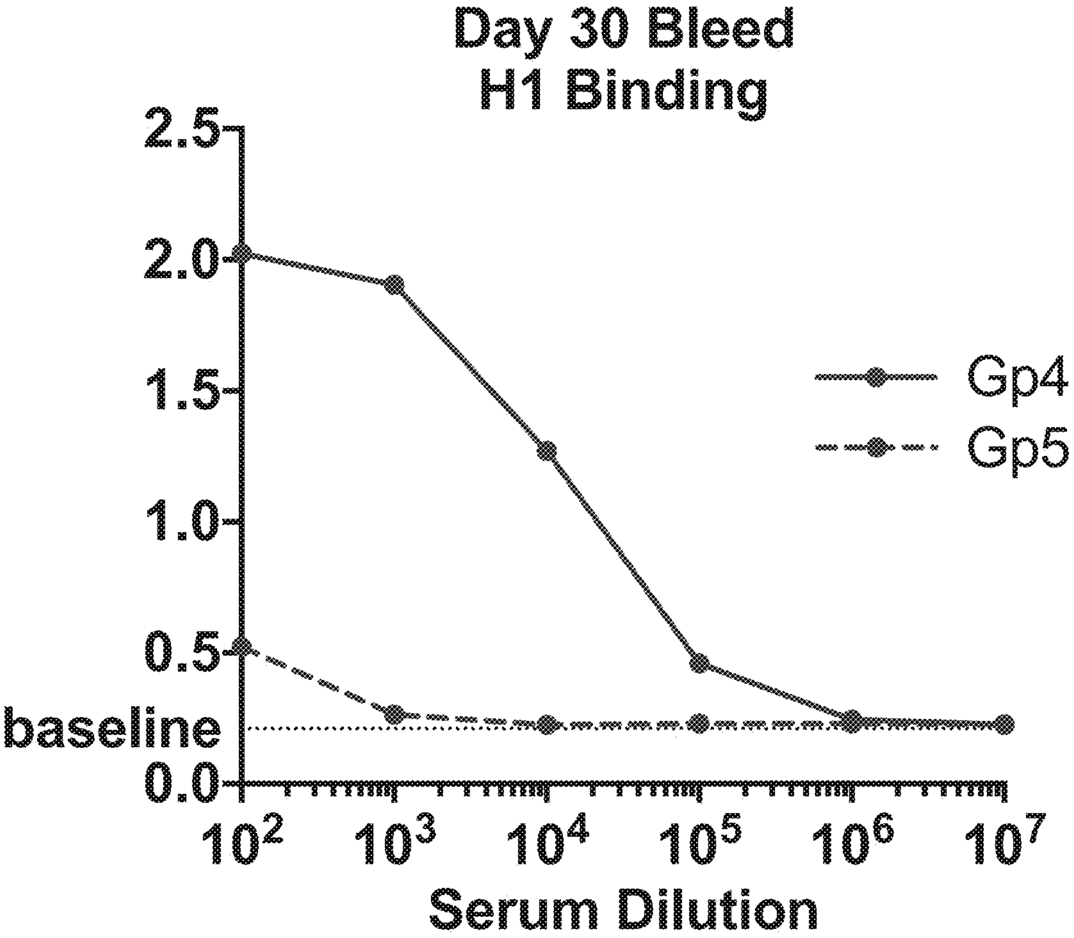
FIG. 14 shows an ELISA analysis comparing binding to H1 ectodomain of serum from guinea pig 5 ("GP5"; dashed line) and serum from guinea pig 4 ("GP4"; solid line), both immunized with H1+9+PEG, according to aspects of this disclosure. The extent of binding observed for GP4 serum is representative of other immunized animals. In comparison, serum from GP5 had substantially less binding to H1 ectodomain, indicating that GP5 produced a weak immune response. As such, this animal was excluded from further analysis (shown below in FIGS. 15A-15D, FIGS. 16-16B, and FIGS. 17A-17B).

Based on the above analysis, guinea pig 5 (a H1+9+PEG immunized animal from the first immunization) ("GP5") was excluded from further data analysis given that its serum response was overall quite weak and was considered to be an outlier as compared to other PMD animals. This can be seen in the ELISA data shown in FIG. 14, which shows the binding of GP5 serum dilutions to plates coated with H1 ectodomain containing the GT-IZ-his tag was assessed by ELISA. The serum binding curve for GP5 is shifted substantially to the left indicating that further dilution of the serum would eliminate antigen binding. In comparison, the curve for serum dilutions from guinea pig 4 ("GP4"), a representative animal immunized with H1+9+PEG showing average serum reactivity, is shifted substantially to the right, indicating that the serum can be diluted further while maintaining antigen specific binding. Thus, the serum from GP4 binds significantly better to the H1 antigen than the serum from GP5. GP5 was concluded to have a weak response relative to other immunized animals.

Figure 15A:
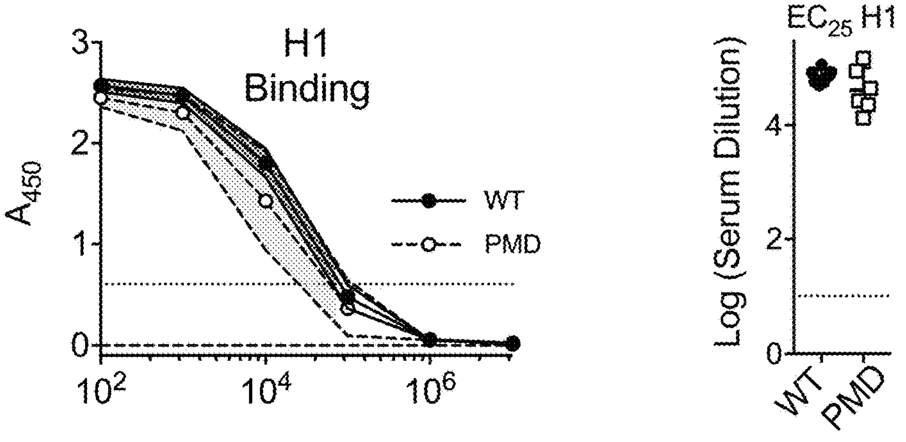
FIGS. 15A-15D.
Figure 15B:
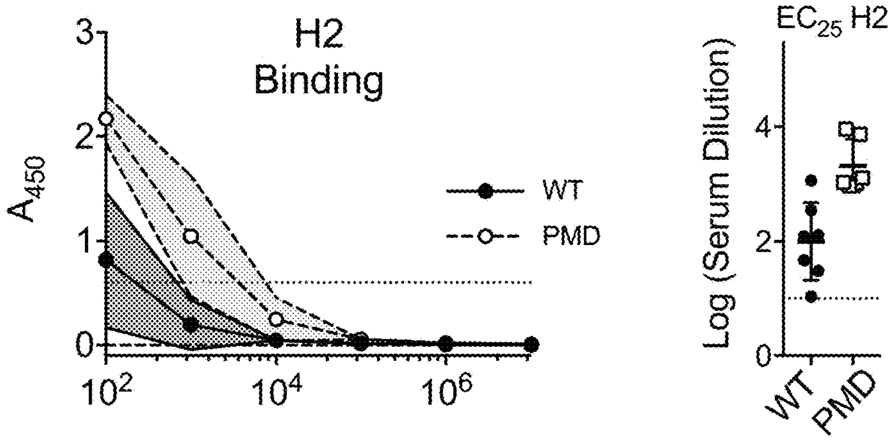
Figure 15C:
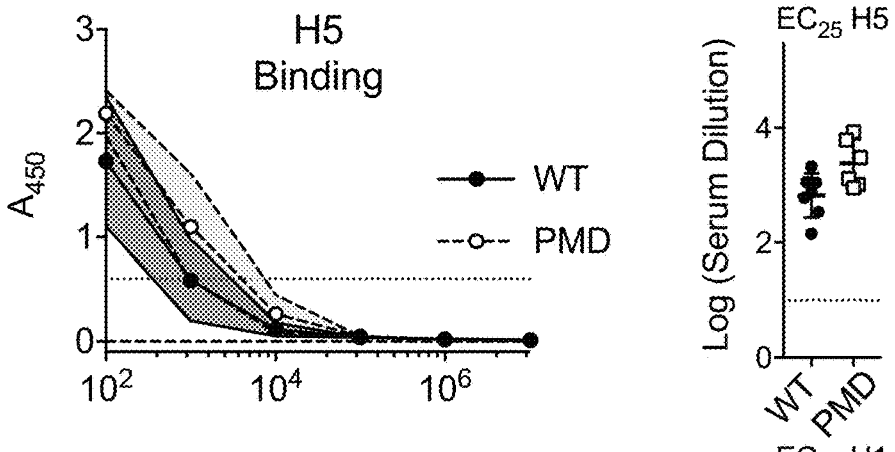
Figure 15D:
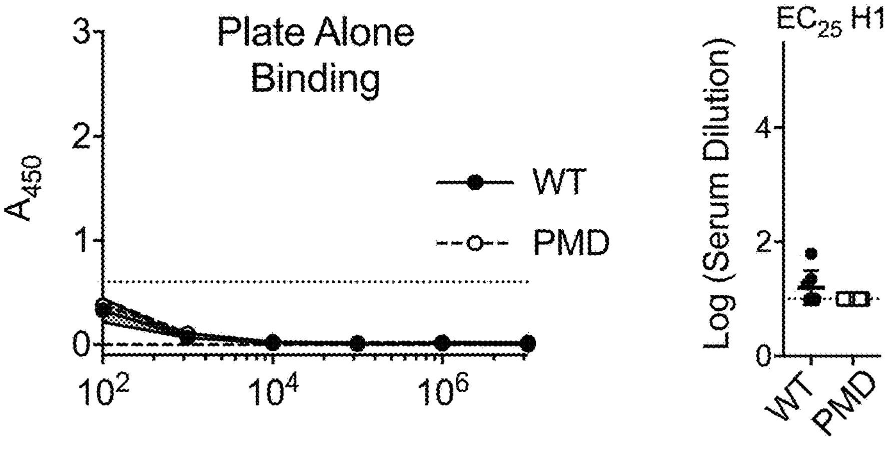

Looking at serum from the animals in both the first and second immunizations, the extent of binding to H1, H2, or H5 ectodomains (GT-IZ-his tagged) of serum from the animals in either the H1 WT immunization group or the H1+9+PEG immunization group was plotted as average $A_{450}$ vs. serum dilution as shown in FIGS. 15A-15D (graphs on left). The data plotted is for all animals that were included in the analysis. A total of 7 animals are plotted in the WT group (3 from the first immunization, 4 from the second) and a total of 6 animals are plotted in the H1+9+PEG group (2 from the first immunization, 4 from the second). Serum having curves that are shifted more to the right can be diluted further and still maintain antigen binding. This reflects that the animal from which the serum was obtained had a relatively strong immune response towards that antigen. Conversely, serum with curves that are shifted more the left cannot be diluted further without loss of antigen binding. As shown in FIG. 15A, the animals immunized with H1+9+PEG have a slightly weaker immune response towards the H1 ectodomain. This is not surprising given that the H1+9+PEG immunogen was highly PEGylated, which is known to decrease the immune response. However, the serum from these animals exhibited better binding to the H2 and H5 ectodomains, as reflected by a curve shifted more to the right as shown in FIG. 15B and FIG. 15C, respectively. This shows that despite having a weaker overall binding to H1 ectodomain, these animals produced more cross reactive serum that is better able to bind to other strains of hemagglutinin. The animals do not show a largely nonspecific response, as none of their curves were insignificant on the negative control plate (FIG. 15D).

Because the above analysis is based on an average observed binding for all the animals in a respective immunization group, the EC25 for each animal is also assessed to confirm that the results were reproducible and not due to a few exceptionally cross reactive animals. The EC25 was calculated for each individual animal by doing a Sigmoidal, 4PL fit on Prism Graph pad and solving for the unknown value of $OD_{450}$=0.602. The resulting curve fit determined the EC25 as shown in FIGS. 15A-15D (graphs on right). A higher EC25 value means that the serum can be diluted further and still reach a value of $OD_{450}$=0.602, which reflects that the serum is binding to antigen more strongly. The animals immunized with H1 WT had higher EC25 values for H1 ectodomain and lower EC25 values for H2 and H5 ectodomains compared to H1+9+PEG immunized animals, as shown in FIGS. 15A-15C, respectively. This indicates that the serum from animals immunized with H1 WT bound better to H1 WT, but their serum was overall less cross reactive than the animals immunized with H1+9+PEG, which bound worse to H1, but better to H2 and H5. Use of antigens having the GT-IZ-his tag had comparable serum binding relative to antigens having the foldon-avi-his tag (data not shown).

3. Biolayer Interferometry Cross Reactivity Analysis of Immune Serum

Figure 16A:
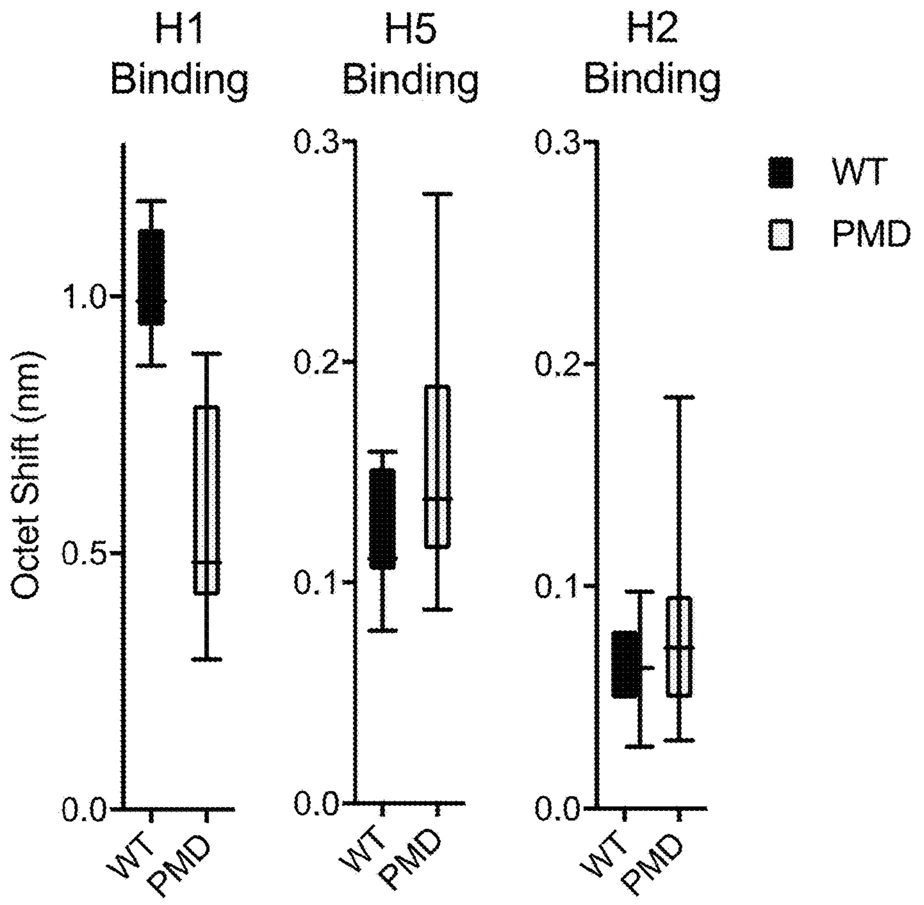
FIGS. 16A-16B show biolayer interferometry binding analysis of individual guinea pig serum immunized with either H1 WT or H1+9+PEG or pooled serum from guinea pigs immunized with either H1 WT or H1+9+PEG, respectively, according to aspects of this disclosure. HIS1K Octet tips were loaded with H1, H2, or H5 incubated with a 1:20 dilution of serum from each animal from each immunization group or a 1:20 dilution of pooled serum from each immunization group (H1 WT group, black box or line; H1+9+PEG group, white box or grey line). Association was conducted for 5 mins in the serum and then dissociation was conducted for 1 min in PBST BSA. Negative control tips did not have antigen loaded thereon but was incubated with serum simultaneously with the loaded tips. All samples were baseline subtracted with the unloaded tip to account for any non-specific binding to the sensor tips. Values plotted in FIG. 16A are the baseline subtracted final time point in the association step, which lasted for 5 mins.

To further confirm the results that the serum of animals immunized with H1+9+PEG was more cross reactive than the serum of animals immunized with H1 WT, a biolayer interferometry ("Octet binding") experiments was conducted with either individual animal serum or pooled serum from each of the immunization groups (H1 WT and H1+9+PEG). The goal of this experiment was to demonstrate the same level of improved cross reactivity in an orthogonal method which also analyzes binding. Biolayer interferometry assessment of individual animals was conducted by loading HIS1K octet biosensors with H1, H2, or H5 (each having a C' terminal GT-IZ-his tag) at 50 nM to a 0.8 nm shift. Negative control tips were simultaneously incubated in PBST BSA for the same duration of time. Tips immersed in a 1:20 serum dilution of each animal serum (in PBST BSA) from the immunized animals and incubated for 5 mins. In post-processing, the octet binding shift for each sample was baseline subtracted using the negative control tip value to remove trends due to any nonspecific binding. The value plotted is the final response at the 5 min timepoint. The interferometer records wavelength shift (nm) as a surrogate for binding such that a higher shift reflects more protein binding to the tip. Thus, the higher the octet shift, the better binding of the serum from that animal to the antigen on the tip. The results of this experiment are shown in FIG. 16A. The animals immunized with H1+9+PEG show weaker binding to the H1 ectodomain (FIG. 16A, left), which is similar to the reactivity seen by ELISA where the H1+9+PEG immunized animals produced a weaker immune response towards H1 IZ. However, H1+9+PEG immunized animals show a better cross reactive immune response towards the H5 ectodomain (FIG. 16A, middle) and H2 ectodomain (FIG. 16A, right). This is clear because their nm shift is higher on the octet, demonstrating that they are better binders.

Figure 16B:
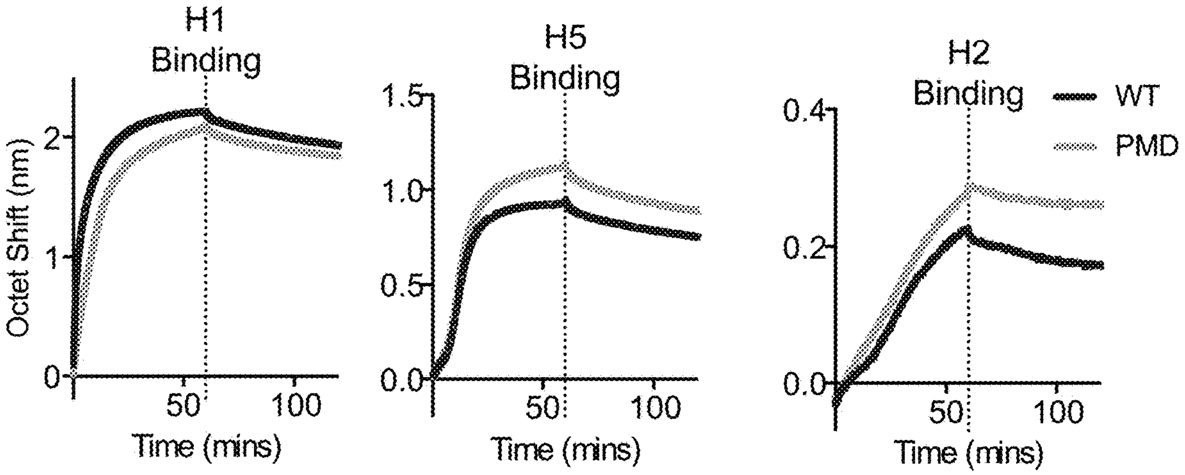

A second Octet experiment was conducted using pooled serum from each immunization group. Pooled serum for each group was produced by combining equal volumes of serum from each animal. HIS1K tips were loaded with antigen (2 per antigen) as described in the prior experiment and then immersed in a 1:20 dilution of pooled serum (one antigen-loaded tip per pooled serum sample). Negative control tips (2) were also included. The association with serum was left to run for 1 hour and then dissociation was left to run for 1 hour. The resulting curves were then baseline subtracted using the unloaded tip that was simultaneously immersed in serum, ensuring that any nonspecific binding to the tip was accounted for. The binding curves from this analysis are shown in FIG. 16B. As discussed above, a higher shift is reflective of better binding of the pooled serum to the antigen on the tip. Similar to the results seen in the prior Octet experiment, the pooled serum from animals immunized with H1+9+PEG show weaker binding to the H1 ectodomain (FIG. 16B, left) but a better cross reactive immune response towards the H5 ectodomain (FIG. 16B, middle) and H2 ectodomain (FIG. 16B, right).

4. Biolayer Interferometry Competition with Mab of Immune Serum

To probe the serum antibody response against individual epitopes and understand the epitopes most targeted by the polyclonal serum, an Octet competition experiment was developed. SA octet biosensors (tips) were loaded with 0.8 nM of biotinylated H1 WT. Tips were immersed in a 1:20 serum dilution of each individual animal for 25 mins and then washed twice. Tips were then immersed in monoclonal antibodies CH65 (60 nM), H2897 (60 nM), MEDI8852 (10 nM), CR9114 (10 nM), MAb 3.1 (10 nM) and left to associate for 2 mins. Two sets of control tips were included: a first control that was incubated only with buffer and a second control that was incubated with a 1:20 dilution of serum and washed twice, but that was not incubated with a monoclonal antibody. Measured antibody binding to the test tips was baseline subtracted to a measured binding from the second control tip to account for any serum dissociation over the course of the assay. An appreciable shift (greater than zero) was observed for antigen-coated tips that were not incubated with serum when the tips were incubated with the monoclonal antibodies, reflecting binding of the antibody to the antigen on the tip. However, for tips incubated first with serum, a lower shift was expected when the tips were incubated with the antibodies, reflecting competition at the antigen epitope of the monoclonal antibody by antibodies in the serum. The observed values were baseline subtracted by taking the Octet shift of the pre-serum bound antibody binding at 40 seconds and dividing it by the Octet shift of the no-serum bound antibody binding. This ratio was multiplied by 100 to give the relative binding. A value of 100 would be consistent with the serum not competing at all for antibody binding; conversely, a value of 0 would be consistent with the serum fully competing the antibody away.

Figure 17A:
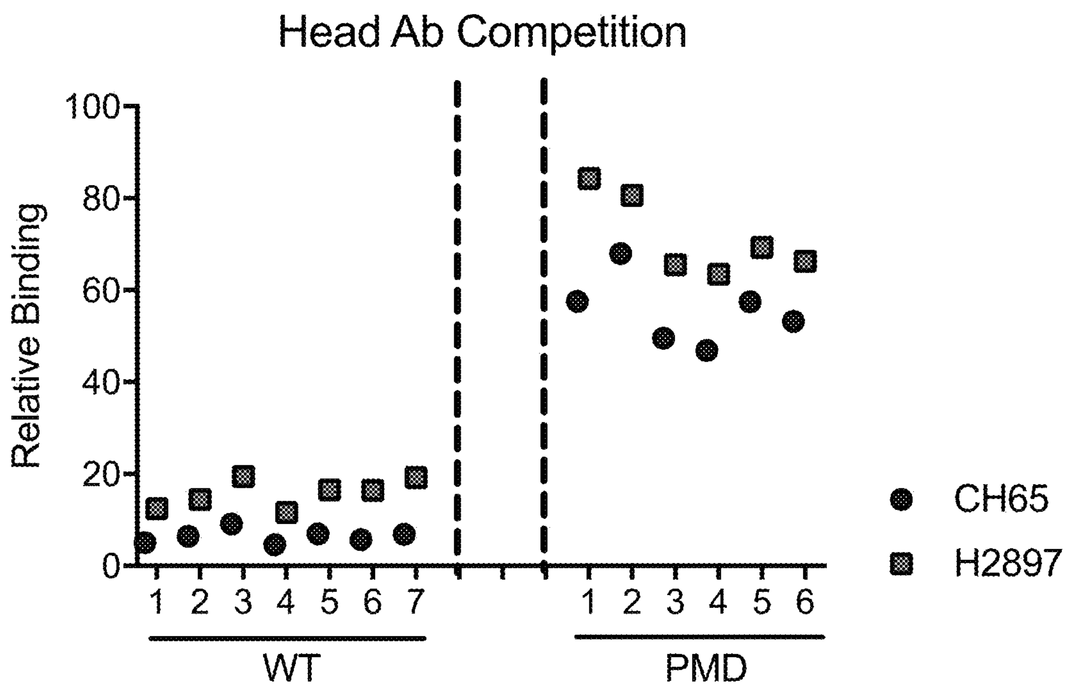
FIGS. 17A-17B show Octet competition experiments assessing the serum of guinea pig immunized with either H1 WT or H1+9+PEG with monoclonal antibodies targeting either the head region of HA H1 or the stem region of HA H1, respectively, according to aspects of this disclosure. Octet SA biosensors (tips) were loaded with biotinylated H1 WT and incubated with head targeted monoclonal antibodies (60 nM CH65 or H2897) or stem targeted monoclonal antibodies (10 nm MEDI8825, CR9114, or MAb 3.1) to set a standard for the amount of binding. Samples were baseline subtracted using negative control values (a tip loaded with H1 WT and serum but not incubated with monoclonal antibody). The resulting decrease in monoclonal antibody binding (due to the fact that serum was pre-associated to the tip) is plotted as 'relative competition'. A value of 100 indicates that the monoclonal antibody binding was not impacted by the association with serum (i.e., the serum did not compete at that epitope), while a value of 0 means that all monoclonal antibody binding is entirely lost after serum association (i.e., the serum competed completely with that antibody). An average of two replicates is shown. The data in FIG. 17A shows that the relative competition of the serum from H1 WT immunized animals for antibodies CH65 and H2897 is a much lower value as compared to the serum from animals immunized with H1+9+PEG. This indicates that the H1 WT immunized animals produced a significantly better anti-head antibody response. The data in FIG. 17B shows that the relative competition of serum from animals immunized with H1 WT is similar towards the stem monoclonal antibodies, indicating that both H1 WT and H1+9+PEG produced a similar immune response targeting the stem. Taken together, this data shows that the immunogenicity of the head was largely decreased, while the immunogenicity of the stem was largely maintained, in animals immunized with H1+9+PEG.
Figure 17B:
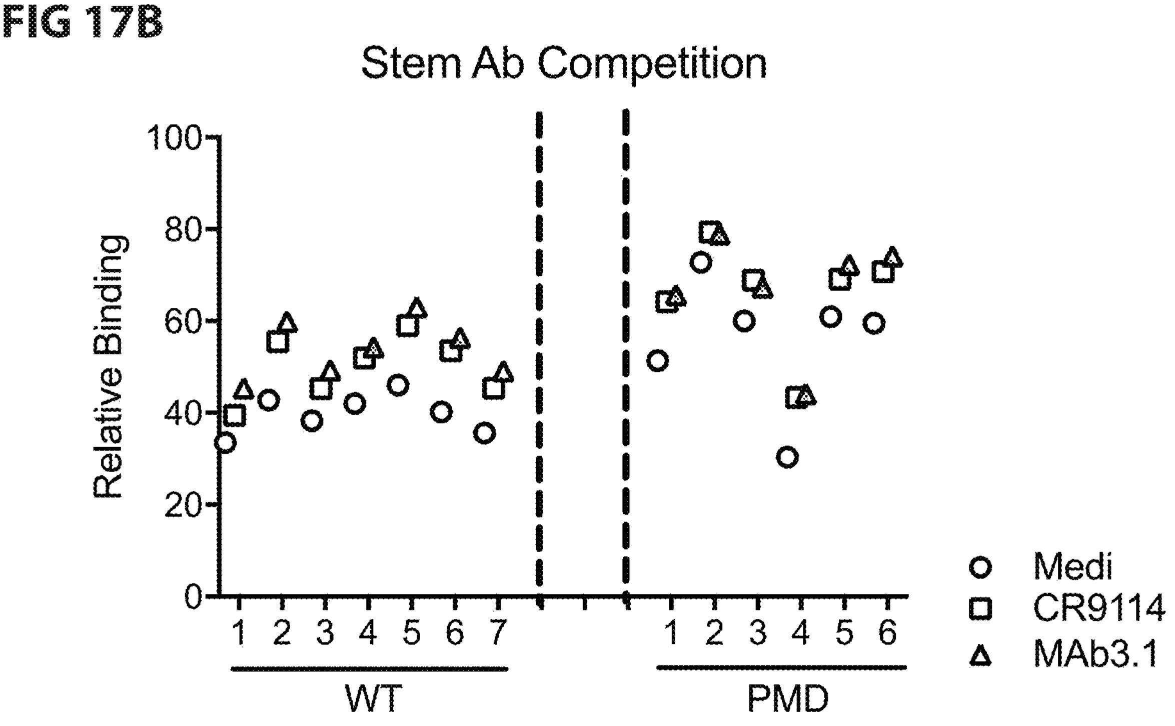

The relative binding determinations for H1 head-binding monoclonal antibodies (CH65 and H2897) and H1 stem-binding monoclonal antibodies (Medi, CR9114, and Mab3.1) are shown in FIG. 17A and FIG. 17B, respectively. The animals immunized with H1+9+PEG show a significantly reduced response to the head as reflected by much higher values of relative binding as compared to H1 WT immunized animals (FIG. 17A). The serum response for the stem is quite similar as the relative competition is at approximately the same level (FIG. 17B). This demonstrates that the H1+9+PEG immunized animals retained binding at the stem but decreased an antibody response against the head.

Taken together, the ELISA and biolayer interferometry experiments clearly indicate that animals immunized with the PMD antigen, H1+9+PEG, show a weaker immune response towards H1 but a better cross reactive immune response and that this immune response is targeted at the stem region of the protein, given that the serum does not compete as strongly at the head region as the WT serum but does compete comparably at the stem region.

Example 3. ERAS Using HIV Antigens

An experiment may be conducted to assess the Protect, Modify, Deprotect ERAS method of making an antigenic protein based on an HIV protein such as gp120. For example, the CD4 binding site on gp120 may be protected with a site specific antibody such as VRC01 or Soluble 1 or 4 domain CD4. Such an experiment is described below.

Gp120 will be cloned into pADD2 vector and expressed in Expi293 HEK cells as previously described. Additional lysine residues will be added to gp120 as needed to incorporate a desirable number of reactive functional groups the non-target region outside of the CD4 binding site. This gp120 or mutant gp120 will be purified using NiNTA chromatography. The resulting gp120 will be batch bound to a resin that had previously been coupled with either VRC01, a VRC01 mutant to lower its binding affinity, CD4 ectodomain with either 1 or 4 domains, or CD4 ectodomain with mutations made to lower its binding affinity. After batch binding of gp120 to the resin, unbound gp120 will be flowed out of the resin with 1×PB S. The resulting complexes containing gp120 and ligands that bind at the CD4 binding site on gp120 will be reacted with 3 mM NHS-PEG$_4$-Methyl in 1×PBS for 45 mins. This reaction will be repeated again and then the reaction will be quenched by flowing 100 mM tris pH 8.0 over the resin. The resulting antigen will be eluted off of the resin using 2M KSCN or another eluent that retains the integrity of gp120, and immediately dialyzed overnight. This modified immunogen will then be used, as in the above studies, to demonstrate selective antibody ablation binding at sites outside of the CD4 binding site, to isolate human B cells that target this region, and to immunize animals to elicit a focused immune response.

Example 4. Modification of HA Target Binding Site to Eliminate Modifiable Amino Acid Residue Conservative mutations can be made within the epitope of the protecting group. In some cases it is possible that the reactive residues, for example a lysine residue, within the binding site of the protecting group may not be necessary for the desired immune response. In these cases it would be possible to remove the lysine residues entirely, thereby improving the protection by limiting the risk of target epitope modification.

H1+9 as described above in Example 2 has a lysine residue within or immediately at the edge of the epitope of the Medi8852 antibody at amino acid residue position 365. Sequence conservation analysis of this lysine reveals that this lysine residue may not be highly conserved and, therefore, could be mutated to a non-reactive amino acid that is not modifiable by the NHS amine chemistry described in the examples above, such as a glutamine residue. This mutation may be introduced using stitching PCR method. Primers will be designed that overlap the site of interest, K365, that will install produce the K365Q point mutation. This PCR will be done using the HiFi PCR premix (Clontech), as described above, and the resulting PCR product will be cloned into pADD2 using the In-Fusion® HD Cloning Kit (Clontech), as described above. The sequence of the resulting construct will be confirmed by DNA sequencing, and then the plasmid will be transfected and expressed in Expi Cells as described above. The supernatant from the Expi Cells will then be harvested, and the H1+9 K365Q mutant will be purified using NiNTA affinity chromatography. This construct will then undergo the same protect, modify, deprotect method that was described above with Medi8852 as the protecting antibody to produce an immunogen that retains the now modified binding site of Medi8852. This resulting product, H1+9 K365Q+PEG, will be validated in the same way that the H1+9+PEG was validated, using biolayer interferometry (Octet Red96™) to demonstrate that the modification within the binding site does not alter its properties significantly but improved the modification specificity.

Example 5. Epitope Focusing—Modification of Target Site Adjacent Amino Acids to Reduce Binding Affinity of Non-Neutralizing Antibodies/B Cell Receptors There may be examples of antigenic proteins containing two or more antibody epitopes that overlap substantially but for which only one of the epitopes has the desirable property of being able to elicit a neutralizing immune response against the antigenic protein in a subject following immunization. For example, a non-neutralizing antibody and a broadly neutralizing antibody may share a significant amount of their epitopes on the antigenic protein. In this scenario, it would be desirable in a vaccination setting to ablate the binding of the non-neutralizing antibody to the immunogen, and by extension its BCR, while retaining the ability of the immunogen to bind to the broadly neutralizing antibody. Such specific epitope focusing may be performed by mutating amino acid residues of the non-neutralizing antibody epitope that are not shared with the neutralizing antibody epitope to non-native amino acids that are modifiable by the selected modification chemistry used in a PMD based method of making an antigenic protein.

A proof of concept study can be performed using the HA protein ectodomain as the antigenic protein, Medi8852 as the neutralizing antibody, and CR9114 as the non-neutralizing antibody. The ectodomain of the HA protein is a trimeric complex of HA1-HA2 heterodimers, wherein the HA2 subunit is a C' terminally truncated variant lacking the transmembrane region and the cytoplasmic region of the protein. The epitope of the CR9114 antibody overlaps significantly with the epitope of the Medi8852 antibody in the HA1 protein (>50% amino acids shared). However, there are regions of the CR9114 epitope that are not shared with the Medi8852 epitope. A S288K mutation will be made within the H1+9 protein. It is expected that this mutation will result in an antigenic protein that, when modified as described in the examples above, will contain a modified amino acid residue (lysine) in the CR9114 epitope. It is expected that binding to the CR9114 epitope will be ablated as a result of this mutation and, thereby, binding of CR9114 will be ablated, but binding to the Medi8852 epitope will be retained. Stitching PCR will be conducted with primers designed such that they overlap the site of interest, S288, and will produce the S288K point mutation in the H1+9 protein. This PCR will be done using the HiFi PCR premix (Clontech), as described above, and the resulting PCR product will be cloned into pADD2 using In-Fusion® HD Cloning Kit (Clontech), as described above. The sequence of the resulting construct will be confirmed by DNA sequencing, and then the plasmid will be transfected and expressed in Expi Cells as described above. The supernatant from the Expi cells will then be harvested and the H1+9 S288K mutant will be purified using NiNTA affinity chromatography. This construct will then undergo the same protect, modify, deprotect method that was described above with Medi8852 as the binding partner to produce an immunogen that retains binding to Medi8852 but for which binding of CR9114, and other antibodies that overlap more significantly with the CR9114 eptiope, is ablated. The resulting product, H1+9 S288K+PEG, will be validated in the same way that the H1+9+PEG was validated using biolayer interferometry (Octet Red 96™) to demonstrate that the point mutation does not alter Medi8852 binding properties but does ablate the binding of other stem-directed antibodies, in this case CR9114.

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

In the foregoing description, numerous specific details are set forth to provide a more thorough understanding of the present invention. However, it will be apparent to one of skill in the art that the invention described in this disclosure may be practiced without one or more of these specific details. In other instances, well-known features and procedures well known to those skilled in the art have not been described in order to avoid obscuring the invention. Embodiments of the disclosure have been described for illustrative and not restrictive purposes. Although the present invention is described primarily with reference to specific embodiments, it is also envisioned that other embodiments will become apparent to those skilled in the art upon reading the present disclosure, and it is intended that such embodiments be contained within the present inventive methods. Accordingly, the present disclosure is not limited to the embodiments described above or depicted in the drawings, and various embodiments and modifications can be made without departing from the scope of the claims below.

What is claimed is:

1. A method of making a modified hemagglutinin influenza virus protein, or a fragment or a variant thereof, the method comprising the steps of:

(a) providing a hemagglutinin influenza virus protein, or the fragment or the variant thereof, comprising a target region comprising an epitope of interest and a non-target region;

(b) providing a binding partner, wherein the binding partner binds specifically to the target region;

(c) contacting the hemagglutinin influenza virus protein, or the fragment or the variant thereof, with the binding partner under conditions in which the binding partner binds specifically to the target region, thereby forming a protein complex comprising the hemagglutinin influenza virus protein, or the fragment or the variant thereof, and the binding partner;

(d) contacting amino acid residues of the hemagglutinin influenza virus protein, or the fragment or the variant thereof, in the protein complex with a modifying reagent under conditions sufficient to form the modified hemagglutinin influenza virus protein, or the fragment or the variant thereof, thereby forming the modified hemagglutinin influenza virus protein, or the fragment or the variant thereof, in the protein complex, wherein each of a plurality of amino acid residues in the non-target region of the hemagglutinin influenza virus protein, or the fragment or the variant thereof, have a modifying component covalently attached thereto, and wherein amino acid residues of the target region of the hemagglutinin influenza virus protein, or the fragment or the variant thereof, do not have the modifying component attached thereto; and (e) separating the modified hemagglutinin influenza virus protein, or the fragment or the variant thereof, from the binding partner in the protein complex, thereby providing the modified hemagglutinin influenza virus protein, or the fragment or the variant thereof, with reduced or ablated immunogenicity of the non-target region.

2. The method of claim 1, wherein in step (c) the binding partner or the hemagglutinin influenza virus protein, or the fragment or the variant thereof, is attached to a solid support.

3. The method of claim 1, wherein step (d) comprises reacting the protein complex with the modifying reagent and a coupling reagent under conditions sufficient to form the modified hemagglutinin influenza virus protein, or the fragment or the variant thereof.

4. The method of claim 1, wherein the modifying component is a polyethylene glycol polymer, a glycopolymer (polysaccharide), a polysialic acid, a hyaluronic acid, a peptide, a protein, a polynucleotide, or a combination of any thereof.

5. The method of claim 1, wherein the binding partner comprises at least one of a protein, a peptide, an aptamer, a chemical ligand, a lectin, or a combination of any thereof.

6. The method of claim 5, wherein the binding partner comprises at least one of an antibody or a receptor.

7. The method of claim 6, wherein the binding partner is a recombinant multivalent antibody.

8. The method of claim 1, wherein the target region is conserved across at least one of influenza A viruses, influenza B viruses, or influenza C viruses.

9. The method of claim 1, wherein the influenza virus hemagglutinin protein, or the fragment or the variant thereof, comprises a head region and a stem region, wherein the head region is the non-target region, and the target region comprises the stem region or a portion thereof.

10. The method of claim 1, wherein the influenza virus hemagglutinin protein, or the fragment or the variant thereof, comprises a head region that comprises a hemagglutinin receptor binding site, wherein the hemagglutinin receptor binding site is the target region.

11. The method of claim 1, wherein the influenza virus hemagglutinin protein, or the fragment or the variant thereof, is a hemagglutinin protein fragment, or a variant thereof, comprising a stem region and lacking, or substantially lacking all, of a head region.

12. The method of claim 1, wherein the influenza virus hemagglutinin protein, or the fragment or the variant thereof, comprises at least one amino acid substitution in the non-target region, wherein the at least one amino acid substitution incorporates at least one non-native amino acid residue that increases or decreases affinity of the binding partner to the non-target region.

13. The method of claim 1, wherein the influenza virus hemagglutinin protein, or the fragment or the variant thereof, comprises at least one amino acid substitution in the non-target region, wherein the at least one amino acid substitution incorporates at least one non-native amino acid residue to which the modifying reagent is attachable.

* * * * *

SEQUENCE LISTING

<160> NUMBER OF SEQ ID NOS: 28

<210> SEQ ID NO 1
<211> LENGTH: 545
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Ser Glu Val Gln Leu Gln Gln Ser Gly Ala Glu Leu Met Lys Pro Gly
1 5 10 15

Ala Ser Val Lys Ile Ser Cys Lys Ala Ser Gly Tyr Thr Phe Ser Asp
20 25 30

Tyr Trp Ile Glu Trp Val Lys Gln Arg Pro Gly His Gly Leu Glu Trp
35 40 45

Ile Gly Glu Ile Leu Pro Gly Ser Gly Ser Thr Asn Tyr His Glu Arg
50 55 60

Phe Lys Gly Lys Ala Thr Phe Thr Ala Asp Thr Ser Ser Ser Thr Ala
65 70 75 80

Tyr Met Gln Leu Asn Ser Leu Thr Ser Glu Asp Ser Gly Val Tyr Tyr
85 90 95

Cys Leu His Gly Asn Tyr Asp Phe Asp Gly Trp Gly Gln Gly Thr Thr
100 105 110

Leu Thr Val Ser Ser Ala Ser Thr Lys Gly Pro Ser Val Lys Leu Glu
115 120 125

Glu Gly Glu Phe Ser Glu Ala Arg Val Ser Met Asp Ile Val Leu Thr
130 135 140

Gln Ser Pro Ala Ile Met Ser Ala Ser Pro Gly Glu Lys Val Thr Met
145 150 155 160

Thr Cys Ser Ala Ser Ser Ser Val Asn Tyr Met Tyr Trp Tyr Gln Gln
165 170 175

Lys Ser Gly Thr Ser Pro Lys Arg Trp Ile Tyr Asp Thr Ser Lys Leu
180 185 190

Ala Ser Gly Val Pro Val Arg Phe Ser Gly Ser Gly Ser Gly Thr Ser
195 200 205

Tyr Ser Leu Thr Ile Ser Ser Met Glu Thr Glu Asp Ala Ala Thr Tyr

```
    210                 215                 220

Tyr Cys Gln Gln Trp Gly Arg Asn Pro Thr Phe Gly Gly Gly Thr Lys
225                 230                 235                 240

Leu Glu Ile Lys Arg Thr Val Ala Ala Pro Ser Gly Gly Ser Pro Ser
                245                 250                 255

Gly Gln Ala Gly Ala Ala Ala Ser Glu Ser Leu Phe Val Ser Asn His
            260                 265                 270

Ala Tyr Gly Gly Ser Ser Gln Val Gln Leu Gln Gln Ser Gly Ala Glu
        275                 280                 285

Leu Val Arg Pro Gly Ala Ser Val Lys Leu Ser Cys Lys Ala Ser Gly
    290                 295                 300

Tyr Thr Phe Ile Ser Tyr Trp Ile Asn Trp Val Lys Gln Arg Pro Gly
305                 310                 315                 320

Gln Gly Leu Glu Trp Ile Gly Asn Ile Tyr Pro Ser Asp Ser Tyr Thr
                325                 330                 335

Asn Tyr Asn Gln Lys Phe Lys Asp Lys Ala Thr Leu Thr Val Asp Lys
            340                 345                 350

Ser Ser Ser Thr Ala Tyr Met Gln Leu Ser Ser Pro Thr Ser Glu Asp
        355                 360                 365

Ser Ala Val Tyr Tyr Cys Thr Arg Asp Asp Asn Tyr Gly Ala Met Asp
    370                 375                 380

Tyr Trp Gly Gln Gly Thr Thr Val Thr Val Ser Ser Ala Ser Thr Lys
385                 390                 395                 400

Gly Pro Ser Val Lys Leu Glu Glu Gly Glu Phe Ser Glu Ala Arg Val
                405                 410                 415

Ser Asp Ile Glu Leu Thr Gln Ser Pro Ser Tyr Leu Val Ala Ser Pro
            420                 425                 430

Gly Glu Thr Ile Thr Ile Asn Cys Arg Ala Ser Lys Ser Ile Ser Lys
        435                 440                 445

Ser Leu Ala Trp Tyr Gln Glu Lys Pro Gly Lys Thr Asn Asn Leu Leu
    450                 455                 460

Ile Tyr Ser Gly Ser Thr Leu Gln Ser Gly Ile Pro Ser Arg Phe Ser
465                 470                 475                 480

Gly Ser Gly Ser Gly Thr Asp Phe Thr Leu Thr Ile Ser Ser Leu Glu
                485                 490                 495

Pro Glu Asp Phe Ala Met Tyr Ile Cys Gln Gln His Asn Glu Tyr Pro
            500                 505                 510

Trp Thr Phe Gly Gly Gly Thr Lys Leu Glu Ile Lys Arg Lys Arg Thr
        515                 520                 525

Val Ala Ala Pro Ser Gly Ala Ala Ala Leu Glu His His His His His
    530                 535                 540

His
545


<210> SEQ ID NO 2
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Tyr Leu Leu Pro Thr Ala Ala Ala Gly Leu Leu Leu Leu Ala
1               5                   10                  15
```

-continued

```
Ala Gln Pro Ala Met Ala Ser Glu Val Gln Leu Gln Gln Ser Gly Ala
            20                  25                  30

Glu Leu Met Lys Pro Gly Ala Ser Val Lys Ile Ser Cys Lys Ala Ser
        35                  40                  45

Gly Tyr Thr Phe Ser Asp Tyr Trp Ile Glu Trp Val Lys Gln Arg Pro
    50                  55                  60

Gly His Gly Leu Glu Trp Ile Gly Glu Ile Leu Pro Gly Ser Gly Ser
65                  70                  75                  80

Thr Asn Tyr His Glu Arg Phe Lys Gly Lys Ala Thr Phe Thr Ala Asp
                85                  90                  95

Thr Ser Ser Ser Thr Ala Tyr Met Gln Leu Asn Ser Leu Thr Ser Glu
            100                 105                 110

Asp Ser Gly Val Tyr Tyr Cys Leu His Gly Asn Tyr Asp Phe Asp Gly
        115                 120                 125

Trp Gly Gln Gly Thr Thr Leu Thr Val Ser Ser Ala Ser Thr Lys Gly
    130                 135                 140

Pro Ser Val Lys Leu Glu Glu Gly Glu Phe Ser Glu Ala Arg Val Ser
145                 150                 155                 160

Met Asp Ile Val Leu Thr Gln Ser Pro Ala Ile Met Ser Ala Ser Pro
                165                 170                 175

Gly Glu Lys Val Thr Met Thr Cys Ser Ala Ser Ser Ser Val Asn Tyr
            180                 185                 190

Met Tyr Trp Tyr Gln Gln Lys Ser Gly Thr Ser Pro Lys Arg Trp Ile
        195                 200                 205

Tyr Asp Thr Ser Lys Leu Ala Ser Gly Val Pro Val Arg Phe Ser Gly
    210                 215                 220

Ser Gly Ser Gly Thr Ser Tyr Ser Leu Thr Ile Ser Ser Met Glu Thr
225                 230                 235                 240

Glu Asp Ala Ala Thr Tyr Tyr Cys Gln Gln Trp Gly Arg Asn Pro Thr
                245                 250                 255

Phe Gly Gly Gly Thr Lys Leu Glu Ile Lys Arg Thr Val Ala Ala Pro
            260                 265                 270

Ser Gly Gly Ser Pro Ser Gly Gln Ala Gly Ala Ala Ala Ser Glu Ser
        275                 280                 285

Leu Phe Val Ser Asn His Ala Tyr Gly Gly Ser Ser Gln Val Gln Leu
    290                 295                 300

Gln Gln Ser Gly Ala Glu Leu Val Arg Pro Gly Ala Ser Val Lys Leu
305                 310                 315                 320

Ser Cys Lys Ala Ser Gly Tyr Thr Phe Ile Ser Tyr Trp Ile Asn Trp
                325                 330                 335

Val Lys Gln Arg Pro Gly Gln Gly Leu Glu Trp Ile Gly Asn Ile Tyr
            340                 345                 350

Pro Ser Asp Ser Tyr Thr Asn Tyr Asn Gln Lys Phe Lys Asp Lys Ala
        355                 360                 365

Thr Leu Thr Val Asp Lys Ser Ser Ser Thr Ala Tyr Met Gln Leu Ser
    370                 375                 380

Ser Pro Thr Ser Glu Asp Ser Ala Val Tyr Tyr Cys Thr Arg Asp Asp
385                 390                 395                 400

Asn Tyr Gly Ala Met Asp Tyr Trp Gly Gln Gly Thr Thr Val Thr Val
                405                 410                 415

Ser Ser Ala Ser Thr Lys Gly Pro Ser Val Lys Leu Glu Glu Gly Glu
            420                 425                 430

Phe Ser Glu Ala Arg Val Ser Asp Ile Glu Leu Thr Gln Ser Pro Ser
```

-continued

```
        435                 440                 445

Tyr Leu Val Ala Ser Pro Gly Glu Thr Ile Thr Ile Asn Cys Arg Ala
    450                 455                 460

Ser Lys Ser Ile Ser Lys Ser Leu Ala Trp Tyr Gln Glu Lys Pro Gly
465                 470                 475                 480

Lys Thr Asn Asn Leu Leu Ile Tyr Ser Gly Ser Thr Leu Gln Ser Gly
                485                 490                 495

Ile Pro Ser Arg Phe Ser Gly Ser Gly Ser Gly Thr Asp Phe Thr Leu
            500                 505                 510

Thr Ile Ser Ser Leu Glu Pro Glu Asp Phe Ala Met Tyr Ile Cys Gln
        515                 520                 525

Gln His Asn Glu Tyr Pro Trp Thr Phe Gly Gly Gly Thr Lys Leu Glu
    530                 535                 540

Ile Lys Arg Lys Arg Thr Val Ala Ala Pro Ser Gly Ala Ala Ala Leu
545                 550                 555                 560

Glu His His His His His His
                565


<210> SEQ ID NO 3
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Gly
1               5                   10                  15

Thr Val Ser Leu Thr Cys Ala Val Ser Gly Gly Ser Ile Ser Ser Ser
            20                  25                  30

Tyr Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Leu Phe Ser
65                  70                  75                  80

Leu Lys Leu Ser Ser Val Thr Ala Ala Asp Thr Ala Val Tyr Tyr Cys
                85                  90                  95

Ala Arg Val Ala Leu Phe Asp Ile Leu Thr Gly Gly Trp Phe Asp Pro
            100                 105                 110

Trp Gly Gln Gly Thr Leu Val Thr Val Ser Ser Ala Ser Thr Lys Gly
        115                 120                 125

Pro Ser Val Lys Leu Glu Glu Gly Glu Phe Ser Glu Ala Arg Val Tyr
    130                 135                 140

Glu Leu Thr Gln Pro Pro Ser Val Ser Val Ser Pro Gly Gln Thr Val
145                 150                 155                 160

Asn Ile Thr Cys Ser Gly Asp Thr Leu Gly Asp Lys Tyr Val Cys Trp
                165                 170                 175

Tyr Gln Gln Lys Pro Gly Gln Ser Pro Val Leu Val Ile Tyr Gln Asp
            180                 185                 190

Thr Lys Arg Pro Ser Gly Ile Pro Glu Arg Phe Ser Gly Ser Asn Ser
        195                 200                 205

Gly Asp Thr Ala Thr Leu Thr Val Ser Gly Thr Gln Ala Met Asp Glu
    210                 215                 220
```

Ala Asp Tyr Tyr Cys Gln Ala Trp Asp Ser Ser Ser Phe Val Phe Gly
225 230 235 240

Thr Gly Thr Lys Val Thr Val Leu Gly Gly Ser Gly Gly Pro Ser Gly
245 250 255

Gln Ala Gly Ala Ala Ala Ser Glu Ser Leu Phe Val Ser Asn His Ala
260 265 270

Tyr Gly Gly Ser Gly Gly Glu Val His Leu Gln Gln Ser Gly Pro Glu
275 280 285

Leu Val Lys Pro Gly Ala Ser Val Lys Met Ser Cys Lys Thr Ser Gly
290 295 300

Tyr Thr Phe Thr Glu Tyr Thr Ile His Trp Met Lys Gln Ser His Gly
305 310 315 320

Lys Ser Leu Glu Trp Ile Gly Gly Ile Phe Pro Asn Asn Gly Asp Thr
325 330 335

Thr Tyr Asn Gln Lys Phe Lys Val Arg Ala Thr Leu Thr Val Gly Arg
340 345 350

Ser Ser Ser Thr Ala Tyr Met Asp Leu Arg Ser Leu Thr Ser Glu Asp
355 360 365

Ser Ala Val Tyr Tyr Cys Val Arg Asn Tyr Gly Ser Ser Tyr Gly Tyr
370 375 380

Phe Asp Val Trp Gly Ala Gly Thr Thr Val Thr Val Ser Ser Ala Ser
385 390 395 400

Thr Lys Gly Pro Ser Val Phe Pro Leu Ala Pro Ser Ser Lys Ser Thr
405 410 415

Ser Gly Gly Thr Ala Ala Leu Gly Cys Leu Val Lys Asp Tyr Phe Pro
420 425 430

Glu Pro Val Thr Val Ser Trp Asn Ser Gly Ala Leu Thr Ser Gly Val
435 440 445

His Thr Phe Pro Ala Val Leu Gln Ser Ser Gly Leu Tyr Ser Leu Ser
450 455 460

Ser Val Val Thr Val Pro Ser Ser Ser Leu Gly Thr Gln Thr Tyr Ile
465 470 475 480

Cys Asn Val Asn His Lys Pro Ser Asn Thr Lys Val Asp Lys Lys Val
485 490 495

Glu Pro Lys Ser Cys Asp Lys Thr His Thr
500 505

<210> SEQ ID NO 4
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Gly Thr Val Ser Leu Thr Cys Ala Val Ser Gly Gly Ser Ile
35 40 45

Ser Ser Ser Tyr Trp Trp Ser Trp Val Arg Gln Pro Pro Gly Lys Gly
50 55 60

Leu Glu Trp Ile Gly Glu Ile Tyr His Ser Gly Asn Thr Asn Tyr Asn
65 70 75 80

-continued

```
Pro Ser Leu Lys Ser Arg Val Thr Ile Ser Val Asp Lys Ser Lys Asn
                85                  90                  95

Leu Phe Ser Leu Lys Leu Ser Ser Val Thr Ala Ala Asp Thr Ala Val
            100                 105                 110

Tyr Tyr Cys Ala Arg Val Ala Leu Phe Asp Ile Leu Thr Gly Gly Trp
        115                 120                 125

Phe Asp Pro Trp Gly Gln Gly Thr Leu Val Thr Val Ser Ser Ala Ser
    130                 135                 140

Thr Lys Gly Pro Ser Val Lys Leu Glu Glu Gly Glu Phe Ser Glu Ala
145                 150                 155                 160

Arg Val Tyr Glu Leu Thr Gln Pro Pro Ser Val Ser Val Ser Pro Gly
                165                 170                 175

Gln Thr Val Asn Ile Thr Cys Ser Gly Asp Thr Leu Gly Asp Lys Tyr
            180                 185                 190

Val Cys Trp Tyr Gln Gln Lys Pro Gly Gln Ser Pro Val Leu Val Ile
        195                 200                 205

Tyr Gln Asp Thr Lys Arg Pro Ser Gly Ile Pro Glu Arg Phe Ser Gly
    210                 215                 220

Ser Asn Ser Gly Asp Thr Ala Thr Leu Thr Val Ser Gly Thr Gln Ala
225                 230                 235                 240

Met Asp Glu Ala Asp Tyr Tyr Cys Gln Ala Trp Asp Ser Ser Ser Phe
                245                 250                 255

Val Phe Gly Thr Gly Thr Lys Val Thr Val Leu Gly Gly Ser Gly Gly
            260                 265                 270

Pro Ser Gly Gln Ala Gly Ala Ala Ala Ser Glu Ser Leu Phe Val Ser
        275                 280                 285

Asn His Ala Tyr Gly Gly Ser Gly Gly Glu Val His Leu Gln Gln Ser
    290                 295                 300

Gly Pro Glu Leu Val Lys Pro Gly Ala Ser Val Lys Met Ser Cys Lys
305                 310                 315                 320

Thr Ser Gly Tyr Thr Phe Thr Glu Tyr Thr Ile His Trp Met Lys Gln
                325                 330                 335

Ser His Gly Lys Ser Leu Glu Trp Ile Gly Gly Ile Phe Pro Asn Asn
            340                 345                 350

Gly Asp Thr Thr Tyr Asn Gln Lys Phe Lys Val Arg Ala Thr Leu Thr
        355                 360                 365

Val Gly Arg Ser Ser Ser Thr Ala Tyr Met Asp Leu Arg Ser Leu Thr
    370                 375                 380

Ser Glu Asp Ser Ala Val Tyr Tyr Cys Val Arg Asn Tyr Gly Ser Ser
385                 390                 395                 400

Tyr Gly Tyr Phe Asp Val Trp Gly Ala Gly Thr Thr Val Thr Val Ser
                405                 410                 415

Ser Ala Ser Thr Lys Gly Pro Ser Val Phe Pro Leu Ala Pro Ser Ser
            420                 425                 430

Lys Ser Thr Ser Gly Gly Thr Ala Ala Leu Gly Cys Leu Val Lys Asp
        435                 440                 445

Tyr Phe Pro Glu Pro Val Thr Val Ser Trp Asn Ser Gly Ala Leu Thr
    450                 455                 460

Ser Gly Val His Thr Phe Pro Ala Val Leu Gln Ser Ser Gly Leu Tyr
465                 470                 475                 480

Ser Leu Ser Ser Val Val Thr Val Pro Ser Ser Ser Leu Gly Thr Gln
                485                 490                 495
```

-continued

```
Thr Tyr Ile Cys Asn Val Asn His Lys Pro Ser Asn Thr Lys Val Asp
            500                 505                 510

Lys Lys Val Glu Pro Lys Ser Cys Asp Lys Thr His Thr
        515                 520                 525
```

<210> SEQ ID NO 5
<211> LENGTH: 501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Glu Val Gln Leu Val Gln Ser Gly Ala Glu Val Lys Lys Pro Gly Glu
1               5                   10                  15

Ser Leu Arg Ile Ser Cys Ala Gly Phe Ala Tyr Ser Ser Thr Tyr Phe
            20                  25                  30

Trp Ile Ser Trp Val Arg Gln Met Pro Gly Lys Cys Pro Glu Trp Met
        35                  40                  45

Gly Arg Ile Asp Pro Thr Asp Ser Tyr Ile Asn Tyr Ser Pro Ser Phe
    50                  55                  60

Gln Gly His Val Thr Ile Ser Val Asp Arg Ser Ala Ser Thr Val Tyr
65                  70                  75                  80

Leu Gln Trp Ser Ser Leu Lys Ala Ser Asp Thr Ala Met Tyr Tyr Cys
                85                  90                  95

Ala Tyr His Arg Arg Gly His Phe Tyr Gly Ser Gly Ser Ala Trp Asp
            100                 105                 110

Trp Phe Glu Ser Trp Gly Gln Gly Thr Leu Val Thr Val Ser Ser Arg
        115                 120                 125

Thr Val Gly Pro Ser Val Lys Leu Glu Glu Gly Glu Phe Ser Glu Ala
    130                 135                 140

Arg Val Glu Ile Val Leu Thr Gln Ser Pro Leu Thr Leu Ser Val Ser
145                 150                 155                 160

Pro Gly Glu Arg Ala Thr Leu Ser Cys Arg Ala Ser Gln Ser Val Ser
                165                 170                 175

Ser Asn Leu Ala Trp Tyr Gln Gln Met Pro Gly Gln Ala Pro Arg Leu
            180                 185                 190

Leu Ile Tyr Gly Ala Ser Thr Arg Ala Thr Gly Ile Pro Ala Arg Leu
        195                 200                 205

Ser Gly Ser Ala Ser Gly Thr Glu Phe Thr Leu Thr Ile Ser Ser Leu
    210                 215                 220

Gln Ser Glu Asp Phe Ala Val Tyr Tyr Cys Gln Gln Tyr Asn Asn Trp
225                 230                 235                 240

Pro Tyr Thr Phe Gly Cys Gly Thr Lys Leu Glu Ile Lys Gly Gly Ser
                245                 250                 255

Gly Gly Pro Ser Gly Gln Ala Gly Ala Ala Ala Ser Glu Ser Leu Phe
            260                 265                 270

Val Ser Asn His Ala Tyr Gly Gly Ser Gly Gly Asp Ile Val Leu Thr
        275                 280                 285

Gln Ser Pro Gly Ser Leu Thr Val Ser Leu Gly Gln Arg Ala Thr Ile
    290                 295                 300

Ser Cys Arg Ala Ser Glu Ser Val Asp Asn Phe Gly Lys Ser Phe Met
305                 310                 315                 320

His Trp Tyr Gln Gln Lys Pro Gly Gln Ser Pro Lys Leu Leu Ile Tyr
                325                 330                 335
```

```
Arg Ala Ser Asn Arg Glu Phe Gly Ile Pro Ala Arg Phe Asn Gly Ser
            340                 345                 350

Gly Ser Gly Thr Asp Phe Ala Leu Thr Ile Asn Pro Val Glu Ala Asp
        355                 360                 365

Asp Val Ala Thr Tyr Phe Cys Gln Gln Ser Asn Glu Asp Pro Arg Thr
    370                 375                 380

Phe Gly Gly Gly Thr Lys Leu Glu Ile Lys Arg Thr Val Ala Ala Pro
385                 390                 395                 400

Ser Val Phe Ile Phe Pro Pro Ser Asp Glu Gln Leu Lys Ser Gly Thr
                405                 410                 415

Ala Ser Val Val Cys Leu Leu Asn Asn Phe Tyr Pro Arg Glu Ala Lys
            420                 425                 430

Val Gln Trp Lys Val Asp Asn Ala Leu Gln Ser Gly Asn Ser Gln Glu
        435                 440                 445

Ser Val Thr Glu Gln Asp Ser Lys Asp Ser Thr Tyr Ser Leu Ser Ser
    450                 455                 460

Thr Leu Thr Leu Ser Lys Ala Asp Tyr Glu Lys His Lys Val Tyr Ala
465                 470                 475                 480

Cys Glu Val Thr His Gln Gly Leu Ser Ser Pro Val Thr Lys Ser Phe
                485                 490                 495

Asn Arg Gly Glu Cys
            500


<210> SEQ ID NO 6
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Glu Ser Leu Arg Ile Ser Cys Ala Gly Phe Ala Tyr Ser Ser
        35                  40                  45

Thr Tyr Phe Trp Ile Ser Trp Val Arg Gln Met Pro Gly Lys Cys Pro
    50                  55                  60

Glu Trp Met Gly Arg Ile Asp Pro Thr Asp Ser Tyr Ile Asn Tyr Ser
65                  70                  75                  80

Pro Ser Phe Gln Gly His Val Thr Ile Ser Val Asp Arg Ser Ala Ser
                85                  90                  95

Thr Val Tyr Leu Gln Trp Ser Ser Leu Lys Ala Ser Asp Thr Ala Met
            100                 105                 110

Tyr Tyr Cys Ala Tyr His Arg Arg Gly His Phe Tyr Gly Ser Gly Ser
        115                 120                 125

Ala Trp Asp Trp Phe Glu Ser Trp Gly Gln Gly Thr Leu Val Thr Val
    130                 135                 140

Ser Ser Arg Thr Val Gly Pro Ser Val Lys Leu Glu Glu Gly Glu Phe
145                 150                 155                 160

Ser Glu Ala Arg Val Glu Ile Val Leu Thr Gln Ser Pro Leu Thr Leu
                165                 170                 175

Ser Val Ser Pro Gly Glu Arg Ala Thr Leu Ser Cys Arg Ala Ser Gln
```

```
            180                 185                 190

Ser Val Ser Ser Asn Leu Ala Trp Tyr Gln Gln Met Pro Gly Gln Ala
        195                 200                 205

Pro Arg Leu Leu Ile Tyr Gly Ala Ser Thr Arg Ala Thr Gly Ile Pro
    210                 215                 220

Ala Arg Leu Ser Gly Ser Ala Ser Gly Thr Glu Phe Thr Leu Thr Ile
225                 230                 235                 240

Ser Ser Leu Gln Ser Glu Asp Phe Ala Val Tyr Tyr Cys Gln Gln Tyr
                245                 250                 255

Asn Asn Trp Pro Tyr Thr Phe Gly Cys Gly Thr Lys Leu Glu Ile Lys
            260                 265                 270

Gly Gly Ser Gly Gly Pro Ser Gly Gln Ala Gly Ala Ala Ala Ser Glu
        275                 280                 285

Ser Leu Phe Val Ser Asn His Ala Tyr Gly Gly Ser Gly Gly Asp Ile
    290                 295                 300

Val Leu Thr Gln Ser Pro Gly Ser Leu Thr Val Ser Leu Gly Gln Arg
305                 310                 315                 320

Ala Thr Ile Ser Cys Arg Ala Ser Glu Ser Val Asp Asn Phe Gly Lys
                325                 330                 335

Ser Phe Met His Trp Tyr Gln Gln Lys Pro Gly Gln Ser Pro Lys Leu
            340                 345                 350

Leu Ile Tyr Arg Ala Ser Asn Arg Glu Phe Gly Ile Pro Ala Arg Phe
        355                 360                 365

Asn Gly Ser Gly Ser Gly Thr Asp Phe Ala Leu Thr Ile Asn Pro Val
    370                 375                 380

Glu Ala Asp Asp Val Ala Thr Tyr Phe Cys Gln Gln Ser Asn Glu Asp
385                 390                 395                 400

Pro Arg Thr Phe Gly Gly Gly Thr Lys Leu Glu Ile Lys Arg Thr Val
                405                 410                 415

Ala Ala Pro Ser Val Phe Ile Phe Pro Pro Ser Asp Glu Gln Leu Lys
            420                 425                 430

Ser Gly Thr Ala Ser Val Val Cys Leu Leu Asn Asn Phe Tyr Pro Arg
        435                 440                 445

Glu Ala Lys Val Gln Trp Lys Val Asp Asn Ala Leu Gln Ser Gly Asn
    450                 455                 460

Ser Gln Glu Ser Val Thr Glu Gln Asp Ser Lys Asp Ser Thr Tyr Ser
465                 470                 475                 480

Leu Ser Ser Thr Leu Thr Leu Ser Lys Ala Asp Tyr Glu Lys His Lys
                485                 490                 495

Val Tyr Ala Cys Glu Val Thr His Gln Gly Leu Ser Ser Pro Val Thr
            500                 505                 510

Lys Ser Phe Asn Arg Gly Glu Cys
        515                 520


<210> SEQ ID NO 7
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Ala Glu Val Lys Lys Pro Gly Ser
1               5                   10                  15
```

-continued

```
Ser Val Lys Val Ser Cys Arg Ala Ser Gly Thr Phe Tyr Lys Tyr Ala
            20                  25                  30

Ile Asn Trp Val Arg Gln Ala Pro Gly Gln Cys Leu Glu Trp Met Gly
        35                  40                  45

Gly Ile Ile Pro Phe Phe Gly Thr Thr Asn Tyr Ala Ala Lys Phe Gln
    50                  55                  60

Gly Arg Leu Thr Ile Thr Ala Asp Gly Ser Thr Asn Thr Ala Tyr Met
65                  70                  75                  80

Gln Leu Asp Ser Leu Arg Ser Glu Asp Thr Ala Val Tyr Tyr Cys Ala
                85                  90                  95

Gly Pro Ser Ile Thr Glu Ser His Tyr Cys Leu Asp Cys Ala Ala Lys
            100                 105                 110

Asp Tyr Tyr Tyr Gly Leu Asp Val Trp Gly Gln Gly Thr Thr Val Thr
        115                 120                 125

Val Ser Ser Ala Ser Thr Lys Gly Pro Ser Val Lys Leu Glu Glu Gly
    130                 135                 140

Glu Phe Ser Glu Ala Arg Val Gln Ser Val Leu Thr Gln Pro Pro Ser
145                 150                 155                 160

Ala Ser Gly Thr Pro Gly Gln Ser Val Thr Ile Ser Cys Ser Gly Ser
                165                 170                 175

Arg Ser Asn Ile Gly Gly Asn Thr Val Asn Trp Tyr Gln His Leu Pro
            180                 185                 190

Gly Met Ala Pro Lys Leu Leu Ile Tyr Ser Ser Asn Gln Arg Ser Ser
        195                 200                 205

Gly Val Pro Asp Arg Phe Ser Gly Ser Lys Ser Gly Thr Ser Ala Ser
    210                 215                 220

Leu Ala Ile Ser Gly Leu Gln Ser Glu Asp Asp Ala Asp Tyr Tyr Cys
225                 230                 235                 240

Ala Ser Trp Asp Asp Ser Leu Asn Gly Val Val Phe Gly Cys Gly Thr
                245                 250                 255

Lys Leu Thr Val Leu Gly Gly Gly Ser Gly Gly Pro Ser Gly Gln Ala
            260                 265                 270

Gly Ala Ala Ala Ser Glu Ser Leu Phe Val Ser Asn His Ala Tyr Gly
        275                 280                 285

Gly Ser Gly Gly Glu Val His Leu Gln Gln Ser Gly Pro Glu Leu Val
    290                 295                 300

Lys Pro Gly Ala Ser Val Lys Met Ser Cys Lys Thr Ser Gly Tyr Thr
305                 310                 315                 320

Phe Thr Glu Tyr Thr Ile His Trp Met Lys Gln Ser His Gly Lys Ser
                325                 330                 335

Leu Glu Trp Ile Gly Gly Ile Phe Pro Asn Asn Gly Asp Thr Thr Tyr
            340                 345                 350

Asn Gln Lys Phe Lys Val Arg Ala Thr Leu Thr Val Gly Arg Ser Ser
        355                 360                 365

Ser Thr Ala Tyr Met Asp Leu Arg Ser Leu Thr Ser Glu Asp Ser Ala
    370                 375                 380

Val Tyr Tyr Cys Val Arg Asn Tyr Gly Ser Ser Tyr Gly Tyr Phe Asp
385                 390                 395                 400

Val Trp Gly Ala Gly Thr Thr Val Thr Val Ser Ser Ala Ser Thr Lys
                405                 410                 415

Gly Pro Ser Val Phe Pro Leu Ala Pro Ser Ser Lys Ser Thr Ser Gly
            420                 425                 430

Gly Thr Ala Ala Leu Gly Cys Leu Val Lys Asp Tyr Phe Pro Glu Pro
```

```
        435                 440                 445

Val Thr Val Ser Trp Asn Ser Gly Ala Leu Thr Ser Gly Val His Thr
    450                 455                 460

Phe Pro Ala Val Leu Gln Ser Ser Gly Leu Tyr Ser Leu Ser Ser Val
465                 470                 475                 480

Val Thr Val Pro Ser Ser Ser Leu Gly Thr Gln Thr Tyr Ile Cys Asn
                485                 490                 495

Val Asn His Lys Pro Ser Asn Thr Lys Val Asp Lys Lys Val Glu Pro
            500                 505                 510

Lys Ser Cys Asp Lys Thr His Thr
        515                 520


<210> SEQ ID NO 8
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Trp Ser Cys Ile Ile Leu Phe Leu Val Ala Thr Ala Thr Gly
1               5                   10                  15

Val His Ser Glu Val Gln Leu Val Glu Ser Gly Ala Glu Val Lys Lys
            20                  25                  30

Pro Gly Ser Ser Val Lys Val Ser Cys Arg Ala Ser Gly Thr Phe Tyr
        35                  40                  45

Lys Tyr Ala Ile Asn Trp Val Arg Gln Ala Pro Gly Gln Cys Leu Glu
    50                  55                  60

Trp Met Gly Gly Ile Ile Pro Phe Phe Gly Thr Thr Asn Tyr Ala Ala
65                  70                  75                  80

Lys Phe Gln Gly Arg Leu Thr Ile Thr Ala Asp Gly Ser Thr Asn Thr
                85                  90                  95

Ala Tyr Met Gln Leu Asp Ser Leu Arg Ser Glu Asp Thr Ala Val Tyr
            100                 105                 110

Tyr Cys Ala Gly Pro Ser Ile Thr Glu Ser His Tyr Cys Leu Asp Cys
        115                 120                 125

Ala Ala Lys Asp Tyr Tyr Tyr Gly Leu Asp Val Trp Gly Gln Gly Thr
    130                 135                 140

Thr Val Thr Val Ser Ser Ala Ser Thr Lys Gly Pro Ser Val Lys Leu
145                 150                 155                 160

Glu Glu Gly Glu Phe Ser Glu Ala Arg Val Gln Ser Val Leu Thr Gln
                165                 170                 175

Pro Pro Ser Ala Ser Gly Thr Pro Gly Gln Ser Val Thr Ile Ser Cys
            180                 185                 190

Ser Gly Ser Arg Ser Asn Ile Gly Gly Asn Thr Val Asn Trp Tyr Gln
        195                 200                 205

His Leu Pro Gly Met Ala Pro Lys Leu Leu Ile Tyr Ser Ser Asn Gln
    210                 215                 220

Arg Ser Ser Gly Val Pro Asp Arg Phe Ser Gly Ser Lys Ser Gly Thr
225                 230                 235                 240

Ser Ala Ser Leu Ala Ile Ser Gly Leu Gln Ser Glu Asp Asp Ala Asp
                245                 250                 255

Tyr Tyr Cys Ala Ser Trp Asp Asp Ser Leu Asn Gly Val Val Phe Gly
            260                 265                 270
```

-continued

```
Cys Gly Thr Lys Leu Thr Val Leu Gly Gly Gly Ser Gly Gly Pro Ser
        275                 280                 285

Gly Gln Ala Gly Ala Ala Ala Ser Glu Ser Leu Phe Val Ser Asn His
    290                 295                 300

Ala Tyr Gly Gly Ser Gly Gly Glu Val His Leu Gln Gln Ser Gly Pro
305                 310                 315                 320

Glu Leu Val Lys Pro Gly Ala Ser Val Lys Met Ser Cys Lys Thr Ser
                325                 330                 335

Gly Tyr Thr Phe Thr Glu Tyr Thr Ile His Trp Met Lys Gln Ser His
            340                 345                 350

Gly Lys Ser Leu Glu Trp Ile Gly Gly Ile Phe Pro Asn Asn Gly Asp
        355                 360                 365

Thr Thr Tyr Asn Gln Lys Phe Lys Val Arg Ala Thr Leu Thr Val Gly
    370                 375                 380

Arg Ser Ser Ser Thr Ala Tyr Met Asp Leu Arg Ser Leu Thr Ser Glu
385                 390                 395                 400

Asp Ser Ala Val Tyr Tyr Cys Val Arg Asn Tyr Gly Ser Ser Tyr Gly
                405                 410                 415

Tyr Phe Asp Val Trp Gly Ala Gly Thr Thr Val Thr Val Ser Ser Ala
            420                 425                 430

Ser Thr Lys Gly Pro Ser Val Phe Pro Leu Ala Pro Ser Ser Lys Ser
        435                 440                 445

Thr Ser Gly Gly Thr Ala Ala Leu Gly Cys Leu Val Lys Asp Tyr Phe
    450                 455                 460

Pro Glu Pro Val Thr Val Ser Trp Asn Ser Gly Ala Leu Thr Ser Gly
465                 470                 475                 480

Val His Thr Phe Pro Ala Val Leu Gln Ser Ser Gly Leu Tyr Ser Leu
                485                 490                 495

Ser Ser Val Val Thr Val Pro Ser Ser Ser Leu Gly Thr Gln Thr Tyr
            500                 505                 510

Ile Cys Asn Val Asn His Lys Pro Ser Asn Thr Lys Val Asp Lys Lys
        515                 520                 525

Val Glu Pro Lys Ser Cys Asp Lys Thr His Thr
    530                 535


<210> SEQ ID NO 9
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Ala
            20                  25                  30

Thr His Trp Tyr Gln Gln Lys Pro Gly Lys Ala Pro Lys Leu Leu Ile
        35                  40                  45

Tyr Ala Ala Ser Ser Arg Gly Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95
```

```
Gly Thr Lys Val Glu Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210


<210> SEQ ID NO 10
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Thr Ser Gln Ser Leu
        35                  40                  45

Ser Ser Ala Thr His Trp Tyr Gln Gln Lys Pro Gly Lys Ala Pro Lys
    50                  55                  60

Leu Leu Ile Tyr Ala Ala Ser Ser Arg Gly Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Arg Thr
            100                 105                 110

Phe Gly Gln Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
```

225

<210> SEQ ID NO 11
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30

Asn Ala Val Trp Asn Trp Ile Arg Gln Ser Pro Ser Arg Gly Leu Glu
        35                  40                  45

Trp Leu Gly Ala Thr Ala Tyr Arg Ser Gly Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350
```

```
Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 12
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Tyr Asn Ala Val Trp Asn Trp Ile Arg Gln Ser Pro Ser Arg
    50                  55                  60

Gly Leu Glu Trp Leu Gly Ala Thr Ala Tyr Arg Ser Gly Trp Tyr Asn
65                  70                  75                  80

Asp Tyr Ala Glu Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Ser Gly His Ile Thr Val Phe Gly
        115                 120                 125

Val Asn Val Asp Ala Phe Asp Met Trp Gly Gln Gly Thr Met Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255
```

```
Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475
```

<210> SEQ ID NO 13
<211> LENGTH: 553
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Lys Leu Lys Gly Ile Ala
        35                  40                  45

Pro Leu Gln Leu Gly Lys Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Phe Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Lys Gly Val Ser Ala Ser Cys Ser His Lys Gly Lys Ser Ser Phe Tyr
```

```
    130                 135                 140

Lys Asn Leu Leu Trp Leu Thr Gly Lys Asn Gly Leu Tyr Pro Lys Leu
145                 150                 155                 160

Ser Lys Ser Tyr Lys Asn Asn Lys Glu Lys Glu Val Leu Val Leu Trp
                165                 170                 175

Gly Val His His Pro Pro Asn Ile Lys Asn Gln Lys Ala Leu Tyr His
            180                 185                 190

Thr Glu Asn Ala Tyr Val Ser Val Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Gln Arg Glu Thr Gly Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Ser Gly Tyr Ile Pro Glu Ala Pro Arg Asp Gly
            500                 505                 510

Gln Ala Tyr Val Arg Lys Asp Gly Glu Trp Val Leu Leu Ser Thr Phe
        515                 520                 525

Leu Gly Ser Gly Leu Asn Asp Ile Phe Glu Ala Gln Lys Ile Glu Trp
    530                 535                 540

His Glu Gly His His His His His His
545                 550
```

<210> SEQ ID NO 14
<211> LENGTH: 573
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Met Tyr Arg Met Gln Leu Leu Ser Cys Ile Ala Leu Ser Leu Ala Leu
1               5                   10                  15

Val Thr Asn Ser Asp Thr Ile Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Ser His Asn Gly Lys Leu Cys Lys Leu
    50                  55                  60

Lys Gly Ile Ala Pro Leu Gln Leu Gly Lys Cys Ser Val Ala Gly Trp
65                  70                  75                  80

Ile Leu Gly Asn Pro Glu Cys Glu Leu Leu Ile Ser Lys Glu Ser Trp
                85                  90                  95

Ser Tyr Ile Val Glu Thr Pro Asn Pro Glu Asn Gly Thr Cys Phe Pro
            100                 105                 110

Gly Tyr Phe Ala Asp Tyr Glu Glu Leu Arg Glu Gln Leu Ser Ser Val
        115                 120                 125

Ser Ser Phe Glu Arg Phe Glu Ile Phe Pro Lys Glu Ser Ser Trp Pro
    130                 135                 140

Asn His Thr Val Lys Gly Val Ser Ala Ser Cys Ser His Lys Gly Lys
145                 150                 155                 160

Ser Ser Phe Tyr Lys Asn Leu Leu Trp Leu Thr Gly Lys Asn Gly Leu
                165                 170                 175

Tyr Pro Lys Leu Ser Lys Ser Tyr Lys Asn Asn Lys Glu Lys Glu Val
            180                 185                 190

Leu Val Leu Trp Gly Val His His Pro Pro Asn Ile Lys Asn Gln Lys
        195                 200                 205

Ala Leu Tyr His Thr Glu Asn Ala Tyr Val Ser Val Val Ser Ser His
    210                 215                 220

Tyr Ser Arg Arg Phe Thr Pro Glu Ile Ala Lys Arg Pro Lys Val Arg
225                 230                 235                 240

Asp Gln Glu Gly Arg Ile Asn Tyr Tyr Trp Thr Leu Leu Glu Pro Gly
                245                 250                 255

Asp Thr Ile Ile Phe Glu Ala Asn Gly Asn Leu Ile Ala Pro Trp Tyr
            260                 265                 270

Ala Phe Ala Leu Ser Arg Gly Phe Gly Ser Gly Ile Ile Thr Ser Asn
        275                 280                 285

Ala Pro Met Asp Glu Cys Asp Ala Lys Cys Gln Thr Pro Gln Gly Ala
    290                 295                 300

Ile Asn Ser Ser Leu Pro Phe Gln Asn Val His Pro Val Thr Ile Gly
305                 310                 315                 320

Glu Cys Pro Lys Tyr Val Arg Ser Ala Lys Leu Arg Met Val Thr Gly
                325                 330                 335

Leu Arg Asn Ile Pro Gln Arg Glu Thr Gly Gly Leu Phe Gly Ala Ile
            340                 345                 350

Ala Gly Phe Ile Glu Gly Gly Trp Thr Gly Met Val Asp Gly Trp Tyr
```

-continued

```
        355                 360                 365

Gly Tyr His His Gln Asn Glu Gln Gly Ser Gly Tyr Ala Ala Asp Gln
    370                 375                 380

Lys Ser Thr Gln Asn Ala Ile Asn Gly Ile Thr Asn Lys Val Asn Ser
385                 390                 395                 400

Val Ile Glu Lys Met Asn Thr Gln Phe Thr Ala Val Gly Lys Glu Phe
                405                 410                 415

Asn Lys Leu Glu Arg Arg Met Glu Asn Leu Asn Lys Lys Val Asp Asp
            420                 425                 430

Gly Phe Leu Asp Ile Trp Thr Tyr Asn Ala Glu Leu Leu Val Leu Leu
        435                 440                 445

Glu Asn Glu Arg Thr Leu Asp Phe His Asp Ser Asn Val Lys Asn Leu
    450                 455                 460

Tyr Glu Lys Val Lys Ser Gln Leu Lys Asn Asn Ala Lys Glu Ile Gly
465                 470                 475                 480

Asn Gly Cys Phe Glu Phe Tyr His Lys Cys Asn Asn Glu Cys Met Glu
                485                 490                 495

Ser Val Lys Asn Gly Thr Tyr Asp Tyr Pro Lys Tyr Ser Glu Glu Ser
            500                 505                 510

Lys Leu Asn Arg Glu Lys Ile Asp Gly Ser Gly Tyr Ile Pro Glu Ala
        515                 520                 525

Pro Arg Asp Gly Gln Ala Tyr Val Arg Lys Asp Gly Glu Trp Val Leu
    530                 535                 540

Leu Ser Thr Phe Leu Gly Ser Gly Leu Asn Asp Ile Phe Glu Ala Gln
545                 550                 555                 560

Lys Ile Glu Trp His Glu Gly His His His His His His
                565                 570


<210> SEQ ID NO 15
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Phe Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140
```

-continued

```
Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Ser Gly Tyr Ile Pro Glu Ala Pro Arg Asp Gly
            500                 505                 510

Gln Ala Tyr Val Arg Lys Asp Gly Glu Trp Val Leu Leu Ser Thr Phe
        515                 520                 525

Leu Gly Ser Gly Leu Asn Asp Ile Phe Glu Ala Gln Lys Ile Glu Trp
    530                 535                 540

His Glu Gly His His His His His His
545                 550
```

<210> SEQ ID NO 16
<211> LENGTH: 569
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Phe Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365
```

Ser Asn Glu Gln Gly Ser Gly Tyr Ala Ala Asp Lys Glu Ser Thr Gln
370 375 380

Lys Ala Ile Asp Gly Val Thr Asn Lys Val Asn Ser Ile Ile Asp Lys
385 390 395 400

Met Asn Thr Gln Phe Glu Ala Val Gly Arg Glu Phe Asn Asn Leu Glu
405 410 415

Arg Arg Ile Glu Asn Leu Asn Lys Lys Met Glu Asp Gly Phe Leu Asp
420 425 430

Val Trp Thr Tyr Asn Ala Glu Leu Leu Val Leu Met Glu Asn Glu Arg
435 440 445

Thr Leu Asp Phe His Asp Ser Asn Val Lys Asn Leu Tyr Asp Lys Val
450 455 460

Arg Leu Gln Leu Arg Asp Asn Ala Lys Glu Leu Gly Asn Gly Cys Phe
465 470 475 480

Glu Phe Tyr His Lys Cys Asp Asn Glu Cys Met Glu Ser Val Arg Asn
485 490 495

Gly Thr Tyr Asp Tyr Pro Gln Tyr Ser Glu Glu Ala Arg Leu Lys Arg
500 505 510

Glu Glu Ile Ser Gly Ser Gly Tyr Ile Pro Glu Ala Pro Arg Asp Gly
515 520 525

Gln Ala Tyr Val Arg Lys Asp Gly Glu Trp Val Leu Leu Ser Thr Phe
530 535 540

Leu Gly Ser Gly Leu Asn Asp Ile Phe Glu Ala Gln Lys Ile Glu Trp
545 550 555 560

His Glu Gly His His His His His His
565

<210> SEQ ID NO 17
<211> LENGTH: 552
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Val Asn Asp Leu Cys Phe Pro Gly Asp Phe Asn
85 90 95

Asp Tyr Glu Glu Leu Lys His Leu Leu Ser Arg Ile Asn His Phe Glu
100 105 110

Lys Ile Gln Ile Ile Pro Lys Ser Ser Trp Ser Ser His Glu Ala Ser
115 120 125

Leu Gly Val Ser Ser Ala Cys Pro Tyr Gln Gly Lys Ser Ser Phe Phe
130 135 140

Arg Asn Val Val Trp Leu Ile Lys Lys Asn Ser Thr Tyr Pro Thr Ile
145 150 155 160

```
Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Gly Gly Gly Thr Gly Gly Gly Gly Thr Gly Arg
            500                 505                 510

Met Lys Gln Ile Glu Asp Lys Ile Glu Glu Ile Leu Ser Lys Ile Tyr
        515                 520                 525

His Ile Glu Asn Glu Ile Ala Arg Ile Lys Lys Leu Ile Gly Glu Arg
    530                 535                 540

His His His His His His His His
545                 550
```

<210> SEQ ID NO 18
<211> LENGTH: 568

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Met Glu Lys Ile Val Leu Leu Phe Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Asn Pro Val Asn Asp Leu Cys Phe Pro Gly Asp Phe Asn
100 105 110

Asp Tyr Glu Glu Leu Lys His Leu Leu Ser Arg Ile Asn His Phe Glu
115 120 125

Lys Ile Gln Ile Ile Pro Lys Ser Ser Trp Ser Ser His Glu Ala Ser
130 135 140

Leu Gly Val Ser Ser Ala Cys Pro Tyr Gln Gly Lys Ser Ser Phe Phe
145 150 155 160

Arg Asn Val Val Trp Leu Ile Lys Lys Asn Ser Thr Tyr Pro Thr Ile
165 170 175

Lys Arg Ser Tyr Asn Asn Thr Asn Gln Glu Asp Leu Leu Val Leu Trp
180 185 190

Gly Ile His His Pro Asn Asp Ala Ala Glu Gln Thr Lys Leu Tyr Gln
195 200 205

Asn Pro Thr Thr Tyr Ile Ser Val Gly Thr Ser Thr Leu Asn Gln Arg
210 215 220

Leu Val Pro Arg Ile Ala Thr Arg Ser Lys Val Asn Gly Gln Ser Gly
225 230 235 240

Arg Met Glu Phe Phe Trp Thr Ile Leu Lys Pro Asn Asp Ala Ile Asn
245 250 255

Phe Glu Ser Asn Gly Asn Phe Ile Ala Pro Glu Tyr Ala Tyr Lys Ile
260 265 270

Val Lys Lys Gly Asp Ser Thr Ile Met Lys Ser Glu Leu Glu Tyr Gly
275 280 285

Asn Cys Asn Thr Lys Cys Gln Thr Pro Met Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Ser
325 330 335

Pro Gln Arg Glu Thr Arg Gly Leu Phe Gly Ala Ile Ala Gly Phe Ile
340 345 350

Glu Gly Gly Trp Gln Gly Met Val Asp Gly Trp Tyr Gly Tyr His His
355 360 365

Ser Asn Glu Gln Gly Ser Gly Tyr Ala Ala Asp Lys Glu Ser Thr Gln
370 375 380

Lys Ala Ile Asp Gly Val Thr Asn Lys Val Asn Ser Ile Ile Asp Lys
385 390 395 400

Met Asn Thr Gln Phe Glu Ala Val Gly Arg Glu Phe Asn Asn Leu Glu
405 410 415

Arg Arg Ile Glu Asn Leu Asn Lys Lys Met Glu Asp Gly Phe Leu Asp
420 425 430

Val Trp Thr Tyr Asn Ala Glu Leu Leu Val Leu Met Glu Asn Glu Arg
435 440 445

Thr Leu Asp Phe His Asp Ser Asn Val Lys Asn Leu Tyr Asp Lys Val
450 455 460

Arg Leu Gln Leu Arg Asp Asn Ala Lys Glu Leu Gly Asn Gly Cys Phe
465 470 475 480

Glu Phe Tyr His Lys Cys Asp Asn Glu Cys Met Glu Ser Val Arg Asn
485 490 495

Gly Thr Tyr Asp Tyr Pro Gln Tyr Ser Glu Glu Ala Arg Leu Lys Arg
500 505 510

Glu Glu Ile Ser Gly Gly Gly Gly Thr Gly Gly Gly Gly Thr Gly Arg
515 520 525

Met Lys Gln Ile Glu Asp Lys Ile Glu Glu Ile Leu Ser Lys Ile Tyr
530 535 540

His Ile Glu Asn Glu Ile Ala Arg Ile Lys Lys Leu Ile Gly Glu Arg
545 550 555 560

His His His His His His His His
565

<210> SEQ ID NO 19
<211> LENGTH: 551
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Arg Gly Asp Gln Ile Cys Ile Gly Tyr His Ala Asn Asn Ser Thr Glu
1 5 10 15

Lys Val Asp Thr Ile Leu Glu Arg Asn Val Thr Val Thr His Ala Lys
20 25 30

Asp Ile Leu Glu Lys Thr His Asn Gly Lys Leu Cys Lys Leu Asn Gly
35 40 45

Ile Pro Pro Leu Glu Leu Gly Asp Cys Ser Ile Ala Gly Trp Leu Leu
50 55 60

Gly Asn Pro Glu Cys Asp Arg Leu Leu Ser Val Pro Glu Trp Ser Tyr
65 70 75 80

Ile Met Glu Lys Glu Asn Pro Arg Asp Gly Leu Cys Phe Pro Gly Ser
85 90 95

Phe Asn Asp Tyr Glu Glu Leu Lys Tyr Leu Leu Ser Ser Val Lys His
100 105 110

Phe Glu Lys Val Lys Ile Leu Pro Lys Asp Arg Trp Thr Gln His Thr
115 120 125

Thr Thr Gly Gly Ser Arg Ala Cys Ala Val Ser Gly Asn Pro Ser Phe
130 135 140

Phe Arg Asn Met Val Trp Leu Thr Lys Lys Gly Ser Asp Tyr Pro Val
145 150 155 160

Ala Lys Gly Ser Tyr Asn Asn Thr Ser Gly Glu Gln Met Leu Ile Ile

```
                165                 170                 175

Trp Gly Val His His Pro Asn Asp Glu Thr Glu Gln Arg Thr Leu Tyr
            180                 185                 190

Gln Asn Val Gly Thr Tyr Val Ser Val Gly Thr Ser Thr Leu Asn Lys
        195                 200                 205

Arg Ser Thr Pro Glu Ile Ala Thr Arg Pro Lys Val Asn Gly Leu Gly
    210                 215                 220

Ser Arg Met Glu Phe Ser Trp Thr Leu Leu Asp Met Trp Asp Thr Ile
225                 230                 235                 240

Asn Phe Glu Ser Thr Gly Asn Leu Ile Ala Pro Glu Tyr Gly Phe Lys
                245                 250                 255

Ile Ser Lys Arg Gly Ser Ser Gly Ile Met Lys Thr Glu Gly Thr Leu
            260                 265                 270

Glu Asn Cys Glu Thr Lys Cys Gln Thr Pro Leu Gly Ala Ile Asn Thr
        275                 280                 285

Thr Leu Pro Phe His Asn Val His Pro Leu Thr Ile Gly Glu Cys Pro
    290                 295                 300

Arg Tyr Val Lys Ser Glu Lys Leu Val Leu Ala Thr Gly Leu Arg Asn
305                 310                 315                 320

Val Pro Gln Ile Glu Ser Arg Gly Leu Phe Gly Ala Ile Ala Gly Phe
                325                 330                 335

Ile Glu Gly Gly Trp Gln Gly Met Val Asp Gly Trp Tyr Gly Tyr His
            340                 345                 350

His Ser Asn Asp Gln Gly Ser Gly Tyr Ala Ala Asp Lys Glu Ser Thr
        355                 360                 365

Gln Lys Ala Phe Asp Gly Ile Thr Asn Lys Val Asn Ser Val Ile Glu
    370                 375                 380

Lys Met Asn Thr Gln Phe Glu Ala Val Gly Lys Glu Phe Ser Asn Leu
385                 390                 395                 400

Glu Arg Arg Leu Glu Asn Leu Asn Lys Lys Met Glu Asp Gly Phe Leu
                405                 410                 415

Asp Val Trp Thr Tyr Asn Ala Glu Leu Leu Val Leu Met Glu Asn Glu
            420                 425                 430

Arg Thr Leu Asp Phe His Asp Ser Asn Val Lys Asn Leu Tyr Asp Lys
        435                 440                 445

Val Arg Met Gln Leu Arg Asp Asn Val Lys Glu Leu Gly Asn Gly Cys
    450                 455                 460

Phe Glu Phe Tyr His Lys Cys Asp Asp Glu Cys Met Asn Ser Val Lys
465                 470                 475                 480

Asn Gly Thr Tyr Asp Tyr Pro Lys Tyr Glu Glu Glu Ser Lys Leu Asn
                485                 490                 495

Arg Asn Glu Gly Gly Gly Gly Thr Gly Gly Gly Gly Thr Gly Arg Met
            500                 505                 510

Lys Gln Ile Glu Asp Lys Ile Glu Glu Ile Leu Ser Lys Ile Tyr His
        515                 520                 525

Ile Glu Asn Glu Ile Ala Arg Ile Lys Lys Leu Ile Gly Glu Arg His
    530                 535                 540

His His His His His His His
545                 550
```

<210> SEQ ID NO 20
<211> LENGTH: 567
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

```
Met Glu Lys Ile Val Leu Leu Phe Ala Ile Val Ser Leu Val Lys Ser
1               5                   10                  15

Arg Gly Asp Gln Ile Cys Ile Gly Tyr His Ala Asn Asn Ser Thr Glu
            20                  25                  30

Lys Val Asp Thr Ile Leu Glu Arg Asn Val Thr Val Thr His Ala Lys
        35                  40                  45

Asp Ile Leu Glu Lys Thr His Asn Gly Lys Leu Cys Lys Leu Asn Gly
    50                  55                  60

Ile Pro Pro Leu Glu Leu Gly Asp Cys Ser Ile Ala Gly Trp Leu Leu
65                  70                  75                  80

Gly Asn Pro Glu Cys Asp Arg Leu Leu Ser Val Pro Glu Trp Ser Tyr
                85                  90                  95

Ile Met Glu Lys Glu Asn Pro Arg Asp Gly Leu Cys Phe Pro Gly Ser
            100                 105                 110

Phe Asn Asp Tyr Glu Glu Leu Lys Tyr Leu Leu Ser Ser Val Lys His
        115                 120                 125

Phe Glu Lys Val Lys Ile Leu Pro Lys Asp Arg Trp Thr Gln His Thr
    130                 135                 140

Thr Thr Gly Gly Ser Arg Ala Cys Ala Val Ser Gly Asn Pro Ser Phe
145                 150                 155                 160

Phe Arg Asn Met Val Trp Leu Thr Lys Lys Gly Ser Asp Tyr Pro Val
                165                 170                 175

Ala Lys Gly Ser Tyr Asn Asn Thr Ser Gly Glu Gln Met Leu Ile Ile
            180                 185                 190

Trp Gly Val His His Pro Asn Asp Glu Thr Glu Gln Arg Thr Leu Tyr
        195                 200                 205

Gln Asn Val Gly Thr Tyr Val Ser Val Gly Thr Ser Thr Leu Asn Lys
    210                 215                 220

Arg Ser Thr Pro Glu Ile Ala Thr Arg Pro Lys Val Asn Gly Leu Gly
225                 230                 235                 240

Ser Arg Met Glu Phe Ser Trp Thr Leu Leu Asp Met Trp Asp Thr Ile
                245                 250                 255

Asn Phe Glu Ser Thr Gly Asn Leu Ile Ala Pro Glu Tyr Gly Phe Lys
            260                 265                 270

Ile Ser Lys Arg Gly Ser Ser Gly Ile Met Lys Thr Glu Gly Thr Leu
        275                 280                 285

Glu Asn Cys Glu Thr Lys Cys Gln Thr Pro Leu Gly Ala Ile Asn Thr
    290                 295                 300

Thr Leu Pro Phe His Asn Val His Pro Leu Thr Ile Gly Glu Cys Pro
305                 310                 315                 320

Arg Tyr Val Lys Ser Glu Lys Leu Val Leu Ala Thr Gly Leu Arg Asn
                325                 330                 335

Val Pro Gln Ile Glu Ser Arg Gly Leu Phe Gly Ala Ile Ala Gly Phe
            340                 345                 350

Ile Glu Gly Gly Trp Gln Gly Met Val Asp Gly Trp Tyr Gly Tyr His
        355                 360                 365

His Ser Asn Asp Gln Gly Ser Gly Tyr Ala Ala Asp Lys Glu Ser Thr
    370                 375                 380

Gln Lys Ala Phe Asp Gly Ile Thr Asn Lys Val Asn Ser Val Ile Glu
```

385 390 395 400

Lys Met Asn Thr Gln Phe Glu Ala Val Gly Lys Glu Phe Ser Asn Leu
405 410 415

Glu Arg Arg Leu Glu Asn Leu Asn Lys Lys Met Glu Asp Gly Phe Leu
420 425 430

Asp Val Trp Thr Tyr Asn Ala Glu Leu Leu Val Leu Met Glu Asn Glu
435 440 445

Arg Thr Leu Asp Phe His Asp Ser Asn Val Lys Asn Leu Tyr Asp Lys
450 455 460

Val Arg Met Gln Leu Arg Asp Asn Val Lys Glu Leu Gly Asn Gly Cys
465 470 475 480

Phe Glu Phe Tyr His Lys Cys Asp Asp Glu Cys Met Asn Ser Val Lys
485 490 495

Asn Gly Thr Tyr Asp Tyr Pro Lys Tyr Glu Glu Glu Ser Lys Leu Asn
500 505 510

Arg Asn Glu Gly Gly Gly Gly Thr Gly Gly Gly Gly Thr Gly Arg Met
515 520 525

Lys Gln Ile Glu Asp Lys Ile Glu Glu Ile Leu Ser Lys Ile Tyr His
530 535 540

Ile Glu Asn Glu Ile Ala Arg Ile Lys Lys Leu Ile Gly Glu Arg His
545 550 555 560

His His His His His His His
565

<210> SEQ ID NO 21
<211> LENGTH: 554
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ser His Asn Gly Lys Leu Cys Leu Leu Lys Gly Ile Ala
35 40 45

Pro Leu Gln Leu Gly Asn Cys Ser Val Ala Gly Trp Ile Leu Gly Asn
50 55 60

Pro Glu Cys Glu Leu Leu Ile Ser Lys Glu Ser Trp Ser Tyr Ile Val
65 70 75 80

Glu Thr Pro Asn Pro Glu Asn Gly Thr Cys Phe Pro Gly Tyr Phe Ala
85 90 95

Asp Tyr Glu Glu Leu Arg Glu Gln Leu Ser Ser Val Ser Ser Phe Glu
100 105 110

Arg Phe Glu Ile Phe Pro Lys Glu Ser Ser Trp Pro Asn His Thr Val
115 120 125

Thr Gly Val Ser Ala Ser Cys Ser His Asn Gly Lys Ser Ser Phe Tyr
130 135 140

Arg Asn Leu Leu Trp Leu Thr Gly Lys Asn Gly Leu Tyr Pro Asn Leu
145 150 155 160

Ser Lys Ser Tyr Val Asn Asn Lys Glu Lys Glu Val Leu Val Leu Trp
165 170 175

```
Gly Val His His Pro Pro Asn Ile Gly Asn Gln Arg Ala Leu Tyr His
            180                 185                 190

Thr Glu Asn Ala Tyr Val Ser Val Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Gln Arg Glu Thr Gly Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Ser Gly Gly Gly Gly Thr Gly Gly Gly Gly Thr
            500                 505                 510

Gly Arg Met Lys Gln Ile Glu Asp Lys Ile Glu Glu Ile Leu Ser Lys
        515                 520                 525

Ile Tyr His Ile Glu Asn Glu Ile Ala Arg Ile Lys Lys Leu Ile Gly
    530                 535                 540

Glu Arg His His His His His His His His
545                 550
```

<210> SEQ ID NO 22
<211> LENGTH: 574
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 22

```
Met Tyr Arg Met Gln Leu Leu Ser Cys Ile Ala Leu Ser Leu Ala Leu
1               5                   10                  15

Val Thr Asn Ser Asp Thr Ile Cys Ile Gly Tyr His Ala Asn Asn Ser
            20                  25                  30

Thr Asp Thr Val Asp Thr Val Leu Glu Lys Asn Val Thr Val Thr His
        35                  40                  45

Ser Val Asn Leu Leu Glu Asp Ser His Asn Gly Lys Leu Cys Leu Leu
    50                  55                  60

Lys Gly Ile Ala Pro Leu Gln Leu Gly Asn Cys Ser Val Ala Gly Trp
65                  70                  75                  80

Ile Leu Gly Asn Pro Glu Cys Glu Leu Leu Ile Ser Lys Glu Ser Trp
                85                  90                  95

Ser Tyr Ile Val Glu Thr Pro Asn Pro Glu Asn Gly Thr Cys Phe Pro
            100                 105                 110

Gly Tyr Phe Ala Asp Tyr Glu Glu Leu Arg Glu Gln Leu Ser Ser Val
        115                 120                 125

Ser Ser Phe Glu Arg Phe Glu Ile Phe Pro Lys Glu Ser Ser Trp Pro
    130                 135                 140

Asn His Thr Val Thr Gly Val Ser Ala Ser Cys Ser His Asn Gly Lys
145                 150                 155                 160

Ser Ser Phe Tyr Arg Asn Leu Leu Trp Leu Thr Gly Lys Asn Gly Leu
                165                 170                 175

Tyr Pro Asn Leu Ser Lys Ser Tyr Val Asn Asn Lys Glu Lys Glu Val
            180                 185                 190

Leu Val Leu Trp Gly Val His His Pro Pro Asn Ile Gly Asn Gln Arg
        195                 200                 205

Ala Leu Tyr His Thr Glu Asn Ala Tyr Val Ser Val Val Ser Ser His
    210                 215                 220

Tyr Ser Arg Arg Phe Thr Pro Glu Ile Ala Lys Arg Pro Lys Val Arg
225                 230                 235                 240

Asp Gln Glu Gly Arg Ile Asn Tyr Tyr Trp Thr Leu Leu Glu Pro Gly
                245                 250                 255

Asp Thr Ile Ile Phe Glu Ala Asn Gly Asn Leu Ile Ala Pro Trp Tyr
            260                 265                 270

Ala Phe Ala Leu Ser Arg Gly Phe Gly Ser Gly Ile Ile Thr Ser Asn
        275                 280                 285

Ala Pro Met Asp Glu Cys Asp Ala Lys Cys Gln Thr Pro Gln Gly Ala
    290                 295                 300

Ile Asn Ser Ser Leu Pro Phe Gln Asn Val His Pro Val Thr Ile Gly
305                 310                 315                 320

Glu Cys Pro Lys Tyr Val Arg Ser Ala Lys Leu Arg Met Val Thr Gly
                325                 330                 335

Leu Arg Asn Ile Pro Gln Arg Glu Thr Gly Gly Leu Phe Gly Ala Ile
            340                 345                 350

Ala Gly Phe Ile Glu Gly Gly Trp Thr Gly Met Val Asp Gly Trp Tyr
        355                 360                 365

Gly Tyr His His Gln Asn Glu Gln Gly Ser Gly Tyr Ala Ala Asp Gln
    370                 375                 380

Lys Ser Thr Gln Asn Ala Ile Asn Gly Ile Thr Asn Lys Val Asn Ser
385                 390                 395                 400
```

-continued

```
Val Ile Glu Lys Met Asn Thr Gln Phe Thr Ala Val Gly Lys Glu Phe
                405                 410                 415

Asn Lys Leu Glu Arg Arg Met Glu Asn Leu Asn Lys Lys Val Asp Asp
            420                 425                 430

Gly Phe Leu Asp Ile Trp Thr Tyr Asn Ala Glu Leu Leu Val Leu Leu
        435                 440                 445

Glu Asn Glu Arg Thr Leu Asp Phe His Asp Ser Asn Val Lys Asn Leu
    450                 455                 460

Tyr Glu Lys Val Lys Ser Gln Leu Lys Asn Asn Ala Lys Glu Ile Gly
465                 470                 475                 480

Asn Gly Cys Phe Glu Phe Tyr His Lys Cys Asn Asn Glu Cys Met Glu
                485                 490                 495

Ser Val Lys Asn Gly Thr Tyr Asp Tyr Pro Lys Tyr Ser Glu Glu Ser
            500                 505                 510

Lys Leu Asn Arg Glu Lys Ile Asp Gly Ser Gly Gly Gly Gly Thr Gly
        515                 520                 525

Gly Gly Gly Thr Gly Arg Met Lys Gln Ile Glu Asp Lys Ile Glu Glu
    530                 535                 540

Ile Leu Ser Lys Ile Tyr His Ile Glu Asn Glu Ile Ala Arg Ile Lys
545                 550                 555                 560

Lys Leu Ile Gly Glu Arg His His His His His His His His
                565                 570
```

<210> SEQ ID NO 23
<211> LENGTH: 502
<212> TYPE: PRT
<213> ORGANISM: Influenza virus

<400> SEQUENCE: 23

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Phe Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Val Asn Asn Lys Glu Lys Glu Val Leu Val Leu Trp
                165                 170                 175

Gly Val His His Pro Pro Asn Ile Gly Asn Gln Arg Ala Leu Tyr His
            180                 185                 190

Thr Glu Asn Ala Tyr Val Ser Val Val Ser Ser His Tyr Ser Arg Arg
        195                 200                 205
```

```
Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Gln Arg Glu Thr Gly Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Ser
            500


<210> SEQ ID NO 24
<211> LENGTH: 499
<212> TYPE: PRT
<213> ORGANISM: Influenza virus

<400> SEQUENCE: 24

Arg Gly Asp Gln Ile Cys Ile Gly Tyr His Ala Asn Asn Ser Thr Glu
1               5                   10                  15

Lys Val Asp Thr Ile Leu Glu Arg Asn Val Thr Val Thr His Ala Lys
            20                  25                  30

Asp Ile Leu Glu Lys Thr His Asn Gly Lys Leu Cys Lys Leu Asn Gly
        35                  40                  45

Ile Pro Pro Leu Glu Leu Gly Asp Cys Ser Ile Ala Gly Trp Leu Leu
    50                  55                  60

Gly Asn Pro Glu Cys Asp Arg Leu Leu Ser Val Pro Glu Trp Ser Tyr
```

-continued

```
65                  70                  75                  80

Ile Met Glu Lys Glu Asn Pro Arg Asp Gly Leu Cys Phe Pro Gly Ser
                85                  90                  95

Phe Asn Asp Tyr Glu Glu Leu Lys Tyr Leu Leu Ser Ser Val Lys His
            100                 105                 110

Phe Glu Lys Val Lys Ile Leu Pro Lys Asp Arg Trp Thr Gln His Thr
        115                 120                 125

Thr Thr Gly Gly Ser Arg Ala Cys Ala Val Ser Gly Asn Pro Ser Phe
    130                 135                 140

Phe Arg Asn Met Val Trp Leu Thr Lys Lys Gly Ser Asp Tyr Pro Val
145                 150                 155                 160

Ala Lys Gly Ser Tyr Asn Asn Thr Ser Gly Glu Gln Met Leu Ile Ile
                165                 170                 175

Trp Gly Val His His Pro Asn Asp Glu Thr Glu Gln Arg Thr Leu Tyr
            180                 185                 190

Gln Asn Val Gly Thr Tyr Val Ser Val Gly Thr Ser Thr Leu Asn Lys
        195                 200                 205

Arg Ser Thr Pro Glu Ile Ala Thr Arg Pro Lys Val Asn Gly Leu Gly
    210                 215                 220

Ser Arg Met Glu Phe Ser Trp Thr Leu Leu Asp Met Trp Asp Thr Ile
225                 230                 235                 240

Asn Phe Glu Ser Thr Gly Asn Leu Ile Ala Pro Glu Tyr Gly Phe Lys
                245                 250                 255

Ile Ser Lys Arg Gly Ser Ser Gly Ile Met Lys Thr Glu Gly Thr Leu
            260                 265                 270

Glu Asn Cys Glu Thr Lys Cys Gln Thr Pro Leu Gly Ala Ile Asn Thr
        275                 280                 285

Thr Leu Pro Phe His Asn Val His Pro Leu Thr Ile Gly Glu Cys Pro
    290                 295                 300

Arg Tyr Val Lys Ser Glu Lys Leu Val Leu Ala Thr Gly Leu Arg Asn
305                 310                 315                 320

Val Pro Gln Ile Glu Ser Arg Gly Leu Phe Gly Ala Ile Ala Gly Phe
                325                 330                 335

Ile Glu Gly Gly Trp Gln Gly Met Val Asp Gly Trp Tyr Gly Tyr His
            340                 345                 350

His Ser Asn Asp Gln Gly Ser Gly Tyr Ala Ala Asp Lys Glu Ser Thr
        355                 360                 365

Gln Lys Ala Phe Asp Gly Ile Thr Asn Lys Val Asn Ser Val Ile Glu
    370                 375                 380

Lys Met Asn Thr Gln Phe Glu Ala Val Gly Lys Glu Phe Ser Asn Leu
385                 390                 395                 400

Glu Arg Arg Leu Glu Asn Leu Asn Lys Lys Met Glu Asp Gly Phe Leu
                405                 410                 415

Asp Val Trp Thr Tyr Asn Ala Glu Leu Leu Val Leu Met Glu Asn Glu
            420                 425                 430

Arg Thr Leu Asp Phe His Asp Ser Asn Val Lys Asn Leu Tyr Asp Lys
        435                 440                 445

Val Arg Met Gln Leu Arg Asp Asn Val Lys Glu Leu Gly Asn Gly Cys
    450                 455                 460

Phe Glu Phe Tyr His Lys Cys Asp Asp Glu Cys Met Asn Ser Val Lys
465                 470                 475                 480

Asn Gly Thr Tyr Asp Tyr Pro Lys Tyr Glu Glu Glu Ser Lys Leu Asn
                485                 490                 495
```

Arg Asn Glu

<210> SEQ ID NO 25
<211> LENGTH: 500
<212> TYPE: PRT
<213> ORGANISM: Influenza virus

<400> SEQUENCE: 25

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Val Asn Asp Leu Cys Phe Pro Gly Asp Phe Asn
85 90 95

Asp Tyr Glu Glu Leu Lys His Leu Leu Ser Arg Ile Asn His Phe Glu
100 105 110

Lys Ile Gln Ile Ile Pro Lys Ser Ser Trp Ser Ser His Glu Ala Ser
115 120 125

Leu Gly Val Ser Ser Ala Cys Pro Tyr Gln Gly Lys Ser Ser Phe Phe
130 135 140

Arg Asn Val Val Trp Leu Ile Lys Lys Asn Ser Thr Tyr Pro Thr Ile
145 150 155 160

Lys Arg Ser Tyr Asn Asn Thr Asn Gln Glu Asp Leu Leu Val Leu Trp
165 170 175

Gly Ile His His Pro Asn Asp Ala Ala Glu Gln Thr Lys Leu Tyr Gln
180 185 190

Asn Pro Thr Thr Tyr Ile Ser Val Gly Thr Ser Thr Leu Asn Gln Arg
195 200 205

Leu Val Pro Arg Ile Ala Thr Arg Ser Lys Val Asn Gly Gln Ser Gly
210 215 220

Arg Met Glu Phe Phe Trp Thr Ile Leu Lys Pro Asn Asp Ala Ile Asn
225 230 235 240

Phe Glu Ser Asn Gly Asn Phe Ile Ala Pro Glu Tyr Ala Tyr Lys Ile
245 250 255

Val Lys Lys Gly Asp Ser Thr Ile Met Lys Ser Glu Leu Glu Tyr Gly
260 265 270

Asn Cys Asn Thr Lys Cys Gln Thr Pro Met Gly Ala Ile Asn Ser Ser
275 280 285

Met Pro Phe His Asn Ile His Pro Leu Thr Ile Gly Glu Cys Pro Lys
290 295 300

Tyr Val Lys Ser Asn Arg Leu Val Leu Ala Thr Gly Leu Arg Asn Ser
305 310 315 320

Pro Gln Arg Glu Thr Arg Gly Leu Phe Gly Ala Ile Ala Gly Phe Ile
325 330 335

Glu Gly Gly Trp Gln Gly Met Val Asp Gly Trp Tyr Gly Tyr His His
340 345 350

Ser Asn Glu Gln Gly Ser Gly Tyr Ala Ala Asp Lys Glu Ser Thr Gln
355 360 365

```
Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser
            500


<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5


<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 27

His His His His His His His His
1               5


<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Ser Gly Gly
1               5
```